(12) United States Patent
Falcenberg et al.

(10) Patent No.: US 9,458,463 B2
(45) Date of Patent: Oct. 4, 2016

(54) METHOD FOR TREATMENT OF DIABETES BY A SMALL MOLECULE INHIBITOR FOR GRK5

(71) Applicant: MAX-PLANCK-GESELLSCHAFT ZUR FÖRDERUNG DER WISSENSCHAFTEN E.V., Munich (DE)

(72) Inventors: Mathias Falcenberg, Martinsried (DE); Axel Ullrich, Munich (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 0 days.

(21) Appl. No.: 14/554,714

(22) Filed: Nov. 26, 2014

(65) Prior Publication Data

US 2015/0079108 A1    Mar. 19, 2015

Related U.S. Application Data

(63) Continuation-in-part of application No. 13/820,226, filed as application No. PCT/EP2011/004567 on Sep. 5, 2011, now abandoned.

(60) Provisional application No. 61/344,668, filed on Sep. 8, 2010.

(30) Foreign Application Priority Data

Sep. 3, 2010   (EP) .................................... 10075383

(51) Int. Cl.
 *A61K 31/00*   (2006.01)
 *C12N 15/113*   (2010.01)

(52) U.S. Cl.
 CPC ............ *C12N 15/1137* (2013.01); *A61K 31/00* (2013.01); *C12Y 207/11016* (2013.01); *C12N 2310/11* (2013.01); *C12N 2310/14* (2013.01)

(58) Field of Classification Search
 CPC .............. C07K 16/40; C07K 2317/76; C12N 15/1137
 See application file for complete search history.

(56) References Cited

U.S. PATENT DOCUMENTS

| | | | |
|---|---|---|---|
| 6,255,069 B1 * | 7/2001 | Benovic | C12N 9/1205 435/252.3 |
| 7,319,093 B2 * | 1/2008 | Fischer | C07H 19/20 514/42 |
| 2002/0034767 A1 * | 3/2002 | Benovic | C12N 9/1205 435/7.1 |
| 2004/0022772 A1 | 2/2004 | Arlinghaus et al. | |
| 2007/0292409 A1 * | 12/2007 | Olefsky | C12Q 1/485 424/130.1 |
| 2008/0160011 A1 | 7/2008 | Chilcote et al. | |

FOREIGN PATENT DOCUMENTS

WO    2005-113799    1/2005

OTHER PUBLICATIONS

International Search Report for PCT/EP2011/004567 mailed on Mar. 23, 2012.
Written Opinion for PCT/EP2011/004567 mailed on Mar. 23, 2012.
U.S. Non-Final Office Action for U.S. Appl. No. 13/820,226, filed Mar. 1, 2013, 19 pages.
U.S. Final Office Action for U.S. Appl. No. 13/820,226, filed Mar. 1, 2013, 11 pages.
Sorriento, et al. "Kinase independent inhibition of NFkB transcriptional activity by GRK5 through IkBα stabilization", Nature Precediings, Sep. 29, 2007, 30 pages.
Usui, et al. "GRK2 is an endogenous protein inhibitor of the insulin signaling pathway for glucose transport stimulation", The European Molecular Biology Organization Journal, 2004, vol. 23, No. 14, 10 pages.
Wang, et al. "GRK5 ablation contributes to insulin resistance", Biochemical and Biophysical Research Communications 429, 2012, pp. 99-104.
Herman, et al. Medizinische Genetik, vol. 22, 2010, P-MoleG-193.
Louvet, et al. "Tyrosine kinase inhibitors reverse type 1 diabetes in nonobese diabetic mice", PNAS, vol. 105, Dec. 2, 2008, pp. 18895-18900.

* cited by examiner

*Primary Examiner* — Gyan Chandra
(74) *Attorney, Agent, or Firm* — Amin, Turocy & Watson, LLP

(57) ABSTRACT

The present invention is related to compound capable of modulating the activity and/or expression of the protein kinase GRK5, thereby enhancing the expression and/or release of insulin. The invention is further related to methods of identifying said compounds for the treatment of diseases of the carbohydrate metabolism. The invention is further related to methods of treatment of diseases of the carbohydrate metabolism, particularly diabetes mellitus type 2.

9 Claims, 22 Drawing Sheets

METHOD FOR TREATMENT OF DIABETES BY A SMALL MOLECULE INHIBITOR FOR GRK5

CROSS REFERENCE TO RELATED APPLICATIONS

This application is a Continuation-in-Part of application Ser. No. 13/820,226 filed Mar. 1, 2013, which is hereby incorporated by reference.

BACKGROUND OF THE INVENTION

1. Field of the Invention

The present invention is related to compound capable of modulating the activity and/or expression of certain protein kinases thereby enhancing the expression and/or release of insulin. The invention is further related to methods of identifying said compounds for the treatment of metabolic diseases. The invention is further related to methods of treatment of metabolic diseases, particularly diabetes mellitus type 2.

Diabetes as a leading cause of death in developed countries is a metabolic condition characterized by high blood sugar levels. There are two main types of diabetes: type 1, resulting from insufficient insulin production of the pancreas beta cells, which requires the person to inject insulin; and type 2, resulting from insensitivity of peripheral tissues (such skeletal muscle, liver or adipose tissue) insulin release alterations, and relative insulin deficiency. Diabetes mellitus type 2 is often acquired and accompanied by obesity; it can be treated in first hand by reducing weight, diet and exercise. Type 1 diabetes is a genetic or autoimmune disease; the only effective therapy to date is the supply of exogenous insulin. This therapy does not cure diabetes; the person needs continuous supply of insulin.

The decreased insulin sensitivity of peripheral tissues in type 2 diabetes which accounts for 90% of all cases of the disease is initially compensated by an increased release of insulin by the beta cells of the pancreas. At a certain stage of the disease, the pancreas cannot maintain the increases release of insulin anymore. As disease progresses, drugs which are currently available and elevate insulin release have led to beta-cell damage and loss of insulin production.

A number of diseases, including cancer, diabetes and inflammation are linked to perturbation of protein kinase mediated cell signaling pathways. For some time, a new class of multiple kinase drugs has been undergoing clinical trials. Some have been approved for various applications, mostly for the treatment of cancer. The targets of these multiple kinase inhibitors like Imanitib or Sunitinib interact at all stages of signal transduction: from the receptor tyrosine kinases which initiate intracellular signaling to second-messenger generators and kinases involved in signaling cascades and finally to those kinases which regulate the cell cycle governing cellular fate.

2. Description of Related Art

Several publications have shown the effect of kinase-inhibitors like Sunitinib (Sutent®) and Imatinib (Gleevec®) on diabetes during a period of treatment which leads to a remission of diabetes type 1 or 2 in patients. However, only few kinases could be identified that affect the insulin release or sensitivity specifically to develop a more specific treatment strategy.

BRIEF SUMMARY OF THE INVENTION

The objective of the present invention is to provide targets for the treatment of metabolic diseases such as diabetes, compounds which are useful for raising the blood insulin level by enhancing the insulin release of the pancreatic beta cells and methods for identifying such compounds. This goal is achieved by the compounds which bind to regulating protein kinases according to claim 1 as well as by the methods for identifying such compounds and the disclosed targets SCYL1, ADCK1, and GRK5. Further advantageous embodiments, aspects and details of the invention are evident from the pending claims, the description, the examples and the figures.

The invention refers particularly to a modulator for the inhibition of the activity of protein kinases, wherein kinases with a molar mass larger than 60 kDa selected from the group consisting of GRK5 are preferred targets for inhibition, and wherein a preferred goal of the inhibition is the treatment of metabolic diseases, more preferred of a disease of the carbohydrate metabolism, more preferred of diabetes, more preferred of diabetes mellitus type 2, and most preferred for the up-regulation of insulin production and/or release of insulin. The invention refers further to a modulator for the inactivation, degradation, downregulation, intercalation of at least one nucleic acid selected from the group consisting of the nucleic acid encoding GRK5 for the treatment of metabolic diseases, more preferred of a disease of the carbohydrate metabolism, more preferred of diabetes, more preferred of diabetes mellitus type 2, and most preferred for the up-regulation of insulin production and/or release of insulin.

The said modulator can be chosen from the group comprising a small molecule, an RNA molecule, a siRNA molecule, a miRNA molecule, or a precursor thereof, an antisense oligonucleotide, an aptamer, a polypeptide, an antibody, or a ribozyme, wherein RNA, peptides, small molecules and aptamers are preferred modulators.

The invention refers further to a pharmaceutical composition comprising a modulator for the treatment of metabolic diseases, more preferred of a disease of the carbohydrate metabolism, more preferred of diabetes, more preferred of diabetes mellitus type 2, and most preferred for the up-regulation of insulin production.

The invention refers further to a method for screening for a modulator for treatment of a metabolic disease, wherein the method comprises providing a test compound for contacting at least one polypeptide or nucleic acid coding for at least one polypeptide of a mass larger than 60 kDa selected from the group consisting of GRK5 polypeptide, detecting the binding of said test compound to the GRK5 polypeptide or nucleic acid coding for at least one polypeptide, and determining the activity of the GRK5 polypeptide in the presence of said test compound.

For identification of an inventive compound the invention further provides a kit comprising the GRK5 polypeptides, the nucleic acid encoding GRK5, a cell line with a glucose dependent insulin production, and a control compound known to affect the insulin production by binding the GRK5 polypeptide.

The invention further provides a method for treatment of a metabolic disease comprising administering a subject in need thereof a therapeutically effective amount of at least one modulator for inhibition or activation of at least one of the kinases selected from the group consisting of GRK5, or inactivation, degradation, downregulation, intercalation or activation of at least one nucleic acid selected from the group consisting of the nucleic acid encoding GRK5.

Furthermore, a list of known small molecule GRK5 inhibitors is disclosed.

BRIEF DESCRIPTION OF THE DRAWINGS

Legend
(FIGS. 20 and 21: Sunitinib is missed9

FIG. 17: Uptake of glucose analogue 2-NBDG after inhibition of GRK5 in C2C12 mouse myoblasts.

FIG. 18: Uptake of glucose analogue 2-NBDG after inhibition of GRK5 in beta TC6 cells.

FIG. 19: Uptake of glucose analogue 2-NBDG after inhibition of GRK5 in beta 3T3-L1 cells.

FIG. 20: Uptake of glucose analogue 2-NBDG after inhibition of GRK5 in matured C2C12 myotubes.

FIG. 21: Uptake of glucose analogue 2-NBDG after inhibition of GRK5 in 3T3-L1 adipocytes.

DETAILED DESCRIPTION OF THE INVENTION

It was surprisingly found that Sunitinib has an effect on insulin release in a dose dependent manner. It was found that this effect was due to the inhibition of certain kinases by Sunitinib. It was further surprisingly found that the inhibition of identified protein kinases of a molar mass larger than 60 kDa by other compounds results in the enhanced release of insulin. It was further found that the combined inhibition of certain protein kinase pairs results in the release of additional insulin. It was further found that the inhibition of certain protein kinase pairs results in an insulin releasing effect which equals the effect after Sunitinib treatment.

Kinases are enzymes which catalyze the transfer of a phosphate group from a donor onto an acceptor. Phosphorylated is a nucleophil functional group, such as hydroxyl-, carboxy-, guanidino-, thiol-, or imidazole groups. Kinases which phosphorylate proteins are called protein kinases. Protein kinases play a particular role in cellular signal transduction. They are usually categorized by their substrate; thus protein kinases may be roughly divided into two groups: protein tyrosine kinases (PTK), which phosphorylate the hydroxyl group of the tyrosine, and serine/threonine kinases (STK), which phosphorylate the hydroxyl groups of the serine or threonine. Examples for PTK are Kinases of the EphA family, Lck, Scyl, HCK, BLK, ITK, TEC, EXK, BTK, CTK, Fyn, Fgr, Src, Yes, Lyn, Tyk, JAK-family, CSK, Arg, Abl, Fes, Fer, Srm, Brk, Syk, ZAP70, FAK, PYK2, DDR, TRK, HER-family, FGFR-family, FLT, Mer, Reg, Axl, Met, Ron, RYK, InsR, IGF1R, LTK, ALK, Ros, Lmr-family. STK are mainly regulated by cAMP, cGMP, DAG, $Ca^{2+}$ or Calmodulin, 1,2-Diacylglycerine, PIP3 and other phospholipid-derivates. Examples for STK include enzymes of the families protein kinase A, B and C, GRK-family, MAST-family, CSNK, PRK, NDR, p70S6K, MSK, MRCK, ROCK, CRIK, DMPK, PKN, Nek, Pim, Aur, SSTK, TSSK, Obscn, skMLCK, DRAK, FAPK, BRSK, MNK, PKD, MAP, PIK3, CHBK, PIP, CERK, TLK, CASK, AKT, KCNH2, GSK, FUK.

Other categorizations are based on the activating compounds of the kinases, or the activating mechanism, or certain catalytic domains or specific amino acid sequences of the kinases. The sum of all kinases in one cell is called kinome.

Based on their function the protein kinases present a very important control mechanism in signal transduction, and are controlling various anabolic and metabolic pathways. On the basis of their importance dysfunctions of protein kinases in cellular pathways are the cause for many diseases, like cancer, metabolic diseases, cardiovascular diseases, arteriosclerosis, thyroid disorders, endocrinological diseases, gastroenterological diseases, inflammation, immune disorders, disorders affecting growth and development, hematological diseases, respiratory diseases, muscle skeleton diseases, neurological diseases, and urological disease. This makes these enzymes attractive molecular targets for therapy.

Figure 1:
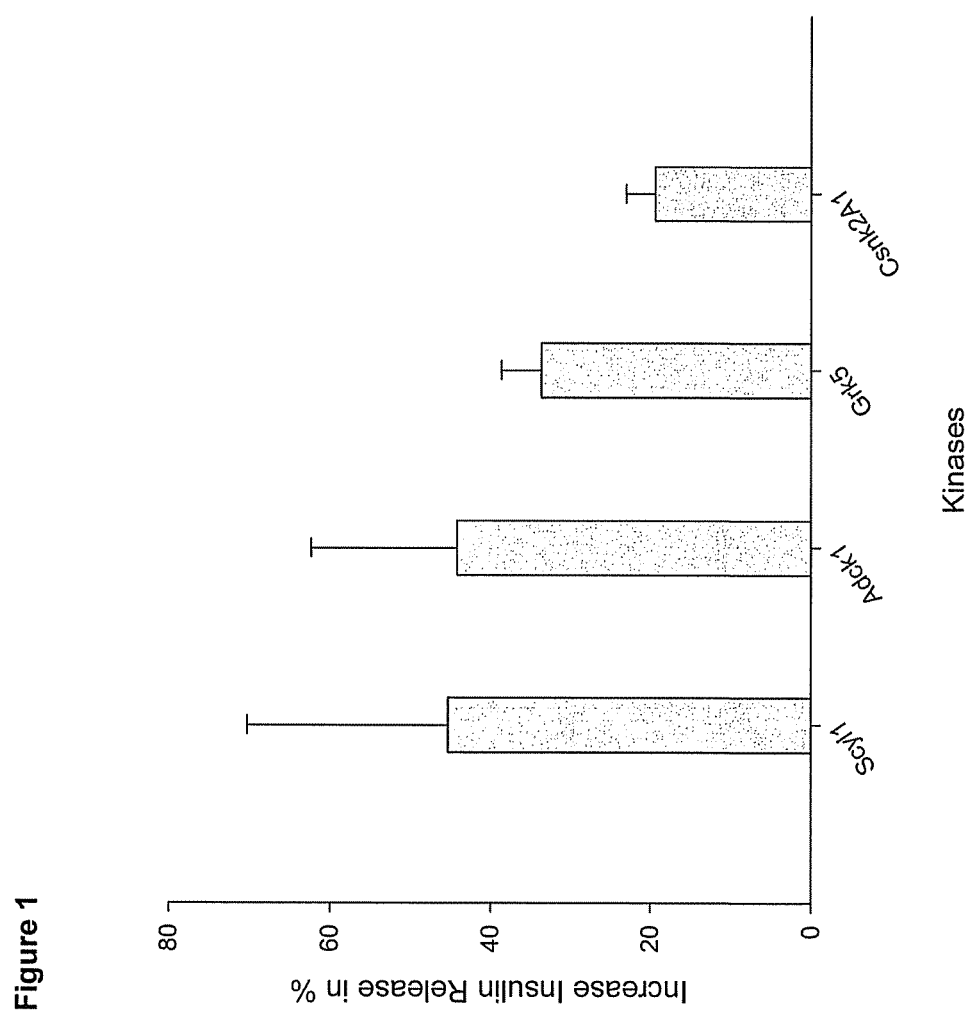
FIG. 1: Assortment of the positive and negative regulating kinases of the kinome screen. The candidate kinases were limited by using hierarchical clustering and proposing and increased insulin release of 15% significant. Additionally, the data were correlated to Sunitinib treatment (5 µM) and a non-targeting siRNA as positive and negative controls. The results are shown for n≥4 biological independent experiments.
Figure 2A:
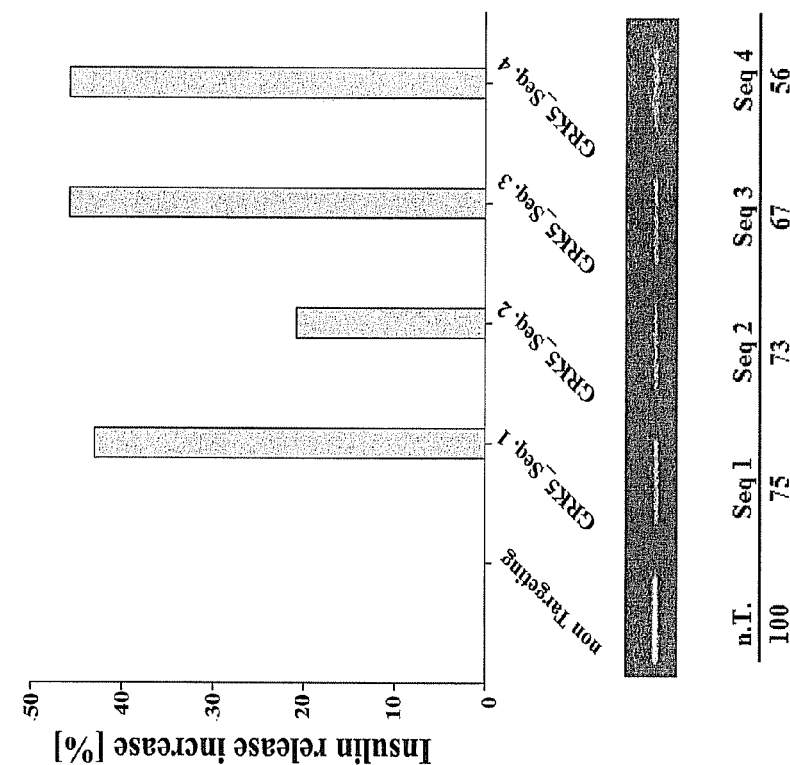
FIG. 2: Correlation of the insulin release increase to the target depletion for each used siRNA sequence for the kinases SCYL1 (FIG. 2A), GRK5 (FIG. 2B), and ADCK1 (FIG. 2C). The insulin release for the kinases (bar chart; upper panel) correlated with their knock-down efficiency, which was monitored by RT-PCR and scanning densitometry (agarose gel; middle panel; depletion; lower panel). The insulin increase as well as the knock-down efficiency is compared to the insulin release or gene depletion of the non-targeting siRNA.
Figure 2B:
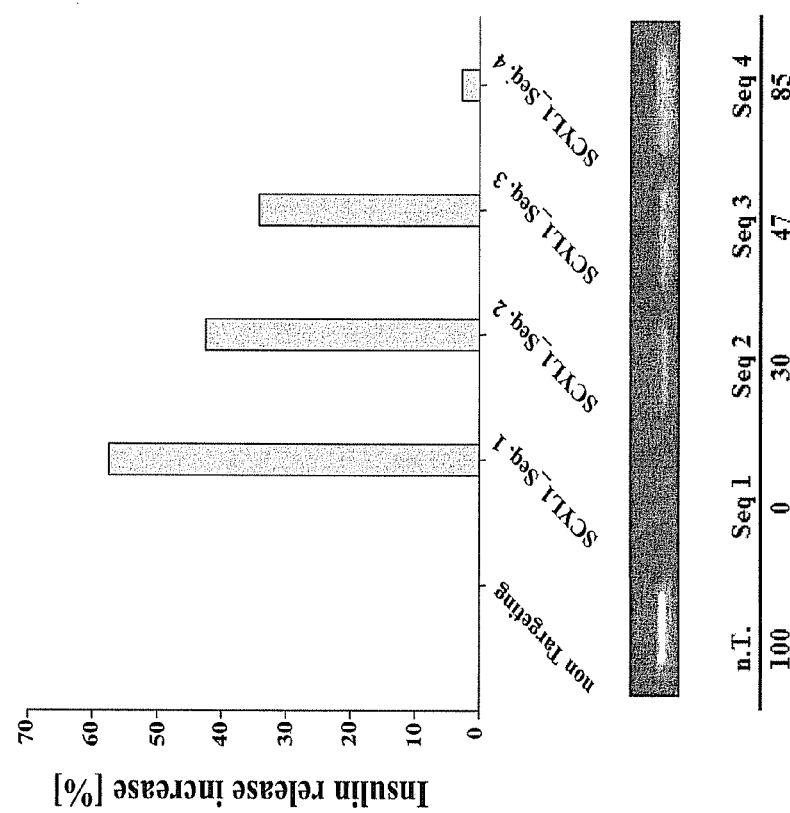
Figure 2C:
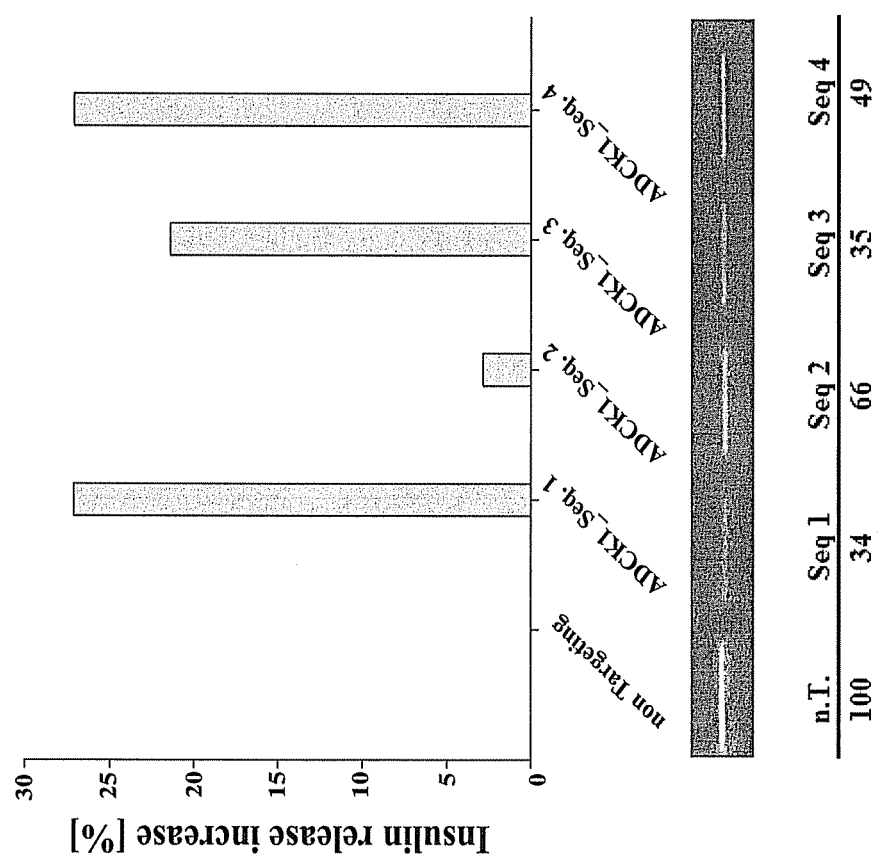
Figure 4:
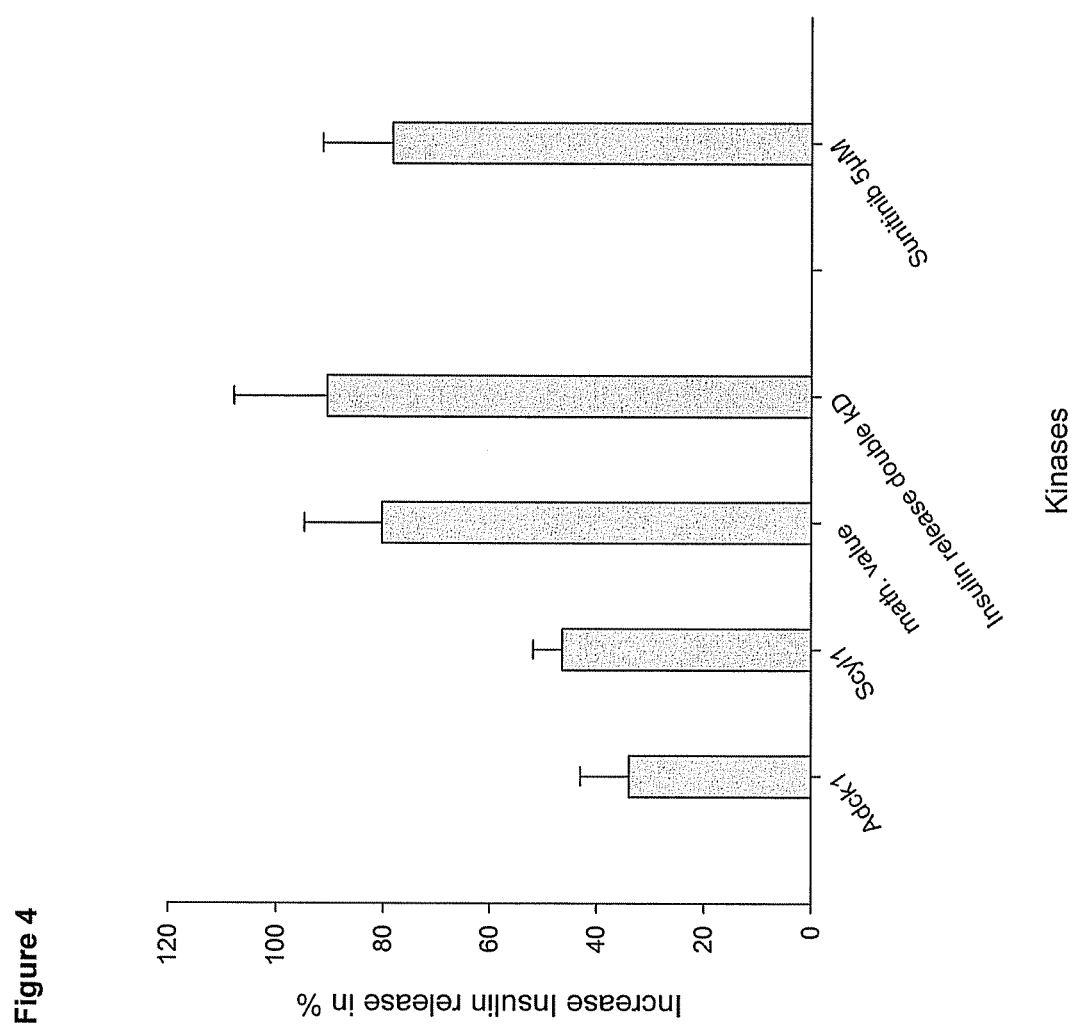
FIG. 4: Additional increase of the insulin release due to a double knock-down for the kinase pair SCYL1 and ADCK1. The depletion resulted in the highest Insulin release (90.64±17.32%), which equaled the insulin after Sunitinib treatment. The figure depicts the values of the single knock-down (light grey and grey), the theoretical mathematical value (changeover dark grey to grey) and the real insulin increase after a double knock-down (dark grey).

Surprisingly the kinase GRK5 was identified to modulate the insulin release in a significant manner (FIGS. 1 and 4). These kinases are preferred targets for the therapy of metabolic disease, preferred of diabetes, more preferred of diabetes type 2, and most preferred to elevate the blood level of insulin. These kinases share the feature of having a molecular mass of at least 60 kDa. Apparently kinases of a certain size are particularly easy inhibited resulting in modulation of insulin release. Kinases which present a target for the therapy of metabolic diseases are basically all kinases which affect metabolic pathways. According to the invention, kinases which have been found to affect or modulate the insulin release or sensitivity and are thus preferred targets for a therapy of diabetes, preferably diabetes type 2, are kinases the inhibition of which is correlated to a significant increase of insulin release, namely GRK5.

The present invention refers particularly to a modulator for
a) inhibition of at least one of the protein kinases selected from the group consisting of GRK5, or
b) inactivation, degradation, downregulation, intercalation of at least one nucleic acid selected from the group consisting of the nucleic acid encoding GRK5,
for the treatment of disease of the carbohydrate metabolism.

Thus, in a preferred embodiment of the invention, the action of the protein kinase GRK5 is blocked by a modulator or even more preferred by an inhibitor.

Hence, the present invention refers preferred to an inhibitor for
a) at least one of the protein kinases selected from the group consisting of GRK5, or
b) inactivation, degradation, downregulation or intercalation of at least one nucleic acid selected from the group consisting of the nucleic acid encoding GRK5,
for the treatment of disease of the carbohydrate metabolism.

It is sufficient to block the kinase GRK5. Enzyme inhibitors are, in general, molecules which bind to enzymes and decrease their activity. The binding of an inhibitor can stop a substrate from entering the enzymes active site, compete with the substrate for the binding site, or hinder the enzyme from catalyzing its reaction. Inhibitor binding can be reversible or irreversible. Protein kinase inhibitors are a type of enzyme inhibitors which specifically block the action of one or more protein kinases. Inhibition of protein kinases can be achieved using a pseudosubstrate binding to the active site of these kinases mimicking the target sequence of the corresponding kinase, but having no serine or threonine.

In another preferred embodiment, the action of the protein kinase GRK5 is impeded by interference of their nucleic acid, which can be both DNA and RNA, by inactivation, degradation, downregulation, or intercalation. Inactivation of a nucleic acid can happen for instance by methylation of nucleotides, insertion, deletion, nucleotide exchange, cross linkage, or strand break/damage. Nucleic acids can be degraded down to single nucleotides by temperature, chemicals, enzymes, and particularly RNA by deadenylation or 5'decay or 3'decay. Downregulation of DNA or RNA is referred to as diminished expression of these nucleic acids and can happen by binding of repressors, which are usually polypeptides, but can also happen by chemical or structural changes or modifications of the nucleic acids. Intercalation is the reversible inclusion of a molecule between two other molecules. In nucleic acids, intercalation occurs when ligands of an appropriate size and chemical nature fit themselves in between base pairs.

The term modulator as it appears herein refers to a molecule that is able to change the activity of the GRK5 polypeptide. This change may be an increase or a decrease in enzymatic activity, binding characteristics, or functional, immunological or any other biological property of the polypeptides. In order to enhance the insulin release, a decrease of the enzymatic activity is advantageous.

According to the invention, modulators for the inhibition of GRK5 can be molecules like small molecules, RNA or DNA molecules, siRNA or precursor thereof, miRNA or precursors thereof, ribozymes, DNA or RNA antisense oligonucleotides, aptamers, antibodies or fragments thereof, peptides, polypeptides, cyclopeptides, or drugs like imatinib, dasanitib, and sorafenib.

The inventive modulators are also referred to as compounds or test compounds. They modulate the expression and/or activity of the polypeptides of the invention and can be identified using one or more assays, alone or in combination. Test compounds used in the screening are not particularly limited. They can be either artificial or natural.

The term small molecule refers to low molecular weight organic compound which is by definition not a polymer. In the field of pharmacology, it is usually restricted to a molecule that also binds with high affinity to a biopolymer such as proteins, nucleic acids, or polysaccharides. The upper molecular weight limit for a small molecule is approximately 200 Da which allows for the possibility to rapidly diffuse across cell membranes. Small molecules are broadly used as enzyme inhibitors, thus they are preferred modulators for the inhibition of the preferred kinases in the present invention.

Small interfering RNA (short interfering RNA, silencing RNA, siRNA) is a class of double-stranded RNA-molecules, which are 19-30 nucleotides, preferably 20-25 nucleotides long. SiRNAs are involved in the RNA-interference of the expression of a specific gene. SiRNAs are cut from long doublestranded RNAs by the RNase III Dicer. They can also be derived by chemical synthesis. They also play a role in antiviral mechanisms or in shaping the chromatin structure of a genome. In molecular research, synthetic siRNAs can also be used in RNA-interference (RNAi) to regulate down the expression of specific target genes. With their ability to knock down essentially any gene of interest, siRNAs have been used to knock down protein kinases to investigate their role in insulin production (FIG. 1-FIG. 4). SiRNAs are preferred modulators for inhibition of the preferred kinases in the present invention.

MicroRNAs (miRNAs) are posttranscriptional regulators that bind to complementary sequences in the 3'UTR of mRNA transcripts, usually resulting in gene silencing. They are short RNA molecules which are about 22 nucleotides long. As miRNAs have been shown to play multiple roles in transcript degradation, sequestering and transcriptional suppression, they are also preferred modulators for inhibition of the preferred kinases in the present invention.

Precursor molecules, e.g. precursor molecules of siRNA and/or miRNA may be a substrate for the siRNA/miRNA-biogenesis-apparatus of the target cell. This comprises, for example, RNA precursor molecules such as double-stranded RNA (dsRNA) or short hairpin RNA-molecules (shRNA), which are processed by endonucleases such as Drosha and/or Pasha to siRNA-molecules or miRNA-molecules, respectively. For this reason, for example dsRNA-molecules or short hairpin RNA-molecules (shRNA) having a length of more than 27 nucleotides, preferably more than 30 up to 100 nucleotides or longer, and mostly preferred dsRNA-molecules having a length of 30-50 nucleotides, can be used.

Further precursor molecules according to the invention may be DNA constructs encoding dsRNA, shRNA, siRNA and/or miRNA, whereby the coding elements are controlled by regulatory elements allowing an expression of dsRNA, shRNA, siRNA and/or miRNA in the target cell. Examples for such control elements are polymerase II promoters or polymerase III promoters such as, for example, U6 or H1.

Ribozymes are catalytic RNAs which possess a well-defined structure that enables them to catalyze a chemical reaction. Apart from naturally occurring ribozymes they can be made artificially and be tailored to interact with nucleic acids and proteins. Ribozymes are also preferred modulators for inhibition of the preferred kinases in the present invention.

Antisense oligonucleotides are single strands of DNA or RNA that are complementary to a chosen sequence. They are between 10 and 35 nucleotides long, preferably about 20-25 nucleotides. Antisense DNA oligonucleotides can target specific, complementary RNA, and upon binding DNA/RNA hybrids are formed. Antisense RNA oligonucleotides can bind to mRNA by binding to mRNA strands. Antisense oligonucleotides are also preferred modulators for inhibition of the preferred kinases in the present invention.

Aptamers are oligonucleic acid (DNA or RNA aptamers) or peptide molecules (peptide aptamers) that bind to a specific target molecule. Aptamers can be used for therapeutic purposes as macromolecular drugs. Aptamers can be created by selecting them from a large random sequence pool. Aptamers are also preferred modulators for inhibition of the preferred kinases in the present invention.

Antibodies are proteins which bind very specifically to antigens. They are formed by the immune system of the body in response to antigen presence. They can be formed for virtually any structure and are thus valuable tools for direct interaction with certain molecules. Recombinant techniques are used to generate antibodies and antibody fragments which basically consist of the binding moieties of the antibodies, such as single chain antibodies. They can be applied in vivo in extracellular and intracellular applications. Antibodies are also preferred modulators for inhibition of the preferred kinases in the present invention. Various antibodies binding to the kinase GRK5 are commercially available. Alternatively, specific inhibitor antibodies against the kinases can by generated by technology known in the art, so that antibody generation does not represent an undue experimental burden for use of the invention.

Peptides are stretches of amino acid residues which are connected by peptide bonds. They can be seen as little proteins. Peptides are usually up to 100 amino acids long, from which on the compound is referred to as a protein. Polypeptides are peptides of at least 10 amino acids. Cyclopeptides are formed by two, three or more amino acids, which form ring structures and have thus no C- and N-terminal amino acids. Peptides are preferred, polypeptides more preferred modulators for inhibition of the preferred kinases in the present invention.

The drugs sunitinib, imatinib, dasatinib, and sorafenib are small molecules which inhibit protein kinases which are mainly used in cancer treatment. However, in the present invention the drug sunitinib is not a preferred modulator for inhibition of the preferred kinases as one major side effect under sunitinib treatment is high blood pressure. People who have diabetes tend to have more trouble with high blood pressure than people who don't have the disease. Having both diabetes and high blood pressure can pack a damaging one-two punch as far as increasing the risk of heart disease, stroke, and eye, kidney and nerve complications. There are particularly common diabetes complications associated with elevated blood pressure. These complications include diabetic retinopathy and diabetic nephropathy. Controlling blood pressure of people with diabetes reduces the risk of future complications as established by a study done by the UK Prospective Diabetes Study.

Metabolic diseases refer to diseases and conditions characterized by pathological disorders of the metabolism. They are mainly characterized by enzyme defects and abnormalities in the regulating system leading to a pathological enrichment of substrates, lack of metabolic products, failure of producing energy, of regeneration of cellular constituents, of elimination of metabolic products, and of maintenance of homeostasis. They can be acquired or be a genetic disease. Metabolic disorders include, but are not limited to, obesity and diabetes (e.g., diabetes type I, diabetes type II, MODY, and gestational diabetes), hypoglycemia, amyloidosis, branched chain disease, hyperaminoacidemia, hyperaminoaciduria, disturbances of the metabolism of urea, hyperammonemia, mucopolysaccharidoses e. g. Maroteaux-Lamy syndrom, glycogen storage diseases and lipid storage diseases, Cori's disease, intestinal carbohydrate malabsorption, maltase-, lactase-, sucrase-insufficiency, disorders of the metabolism of fructose, disorders of the metabolism of galactose, galactosaemia, disturbances of pyruvate metabolism, hypolipidemia, hypolipoproteinemia, hyperlipidemia, hyperlipoproteinemia, camitine or camitine acyltransferase deficiency, porphyrias, disturbances of the purine metabolism, lysosomal diseases, metabolic diseases of nerves and nervous systems like gangliosidoses, sphingolipidoses, sulfatidoses, leucodystrophies, Lesch-Nyhan syndrome, dysfunction of the parathyroid glands, pancreatic islet cell dysfunction, carbohydrate and lipid storage myopathies, glycogenoses, myoglobinuria, alkaptonuria, adrenogenital syndrome, ketosis, ketoacidosis, methylmalonaciduria, Morbus Addison, Morbus Conn, Morbus Cushing, Morbus Fabry, Morbus Gaucher, Morbus Hunter, cystic fibrosis, phenylketonuria, thesaurismosis, uricopathia. Carbohydrate metabolism denotes the various biochemical processes responsible for the formation, breakdown and interconversion of carbohydrates in living organisms, wherein the most important carbohydrate is glucose. The hormone insulin is the primary regulatory signal in animals; when present, it causes many tissue cells to take up glucose from the circulation, causes some cells to store glucose internally in the form of glycogen, causes some cells to take in and hold lipids, and in many cases controls cellular electrolyte balances and amino acid uptake as well. Diseases of the carbohydrate metabolism refer to diseases and conditions characterized in pathophysiological alterations in the metabolism of one or more carbohydrates. It is preferred if the disease of the carbohydrate metabolism is chosen of one disease of the group comprising or consisting of Diabetes mellitus, Lactose intolerance, Fructose intolerance, Galactosemia, Glycogen storage disease, diabetic ketoacidosis, hyperosmolar coma and hypoglycemia.

The invention relates also to pharmaceutical compositions comprising or consisting of an effective amount of at least one inventive compound, and at least one pharmaceutically acceptable carrier, excipient, binders, disintegrates, glidents, diluents, lubricants, coloring agents, sweetening agents, flavoring agents, preservatives, solvent or the like. The pharmaceutical compositions of the present invention can be prepared in a conventional solid or liquid carrier or diluents and a conventional pharmaceutically-made adjuvant at suitable dosage level in a known way.

According to the invention, the inventive compound or the pharmaceutical composition can be used for the treatment of diseases of the carbohydrate metabolism, preferably of diabetes mellitus, more preferably of diabetes mellitus type 2, and most preferably to increase the level of insulin release from pancreas cells.

The inventive pharmaceutical composition is formulated to be compatible with its intended route of administration. Administration forms include, for example, pills, tablets, film tablets, coated tablets, capsules, liposomal formulations, micro- and nano-formulations, powders and deposits. Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain the compound according to the present invention. Intravenous and oral applications are preferred forms of administration in the present invention, wherein oral application is particularly preferred.

The present invention also includes the mammalian milk, artificial mammalian milk as well as mammalian milk substitutes as a formulation for oral administration of the inventive compound to newborns, toddlers, and infants, either as pharmaceutical preparations, and/or as dietary food supplements.

The inventive compound can also be administered in form of its pharmaceutically active salts. Suitable pharmaceutically active salts comprise acid addition salts and alkali or earth alkali salts. For instance, sodium, potassium, lithium, magnesium or calcium salts can be obtained.

The pharmaceutical compositions according to the present invention will typically be administered together with suitable carrier materials selected with respect to the intended form of administration, i.e. for oral administration in the form of tablets, capsules (either solid filled, semi-solid filled or liquid filled), powders for constitution, aerosol preparations consistent with conventional pharmaceutical practices. Other suitable formulations are gels, elixirs, dispersible granules, syrups, suspensions, creams, lotions, solutions, emulsions, suspensions, dispersions, and the like. Suitable dosage forms for sustained release include tablets having layers of varying disintegration rates or controlled release polymeric matrices impregnated with the active components and shaped in tablet form or capsules containing such impregnated or encapsulated porous polymeric matrices. The pharmaceutical compositions may be comprised of 5 to 95% by weight of the inventive compound.

As pharmaceutically acceptable carrier, excipient and/or diluents can be used lactose, starch, sucrose, cellulose, magnesium stearate, dicalcium phosphate, calcium sulfate, talc, mannitol, ethyl alcohol (liquid filled capsules).

Suitable binders include starch, gelatin, natural sugars, corn sweeteners, natural and synthetic gums such as acacia, sodium alginate, carboxymethyl-cellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions or modulators of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The inventive compound may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refer to the active ingredients dispersed or solubilized in a hydrophilic semi-solid matrix.

Powders for constitution refer to powder blends containing the active ingredients and suitable diluents which can be suspended in water or juices. One example for such an oral administration form for newborns, toddlers and/or infants is a human breast milk substitute which is produced from milk powder and milk whey powder, optionally and partially substituted with lactose.

Human breast milk is a complex fluid, rich in nutrients and in non-nutritional bioactive components. It contains all of the nutrients needed by the newborn baby. These include the metabolic components (fat, protein, and carbohydrates), water, and the raw materials for tissue growth and development, such as fatty acids, amino acids, minerals, vitamins, and trace elements.

More than 98% of the fat is in the form of triglycerides. Oleic acid and palmitic acid are the most abundant fatty acids in breastmilk triglycerides, with comparatively high proportions of the essential fatty acids, and linolenic acid, followed by long-chain polyunsaturated fatty acids, such as arachidonic acid and docosahexaenoic acid. These long-chain fatty acids are constituents of brain and neural tissue and are needed in early life for mental and visual development. The lipid component of breast milk is the transport vehicle for fat-soluble micronutrients such as prostaglandins and vitamins A, D, E, and K.

Proteins account for approximately 75% of the nitrogen-containing compounds in breast milk. Non-protein nitrogen substances include urea, nucleotides, peptides, free amino acids, and DNA. The proteins of breast milk can be divided into two categories: micellar caseins and aqueous whey proteins, present in the ratio of about 40:60. Casein forms micelles of relatively small volume and produces a soft, flocculent curd in the infant's stomach. The major whey proteins are lactalbumin, lactoferrin, secretory IgA, and serum albumin, with a large number of other proteins and peptides present in smaller amounts.

The principal carbohydrate is lactose, a disaccharide produced in the mammary epithelial cell from glucose by a reaction involving lactalbumin.

In addition to the nutritional components, breast milk contains a wealth of bioactive components that have beneficial non-nutritional functions. These include a wide range of specific and non-specific antimicrobial factors; cytokines and anti-inflammatory substances; and hormones, growth modulators, and digestive enzymes, many of which have multiple activities. These components may be of particular importance for young infants because of the immaturity of the host defense and digestive systems early in life.

The artificial mother milk formulations or mother milk substitutes of the present invention are preferably prepared by adding to a mother milk formulation including commercially available mother milk formulations especially in powder form of the compound of the present invention. The inventive compound is preferably added in an amount of 3-100 µg compound or per 100 ml (commercially available) mother milk formulation, more preferably in an amount of 5-70 µg/100 ml and most preferably in an amount of 10-40 µg/100 ml mother milk formulation.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose. The amount of diluents in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to 10% by weight of the composition, preferably 0.1% to about 7% by weight of the total composition, more preferably from about 0.2 to 5% by weight, and most preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.01 to 10% by weight of the composition, preferably from about 0.05 to 6% by weight, more preferably from about 0.1 to about 4% by weight of the composition, and most preferably from about 0.1 to about 1%.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Other preferred pharmaceutical compositions are buffered solutions. The term buffer, buffer system, buffer solution and buffered solution, when used with reference to hydrogen-ion concentration or pH, refers to the ability of a system, particularly an aqueous solution, to resist a change of pH on adding acid or alkali, or on dilution with a solvent. Preferred buffer systems can be selected from the group consisting of formate (pKa=3.75), lactate (pKa=3.86), benzoic acid (pKa=4.2) oxalate (pKa=4.29), fumarate (pKa=4.38), aniline (pKa=4.63), acetate buffer (pKa=4.76), citrate buffer (pKa2=4.76, pKa3=6.4), glutamate buffer (pKa=4.3), phosphate buffer (pKa=7.20), succinate (pKa1=4.93; pKa2=5.62), pyridine (pKa=5.23), phthalate (pKa=5.41); histidine (pKa=6.04), MES (2-(N-morpholino)ethanesulphonic acid; pKa=6.15); maleic acid (pKa=6.26); cacodylate (dimethylarsinate, pKa=6.27), carbonic acid (pKa=6.35), ADA (N-(2-acetamido)imino-diacetic acid (pKa=6.62); PIPES (4-piperazinebis-(ethanesulfonic acid; BIS-TRIS-propane (1,3-bis[tris(hydroxymethyl)methylamino]-propane), pKa=6.80), ethylendiamine (pKa=6.85), ACES 2-[(2-amino-2-oxoethyl)amino]ethanesulphonic acid; pKa=6.9), imidazole (pKa=6.95), MOPS (3-(N-morphin)-propansulfonic acid; pKa=7.20), diethylmalonic acid (pKa=7.2), TES (2-[tris(hydroxymethyl)methyl]amino ethanesulphonic acid; pKa=7.50) and HEPES (N-2-hydroxylethylpiperazin-N'-2-ethanesulfonic acid; pKa=7.55) buffers or other buffers having a pKa between 3.8 to 7.7.

Preferred is the group of carboxylic acid buffers such as acetate and carboxylic diacid buffers such as fumarate, tartrate and phthalate and carboxylic triacid buffers such as citrate. Another group of preferred buffers is represented by inorganic buffers such as sulfate, borate, carbonate, oxalate, calcium hydroxyde and phosphate buffers. Another group of preferred buffers are nitrogen containing buffers such as imidazole, diethylenediamine, and piperazine.

Also preferred are sulfonic acid buffers such as TES, HEPES, ACES, PIPES, [(2-hydroxy-1,1-bis(hydroxymethyl)ethyl)amino]-1-propanesulfonic acid (TAPS), 4-(2-hydroxyethyl)piperazine-1-propanesulfonic acid (EPPS), 4-Morpholinepropanesulfonic acid (MOPS) and N,N-bis(2-hydroxyethyl)-2-aminoethanesulfonic acid (BES).

Another group of preferred buffers are glycine buffers such as glycine, glycyl-glycine, glycyl-glycyl-glycine, N,N-bis(2-hydroxyethyl)glycine and N-[2-hydroxy-1,1-bis(hydroxy-methyl)ethyl]glycine (Tricine).

Preferred are also amino acid buffers such as glycine, alanine, valine, leucine, isoleucine, serine, threonine, phenylalanine, tyrosine, tryptophane, lysine, arginine, histidine, aspartate, glutamate, asparagine, glutamine, cysteine, methionine, proline, 4-hydroxyproline, N,N,N-trimethyllysine, 3-methylhistidine, 5-hydroxylysine, O-phosphoserine, □-carboxyglutamate, □-N-acetyllysine, □-N-methylarginine, citrulline, ornithine and derivatives thereof.

Preferred are the buffers having an effective pH range of from 2.7 to 8.5, and more preferred of from 3.8 to 7.7. The effective pH range for each buffer can be defined as pKa−1 to pKa+1, where Ka is the ionization constant for the weak acid in the buffer and pKa=−log K.

Most preferred are buffers suitable for pharmaceutical use e.g. buffers suitable for administration to a patient such as acetate, carbonate, citrate, fumarate, glutamate, lactate, phosphate, phthalate, and succinate buffers. Particularly preferred examples of commonly used pharmaceutical buffers are acetate buffer, citrate buffer, glutamate buffer and phosphate buffer. Also most preferred is the group of carboxylic acid buffers. The term "carboxylic acid buffers" as used herein shall refer to carboxylic mono acid buffers and carboxylic diacid buffers as well as carboxylic triacid buffers. Of course also combinations of buffers, especially of the buffers mentioned herein are useful for the present invention.

Some suitable pharmaceutical buffers are a citrate buffer (preferably at a final formulation concentration of from about 20 to 200 mM, more preferably at a final concentration of from about 30 to 120 mM) or an acetate buffer (preferably at a final formulation concentration of about 20 to 200 mM) or a phosphate buffer (preferably at a final formulation concentration of about 20 to 200 mM).

Techniques for the formulation and administration of the compound of the present invention may be found in "Remington's Pharmaceutical Sciences" Mack Publishing Co., Easton Pa. A suitable composition comprising the compound mentioned herein may be a solution of the compound in a suitable liquid pharmaceutical carrier or any other formulation such as tablets, pills, film tablets, coated tablets, dragees, capsules, powders and deposits, gels, syrups, slurries, suspensions, emulsions, and the like.

A particularly preferred pharmaceutical composition is a lyophilised (freeze-dried) preparation (lyophilisate) suitable for administration by inhalation or for intravenous administration. To prepare the preferred lyophilised preparation the compound of the invention is solubilised in a 4 to 5% (w/v) mannitol solution and the solution is then lyophilised. The mannitol solution can also be prepared in a suitable buffer solution as described above.

Further examples of suitable cryo-/lyoprotectants (otherwise referred to as bulking agents or stabilizers) include thiol-free albumin, immunoglobulins, polyalkyleneoxides (e.g. PEG, polypropylene glycols), trehalose, glucose, sucrose, sorbitol, dextran, maltose, raffinose, stachyose and other saccharides (cf. for instance WO 97/29782), while mannitol is used preferably. These can be used in conventional amounts in conventional lyophilization techniques. Methods of lyophilisation are well known in the art of preparing pharmaceutical formulations.

For administration by inhalation the particle diameter of the lyophilised preparation is preferably between 2 to 5 μm, more preferably between 3 to 4 μm. The lyophilised preparation is particularly suitable for administration using an inhalator, for example the OPTINEB® or VENTA-NEB® inhalator (NEBU-TEC, Elsenfeld, Germany). The lyophilised product can be rehydrated in sterile distilled water or any other suitable liquid for inhalation administration.

Alternatively for intravenous administration the lyophilised product can be rehydrated in sterile distilled water or any other suitable liquid for intravenous administration.

After rehydration for administration in sterile distilled water or another suitable liquid the lyophilised preparation should have the approximate physiological osmolality of the target tissue for the rehydrated compound preparation i.e. blood for intravenous administration or lung tissue for inhalation administration. Thus it is preferred that the rehydrated formulation is substantially isotonic.

The preferred dosage concentration for either intravenous, oral, or inhalation administration is between 100 to 2000 μmol/ml, and more preferably is between 200 to 800 μmol/ml. These are also the preferred ranges of the compound in the mother milk substitute or artificial mother milk formulation or the pharmaceutical compositions disclosed herein.

Still another aspect of the present invention relates to the use of the inventive compound as a dietary supplement. That dietary supplement is preferably for oral administration and especially but not limited to administration to newborns, toddlers, and/or infants. A dietary supplement is intended to supplement the diet. The "dietary ingredients" in these products may in addition include: vitamins, minerals, herbs or other botanicals, amino acids, and substances such as enzymes, organ tissues, glandulars, and metabolites. Dietary supplements may be manufactured in forms such as tablets, capsules, softgels, gelcaps, liquids, or powders.

The invention further relates to a method for screening for a modulator for treatment of a metabolic disease, the method comprising
  a) contacting a test compound with at least one polypeptide selected from the group consisting of GRK5 polypeptide,
  b) detecting the binding of said test compound to the GRK5 polypeptide, and
  c) determining the activity of the GRK5 polypeptide in the presence of said test compound.

The screening method of the present invention apparently consists of three steps. The term test compound may be any of the potential modulators listed above. The contacting of the test compound with at least one of the polypeptides can happen e.g. in the form of a compound library, in physiological or non-physiological solution, or solid phase systems, however a liquid environment is preferred. The conditions and the time need to be sufficient to allow the test compound to bind to the polypeptide(s). The method is normally carried our in solution at room temperature and at a suitable pH value normally between pH 5 and 9, all parameters which are easily selected by a skilled person.

The polypeptide GRK5 can be obtained by purification from primary human cells, cell lines, from cells which have been transfected with expression constructs which contain the nucleic acid sequences encoding one or more of the polypeptide GRK5, or by direct chemical synthesis.

The nucleic acid sequences encoding the polypeptide GRK5 can be obtained by cloning the relevant genes, amplification of the cDNAs or chemical synthesis of the nucleic sequences. For the expression of the corresponding polypeptides the nucleic acid sequences can be inserted into expression vectors, such as recombinant bacteriophage, plasmid, or cosmid DNA expression vectors.

The term binding refers to an interaction between the test compound and one or more of the polypeptide GRK5 or the nucleic acids encoding one or more of the polypeptide GRK5. For binding to a protein, the binding interaction is dependent upon the presence of a particular structure of the kinase, e.g. the antigenic determinant or epitope, recognized by the binding molecule. For binding of compounds to nucleic acids, test compounds need to have a complementary sequence to the nucleic acids, or fit into certain secondary or tertiary structures of the nucleic acids.

The binding of the test compounds to the polypeptides or nucleic acids can be checked by any convenient method known in the art. A separation step may be included to separate bound from unbound components. To check whether the test compound has been bound by the polypeptide or nucleic acid, it is advantageous if the test compound is labeled for direct detection (radioactivity, luminescence, fluorescence, optical or electron density etc.) or indirect detection (e.g., epitope tag such as the FLAG, V5 or myc epitopes, an enzyme tag such as horseradish peroxidase or luciferase, a transcription product, etc.). The label may be bound to a substrate, to the proteins employed in the assays, or to the candidate pharmacological agent. The binding of a test compound can also be conveniently checked if one of the components is immobilized on a solid substrate. The substrate can be made of a wide variety of materials and in various shapes, e.g. tubes, microtiter plates, microbeads, dipsticks and the like. It is also advantageous if one of the components is modified by biotinylation, so that the components can be immobilized on streptavidin-covered surfaces.

Protein-DNA interactions can be for instance checked by gel shift or band shift assays or elektrophoretic mobility shift assays (EMSA), which is based on the observation that complexes of protein and DNA migrate through a non-denaturing polyacrylamide gel more slowly that a free DNA fragments.

Protein-RNA interactions can be investigated by RNA electrophoretic mobility shift assays which are an in vitro technique used to detect protein-RNA interactions through changes in migration speed during gel electrophoresis. After incubation, the binding reaction is then separated via non-denaturing polyacrylamide gel electrophoresis. Like protein-DNA complexes, a protein-RNA complex migrates more slowly than a free RNA probe through a gel matrix. This causes a migration shift relative to the nonbound RNA probe. Specificity is determined through a competition reaction, where excess unlabeled RNA is incubated in the binding reaction, resulting in a decrease in the shifted signal if the labeled and unlabeled RNA sequences compete for binding of the same protein. Alternatively, the protein-RNA complex may be crosslinked and the reaction run on a denaturing gel. Specificity is determined through visualization of a single shifted band. Traditionally, RNA probes are radioactively labeled for detection, although fluorescent and chemiluminescent detection is also possible. Non-radioactive RNA end-labeling techniques are limited, but more versatile biotin and fluorescent labeling methods are now available. Alternatively, RNA Pull-down assays can be carried out which selectively extract a Protein-RNA complex from a sample. This method has the advantage that several RNAs can be used with the target protein(s), and selectively binding RNAs can be identified. Typically, the RNA pull-down assay takes advantage of high affinity tags, such as biotin or azido-phosphine chemistry. RNA probes can be biotinylated, complexed with a protein from a cell lysate and then purified using agarose or magnetic beads. Alternatively, the protein may be labeled, or the RNA-Protein complex may be isolated using an antibody against the protein of interest. The RNA is then detected by Northern blot or through RT-PCR analysis and the proteins detected by Western blotting or mass spectrometry. Protein-RNA interactions can also be identified by oligonucleotide-targeted RNase H protection assays (RPA), which is a powerful method for detecting RNA and RNA fragments in cell extracts. Unlike Northern blotting or RT-PCR analysis, RPA assays allow greater flexibility in the integrity of target RNA, requiring very short segments for hybridization and detection. RPA assays can also be used to map protein-RNA interactions. In this adaptation of the RPA, RNase H is used to cleave a target RNA molecule at a specific site hybridized with a DNA probe. If a protein is bound to the RNA at the target sequence, it will prevent will block probe hybridization, prevent cleavage by RNase H and indicate a site of interaction between protein and RNA. RNase H requires only a four basepair hybrid with a DNA probe in order to cleave the RNA molecule of interest. Using many small probes allows the entire sequence of RNA to be mapped for sites of interaction.

The interactions between peptides and proteins, respectively, can be investigated by various methods, which include, but are not limited to, protein binding microarray, antibody microarrays, protein chips, and a variety of assays, UV-crosslink experiments.

The interactions between nucleic acids can be checked for instance by hybridization, which is based on the annealing of complementary DNA-DNA or DNA-RNA or RNA-RNA-sequences. The nucleotide sequences encoding GRK5 may be labeled by standard methods and added to a sample of nucleic acids to be used as test compounds under conditions suitable for the formation of hybridization complexes. After a suitable incubation period, the sample is washed and the signal is quantified and compared with a standard value. If the amount of signal in the patient sample is significantly altered from that of a comparable control sample, the nucleotide sequences have hybridized with nucleotide sequences in the sample, and the presence of altered levels of nucleotide sequences encoding GRK5 in the sample indicates the presence of the associated disorder. Such assays may also be used to evaluate the efficacy of a particular therapeutic treatment regimen in animal studies, in clinical trials, or in monitoring the treatment of an individual patient. Interactions between nucleic acids can also be investigated by microarrays. A further way of testing the binding between nucleic acids is the use of gel shift assays, in which hybrid molecules are moving slower in a denaturating gels in electrophoresis.

In all methods to identify compounds that modulate (stimulate or inhibit) the expression and kinase activity of the polypeptides of the invention, the expression level and kinase activity are compared to those detected in the absence of the test compound. The present invention is related particularly to the identification of compounds which have inhibitory activity on the kinase activity of the polypeptides of the invention. Consequently, it is particularly the inhibition of expression and activity that is measured.

The inhibition of nucleic acids on the mRNA-level encoding the polypeptides can be checked by investigating the expression of the polypeptides by quantitative methods, e.g. Western blot or enzyme-linked immune-adsorbent assay (ELISA). A way to quantify the protein expression is further the measuring of fusion proteins, wherein the polypeptides of the invention are fused to proteins or protein fragments which are easy to quantify, like fluorescent proteins. The inhibition of DNA and thus the production of mRNA can be checked by mRNA-quantification. Levels of mRNA can be quantitatively measured by Northern blotting. Another way is the reverse transcription quantitative polymerase chain reaction (RT-PCR followed by qPCR). Another way of quantifying mRNA is the use of microarrays, which are, however, more practical if a large set of mRNAs is investigated.

The inhibition of the polypeptides on the protein-level can be investigated by measuring their activity. The determination of the activity of a polypeptide/protein/enzyme depends on its specificity. Consequently, the activity of kinases is measured in phosphorylation assays, wherein a substrate is phosphorylated by a kinase. The kinase activity of GRK5 can be detected, for example, by adding ATP having radioactively labeled phosphate to the system containing the polypeptide GRK5 and the substrate and measuring the radioactivity of the phosphate attached to the substrate.

According to the invention, the effect of a test compound on the kinase activity of the polypeptides of the invention can be estimated in a system using an insulin-producing cell line, or primary cells, which are or are derived from pancreatic cells. Therein the change of the insulin release level compared to the level without the compound. The release level of insulin can be estimated with the mRNA and protein quantification levels identified above.

Polypeptide of GRK5 can be used in high-throughput screens to assay test compounds for the ability to modulate the kinase activity. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree. Further, GRK5 can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Polypeptide of GRK5 is also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase.

To facilitate the identification of modulators of the expression and activity of the peptides of the invention, the invention further provides, in a preferred embodiment, a kit comprising
  a) GRK5 polypeptides, and/or
  b) a nucleic acid encoding GRK5, and
  c) a control compound known to affect the insulin production by binding the GRK5 polypeptide or the corresponding nucleic acid.

In a further preferred embodiment, the invention provides a kit comprising
  a) the GRK5 polypeptides, and/or
  b) the nucleic acid encoding GRK5 and
  c) a control compound known to affect the insulin production by binding the GRK5 polypeptide or the corresponding nucleic acid, and further comprising
  d) a cell line with insulin production.

In a further preferred embodiment, the invention provides a kit comprising
  a) the GRK5 polypeptides, and/or
  b) the nucleic acid encoding GRK5 and
  c) a control compound for the kinase GRK5 known to affect the insulin production by binding the GRK5 polypeptide or the corresponding nucleic acid.

In a further preferred embodiment, the invention provides a kit comprising
  a) GRK5 polypeptides, and/or
  b) a nucleic acid encoding GRK5, and
  c) a control compound for the kinase GRK5 known to affect the insulin production by binding the GRK5 polypeptide or the corresponding nucleic acid, and further comprising
  d) a cell line with insulin production.

In all embodiments of the kit, the control compounds can be any of the test compounds characterized above. A control compound is used as a reference for the binding/inhibitory efficiency of a test compound because it is known for its binding to a chosen polypeptide or the corresponding nucleic acid which encode the chosen polypeptide, thereby inhibiting the activity or the expression of the polypeptides. A chosen control compound refers to the same polypeptide for which inhibitory compounds are tested; e.g. if compounds for the inhibition of GRK5 are tested, then the control compound is one which inhibits GRK5.

In a further preferred embodiment, it is particularly preferred if the kit comprises the polypeptide GRK5 and/or their corresponding nucleic acids.

Control compounds that affect the insulin release by binding to the polypeptides of GRK5 are e.g. Sunitinib and inventive siRNAs or any other compound which has proved to modulate the insulin production.

The invention is further related to a method for treatment of a disease of the carbohydrate metabolism, preferably diabetes mellitus, more preferably diabetes mellitus type 2, and most preferably for increasing the level of insulin release from pancreas cells comprising:

administering a subject in need thereof a therapeutically effective amount of at least one modulator for:

a) inhibition or activation of at least one of the tyrosine kinases selected from the group consisting of GRK5 or b) inactivation, degradation, downregulation, intercalation or activation of at least one nucleic acid selected from the group consisting of the nucleic acid encoding GRK5.

An inventive compound known to affect the expression and/or activity of the polypeptide of GRK5 can be used for the treatment of a metabolic disease, preferably diabetes mellitus, more preferably diabetes mellitus type 2, and most preferably for increasing the level of insulin release from pancreas cells by administration of the inventive compound(s) within pharmaceutical compositions as outline above.

The inventive compounds or inventive compositions are according to the invention useful for each single disease of the group of diseases consisting of metabolic diseases, preferably diseases of the carbohydrate metabolism.

The influence of the kinase GRK5 on insulin release suggests a particular, but not limited to, utilization of the polypeptides for diagnosis of disease of the carbohydrate metabolism, preferably of diabetes mellitus, more preferably of diabetes mellitus type 2.

The embodiments in the description and the following examples are provided by way of illustration of the invention and are not included for the purpose of limiting the invention. The variations and changes of the invention which are obvious to a person skilled in the field and solutions equivalent to embodiments described herein fall within the scope of protection of the patent claims.

TABLE 1

Sequence identities of the target gene and target protein

| SeqIdNo | Sequence Name | Gene Accession |
|---|---|---|
| 9 | GRK5 gene | NM_018869 |
| 12 | GRK5 protein | NM_018869 |

Small Molecules:

Further small molecules inhibiting GRK5 consist of the groups I, II, and III:

Wherein group I comprises:
Compounds of the General Formula (I)

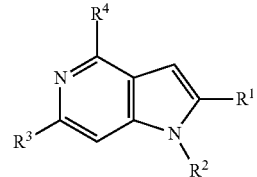

(I)

wherein
$R^1$ represents —$(CH_2)_n$—$R^5$ or —NH—$(CH_2)_n$—$R^5$; and $R^1$ is not —H;
$R^2$ represents —H, —$CH_3$, —$(CH_2)_k$—O—$CH_3$, —$(CH_2)_k$—$NHCOCH_3$, —$(CH_2)_k$-cyclo-$C_3H_5$, —$(CH_2)_k$-Ph, or —$(CH_2)_k$—R*;
R* represents

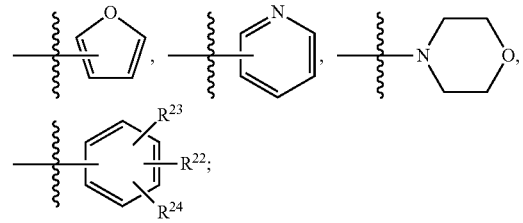

$R^3$ represents —H, —$(CH_2)_m$—$R^6$, or —$NR^7((CH_2)_m$—$R^6)$, $R^4$ represents —H, —$(CH_2)_p$—$R^8$, or —$NR^9((CH_2)_p$—$R^8)$, wherein $R^3$ or $R^4$ represents —H,
$R^5$ represents —H, —F, —Cl, —Br, —I, —CN, —$NO_2$, —$NHCH_3$, —$N(CH_3)_2$, —CH=CH—$C_4H_9$, —CH=CH—$C_5H_{11}$, —CH=CH-Ph, —CH=CH—$C_6H_{13}$, —$CH_2$—OH, —$C_2H_4$—OH, —$C_3H_6$—OH, —$C_4H_9$—OH, —$C_5H_{10}$—OH, —$C_6H_{12}$—OH, —$C_7H_{14}$—OH, —$C_8H_{16}$—OH, —CH=CH—$C_3H_6$—OH, —CH=CH—$C_4H_8$—OH, —CH($CH_2OH)_2$, —CH($C_2H_5$)—$CH_2$—OH, —CH($CH_3$)—$C_2H_4$—OH, —C($CH_3)_2$—OH, —C($CH_3)_2$—$CH_2$—OH, —CH($CH_3$)OH, —$CH_2$—CH($CH_3$)OH, —C(OH)($CH_3$)—$C_2H_5$, —C(OH)($CH_3$)—$C_3H_7$, —$CH_2$—C(OH)($CH_3$)—$C_2H_5$, —CH($CH_3$)—CH($CH_3$)OH, —C($CH_3)_2$—$C_2H_4OH$, —$CH_2$—C($CH_3)_2OH$, —C(OH)($C_2H_5)_2$, —$C_2H_4$—C(OH)($CH_3)_2$, —C(CH($CH_3)_2)CH_2OH$, —$C_3H_6$—C(OH)($CH_3)_2$, —CH(CH($CH_3)_2)CH_2$—OH, —OH, —$OCH_3$, —$OC_2H_5$, —$OC_3H_7$, —O-cyclo-$C_3H_5$, —OCH($CH_3)_2$, —OC($CH_3)_3$, —$OC_4H_9$, —OPh, —$OCH_2$-Ph, —$OCPh_3$, —SH, —$SCH_3$, —$SC_2H_5$, —$SO_3H$, —$OCF_3$, —$CH_2$—$OCF_3$, —$C_2H_4$—$OCF_3$, —$C_3H_6$—$OCF_3$, —$OC_2F_5$, —OOC—$CH_3$, —OOC—$C_2H_5$, —OOC—$C_3H_7$, —OOC-cyclo-$C_3H_5$, —OOC—CH($CH_3)_2$, —OOC—C($CH_3)_3$, —$NHCOCH_3$, —$NHCOC_2H_5$, —$NHCOC_3H_7$, —NHCO-cyclo-$C_3H_5$, —NHCO—CH($CH_3)_2$, —NHCO—C($CH_3)_3$, —NHCO—$OCH_3$, —NHCO—$OC_2H_5$, —NHCO—$OC_3H_7$, —NHCO—O-cyclo-$C_3H_5$, —NHCO—OCH($CH_3)_2$, —NHCO—OC($CH_3)_3$, —$NH_2$, —$NHCH_3$, —$NHC_2H_5$, —$NHC_3H_7$, —NH-cyclo-$C_3H_5$, —NHCH($CH_3)_2$, —NHC($CH_3)_3$, —$N(CH_3)_2$, —$N(C_2H_5)_2$, —$N(C_3H_7)_2$, —N(cyclo-$C_3H_5)_2$, —$N[CH(CH_3)_2]_2$, —$N[C(CH_3)_3]_2$, —$R^{10}$, —$R^{11}$,

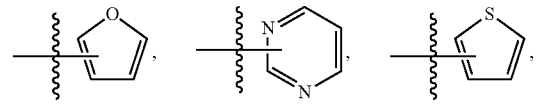

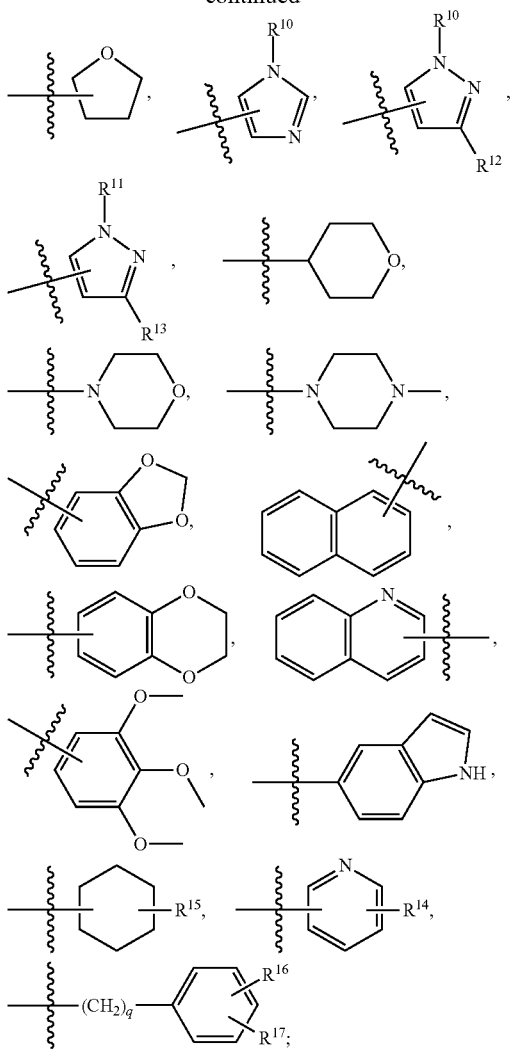

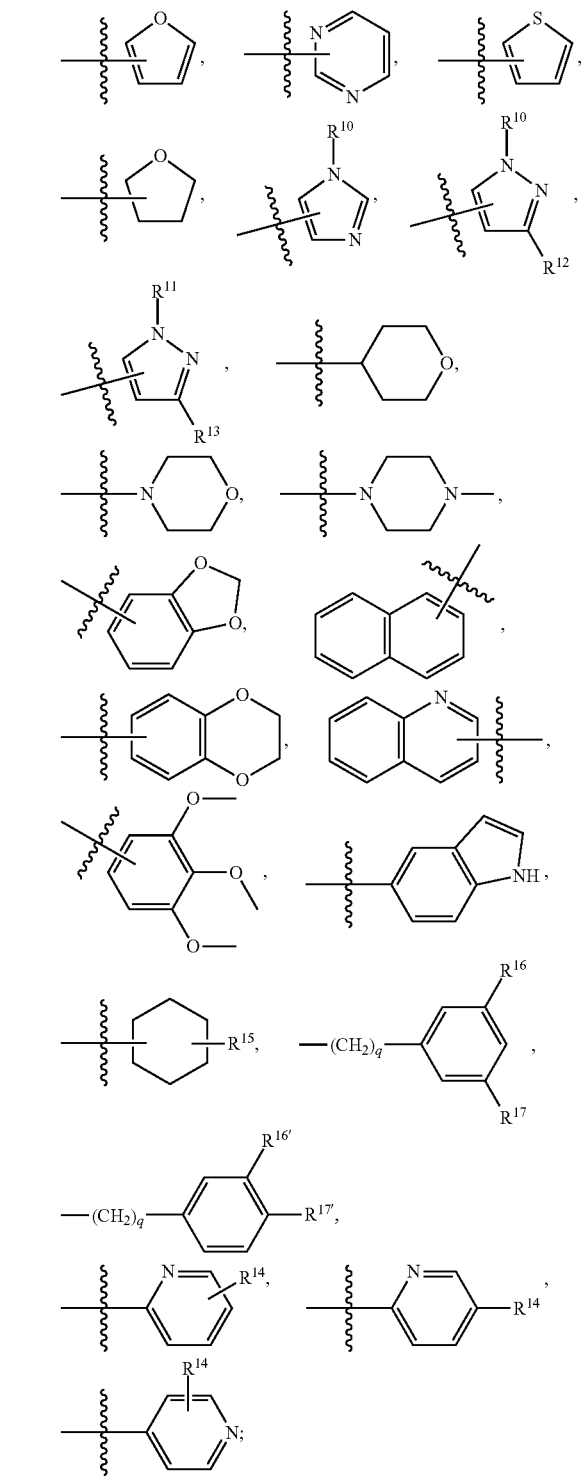

R[6] represents —H, —F, —CN, —NO$_2$, —NHCH$_3$, —N(CH$_3$)$_2$, —CH=CH—C$_4$H$_9$, —CH=CH—C$_5$H$_{11}$, —CH=CH-Ph, —CH=CH—C$_6$H$_{13}$, —CH$_2$—OH, —C$_2$H$_4$—OH, —C$_3$H$_6$—OH, —C$_4$H$_8$—OH, —C$_5$H$_{10}$—OH, —C$_6$H$_{12}$—OH, —C$_7$H$_{14}$—OH, —C$_8$H$_{16}$—OH, —CH=CH—C$_3$H$_6$—OH, —CH=CH—C$_4$H$_8$—OH, —CH(CH$_2$OH)$_2$, —CH(C$_2$H$_5$)—CH$_2$—OH, —CH(CH$_3$)—C$_2$H$_4$—OH, —C(CH$_3$)$_2$—OH, —C(CH$_3$)$_2$—CH$_2$—OH, —CH(CH$_3$)OH, —CH$_2$—CH(CH$_3$)OH, —C(OH)(CH$_3$)—C$_2$H$_5$, —C(OH)(CH$_3$)—C$_3$H$_7$, —CH$_2$—C(OH)(CH$_3$)—C$_2$H$_5$, —CH(CH$_3$)—CH(CH$_3$)OH, —C(CH$_3$)$_2$—C$_2$H$_4$OH, —CH$_2$—C(CH$_3$)$_2$OH, —C(OH)(C$_2$H$_5$)$_2$, —C$_2$H$_4$—C(OH)(CH$_3$)$_2$, —C(CH(CH$_3$)$_2$)CH$_2$OH, —C$_3$H$_6$—C(OH)(CH$_3$)$_2$, —CH(CH(CH$_3$)$_2$)CH$_2$—OH, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OPh$_3$, —SH, —SCH$_3$, —SC$_2$H$_5$, —SO$_3$H, —OCF$_3$, —CH$_2$—OCF$_3$, —C$_2$H$_4$—OCF$_3$, —C$_3$H$_6$—OCF$_3$, —OC$_2$F$_5$, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON (cyclo-C$_3$H$_5$)$_2$, —CON[CH(CH$_3$)$_2$]$_2$, —CON[C(CH$_3$)$_3$]$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —R[10], —R[11], R[8] represents —H, —F, —CN, —NO$_2$, —NHCH$_3$, —N(CH$_3$)$_2$, —CH=CH—C$_4$H$_9$, —CH=CH—C$_5$H$_{11}$, —CH=CH-Ph, —CH=CH—C$_6$H$_{13}$, —CH$_2$—OH, —C₂H₄—OH, —C₃H₆—OH, —C₄H₉—OH, —C₅H₁₀—OH, —C₆H₁₂—OH, —C₇H₁₄—OH, —C₈H₁₆—OH, —CH=CH—C₃H₆—OH, —CH=CH—C₄H₈—OH, —CH(CH₂OH)₂, —CH(C₂H₅)—CH₂—OH, —CH(CH₃)—C₂H₄—OH, —C(CH₃)₂—OH, —C(CH₃)₂—CH₂—OH, —CH(CH₃)OH, —CH₂—CH(CH₃)OH, —C(OH)(CH₃)—C₂H₅, —C(OH)(CH₃)—C₃H₇, —CH₂—C(OH)(CH₃)—C₂H₅, —CH(CH₃)—CH(CH₃)OH, —C(CH₃)₂—C₂H₄OH, —CH₂—C(CH₃)₂OH, —C(OH)(C₂H₅)₂, —C₂H₄—C(OH)(CH₃)₂, —C(CH(CH₃)₂)CH₂OH, —C₃H₆—C(OH)(CH₃)₂, —CH(CH(CH₃)₂)CH₂—OH, —OH, —OCH₃, —OC₂H₅, —OC₃H₇, —O-cyclo-C₃H₅, —OCH(CH₃)₂, —OC(CH₃)₃, —OC₄H₉, —OPh, —OCH₂-Ph, —OCPh₃, —SH, —SCH₃, —SC₂H₅, —SO₃H, —OCF₃, —CH₂—OCF₃, —C₂H₄—OCF₃, —C₃H₆—OCF₃, —OC₂F₅, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —R¹⁰, —R¹¹,

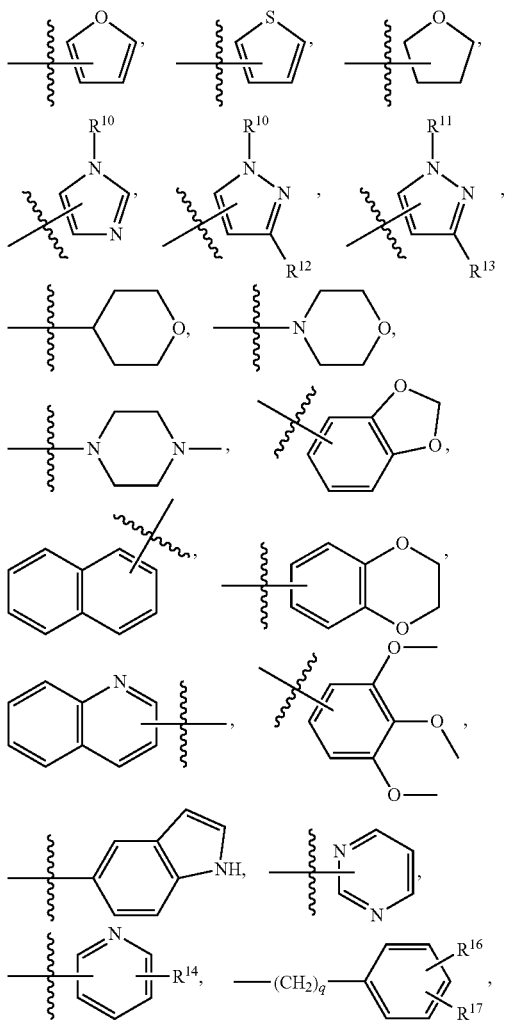

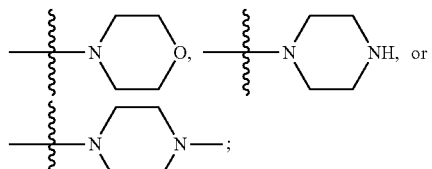

$R^7$ and $R^9$ are independently of each other —H, —CH₃, —C₂H₅, —C₃H₇, —CH(CH₃)₂, —C₄H₉, —CH₂—CH(CH₃)₂, —CH(CH₃)—C₂H₅, or —C(CH₃)₃;

$R^{14}$ and $R^{15}$ are independently of each other —H, —NH₂, —OH, or —OMe;

$R^{16}$ and $R^{16'}$ are independently of each other —H, —F, —Br, —Cl, —OH, —CN, —$R^{18}$, —$R^{19}$, —O$R^{18}$, —O$R^{19}$, —CH₂OH, —CH₂NH₂, —CH₂CN; —CH₂N($R^{18}$)₂, —CH₂N($R^{19}$)₂, —CH₂NH($R^{18}$), —CH₂NH($R^{19}$), —O(CH₂)₃N(CH₃)₂, —SCH₃, —NH₂, —NH($R^{18}$), —NH($R^{19}$), —N$R^{18}$CO$R^{19}$, —NHSO₂CH₃, —N($R^{18}$)₂, —N($R^{19}$)₂, —SO₂CH₃, —SO₂NH₂, —CH₂CO₂H, —C₂H₄CO₂H, —CH=CH—CO₂H, —COR²⁰,

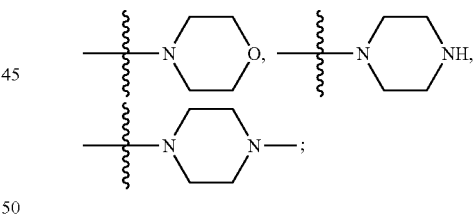

$R^{17}$ and $R^{17'}$ are independently of each other —H, —F, —Br, —Cl, —OH, —CN, —$R^{18}$, —$R^{19}$, —O$R^{18}$, —O$R^{19}$, —CH₂OH, —CH₂NH₂, —CH₂CN; —CH₂N($R^{18}$)₂, —CH₂N($R^{19}$)₂, —CH₂NH($R^{18}$), —CH₂NH($R^{19}$), —O(CH₂)₃N(CH₃)₂, —SCH₃, —NH₂, —NH($R^{18}$), —NH($R^{19}$), —N$R^{18}$CO$R^{19}$, —NHSO₂CH₃, —N($R^{18}$)₂, —N($R^{19}$)₂, —SO₂CH₃, —SO₂NH₂, —CH₂CO₂H, —C₂H₄CO₂H, —CH=CH—CO₂H, —COR²⁰,

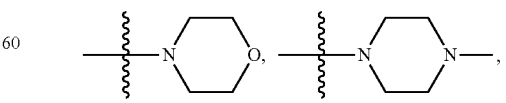

and $R^{17'}$ is not —F, —CN, —OCH₃, —OC₂H₄OCH₃, —CON(CH₃)₂ or —CF₃, when $R^5$ is 1H-pyrazol-4-yl or 1-methyl-1H-pyrazol-4-yl;

$R^{20}$ is —OH, —$R^{21}$, —O$R^{21}$, —NH₂, —NH$R^{21}$, —N($R^{21}$)₂, —NHC₂H₄OH,

—NHC₂H₄OCH₃, or —NH(CH₂)ᵣN($R^{21}$)₂;

$R^{10}$, $R^{11}$, $R^{12}$, $R^{13}$, $R^{18}$, $R^{19}$, and $R^{21}$ are independently of each other

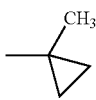

cyclo-$C_3H_5$, cyclo-$C_4H_7$, cyclo-$C_5H_9$, cyclo-$C_6H_{11}$, cyclo-$C_7H_{13}$, —H, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, —$C_3H_6$—$OC_2H_5$, —$CH_2$—$OC_3H_7$, —$C_2H_4$—$OC_3H_7$, —$C_3H_6$—$OC_3H_7$, —$CH_2$—O-cyclo-$C_3H_5$, —$C_2H_4$—O-cyclo-$C_3H_5$, —$C_3H_6$—O-cyclo-$C_3H_5$, —$CH_2$—$OCH(CH_3)_2$, —$C_2H_4$—$OCH(CH_3)_2$, —$C_3H_6$—$OCH(CH_3)_2$, —$CH_2$—$OC(CH_3)_3$, —$C_2H_4$—$OC(CH_3)_3$, —$C_3H_6$—$OC(CH_3)_3$, —$CH_2$—$OC_4H_9$, —$C_2H_4$—$OC_4H_9$, —$C_3H_6$—$OC_4H_9$, —$CH_2$—OPh, —$C_2H_4$—OPh, —$C_3H_6$—OPh, —$CH_2$—$OCH_2$-Ph, —$C_2H_4$—$OCH_2$-Ph, —$C_3H_6$—$OCH_2$-Ph, —$CH_2F$, —$CHF_2$, —$CF_3$, —$CH_2Cl$, —$CH_2Br$, —$CH_2I$, —$CH_2$—$CH_2F$, —$CH_2$—$CHF_2$, —$CH_2$—$CF_3$, —$CH_2$—$CH_2Cl$, —$CH_2$—$CH_2Br$, —$CH_2$—$CH_2I$, cyclo-$C_8H_{15}$, -Ph, —$CH_2$—$CH_2$-Ph, —CH=CH-Ph, —$CPh_3$, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_7H_{15}$, —$C_8H_{17}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$CH$=$CH_2$, —$CH_2$—CH=$CH_2$, —$C(CH_3)$=$CH_2$, —CH=CH—$CH_3$, —$C_2H_4$—CH=$CH_2$, —$CH_2$—CH=CH—$CH_3$, —CH=CH—$C_2H_5$, —$CH_2$—$C(CH_3)$=$CH_2$, —$CH(CH_3)$—CH=CH, —CH=$C(CH_3)_2$, —$C(CH_3)$=CH—$CH_3$, —CH=CH—CH=$CH_2$, —C≡CH, —C≡C—$CH_3$, —$CH_2$—C≡CH, —$C_2H_4$—C≡CH, —$CH_2$—C≡C—$CH_3$, —C≡C—$C_2H_5$, —$CH(CH_3)$Ph, or —$C(CH_3)_2$Ph;

$R^{22}$, $R^{23}$ and $R^{24}$ represent independently of each other —H, —F, —Cl, —Br, —$OCH_3$, or —$CF_3$;

k is the integer 0, 1 or 2;

m, n, p, q and r are independently of each other integer selected from 0, 1, 2, or 3;

and enantiomers, stereoisomeric forms, mixtures of enantiomers, anomers, diastereomers, mixtures of diastereomers, tautomers, hydrates, solvates and racemates of the above mentioned compounds and pharmaceutically acceptable salts thereof.

According to group I further small molecules for inhibition of GRK5 consist of Compounds of the formula (II)

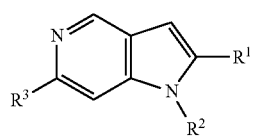

(II)

wherein $R^1$ represents —$R^5$;

$R^2$ represents —H, —$CH_3$, or —$CH_2Ph$;

$R^3$ represents —$R^6$, or —$NR^7R^6$;

$R^5$ represents

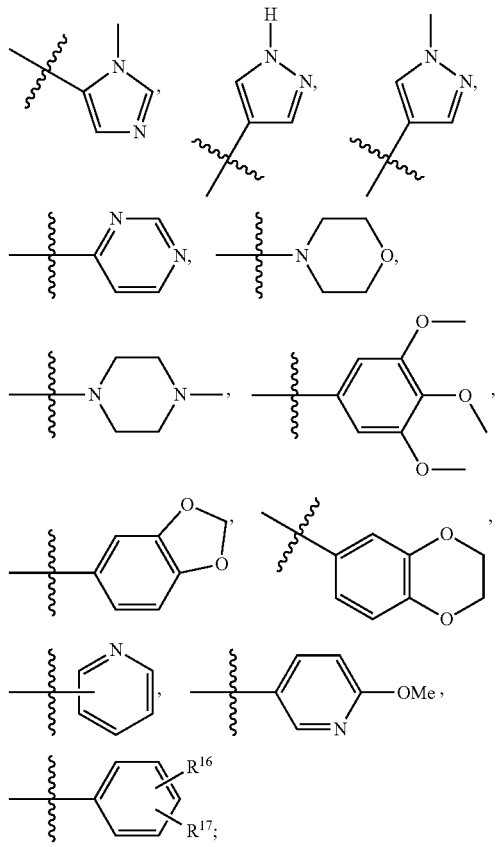

$R^6$ represents

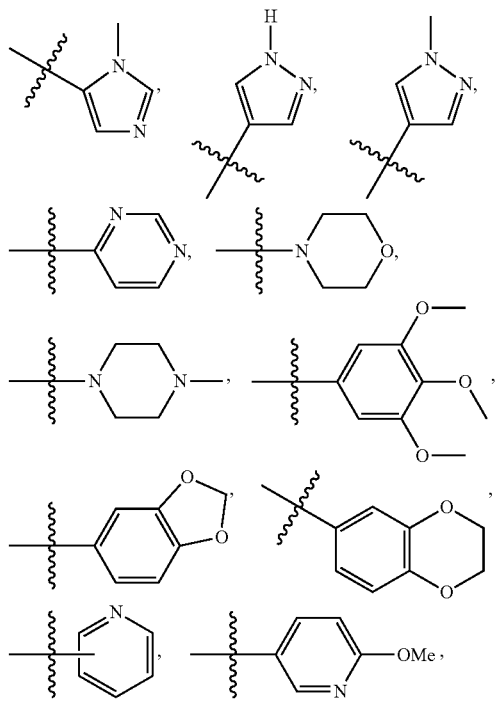

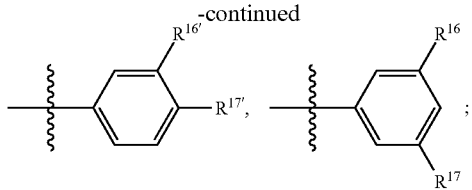

R⁷ is —H or —CH₃;
R¹⁶, R¹⁶', R¹⁷ and R¹⁷' are independently of each other —H, —F, —Cl, —OH, —CN, —NH₂, —CH₃, —CH(CH₃)₂, —CF₃, —OCH₃, —OCH(CH₃)₂, —OCF₃, —OPh, —SCH₃, —N(CH₃)₂, —NHCOCH₃, —NHSO₂CH₃, —N(CH₃)COCH₃, —SO₂CH₃, —COCH₃, —CONH₂, —CON(OH₃)₂, —CO₂CH₃,

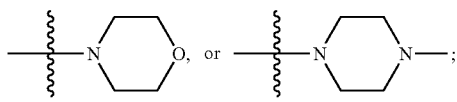

and R¹⁷' is not —F, —CN, —OCH₃, —CON(OH₃)₂, or —CF₃, when R⁵ is 1H-pyrazol-4-yl or 1-methyl-1H-pyrazol-4-yl.

According to group I further small molecules for inhibition of GRK5 consist of compounds of the formula (III)

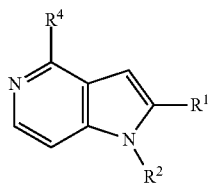
(III)

wherein
R¹ represents —R⁵;
R² represents —H or —CH₃;
R⁴ represents —R⁸ or —NH—R⁸;
R⁵ and R⁸ are independently of each other

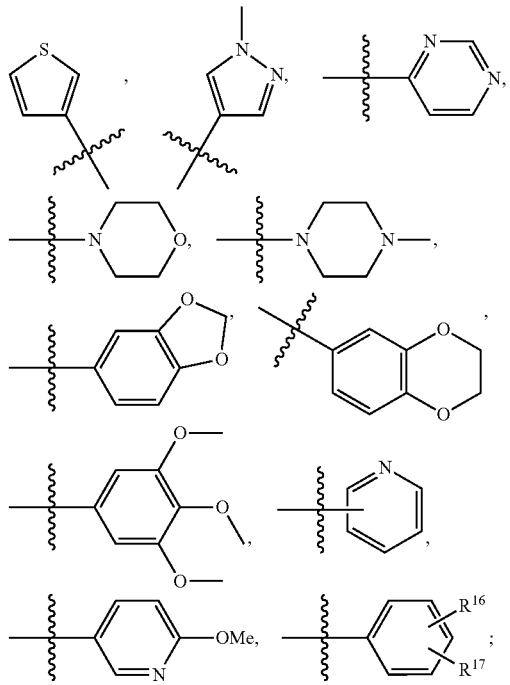

R¹⁶ and R¹⁷ are independently of each other —H, —F, —Cl, —OH, —CN, —CH₃, —CH(CH₃)₂, —CF₃, —OCH₃, —OCH(CH₃)₂, —OCF₃, —OPh, —SCH₃, —N(CH₃)₂, —NHCOCH₃, —N(CH₃)COCH₃, —NHSO₂CH₃, —SO₂CH₃, —COCH₃, —CONH₂, —CON(CH₃)₂, —CO₂CH₃,

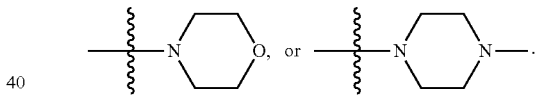

Small molecule GRK5 inhibitors according to group I. are listed in the following table 2:

| | compound name |
|---|---|
| 1 | 2-(3-aminophenyl)-N-(6-methoxy-3-pyridyl)-1H-pyrrolo[3,2-c]pyridin-6-amine |
| 2 | 2-(3-aminophenyl)-N-(3-pyridyl)-1H-pyrrolo[3,2-c]pyridin-6-amine |
| 3 | 2-(3-aminophenyl)-N-[4-(4-methylpiperazin-1-yl)phenyl]-1H-pyrrolo[3,2-c]pyridin-6-amine |
| 4 | 6-(4-methylpiperazin-1-yl)-2-[3-(trifluoromethyl)phenyl]-1H-pyrrolo[3,2-c]pyridine |
| 5 | N-[3-[[2-[3-(trifluoromethyl)phenyl]-1H-pyrrolo[3,2-c]pyridin-6-yl]amino]phenyl]methanesulfonamide |
| 6 | 4-[[2-(3-fluorophenyl)-1H-pyrrolo[3,2-c]pyridin-6-yl]amino]benzamide |
| 7 | N-(3,4-dimethoxyphenyl)-2-(3-fluorophenyl)-1H-pyrrolo[3,2-c]pyridin-6-amine |
| 8 | 2-(3-fluorophenyl)-N-(6-methoxy-3-pyridyl)-1H-pyrrolo[3,2-c]pyridin-6-amine |
| 9 | N-(3-chloro-4-fluoro-phenyl)-2-(3-fluorophenyl)-1H-pyrrolo[3,2-c]pyridin-6-amine |
| 10 | 3-[[2-(3-fluorophenyl)-1H-pyrrolo[3,2-c]pyridin-6-yl]amino]phenol |
| 11 | 5-[[2-(3-fluorophenyl)-1H-pyrrolo[3,2-c]pyridin-6-yl]amino]-2-methoxyphenol |
| 12 | 4-[2-(3-fluorophenyl)-1H-pyrrolo[3,2-c]pyridin-6-yl]morpholine |
| 13 | N-[3-[[2-(3-fluorophenyl)-1H-pyrrolo[3,2-c]pyridin-6-yl]amino]phenyl]methanesulfonamide |

-continued

| | compound name |
|---|---|
| 14 | 4-[[2-(3-fluorophenyl)-1H-pyrrolo[3,2-c]pyridin-6-yl]amino]-N,N-dimethyl-benzamide |
| 15 | N-[3-[[2-(3-fluorophenyl)-1H-pyrrolo[3,2-c]pyridin-6-yl]amino]phenyl]acetamide |
| 16 | 2-(3-fluorophenyl)-N-(4-methylsulfonylphenyl)-1H-pyrrolo[3,2-c]pyridin-6-amine |
| 17 | 4-[[2-(3-fluorophenyl)-1-methyl-pyrrolo[3,2-c]pyridin-6-yl]amino]phenol |
| 18 | N,N-dimethyl-4-[6-(3,4,5-trimethoxyanilino)-1H-pyrrolo[3,2-c]pyridin-2-yl]benzamide |
| 19 | 4-[6-(3-methoxyanilino)-1H-pyrrolo[3,2-c]pyridin-2-yl]-N,N-dimethyl-benzamide |
| 21 | 4-[6-(3,4-dimethoxyanilino)-1H-pyrrolo[3,2-c]pyridin-2-yl]-N,N-dimethyl-benzamide |
| 22 | N,N-dimethyl-4-[6-(3-pyridylamino)-1H-pyrrolo[3,2-c]pyridin-2-yl]benzamide |
| 23 | 4-[6-(3-chloroanilino)-1H-pyrrolo[3,2-c]pyridin-2-yl]-N,N-dimethyl-benzamide |
| 24 | 4-(6-anilino-1H-pyrrolo[3,2-c]pyridin-2-yl)-N,N-dimethyl-benzamide |
| 25 | N,N-dimethyl-4-[6-(4-phenoxyanilino)-1H-pyrrolo[3,2-c]pyridin-2-yl]benzamide |
| 26 | N,N-dimethyl-4-[6-[4-(4-methylpiperazin-1-yl)anilino]-1H-pyrrolo[3,2-c]pyridin-2-yl]benzamide |
| 27 | 4-[6-[3-(dimethylamino)anilino]-1H-pyrrolo[3,2-c]pyridin-2-yl]-N,N-dimethyl-benzamide |
| 28 | N,N-dimethyl-4-[6-(3-methylanilino)-1H-pyrrolo[3,2-c]pyridin-2-yl]benzamide |
| 29 | methyl 4-[[2-[4-(dimethylcarbamoyl)phenyl]-1H-pyrrolo[3,2-c]pyridin-6-yl]amino]benzoate |
| 30 | N,N-dimethyl-4-[6-(3-methylsulfonylanilino)-1H-pyrrolo[3,2-c]pyridin-2-yl]benzamide |
| 31 | 4-[6-(3-hydroxyanilino)-1H-pyrrolo[3,2-c]pyridin-2-yl]-N,N-dimethyl-benzamide |
| 32 | N,N-dimethyl-4-[6-[4-(trifluoromethyl)anilino]-1H-pyrrolo[3,2-c]pyridin-2-yl]benzamide |
| 33 | N,N-dimethyl-4-[6-[3-(trifluoromethoxy)anilino]-1H-pyrrolo[3,2-c]pyridin-2-yl]benzamide |
| 34 | N,N-dimethyl-4-[6-[4-(trifluoromethoxy)anilino]-1H-pyrrolo[3,2-c]pyridin-2-yl]benzamide |
| 35 | N,N-dimethyl-4-[6-(3-phenoxyanilino)-1H-pyrrolo[3,2-c]pyridin-2-yl]benzamide |
| 36 | 4-[6-(3-isopropylanilino)-1H-pyrrolo[3,2-c]pyridin-2-yl]-N,N-dimethyl-benzamide |
| 38 | 4-[6-(4-isopropylanilino)-1H-pyrrolo[3,2-c]pyridin-2-yl]-N,N-dimethyl-benzamide |
| 39 | 4-[6-[3-(methanesulfonamido)anilino]-1H-pyrrolo[3,2-c]pyridin-2-yl]-N,N-dimethyl-benzamide |
| 40 | 4-[6-[4-(dimethylcarbamoyl)anilino]-1H-pyrrolo[3,2-c]pyridin-2-yl]-N,N-dimethyl-benzamide |
| 41 | 4-[6-(3-acetamidoanilino)-1H-pyrrolo[3,2-c]pyridin-2-yl]-N,N-dimethyl-benzamide |
| 42 | 4-[6-(3-acetylanilino)-1H-pyrrolo[3,2-c]pyridin-2-yl]-N,N-dimethyl-benzamide |
| 43 | N,N-dimethyl-4-[6-(4-methylsulfonylanilino)-1H-pyrrolo[3,2-c]pyridin-2-yl]benzamide |
| 44 | 4-[6-(3-isopropoxyanilino)-1H-pyrrolo[3,2-c]pyridin-2-yl]-N,N-dimethyl-benzamide |
| 45 | 4-[6-(3-methoxyanilino)-1-methyl-pyrrolo[3,2-c]pyridin-2-yl]-N,N-dimethyl-benzamide |
| 46 | 4-[6-(3,4-dimethoxyanilino)-1-methyl-pyrrolo[3,2-c]pyridin-2-yl]-N,N-dimethyl-benzamide |
| 47 | N,N-dimethyl-4-[1-methyl-6-(3-pyridylamino)pyrrolo[3,2-c]pyridin-2-yl]benzamide |
| 48 | 4-(6-anilino-1-methyl-pyrrolo[3,2-c]pyridin-2-yl)-N,N-dimethyl-benzamide |
| 49 | N,N-dimethyl-4-[1-methyl-6-[4-(4-methylpiperazin-1-yl)anilino]pyrrolo[3,2-c]pyridin-2-yl]benzamide |
| 50 | 4-[6-[3-(dimethylamino)anilino]-1-methyl-pyrrolo[3,2-c]pyridin-2-yl]-N,N-dimethyl-benzamide |
| 51 | N,N-dimethyl-4-[1-methyl-6-(2-pyridylamino)pyrrolo[3,2-c]pyridin-2-yl]benzamide |
| 52 | N,N-dimethyl-4-[1-methyl-6-(N-methylanilino)pyrrolo[3,2-c]pyridin-2-yl]benzamide |
| 53 | 4-[6-(3-hydroxyanilino)-1-methyl-pyrrolo[3,2-c]pyridin-2-yl]-N,N-dimethyl-benzamide |
| 54 | 4-[6-(3-hydroxy-4-methoxy-anilino)-1-methyl-pyrrolo[3,2-c]pyridin-2-yl]-N,N-dimethyl-benzamide |

-continued

| | compound name |
|---|---|
| 55 | 4-[6-[3-(methanesulfonamido)anilino]-1-methyl-pyrrolo[3,2-c]pyridin-2-yl]-N,N-dimethyl-benzamide |
| 56 | 4-[6-(3-acetamidoanilino)-1-methyl-pyrrolo[3,2-c]pyridin-2-yl]-N,N-dimethyl-benzamide |
| 57 | 4-[6-(4-acetamidoanilino)-1-benzyl-pyrrolo[3,2-c]pyridin-2-yl]-N,N-dimethyl-benzamide |
| 58 | 4-[1-benzyl-6-(pyrimidin-4-ylamino)pyrrolo[3,2-c]pyridin-2-yl]-N,N-dimethyl-benzamide |
| 59 | 2-(4-dimethylaminophenyl)-1-methyl-N-(2-pyridyl)pyrrolo[3,2-c]pyridin-6-amine |
| 60 | 3-[[1-benzyl-2-(4-dimethylaminophenyl)pyrrolo[3,2-c]pyridin-6-yl]amino]phenol |
| 61 | 1-benzyl-2-(4-dimethylaminophenyl)-N-pyrimidin-4-yl-pyrrolo[3,2-c]pyridin-6-amine |
| 62 | 2-(2-pyridyl)-N-(3,4,5-trimethoxyphenyl)-1H-pyrrolo[3,2-c]pyridin-6-amine |
| 64 | N-(m-tolyl)-2-(2-pyridyl)-1H-pyrrolo[3,2-c]pyridin-6-amine |
| 65 | N-(4-methoxyphenyl)-2-(2-pyridyl)-1H-pyrrolo[3,2-c]pyridin-6-amine |
| 66 | 2-(2-pyridyl)-N-[3-(trifluoromethyl)phenyl]-1H-pyrrolo[3,2-c]pyridin-6-amine |
| 67 | methyl 4-[[2-(2-pyridyl)-1H-pyrrolo[3,2-c]pyridin-6-yl]amino]benzoate |
| 68 | 4-[[2-(2-pyridyl)-1H-pyrrolo[3,2-c]pyridin-6-yl]amino]benzonitrile |
| 69 | 2-(2-pyridyl)-N-[3-(trifluoromethoxy)phenyl]-1H-pyrrolo[3,2-c]pyridin-6-amine |
| 70 | N,N-dimethyl-4-[[2-(2-pyridyl)-1H-pyrrolo[3,2-c]pyridin-6-yl]amino]benzamide |
| 71 | N-(3-fluorophenyl)-2-(2-pyridyl)-1H-pyrrolo[3,2-c]pyridin-6-amine |
| 72 | N-(4-methylsulfonylphenyl)-2-(2-pyridyl)-1H-pyrrolo[3,2-c]pyridin-6-amine |
| 73 | N-(3-isopropoxyphenyl)-2-(2-pyridyl)-1H-pyrrolo[3,2-c]pyridin-6-amine |
| 74 | N-[4-[[2-(3-pyridyl)-1H-pyrrolo[3,2-c]pyridin-6-yl]amino]phenyl]acetamide |
| 75 | N-(6-methoxy-3-pyridyl)-2-(3-pyridyl)-1H-pyrrolo[3,2-c]pyridin-6-amine |
| 76 | 2-(3-pyridyl)-N-(4-pyridyl)-1H-pyrrolo[3,2-c]pyridin-6-amine |
| 77 | 4-[2-(3-pyridyl)-1H-pyrrolo[3,2-c]pyridin-6-yl]morpholine |
| 80 | N-[3-[[2-(3-pyridyl)-1H-pyrrolo[3,2-c]pyridin-6-yl]amino]phenyl]acetamide |
| 81 | N-(4-isopropoxyphenyl)-2-(3-pyridyl)-1H-pyrrolo[3,2-c]pyridin-6-amine |
| 82 | 1-methyl-2-(3-pyridyl)-N-(3,4,5-trimethoxyphenyl)pyrrolo[3,2-c]pyridin-6-amine |
| 84 | N-(2,3-dihydro-1,4-benzodioxin-6-yl)-1-methyl-2-(3-pyridyl)pyrrolo[3,2-c]pyridin-6-amine |
| 85 | N-(3,4-dimethoxyphenyl)-1-methyl-2-(3-pyridyl)pyrrolo[3,2-c]pyridin-6-amine |
| 86 | N-(6-methoxy-3-pyridyl)-1-methyl-2-(3-pyridyl)pyrrolo[3,2-c]pyridin-6-amine |
| 87 | 1-methyl-N,2-bis(3-pyridyl)pyrrolo[3,2-c]pyridin-6-amine |
| 88 | 1-methyl-N-phenyl-2-(3-pyridyl)pyrrolo[3,2-c]pyridin-6-amine |
| 89 | N1,N1-dimethyl-N3-[1-methyl-2-(3-pyridyl)pyrrolo[3,2-c]pyridin-6-yl]benzene-1,3-diamine |
| 90 | 1-methyl-N-(m-tolyl)-2-(3-pyridyl)pyrrolo[3,2-c]pyridin-6-amine |
| 91 | N-(4-methoxyphenyl)-1-methyl-2-(3-pyridyl)pyrrolo[3,2-c]pyridin-6-amine |
| 92 | N-(4-fluorophenyl)-1-methyl-2-(3-pyridyl)pyrrolo[3,2-c]pyridin-6-amine |
| 93 | N-(1,3-benzodioxol-5-yl)-1-methyl-2-(3-pyridyl)pyrrolo[3,2-c]pyridin-6-amine |
| 94 | 4-[1-methyl-2-(3-pyridyl)pyrrolo[3,2-c]pyridin-6-yl]morpholine |
| 95 | N,N-dimethyl-4-[[1-methyl-2-(3-pyridyl)pyrrolo[3,2-c]pyridin-6-yl]amino]benzamide |
| 96 | N-[3-[[1-methyl-2-(3-pyridyl)pyrrolo[3,2-c]pyridin-6-yl]amino]phenyl]acetamide |
| 97 | 1-[3-[[1-methyl-2-(3-pyridyl)pyrrolo[3,2-c]pyridin-6-yl]amino]phenyl]ethanone |
| 98 | 1-benzyl-N-(2-pyridyl)-2-(3-pyridyl)pyrrolo[3,2-c]pyridin-6-amine |
| 99 | 1-benzyl-2-(3-pyridyl)-N-pyrimidin-4-yl-pyrrolo[3,2-c]pyridin-6-amine |
| 100 | 2-(3-methylimidazol-4-yl)-N-(3,4,5-trimethoxyphenyl)-1H-pyrrolo[3,2-c]pyridin-6-amine |
| 101 | N-(3-methoxyphenyl)-2-(3-methylimidazol-4-yl)-1H-pyrrolo[3,2-c]pyridin-6-amine |
| 103 | N-(3-chlorophenyl)-2-(3-methylimidazol-4-yl)-1H-pyrrolo[3,2-c]pyridin-6-amine |
| 104 | N1,N1-dimethyl-N3-[2-(3-methylimidazol-4-yl)-1H-pyrrolo[3,2-c]pyridin-6-yl]benzene-1,3-diamine |
| 105 | 2-(3-methylimidazol-4-yl)-N-(m-tolyl)-1H-pyrrolo[3,2-c]pyridin-6-amine |
| 107 | 1-[3-[[2-(3-methylimidazol-4-yl)-1H-pyrrolo[3,2-c]pyridin-6-yl]amino]phenyl]ethanone |

| | compound name |
|---|---|
| 108 | N-(3-fluorophenyl)-2-(3-methylimidazol-4-yl)-1H-pyrrolo[3,2-c]pyridin-6-amine |
| 109 | N-(4-isopropoxyphenyl)-2-(3-methylimidazol-4-yl)-1H-pyrrolo[3,2-c]pyridin-6-amine |
| 110 | N-(3-methoxyphenyl)-2-(1H-pyrazol-4-yl)-1H-pyrrolo[3,2-c]pyridin-6-amine |
| 112 | N1,N1-dimethyl-N3-[2-(1H-pyrazol-4-yl)-1H-pyrrolo[3,2-c]pyridin-6-yl]benzene-1,3-diamine |
| 113 | N-(m-tolyl)-2-(1H-pyrazol-4-yl)-1H-pyrrolo[3,2-c]pyridin-6-amine |
| 115 | 2-(1H-pyrazol-4-yl)-N-(2-pyridyl)-1H-pyrrolo[3,2-c]pyridin-6-amine |
| 116 | N-[3-methoxy-5-(trifluoromethyl)phenyl]-2-(1H-pyrazol-4-yl)-1H-pyrrolo[3,2-c]pyridin-6-amine |
| 117 | N-[3-[[2-(1H-pyrazol-4-yl)-1H-pyrrolo[3,2-c]pyridin-6-yl]amino]phenyl]acetamide |
| 118 | 1-[3-[[2-(1H-pyrazol-4-yl)-1H-pyrrolo[3,2-c]pyridin-6-yl]amino]phenyl]ethanone |
| 119 | N-(3-fluorophenyl)-2-(1H-pyrazol-4-yl)-1H-pyrrolo[3,2-c]pyridin-6-amine |
| 120 | N-(4-methylsulfonylphenyl)-2-(1H-pyrazol-4-yl)-1H-pyrrolo[3,2-c]pyridin-6-amine |
| 121 | N-[4-[[2-(1-methylpyrazol-4-yl)-1H-pyrrolo[3,2-c]pyridin-6-yl]amino]phenyl]acetamide |
| 122 | N-(2,3-dihydro-1,4-benzodioxin-6-yl)-2-(1-methylpyrazol-4-yl)-1H-pyrrolo[3,2-c]pyridin-6-amine |
| 124 | 1-[3-[[2-(1-methylpyrazol-4-yl)-1H-pyrrolo[3,2-c]pyridin-6-yl]amino]phenyl]ethanone |
| 125 | 1-methyl-2-(1-methylpyrazol-4-yl)-N-(3,4,5-trimethoxyphenyl)pyrrolo[3,2-c]pyridin-6-amine |
| 126 | N-[4-[[1-methyl-2-(1-methylpyrazol-4-yl)pyrrolo[3,2-c]pyridin-6-yl]amino]phenyl]acetamide |
| 127 | N-(3-methoxyphenyl)-1-methyl-2-(1-methylpyrazol-4-yl)pyrrolo[3,2-c]pyridin-6-amine |
| 128 | N-(2,3-dihydro-1,4-benzodioxin-6-yl)-1-methyl-2-(1-methylpyrazol-4-yl)pyrrolo[3,2-c]pyridin-6-amine |
| 130 | N-(6-methoxy-3-pyridyl)-1-methyl-2-(1-methylpyrazol-4-yl)pyrrolo[3,2-c]pyridin-6-amine |
| 131 | 1-methyl-2-(1-methylpyrazol-4-yl)-N-(3-pyridyl)pyrrolo[3,2-c]pyridin-6-amine |
| 132 | 1-methyl-2-(1-methylpyrazol-4-yl)-N-phenyl-pyrrolo[3,2-c]pyridin-6-amine |
| 133 | 1-methyl-N-[4-(4-methylpiperazin-1-yl)phenyl]-2-(1-methylpyrazol-4-yl)pyrrolo[3,2-c]pyridin-6-amine |
| 134 | N1,N1-dimethyl-N3-[1-methyl-2-(1-methylpyrazol-4-yl)pyrrolo[3,2-c]pyridin-6-yl]benzene-1,3-diamine |
| 135 | 1-methyl-2-(1-methylpyrazol-4-yl)-N-(4-pyridyl)pyrrolo[3,2-c]pyridin-6-amine |
| 136 | 1-methyl-2-(1-methylpyrazol-4-yl)-N-(m-tolyl)pyrrolo[3,2-c]pyridin-6-amine |
| 139 | 1-methyl-2-(1-methylpyrazol-4-yl)-N-(2-pyridyl)pyrrolo[3,2-c]pyridin-6-amine |
| 140 | N,1-dimethyl-2-(1-methylpyrazol-4-yl)-N-phenyl-pyrrolo[3,2-c]pyridin-6-amine |
| 141 | methyl 4-[[1-methyl-2-(1-methylpyrazol-4-yl)pyrrolo[3,2-c]pyridin-6-yl]amino]benzoate |
| 143 | N-(1,3-benzodioxol-5-yl)-1-methyl-2-(1-methylpyrazol-4-yl)pyrrolo[3,2-c]pyridin-6-amine |
| 144 | 3-[[1-methyl-2-(1-methylpyrazol-4-yl)pyrrolo[3,2-c]pyridin-6-yl]amino]phenol |
| 145 | 4-[1-methyl-2-(1-methylpyrazol-4-yl)pyrrolo[3,2-c]pyridin-6-yl]morpholine |
| 146 | 1-methyl-2-(1-methylpyrazol-4-yl)-N-[3-(trifluoromethoxy)phenyl]pyrrolo[3,2-c]pyridin-6-amine |
| 147 | 1-methyl-2-(1-methylpyrazol-4-yl)-N-pyrimidin-4-yl-pyrrolo[3,2-c]pyridin-6-amine |
| 149 | N-[3-[[1-methyl-2-(1-methylpyrazol-4-yl)pyrrolo[3,2-c]pyridin-6-yl]amino]phenyl]acetamide |
| 150 | 1-[3-[[1-methyl-2-(1-methylpyrazol-4-yl)pyrrolo[3,2-c]pyridin-6-yl]amino]phenyl]ethanone |
| 151 | N-(3-fluorophenyl)-1-methyl-2-(1-methylpyrazol-4-yl)pyrrolo[3,2-c]pyridin-6-amine |
| 152 | 1-methyl-2-(1-methylpyrazol-4-yl)-N-(4-methylsulfonylphenyl)pyrrolo[3,2-c]pyridin-6-amine |
| 153 | 1-methyl-2-(1-methylpyrazol-4-yl)-N-(4-methylsulfanylphenyl)pyrrolo[3,2-c]pyridin-6-amine |
| 154 | 1-benzyl-6-(4-methylpiperazin-1-yl)-2-(1-methylpyrazol-4-yl)pyrrolo[3,2-c]pyridine |
| 155 | 4-[1-benzyl-2-(1-methylpyrazol-4-yl)pyrrolo[3,2-c]pyridin-6-yl]morpholine |

-continued

| | compound name |
|---|---|
| 156 | N-[3-[[1-benzyl-2-(1-methylpyrazol-4-yl)pyrrolo[3,2-c]pyridin-6-yl]amino]phenyl]methanesulfonamide |
| 157 | N-[3-[[1-benzyl-2-(1-methylpyrazol-4-yl)pyrrolo[3,2-c]pyridin-6-yl]amino]phenyl]acetamide |
| 158 | N-methyl-N-[3-[1-methyl-6-(3,4,5-trimethoxyanilino)pyrrolo[3,2-c]pyridin-2-yl]phenyl]acetamide |
| 159 | 4-[[2-[3-[acetyl(methyl)amino]phenyl]-1-methyl-pyrrolo[3,2-c]pyridin-6-yl]amino]benzamide |
| 160 | N-[3-[6-(3,4-dimethoxyanilino)-1-methyl-pyrrolo[3,2-c]pyridin-2-yl]phenyl]-N-methyl-acetamide |
| 161 | N-[3-[6-[(6-methoxy-3-pyridyl)amino]-1-methyl-pyrrolo[3,2-c]pyridin-2-yl]phenyl]-N-methyl-acetamide |
| 162 | N-methyl-N-[3-[1-methyl-6-(3-pyridylamino)pyrrolo[3,2-c]pyridin-2-yl]phenyl]acetamide |
| 163 | N-methyl-N-[3-[1-methyl-6-(4-morpholinoanilino)pyrrolo[3,2-c]pyridin-2-yl]phenyl]acetamide |
| 164 | N-methyl-N-[3-[1-methyl-6-[4-(4-methylpiperazin-1-yl)anilino]pyrrolo[3,2-c]pyridin-2-yl]phenyl]acetamide |
| 165 | N-[3-[6-[3-(dimethylamino)anilino]-1-methyl-pyrrolo[3,2-c]pyridin-2-yl]phenyl]-N-methyl-acetamide |
| 166 | N-[3-[6-(4-methoxyanilino)-1-methyl-pyrrolo[3,2-c]pyridin-2-yl]phenyl]-N-methyl-acetamide |
| 167 | N-methyl-N-[3-[1-methyl-6-(2-pyridylamino)pyrrolo[3,2-c]pyridin-2-yl]phenyl]acetamide |
| 168 | N-[3-[6-(4-cyanoanilino)-1-methyl-pyrrolo[3,2-c]pyridin-2-yl]phenyl]-N-methyl-acetamide |
| 169 | N-[3-[6-(1,3-benzodioxol-5-ylamino)-1-methyl-pyrrolo[3,2-c]pyridin-2-yl]phenyl]-N-methyl-acetamide |
| 170 | N-[3-[6-(3-hydroxyanilino)-1-methyl-pyrrolo[3,2-c]pyridin-2-yl]phenyl]-N-methyl-acetamide |
| 171 | N-methyl-N-[3-(1-methyl-6-morpholino-pyrrolo[3,2-c]pyridin-2-yl)phenyl]acetamide |
| 172 | 4-[[2-[3-[acetyl(methyl)amino]phenyl]-1-methyl-pyrrolo[3,2-c]pyridin-6-yl]amino]-N,N-dimethyl-benzamide |
| 173 | N-methyl-N-[3-[1-methyl-6-(4-methylsulfonylanilino)pyrrolo[3,2-c]pyridin-2-yl]phenyl]acetamide |
| 174 | 2-phenyl-N-(3,4,5-trimethoxyphenyl)-1H-pyrrolo[3,2-c]pyridin-6-amine |
| 175 | N-(3,4-dimethoxyphenyl)-2-phenyl-1H-pyrrolo[3,2-c]pyridin-6-amine |
| 176 | N-(4-morpholinophenyl)-2-phenyl-1H-pyrrolo[3,2-c]pyridin-6-amine |
| 177 | N-[4-(4-methylpiperazin-1-yl)phenyl]-2-phenyl-1H-pyrrolo[3,2-c]pyridin-6-amine |
| 178 | 2-phenyl-N-(4-pyridyl)-1H-pyrrolo[3,2-c]pyridin-6-amine |
| 179 | N-(4-fluorophenyl)-2-phenyl-1H-pyrrolo[3,2-c]pyridin-6-amine |
| 180 | 3-[(2-phenyl-1H-pyrrolo[3,2-c]pyridin-6-yl)amino]phenol |
| 181 | 4-(2-phenyl-1H-pyrrolo[3,2-c]pyridin-6-yl)morpholine |
| 182 | N,N-dimethyl-4-[(2-phenyl-1H-pyrrolo[3,2-c]pyridin-6-yl)amino]benzamide |
| 183 | N-[3-[(2-phenyl-1H-pyrrolo[3,2-c]pyridin-6-yl)amino]phenyl]acetamide |
| 184 | 1-benzyl-2-phenyl-N-pyrimidin-4-yl-pyrrolo[3,2-c]pyridin-6-amine |
| 185 | 1-methyl-4-(4-methylpiperazin-1-yl)-2-[3-(trifluoromethyl)phenyl]pyrrolo[3,2-c]pyridine |
| 186 | 2-(3-fluorophenyl)-4-(4-methylpiperazin-1-yl)-1H-pyrrolo[3,2-c]pyridine |
| 187 | 4-[2-(3-fluorophenyl)-1H-pyrrolo[3,2-c]pyridin-4-yl]morpholine |
| 188 | N,N-dimethyl-4-(1-methyl-4-morpholino-pyrrolo[3,2-c]pyridin-2-yl)benzamide |
| 189 | N,N-dimethyl-4-(4-morpholino-1H-pyrrolo[3,2-c]pyridin-2-yl)aniline |
| 190 | 4-(4-methylpiperazin-1-yl)-2-(3-thienyl)-1H-pyrrolo[3,2-c]pyridine |
| 191 | 4-[2-(3-thienyl)-1H-pyrrolo[3,2-c]pyridin-4-yl]morpholine |
| 192 | 4-[2-(3,5-dimethoxyphenyl)-1-methyl-pyrrolo[3,2-c]pyridin-4-yl]morpholine |
| 193 | 4-[2-(2-methoxyphenyl)-1H-pyrrolo[3,2-c]pyridin-4-yl]morpholine |
| 194 | 2-(3-methoxyphenyl)-1-methyl-4-(4-methylpiperazin-1-yl)pyrrolo[3,2-c]pyridine |
| 195 | 4-[2-(3-chlorophenyl)-1-methyl-pyrrolo[3,2-c]pyridin-4-yl]morpholine |
| 196 | N-(3-pyridyl)-2-[3-(trifluoromethyl)phenyl]-1H-pyrrolo[3,2-c]pyridin-4-amine |
| 197 | N-(4-methylsulfonylphenyl)-2-[3-(trifluoromethyl)phenyl]-1H-pyrrolo[3,2-c]pyridin-4-amine |
| 198 | N-[4-[[2-(3-fluorophenyl)-1H-pyrrolo[3,2-c]pyridin-4-yl]amino]phenyl]acetamide |
| 199 | 4-[[2-(3-fluorophenyl)-1H-pyrrolo[3,2-c]pyridin-4-yl]amino]phenol |
| 200 | 2-(3-fluorophenyl)-N-(3-pyridyl)-1H-pyrrolo[3,2-c]pyridin-4-amine |
| 201 | 2-(3-fluorophenyl)-N-[4-(4-methylpiperazin-1-yl)phenyl]-1H-pyrrolo[3,2-c]pyridin-4-amine |
| 202 | 2-(3-fluorophenyl)-N-(3-methylsulfonylphenyl)-1H-pyrrolo[3,2-c]pyridin-4-amine |

-continued

| | compound name |
|---|---|
| 203 | N-(1,3-benzodioxol-5-yl)-2-(3-fluorophenyl)-1H-pyrrolo[3,2-c]pyridin-4-amine |
| 204 | 5-[[2-(3-fluorophenyl)-1H-pyrrolo[3,2-c]pyridin-4-yl]amino]-2-methoxy-phenol |
| 205 | N-[3-[[2-(3-fluorophenyl)-1H-pyrrolo[3,2-c]pyridin-4-yl]amino]phenyl]methanesulfonamide |
| 206 | N-[3-[[2-(3-fluorophenyl)-1H-pyrrolo[3,2-c]pyridin-4-yl]amino]phenyl]acetamide |
| 207 | 2-(3-fluorophenyl)-N-(4-methylsulfonylphenyl)-1H-pyrrolo[3,2-c]pyridin-4-amine |
| 208 | N-(3,4-dimethoxyphenyl)-2-(3-fluorophenyl)-1-methyl-pyrrolo[3,2-c]pyridin-4-amine |
| 209 | 2-(3-fluorophenyl)-1-methyl-N-[4-(4-methylpiperazin-1-yl)phenyl]pyrrolo[3,2-c]pyridin-4-amine |
| 210 | N-[3-[[2-(3-fluorophenyl)-1-methyl-pyrrolo[3,2-c]pyridin-4-yl]amino]phenyl]acetamide |
| 211 | 4-[4-(4-acetamidoanilino)-1-methyl-pyrrolo[3,2-c]pyridin-2-yl]-N,N-dimethyl-benzamide |
| 212 | 4-[4-(3-methoxyanilino)-1-methyl-pyrrolo[3,2-c]pyridin-2-yl]-N,N-dimethyl-benzamide |
| 213 | 4-[4-(4-carbamoylanilino)-1-methyl-pyrrolo[3,2-c]pyridin-2-yl]-N,N-dimethyl-benzamide |
| 214 | 4-[4-(2,3-dihydro-1,4-benzodioxin-6-ylamino)-1-methyl-pyrrolo[3,2-c]pyridin-2-yl]-N,N-dimethyl-benzamide |
| 215 | 4-[4-(3,4-dimethoxyanilino)-1-methyl-pyrrolo[3,2-c]pyridin-2-yl]-N,N-dimethyl-benzamide |
| 216 | 4-[4-[(6-methoxy-3-pyridyl)amino]-1-methyl-pyrrolo[3,2-c]pyridin-2-yl]-N,N-dimethyl-benzamide |
| 217 | N,N-dimethyl-4-[1-methyl-4-(4-phenoxyanilino)pyrrolo[3,2-c]pyridin-2-yl]benzamide |
| 218 | 4-[4-[3-(dimethylamino)anilino]-1-methyl-pyrrolo[3,2-c]pyridin-2-yl]-N,N-dimethyl-benzamide |
| 219 | N,N-dimethyl-4-[1-methyl-4-(2-pyridylamino)pyrrolo[3,2-c]pyridin-2-yl]benzamide |
| 220 | N,N-dimethyl-4-[1-methyl-4-(3-methoxy-5-(trifuloromethyl)phenylamino)pyrrolo[3,2-c]pyridin-2-yl]benzamide |
| 221 | 4-[4-(3-hydroxyanilino)-1-methyl-pyrrolo[3,2-c]pyridin-2-yl]-N,N-dimethyl-benzamide |
| 222 | N,N-dimethyl-4-[1-methyl-4-[3-(trifluoromethoxy)anilino]pyrrolo[3,2-c]pyridin-2-yl]benzamide |
| 223 | N,N-dimethyl-4-[1-methyl-4-(3-phenoxyanilino)pyrrolo[3,2-c]pyridin-2-yl]benzamide |
| 224 | 4-[4-(3-isopropylanilino)-1-methyl-pyrrolo[3,2-c]pyridin-2-yl]-N,N-dimethyl-benzamide |
| 225 | 4-[4-[3-(methanesulfonamido)anilino]-1-methyl-pyrrolo[3,2-c]pyridin-2-yl]-N,N-dimethyl-benzamide |
| 226 | 4-[[2-(4-dimethylaminophenyl)-1-methyl-pyrrolo[3,2-c]pyridin-4-yl]amino]phenol |
| 227 | 4-[[2-(4-dimethylaminophenyl)-1-methyl-pyrrolo[3,2-c]pyridin-4-yl]amino]benzamide |
| 228 | 5-[[2-(4-dimethylaminophenyl)-1-methyl-pyrrolo[3,2-c]pyridin-4-yl]amino]-2-methoxy-phenol |
| 229 | 2-(4-dimethylaminophenyl)-1-methyl-N-pyrimidin-4-yl-pyrrolo[3,2-c]pyridin-4-amine |
| 230 | 2-(4-dimethylaminophenyl)-1-methyl-N-(4-methylsulfonylphenyl)pyrrolo[3,2-c]pyridin-4-amine |
| 231 | N-[4-[[2-(3-pyridyl)-1H-pyrrolo[3,2-c]pyridin-4-yl]amino]phenyl]acetamide |
| 232 | N-(2,3-dihydro-1,4-benzodioxin-6-yl)-2-(3-pyridyl)-1H-pyrrolo[3,2-c]pyridin-4-amine |
| 233 | N-(6-methoxy-3-pyridyl)-2-(3-pyridyl)-1H-pyrrolo[3,2-c]pyridin-4-amine |
| 234 | N,2-bis(3-pyridyl)-1H-pyrrolo[3,2-c]pyridin-4-amine |
| 235 | N-[4-(4-methylpiperazin-1-yl)phenyl]-2-(3-pyridyl)-1H-pyrrolo[3,2-c]pyridin-4-amine |
| 236 | 2-methoxy-5-[[2-(3-pyridyl)-1H-pyrrolo[3,2-c]pyridin-4-yl]amino]phenol |
| 237 | 1-methyl-2-(3-pyridyl)-N-(3,4,5-trimethoxyphenyl)pyrrolo[3,2-c]pyridin-4-amine |
| 238 | N-(3,4-dimethoxyphenyl)-1-methyl-2-(3-pyridyl)pyrrolo[3,2-c]pyridin-4-amine |
| 239 | N1,N1-dimethyl-N3-[1-methyl-2-(3-pyridyl)pyrrolo[3,2-c]pyridin-4-yl]benzene-1,3-diamine |
| 240 | N-(4-methoxy-2-methyl-phenyl)-1-methyl-2-(3-pyridyl)pyrrolo[3,2-c]pyridin-4-amine |
| 241 | 1-methyl-N-(m-tolyl)-2-(3-pyridyl)pyrrolo[3,2-c]pyridin-4-amine |
| 242 | N-(4-fluorophenyl)-1-methyl-2-(3-pyridyl)pyrrolo[3,2-c]pyridin-4-amine |
| 243 | 1-methyl-2-(3-pyridyl)-N-[3-(trifluoromethyl)phenyl]pyrrolo[3,2-c]pyridin-4-amine |

| | compound name |
|---|---|
| 244 | N-[3-[[1-methyl-2-(3-pyridyl)pyrrolo[3,2-c]pyridin-4-yl]amino]phenyl]methanesulfonamide |
| 245 | N-[3-[[1-methyl-2-(3-pyridyl)pyrrolo[3,2-c]pyridin-4-yl]amino]phenyl]acetamide |
| 246 | 2-(1-methylpyrazol-4-yl)-N-(4-methylsulfonylphenyl)-1H-pyrrolo[3,2-c]pyridin-4-amine |
| 247 | 1-methyl-2-(1-methylpyrazol-4-yl)-N-(3-pyridyl)pyrrolo[3,2-c]pyridin-4-amine |
| 248 | N-methyl-N-[3-[1-methyl-4-[4-(trifluoromethoxy)anilino]pyrrolo[3,2-c]pyridin-2-yl]phenyl]acetamide |
| 249 | N-[4-[[2-(3-thienyl)-1H-pyrrolo[3,2-c]pyridin-4-yl]amino]phenyl]acetamide |
| 250 | 4-[[2-(3-thienyl)-1H-pyrrolo[3,2-c]pyridin-4-yl]amino]benzamide |
| 251 | N-(2,4-dimethoxyphenyl)-2-(3-thienyl)-1H-pyrrolo[3,2-c]pyridin-4-amine |
| 252 | N-(2,3-dihydro-1,4-benzodioxin-6-yl)-2-(3-thienyl)-1H-pyrrolo[3,2-c]pyridin-4-amine |
| 253 | N-(3,4-dimethoxyphenyl)-2-(3-thienyl)-1H-pyrrolo[3,2-c]pyridin-4-amine |
| 254 | N-(6-methoxy-3-pyridyl)-2-(3-thienyl)-1H-pyrrolo[3,2-c]pyridin-4-amine |
| 255 | N-(3-pyridyl)-2-(3-thienyl)-1H-pyrrolo[3,2-c]pyridin-4-amine |
| 256 | N-(4-morpholinophenyl)-2-(3-thienyl)-1H-pyrrolo[3,2-c]pyridin-4-amine |
| 257 | N-[4-(4-methylpiperazin-1-yl)phenyl]-2-(3-thienyl)-1H-pyrrolo[3,2-c]pyridin-4-amine |
| 258 | N-(4-pyridyl)-2-(3-thienyl)-1H-pyrrolo[3,2-c]pyridin-4-amine |
| 259 | N-(4-methoxyphenyl)-2-(3-thienyl)-1H-pyrrolo[3,2-c]pyridin-4-amine |
| 260 | N-(2-pyridyl)-2-(3-thienyl)-1H-pyrrolo[3,2-c]pyridin-4-amine |
| 261 | methyl 4-[[2-(3-thienyl)-1H-pyrrolo[3,2-c]pyridin-4-yl]amino]benzoate |
| 262 | N-(3-methylsulfonylphenyl)-2-(3-thienyl)-1H-pyrrolo[3,2-c]pyridin-4-amine |
| 263 | N-(1,3-benzodioxol-5-yl)-2-(3-thienyl)-1H-pyrrolo[3,2-c]pyridin-4-amine |
| 264 | 3-[[2-(3-thienyl)-1H-pyrrolo[3,2-c]pyridin-4-yl]amino]phenol |
| 265 | N-[3-[[2-(3-thienyl)-1H-pyrrolo[3,2-c]pyridin-4-yl]amino]phenyl]methanesulfonamide |
| 266 | N-[3-[[2-(3-thienyl)-1H-pyrrolo[3,2-c]pyridin-4-yl]amino]phenyl]acetamide |
| 267 | 1-[3-[[2-(3-thienyl)-1H-pyrrolo[3,2-c]pyridin-4-yl]amino]phenyl]ethanone |
| 268 | N-(4-methylsulfonylphenyl)-2-(3-thienyl)-1H-pyrrolo[3,2-c]pyridin-4-amine |
| 269 | N-(4-isopropoxyphenyl)-2-(3-thienyl)-1H-pyrrolo[3,2-c]pyridin-4-amine |
| 270 | N-[4-[[1-methyl-2-(3-thienyl)pyrrolo[3,2-c]pyridin-4-yl]amino]phenyl]acetamide |
| 271 | 4-[[1-methyl-2-(3-thienyl)pyrrolo[3,2-c]pyridin-4-yl]amino]phenol |
| 272 | N-(2,4-dimethoxyphenyl)-1-methyl-2-(3-thienyl)pyrrolo[3,2-c]pyridin-4-amine |
| 273 | N-(2,3-dihydro-1,4-benzodioxin-6-yl)-1-methyl-2-(3-thienyl)pyrrolo[3,2-c]pyridin-4-amine |
| 274 | N-(3,4-dimethoxyphenyl)-1-methyl-2-(3-thienyl)pyrrolo[3,2-c]pyridin-4-amine |
| 275 | N-(6-methoxy-3-pyridyl)-1-methyl-2-(3-thienyl)pyrrolo[3,2-c]pyridin-4-amine |
| 276 | 1-methyl-N-(3-pyridyl)-2-(3-thienyl)pyrrolo[3,2-c]pyridin-4-amine |
| 277 | N1,N1-dimethyl-N3-[1-methyl-2-(3-thienyl)pyrrolo[3,2-c]pyridin-4-yl]benzene-1,3-diamine |
| 278 | 1-methyl-N-(4-pyridyl)-2-(3-thienyl)pyrrolo[3,2-c]pyridin-4-amine |
| 279 | N-(4-methoxyphenyl)-1-methyl-2-(3-thienyl)pyrrolo[3,2-c]pyridin-4-amine |
| 280 | 1-methyl-N-(2-pyridyl)-2-(3-thienyl)pyrrolo[3,2-c]pyridin-4-amine |
| 281 | 4-[[1-methyl-2-(3-thienyl)pyrrolo[3,2-c]pyridin-4-yl]amino]benzonitrile |
| 282 | 1-methyl-N-(3-methylsulfonylphenyl)-2-(3-thienyl)pyrrolo[3,2-c]pyridin-4-amine |
| 283 | N-(1,3-benzodioxol-5-yl)-1-methyl-2-(3-thienyl)pyrrolo[3,2-c]pyridin-4-amine |
| 284 | 2-methoxy-5-[[1-methyl-2-(3-thienyl)pyrrolo[3,2-c]pyridin-4-yl]amino]phenol |
| 285 | 1-methyl-N-pyrimidin-4-yl-2-(3-thienyl)pyrrolo[3,2-c]pyridin-4-amine |
| 286 | N-[3-[[1-methyl-2-(3-thienyl)pyrrolo[3,2-c]pyridin-4-yl]amino]phenyl]methanesulfonamide |
| 287 | N-[3-[[1-methyl-2-(3-thienyl)pyrrolo[3,2-c]pyridin-4-yl]amino]phenyl]acetamide |
| 288 | 1-[3-[[1-methyl-2-(3-thienyl)pyrrolo[3,2-c]pyridin-4-yl]amino]phenyl]ethanone |
| 289 | 1-methyl-N-(4-methylsulfonylphenyl)-2-(3-thienyl)pyrrolo[3,2-c]pyridin-4-amine |
| 290 | 4-[[2-(3,5-dimethoxyphenyl)-1H-pyrrolo[3,2-c]pyridin-4-yl]amino]benzamide |
| 291 | 2-(3,5-dimethoxyphenyl)-N-(4-pyridyl)-1H-pyrrolo[3,2-c]pyridin-4-amine |
| 292 | N-[3-[[2-(3,5-dimethoxyphenyl)-1H-pyrrolo[3,2-c]pyridin-4-yl]amino]phenyl]methanesulfonamide |

| | compound name |
|---|---|
| 293 | 2-(3,5-dimethoxyphenyl)-N-(4-methylsulfonylphenyl)-1H-pyrrolo[3,2-c]pyridin-4-amine |
| 294 | 4-[[2-(2-methoxyphenyl)-1H-pyrrolo[3,2-c]pyridin-4-yl]amino]benzamide |
| 295 | 2-(2-methoxyphenyl)-N-(4-pyridyl)-1H-pyrrolo[3,2-c]pyridin-4-amine |
| 296 | N-(1,3-benzodioxol-5-yl)-2-(2-methoxyphenyl)-1H-pyrrolo[3,2-c]pyridin-4-amine |
| 297 | 3-[[2-(2-methoxyphenyl)-1H-pyrrolo[3,2-c]pyridin-4-yl]amino]phenol |
| 298 | N-[3-[[2-(2-methoxyphenyl)-1H-pyrrolo[3,2-c]pyridin-4-yl]amino]phenyl]methanesulfonamide |
| 299 | N-[3-[[2-(2-methoxyphenyl)-1H-pyrrolo[3,2-c]pyridin-4-yl]amino]phenyl]acetamide |
| 300 | 2-(2-methoxyphenyl)-N-(4-methylsulfonylphenyl)-1H-pyrrolo[3,2-c]pyridin-4-amine |
| 301 | N-[4-[[2-(2-methoxyphenyl)-1-methyl-pyrrolo[3,2-c]pyridin-4-yl]amino]phenyl]acetamide |
| 302 | N-(2,4-dimethoxyphenyl)-2-(2-methoxyphenyl)-1-methyl-pyrrolo[3,2-c]pyridin-4-amine |
| 303 | 2-(2-methoxyphenyl)-1-methyl-N-(3-pyridyl)pyrrolo[3,2-c]pyridin-4-amine |
| 304 | 2-(2-methoxyphenyl)-1-methyl-N-(2-pyridyl)pyrrolo[3,2-c]pyridin-4-amine |
| 305 | 2-(2-methoxyphenyl)-1-methyl-N-(4-methylsulfanylphenyl)pyrrolo[3,2-c]pyridin-4-amine |
| 306 | N-[4-[[2-(3-methoxyphenyl)-1H-pyrrolo[3,2-c]pyridin-4-yl]amino]phenyl]acetamide |
| 307 | 2-(3-methoxyphenyl)-N-(6-methoxy-3-pyridyl)-1H-pyrrolo[3,2-c]pyridin-4-amine |
| 308 | 2-(3-methoxyphenyl)-N-(3-pyridyl)-1H-pyrrolo[3,2-c]pyridin-4-amine |
| 309 | 2-(3-methoxyphenyl)-N-phenyl-1H-pyrrolo[3,2-c]pyridin-4-amine |
| 310 | 2-(3-methoxyphenyl)-N-[4-(4-methylpiperazin-1-yl)phenyl]-1H-pyrrolo[3,2-c]pyridin-4-amine |
| 311 | 2-(3-methoxyphenyl)-N-(3-methylsulfonylphenyl)-1H-pyrrolo[3,2-c]pyridin-4-amine |
| 312 | 2-methoxy-5-[[2-(3-methoxyphenyl)-1H-pyrrolo[3,2-c]pyridin-4-yl]amino]phenol |
| 313 | 4-[[2-(3-methoxyphenyl)-1H-pyrrolo[3,2-c]pyridin-4-yl]amino]-N,N-dimethyl-benzamide |
| 314 | N-(3-isopropoxyphenyl)-2-(3-methoxyphenyl)-1-methyl-pyrrolo[3,2-c]pyridin-4-amine |
| 315 | 2-(3-chlorophenyl)-N-(3-pyridyl)-1H-pyrrolo[3,2-c]pyridin-4-amine |
| 316 | 2-(3-chlorophenyl)-1-methyl-N-pyrimidin-4-yl-pyrrolo[3,2-c]pyridin-4-amine |
| 317 | 4-[(2-phenyl-1H-pyrrolo[3,2-c]pyridin-4-yl)amino]phenol |
| 318 | 4-[(2-phenyl-1H-pyrrolo[3,2-c]pyridin-4-yl)amino]benzamide |
| 319 | 2-phenyl-N-(3-pyridyl)-1H-pyrrolo[3,2-c]pyridin-4-amine |
| 320 | N-[4-(4-methylpiperazin-1-yl)phenyl]-2-phenyl-1H-pyrrolo[3,2-c]pyridin-4-amine |
| 321 | 2-phenyl-N-(2-pyridyl)-1H-pyrrolo[3,2-c]pyridin-4-amine |
| 322 | N,N-dimethyl-4-[(2-phenyl-1H-pyrrolo[3,2-c]pyridin-4-yl)amino]benzamide |
| 323 | N-[3-[(2-phenyl-1H-pyrrolo[3,2-c]pyridin-4-yl)amino]phenyl]acetamide |
| 324 | N-(4-methylsulfonylphenyl)-2-phenyl-1H-pyrrolo[3,2-c]pyridin-4-annine |
| 325 | 4-[(1-methyl-2-phenyl-pyrrolo[3,2-c]pyridin-4-yl)amino]benzamide |
| 326 | N-(3,4-dimethoxyphenyl)-1-methyl-2-phenyl-pyrrolo[3,2-c]pyridin-4-amine |
| 327 | 1-methyl-2-phenyl-N-(2-pyridyl)pyrrolo[3,2-c]pyridin-4-amine |
| 328 | 3-[(1-methyl-2-phenyl-pyrrolo[3,2-c]pyridin-4-yl)amino]phenol |

Further small molecules inhibiting GRK5 consist of the group II.

Wherein group II comprises
Compounds of General Formula (IV)

wherein,

B represents:

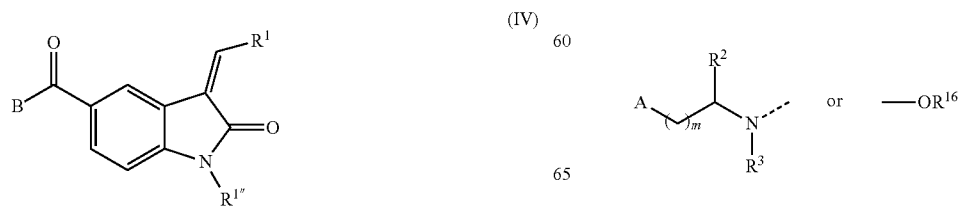

$R^1$ represents

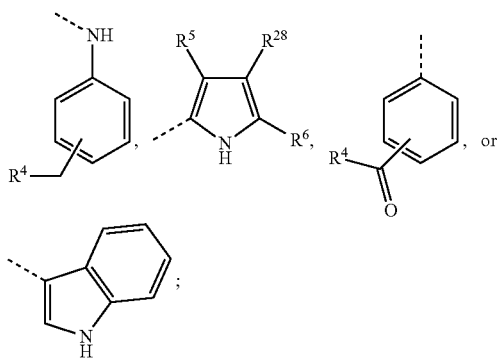

$R^{1''}$ represents —H or —C(O)$R^{18}$;
$R^2$ represents —$R^{19}$, —C(O)NH$_2$, or —CO$_2R^{20}$;
$R^{19}$ and $R^{20}$ are independently of each other selected from —H, —CH$_3$, —C$_2$H$_5$, —C$_3$H$_7$, —C$_4$H$_9$, —C$_5$H$_{11}$, -Ph, and —CH$_2$Ph;
$R^3$, $R^5$ and $R^6$ are independently of each other selected from —H, —CH$_3$, —C$_2$H$_5$, and —C$_3$H$_7$;
$R^{28}$ represents —H or —(CH$_2$)$_q$—C(O)$R^4$;
$R^4$ represents —O$R^{29}$, —$R^7$, —NH—(CH$_2$)$_p$—$R^{17}$, —NH—(CH$_2$)$_n$—$R^7$,

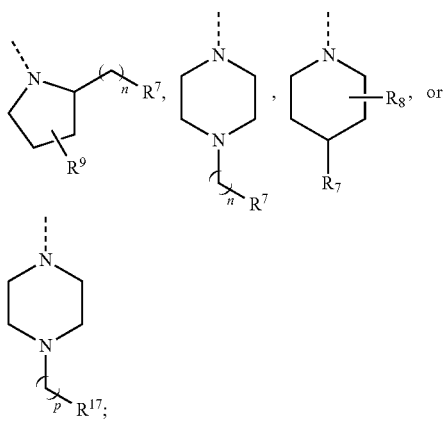

$R^7$ represents: —NH—CH($R^{30}$)—CO$_2R^{31}$, —N$R^{10}R^{11}$, —NH—CH($R^{30}$)Ph,

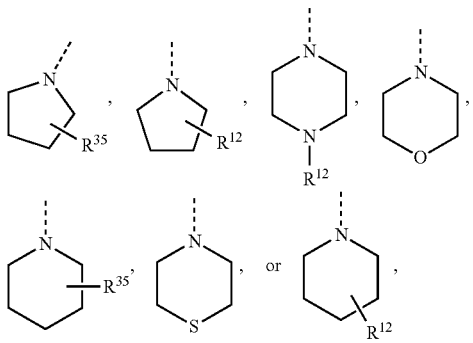

and at least one of the residues $R^{10}$ and $R^{11}$ is different of —H;

$R^{30}$ represents —H, —CH$_2R^{32}$, or —CH$_2$O$R^{33}$;
$R^{32}$ represents —H, —CH$_3$, —C$_2$H$_5$, —C$_3$H$_7$, —CH(CH$_3$)$_2$, —C$_4$H$_9$, —CH(CH$_3$)—C$_2$H$_5$, —CH$_2$—CH(CH$_3$)$_2$, —C(CH$_3$)$_3$, -Ph, —CH$_2$—CO$R^{34}$, —C$_2$H$_4$—CO$R^{34}$, or —C$_3$H$_6$—CO$R^{34}$;
$R^{33}$ represents —H, —CH$_3$, —C$_2$H$_5$, —C$_3$H$_7$, —CH(CH$_3$)$_2$, —C$_4$H$_9$, —CH(CH$_3$)—C$_2$H$_5$, —CH$_2$—CH(CH$_3$)$_2$, —C(CH$_3$)$_3$, -Ph, or —CH$_2$-Ph;
$R^{34}$ represents —N$R^{10}R^{11}$, —OH, —OCH$_3$, —OC$_2$H$_5$, —OC$_3$H$_7$, —OCH(CH$_3$)$_2$, or —OCH$_2$Ph;
$R^{35}$ represents —OH, —OCH$_3$, —OC$_2$H$_5$, —NH$_2$, —N(CH$_3$)$_2$, or —N(CH$_3$)(C$_2$H$_5$);
$R^{17}$ represents:

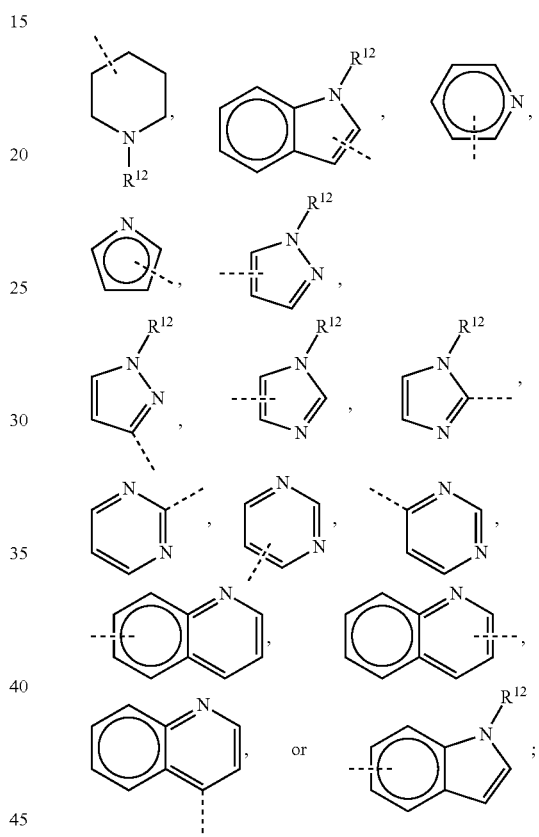

$R^{29}$ and $R^{31}$ are independently of each other selected from —H, —CH$_3$, —C$_2$H$_5$, —C$_3$H$_7$, and —CH$_2$Ph;
A represents

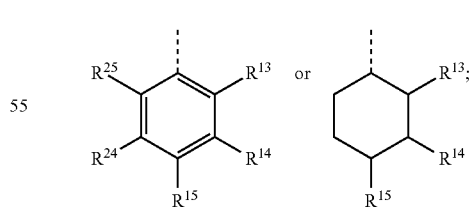

$R^{13}$, $R^{14}$, $R^{15}$, $R^{24}$ and $R^{25}$ are independently of each other selected from the group consisting of: —$R^{21}$, —$R^{22}$, —$R^{23}$, —$R^{26}$, —$R^{27}$, —O$R^{21}$, —O$R^{22}$, —O$R^{23}$, —O$R^{26}$, —O$R^{27}$, —F, —Cl, —Br and —I;
$R^{14}$ together with $R^{15}$ may form with the two carbon of the benzene or cyclohexane they are attached to a carbocyclic 4-, 5- or 6-membered ring and that 4-, 5- or 6-membered ring can be saturated or unsaturated, or a heterocyclic 5- or 6-membered ring and that 5- or 6-membered ring can be saturated or unsaturated;

R$^{13}$ together with R$^2$ may form a carbocyclic 4-, 5- or 6-membered ring and that 4-, 5- or 6-membered ring can be saturated or unsaturated, or a heterocyclic 5- or 6-membered ring and that 5- or 6-membered ring can be saturated or unsaturated;

R$^8$, R$^9$, R$^{10}$, R$^{11}$, R$^{12}$, R$^{16}$, R$^{18}$, R$^{21}$, R$^{22}$, R$^{23}$, R$^{26}$ and R$^{27}$ are independently of each other selected from: —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, -Ph, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —CH$_2$Ph;

m is an integer number selected from 0 and 1,
n is an integer number selected from 1, 2, 3, 4, 5 and 6,
p is an integer number selected from 0, 1, 2, 3 and 4;
q is an integer number selected from 0, 1, 2, 3 and 4;
and enantiomers, mixtures of enantiomers, diastereomers, mixtures of diastereomers, tautomers, hydrates, solvates and racemates of the above mentioned compounds and pharmaceutically acceptable salts thereof.

The expression tautomer is defined as an organic compound that is interconvertible by a chemical reaction called tautomerization. Tautomerization can be catalyzed preferably by bases or acids or other suitable compounds.

Preferred are compounds of general formula (IV), wherein B is

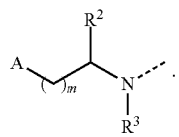

and even more preferred are compounds of general formula

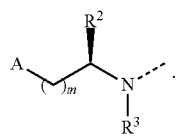

(IV), wherein B is

Thus, the following general formula (V) is preferred:

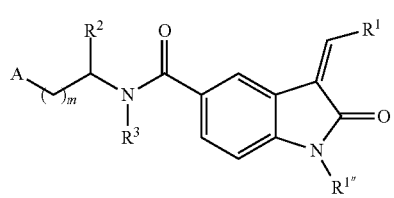

(V)

wherein the substituents A, R$^1$, R$^{1''}$, R$^2$, R$^3$, and the integer m have the meanings as disclosed herein, and even more preferred is the general formula (VI):

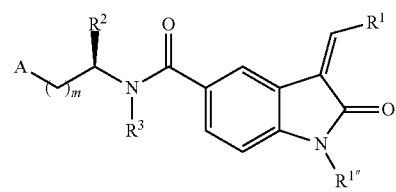

(VI)

wherein the substituents A, R$^1$, R$^{1''}$, R$^2$, R$^3$, and the integer m have the meanings as disclosed herein. Preferred substituents A, R$^1$, R$^{1''}$, R$^2$, and R$^3$ are disclosed below.

A compound of general formula (V) or (VI), wherein m is 0 is especially preferred.

Another aspect of the present invention refers to a compound of general formula (V-a) or a compound of general formula (VII)

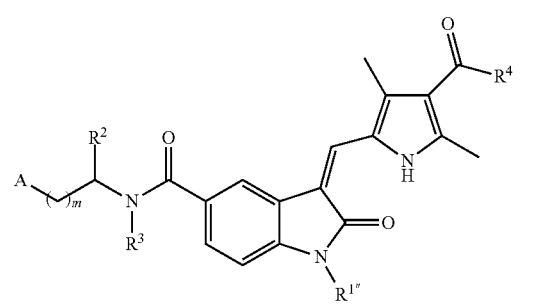

(V-a)

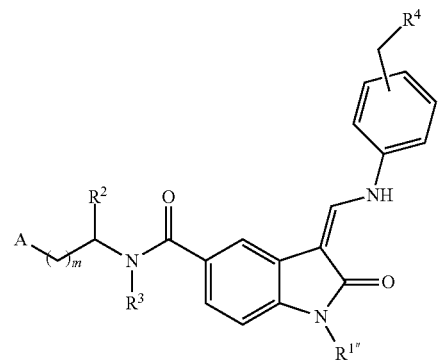

(VI)

wherein the substituents A, R$^{1''}$, R$^2$, R$^3$, R$^4$, and the integer m have the meanings as disclosed herein and more preferably wherein
A represents

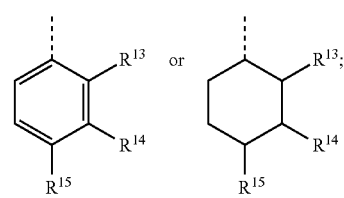 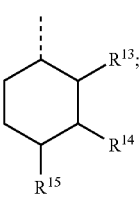 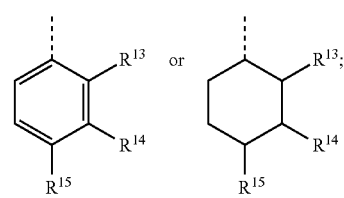

R$^{1''}$ represents —H or —C(O)R$^{18}$;
R$^2$ represents —R$^{19}$, —C(O)NH$_2$, or —CO$_2$R$^{20}$;
R$^3$ represents —H, —CH$_3$, —C$_2$H$_5$, or —C$_3$H$_7$;
R$^4$ represents —R$^7$, —NH—(CH$_2$)$_p$—R$^{17}$,

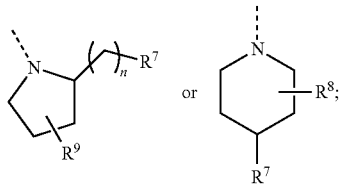

R$^7$ represents:
—NR$^{10}$R$^{11}$,

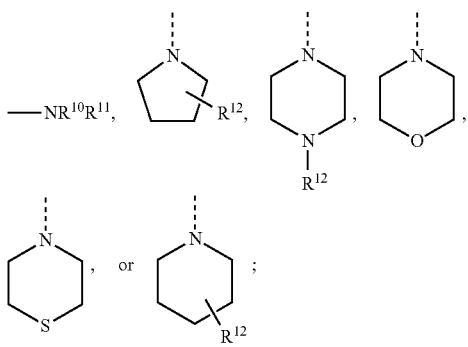

and at least one of R$^{10}$ and R$^{11}$ is different of —H;
R$^{17}$ represents:

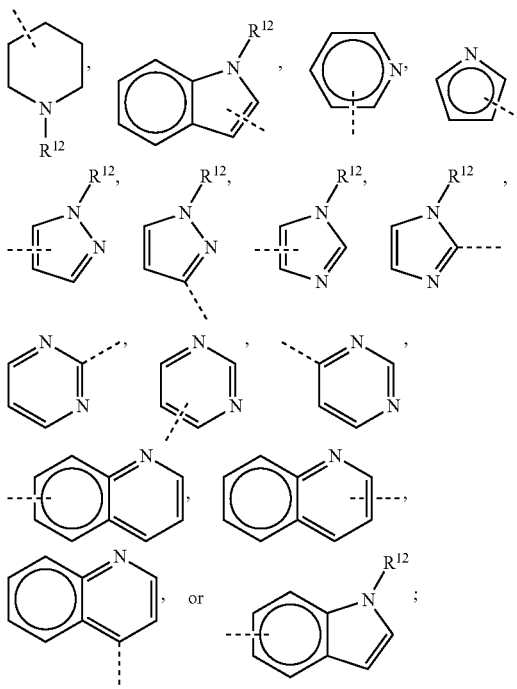

R$^{13}$, R$^{14}$ and R$^{15}$ are each independently selected from the group consisting of: —R$^{21}$, —R$^{22}$, —R$^{23}$, —OR$^{21}$, —OR$^{22}$, —OR$^{23}$, —F, —Cl, —Br, and —I;

R$^{14}$ together with R$^{15}$ may form with the two carbon of the benzene or cyclohexane they are attached to a carbocyclic 4-, 5- or 6-membered ring and that 4-, 5- or 6-membered ring can be saturated or unsaturated, or a heterocyclic 5- or 6-membered ring and that 5- or 6-membered ring can be saturated or unsaturated;

R$^{13}$ together with R$^2$ may form a carbocyclic 4-, 5- or 6-membered ring and that 4-, 5- or 6-membered ring can be saturated or unsaturated, or a heterocyclic 5- or 6-membered ring and that 5- or 6-membered ring can be saturated or unsaturated;

R$^8$, R$^9$, R$^{10}$, R$^{11}$, R$^{12}$, R$^{18}$, R$^{21}$, R$^{22}$ and R$^{23}$ are each independently selected from the group consisting of: —H, —CH$_3$, —C$_2$H$_5$, —C$_3$H$_7$, —C$_4$H$_9$, —C$_5$H$_{11}$, -Ph, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH$_2$Ph, —CH(CH$_3$)—CH=CH, —CH=C(CH$_3$)$_2$, —C(CH$_3$)=CH—CH$_3$, —CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$ and —CH$_2$Ph;

R$^{19}$ and R$^{20}$ are independently of each other selected from: —H, —CH$_3$, —C$_2$H$_5$, —C$_3$H$_7$, —C$_4$H$_9$, —C$_5$H$_{11}$, -Ph, and —CH$_2$Ph;

m is an integer number selected from 0 and 1,
n is an integer number selected from 1, 2, 3, 4, 5 and 6,
p is an integer number selected from 0, 1 and 2,
and enantiomers, mixtures of enantiomers, diastereomers, mixtures of diastereomers, tautomers, hydrates, solvates and racemates of the above mentioned compounds and pharmaceutically acceptable salts thereof.

Preferably, the residue A represents

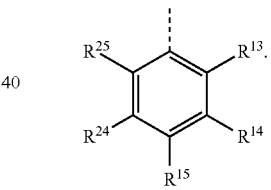

Hence, a compound of general formula (VII) is preferred (VII)

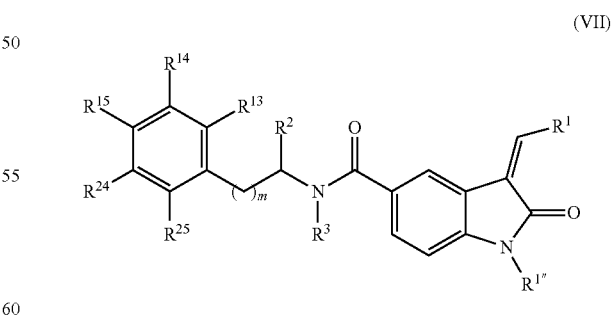

wherein the residues R$^1$, R$^{1''}$, R$^2$, R$^3$, R$^{13}$, R$^{14}$, R$^{15}$, R$^{24}$ and R$^{25}$ and the integer m are defined as disclosed herein. More preferred are compounds of general formula (VII), wherein the integer m is 0.

A preferred embodiment of the present invention is directed to a compound of general formula (VIII)

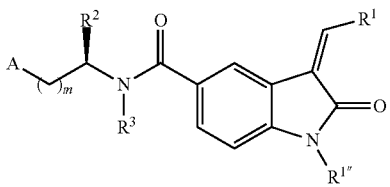

(VIII)

wherein $R^2$ represents: —$R^{19}$, —C(O)NH$_2$, or —CO$_2$R$^{20}$; and $R^{19}$ and $R^{20}$ are independently of each other selected from: —CH$_3$, —C$_2$H$_5$, —C$_3$H$_7$, —C$_4$H$_9$, and —C$_5$H$_{11}$ and the residues A, $R^1$, $R^{1'''}$, $R^3$, and the integer m have the meanings as disclosed herein and preferably the integer m is 0.

Another preferred embodiment according to the present invention refers to a compound of general formula (VII-a)

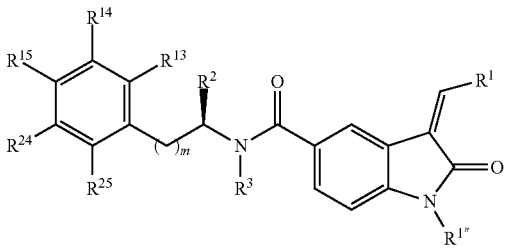

(VII-a)

wherein residue $R^2$ represents —$R^{19}$, —C(O)NH$_2$, or —CO$_2$R$^{20}$; and
the residues $R^{19}$ and $R^{20}$ are independently selected from —CH$_3$, —C$_2$H$_5$, —C$_3$H$_7$, —C$_4$H$_9$, and —C$_5$H$_{11}$,
and the residues $R^1$, $R^{1'''}$, $R^3$, $R^{13}$, $R^{14}$, $R^{15}$, $R^{24}$ and $R^{25}$ and the integer m have the meanings defined herein, and more preferably the integer m is 0.

Preferably, integer m is 0 and residue $R^2$ is selected from —CH$_3$, —C$_2$H$_5$, and —C$_3$H$_7$. Therefore, a compound of general formula (IV), (V), (V-a), (VI), (VII), (VII-a) and (VIII), wherein the integer m is 0 and the residue $R^2$ is selected from —CH$_3$, —C$_2$H$_5$, and —C$_3$H$_7$, and more preferably from —CH$_3$ and —C$_2$H$_5$ is especially preferred.

Also preferably, the residue $R^1$ represents

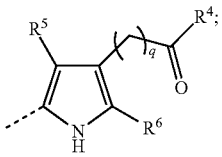

and the residue $R^4$ represents —$R^7$, —NH—(CH$_2$)$_n$—$R^7$,

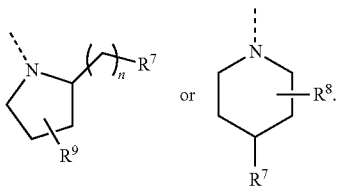

and $R^5$-$R^9$, q, and n have the meanings as defined herein.
Thus, a compound of general formula (IV), (V), (VII), (VII-a) and (VIII), wherein the residue $R^1$ represents:

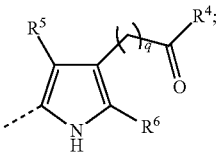

and the residue $R^4$ represents:
—$R^7$, —NH—(CH$_2$)$_n$—$R^7$,

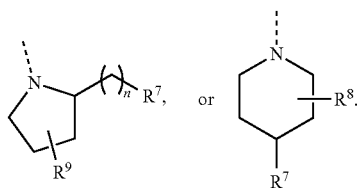

with $R^5$-$R^9$, q and n having the meanings as defined herein is especially preferred Even more preferred is a compound of general formula (IV), (V), (VII), (VII-a) and (VIII), wherein the residue $R^1$ represents:

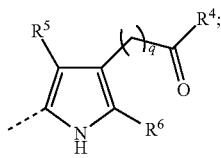

and the residue $R^4$ is selected from

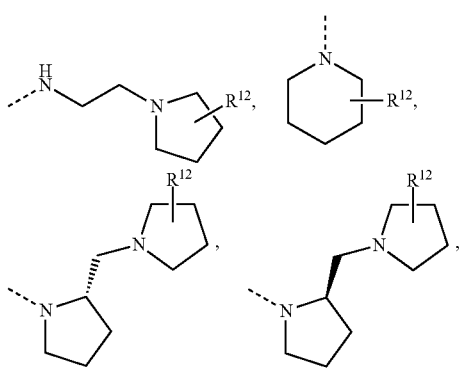

—NH—CH(CH$_3$)—CO$_2$R$^{31}$, or —NH—CH(CH$_3$)Ph.

Also preferred are compounds of general formula (IV), (V), (VII), (VII-a) and (VIII), wherein the residue $R^1$ represents

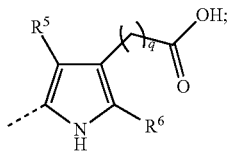

q is an integer number selected from 2, 3 and 4 and residues $R^5$ and $R^6$ have the meanings defined herein.

Preferred are also compounds according to the present invention, wherein the residue $R^1$ represents

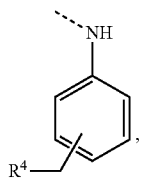

the residue $R^4$ represents $R^7$, and the residue $R^7$ has the meaning as defined herein.

In other words, a compound of general formula (IX)

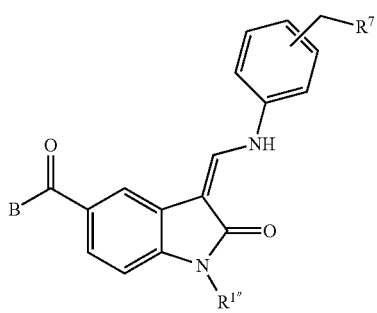

(IX)

wherein the residues B, $R^{1'''}$ and $R^7$ have the meanings defined herein is preferred.

Especially preferred are compounds of general formula (IX) having the residue B selected from:

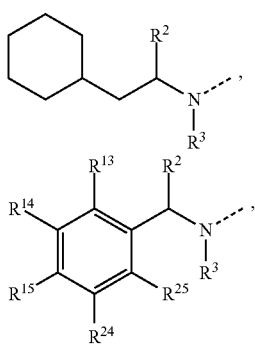

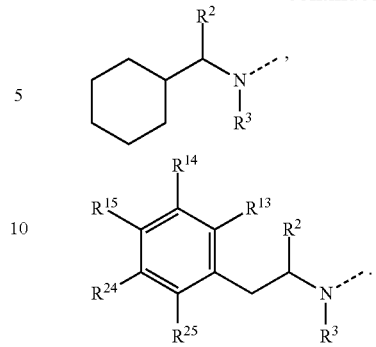

Even more preferred are compounds of general formula (VI), wherein the residue B is selected from:

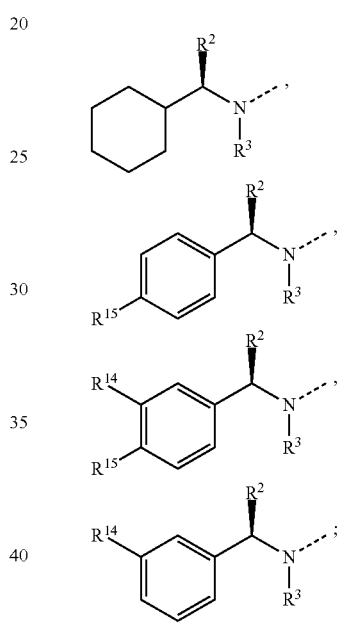

residues $R^{14}$ and $R^{15}$ are independently of each other selected from the group consisting of: —H, -Me, —OMe, —F, —Cl, and —Br;
residue $R^2$ represents: —$R^{19}$, —C(O)NH$_2$, or —CO$_2R^{20}$;
residues $R^{19}$ and $R^{20}$ are independently selected from: —CH$_3$, —C$_2$H$_5$, —C$_3$H$_7$, —C$_4$H$_9$, and —C$_5$H$_{11}$; and residue $R^3$ has the meaning defined herein.

Also preferred are compounds of general formula (IX), wherein the residue $R^7$ is selected from:

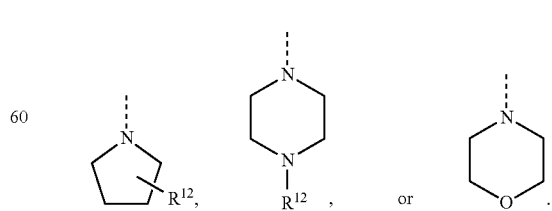

Thus, especially preferred are compounds of general formula (IX), wherein the residue $R^7$ is selected from:

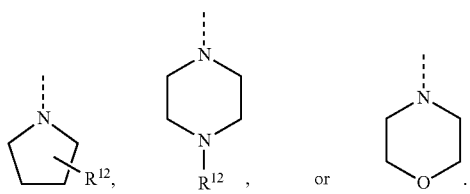

and the residue B is selected from

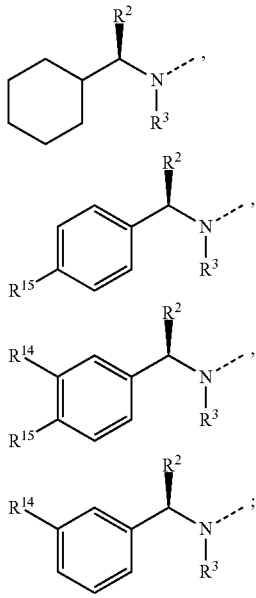

and the residues $R^2$, $R^{14}$ and $R^{15}$ have the meanings as disclosed herein and preferably the residues $R^{14}$ and $R^{15}$ are independently of each other selected from the group consisting of —H, -Me, —OMe, —F, —Cl, and —Br; and residue $R^2$ represents —$R^{19}$, —C(O)NH$_2$, or —CO$_2R^{20}$; and residues $R^{19}$ and $R^{20}$ are independently selected from —CH$_3$, —C$_2$H$_5$, —C$_3$H$_7$, —C$_4$H$_9$, and —C$_5$H$_{11}$; and residue $R^3$ has the meaning defined herein.

The residue $R^2$ is preferably selected from —CH$_3$, —C$_2$H$_5$, —C$_3$H$_7$, —C(O)NH$_2$, —CO$_2$H, —CO$_2$CH$_3$, —CO$_2$C$_2$H$_5$ and even more preferably $R^2$ represents —CH$_3$ or —C$_2$H$_5$. Hence, compounds of general formula (IV), (V), (V-a), (VI), (VII), (VIII), (VII-a) or (IX), wherein the residue $R^2$ is —CH$_3$ or —C$_2$H$_5$ are preferred. Particularly preferred compounds of the present invention are compounds of general formula (VIII) and (VII-a), wherein $R^2$ is —CH$_3$ or —C$_2$H$_5$. Even more preferred compounds according to the present invention are compounds of general formula (VIII) and (VII-a), wherein residue $R^2$ represents —CH$_3$.

The residues $R^{13}$, $R^{14}$, $R^{15}$, $R^{24}$ and $R^{25}$ are preferably independently of each other selected from: —H, —Me, —OMe, —F, —Cl, and —Br. More preferably, residues $R^{13}$ and $R^{25}$ are independently of each other selected from —H and —F; residue $R^{24}$ represents —H and residues $R^{14}$ and $R^{15}$ are independently selected from: —H, —Me, —OMe, —F, —Cl, and —Br. Thus, compounds of general formula (IV), (V), (VI), (VII), (VIII), (VII-a) or (IX), wherein the residue A is selected from:

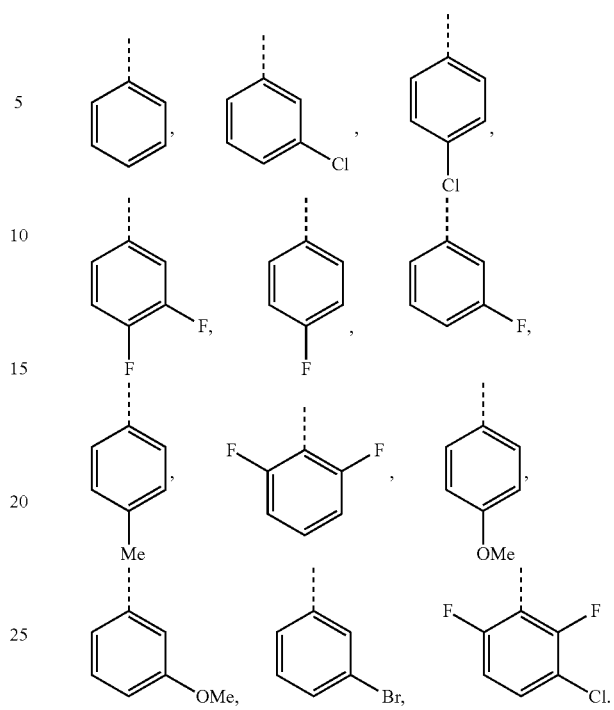

Especially preferred compounds according to the present invention are compounds of general formula (VII) and (VII-a), wherein
$R^2$ is selected from —CH$_3$ or —C$_2$H$_5$;
m represents 0;
A represents

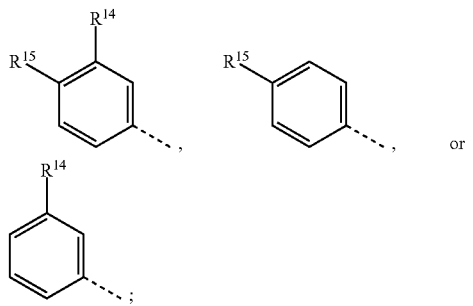

$R^{14}$ is selected from —H, —Cl, or —F;
$R^{15}$ is selected from —H, —Cl, —F, —CH$_3$, or —OCH$_3$;
$R^1$ represents

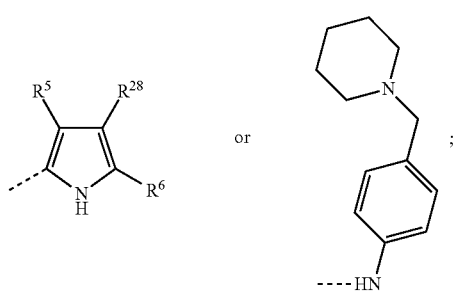

$R^{28}$ is selected from: —$(CH_2)_q$—$CO_2H$, —$(CH_2)_q$—$CONH$—$(CH_2)_n$—$NR^{10}R^{11}$,

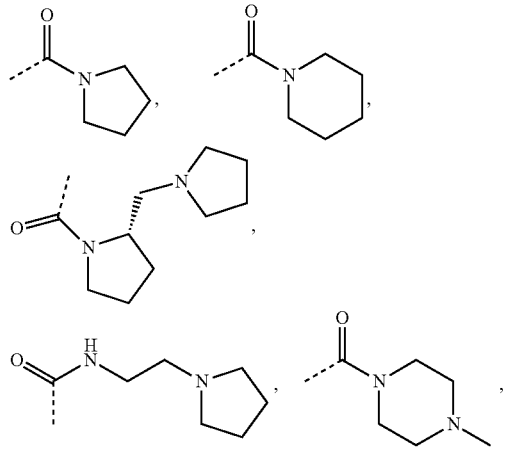

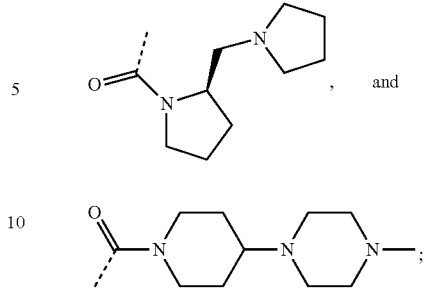

$R^{10}$ and $R^{11}$ are independently of each other selected from —$CH_3$ and —$C_2H_5$.

$R^5$, $R^6$, q and n have the meanings defined herein.

In yet another preferred embodiment of the present invention, the compound according to the general formula (IV) is selected from the group II of compounds depicted in the following Table 3.

TABLE 3

| No. | Compound |
|---|---|
| II.1 | (3Z)-3-{[3,5-dimethyl-4-(piperidin-1-ylcarbonyl)-1H-pyrrol-2-yl]methylene}-2-oxoindoline-5-carboxylic acid |
| II.2 | ((3Z)-3-({3,5-dimethyl-4-[(2-pyrrolidin-1-ylethyl)carbamoyl]-1H-pyrrol-2-yl}methylene)-2-oxoindoline-5-carboxylic acid |

TABLE 3-continued

| No. | Compound |
|---|---|
| II.3 | 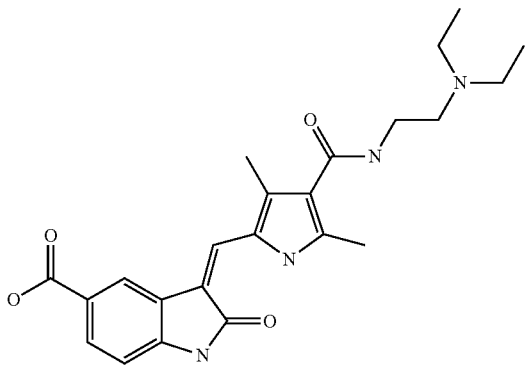 [SMILES: CCN(CC)CCNC(=O)c1c(C)[nH]c(/C=C2\C(=O)Nc3ccc(C(=O)O)cc32)c1C]<br>(3Z)-3-[(4-{[2-(diethylamino)ethyl]carbamoyl}-3,5-dimethyl-1H-pyrrol-2-yl)methylene]-2-oxoindoline-5-carboxylic acid |
| II.4 | 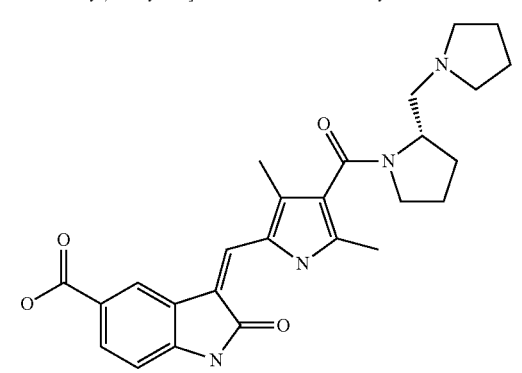<br>(3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxoindoline-5-carboxylic acid |
| II.5 | 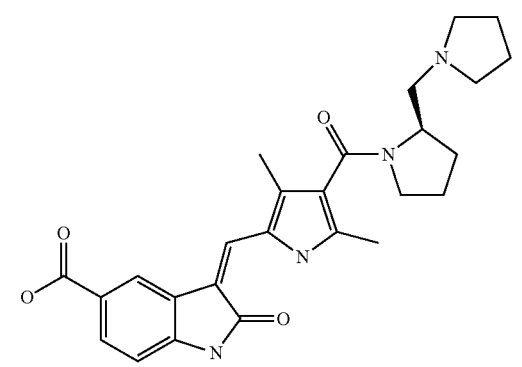 [SMILES: Cc1[nH]c(/C=C2\C(=O)Nc3ccc(C(=O)O)cc32)c(C)c1C(=O)N1CCC[C@@H]1CN1CCCC1]<br>(3Z)-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxylic acid |
| II.6 | 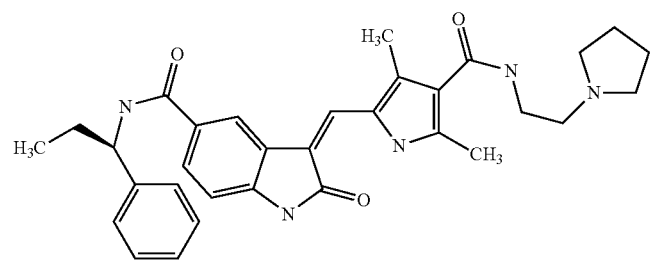 [SMILES: CC[C@@H](NC(=O)c1ccc2c(c1)/C(=C/c1[nH]c(C)c(C(=O)NCCN3CCCC3)c1C)C(=O)N2)c1ccccc1]<br>(3Z)-3-({3,5-dimethyl-4-[(2-pyrrolidin-1-ylethyl)carbamoyl]-1H-pyrrol-2-yl}methylene)-2-oxo-N-[(1R)-1-phenylpropyl]indoline-5-carboxamide |

TABLE 3-continued

| No. | Compound |
|---|---|
| II.7 | 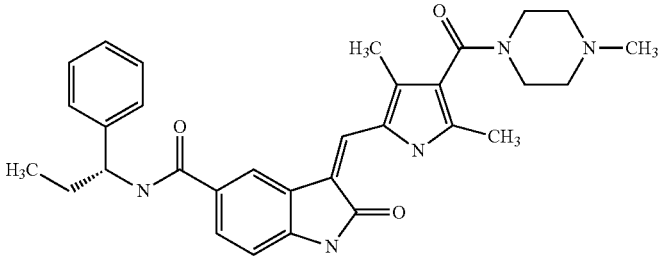 [SMILES: CC[C@@H](NC(=O)c1ccc2c(c1)/C(=C/c1[nH]c(C)c(C(=O)N3CCN(C)CC3)c1C)C(=O)N2)c1ccccc1]<br>(3Z)-3-({3,5-dimethyl-4-[(4-methylpiperazin-1-yl)carbonyl]-1H-pyrrol-2-yl}methylene)-2-oxo-N-[(1R)-1-phenylpropyl]indoline-5-carboxamide |
| II.8 | 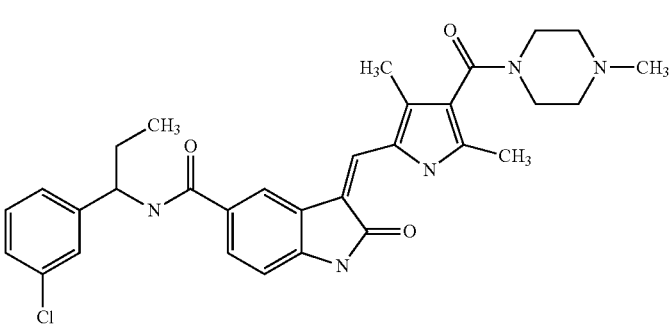 [SMILES: CCC(NC(=O)c1ccc2c(c1)/C(=C/c1[nH]c(C)c(C(=O)N3CCN(C)CC3)c1C)C(=O)N2)c1cccc(Cl)c1]<br>(3Z)-N-[1-(3-chlorophenyl)propyl]-3-({3,5-dimethyl-4-[(4-methylpiperazin-1-yl)carbonyl]-1H-pyrrol-2-yl}methylene)-2-oxoindoline-5-carboxamide |
| II.9 | 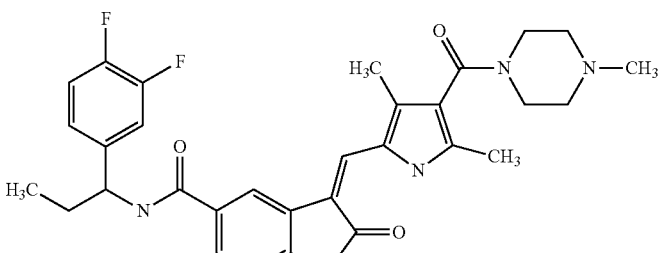<br>(3Z)-N-[1-(3,4-difluorophenyl)propyl]-3-({3,5-dimethyl-4-[(4-methylpiperazin-1-yl)carbonyl]-1H-pyrrol-2-yl}methylene)-2-oxoindoline-5-carboxamide |
| II.10 | 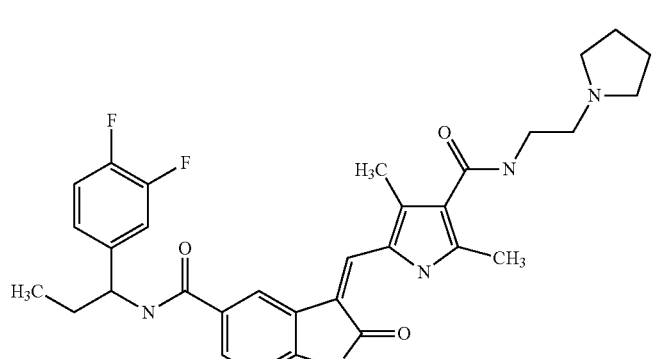<br>(3Z)-N-[1-(3,4-difluorophenyl)propyl]-3-({3,5-dimethyl-4-[(2-pyrrolidin-1-ylethyl)carbamoyl]-1H-pyrrol-2-yl}methylene)-2-oxoindoline-5-carboxamide |

TABLE 3-continued

| No. | Compound |
|---|---|
| II.11 | 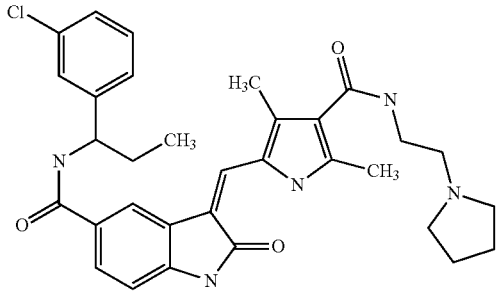 [SMILES: CCC(NC(=O)c1ccc2c(c1)/C(=C/c1[nH]c(C)c(C(=O)NCCN3CCCC3)c1C)C(=O)N2)c1cccc(Cl)c1]<br>(3Z)-N-[1-(3-chlorophenyl)propyl]-3-({3,5-dimethyl-4-[(2-pyrrolidin-1-ylethyl)carbamoyl]-1H-pyrrol-2-yl}methylene)-2-oxoindoline-5-carboxamide |
| II.12 | 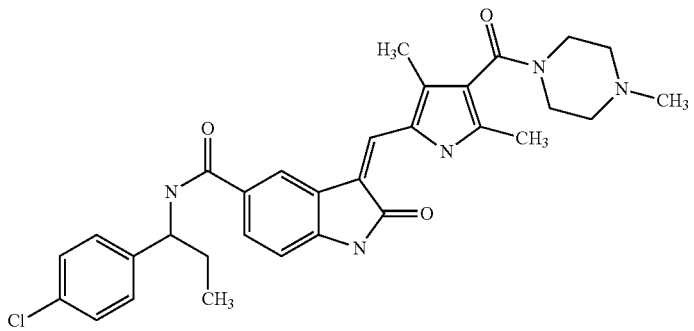 [SMILES: CCC(NC(=O)c1ccc2c(c1)/C(=C/c1[nH]c(C)c(C(=O)N3CCN(C)CC3)c1C)C(=O)N2)c1ccc(Cl)cc1]<br>(3Z)-N-[1-(4-chlorophenyl)propyl]-3-({3,5-dimethyl-4-[(4-methylpiperazin-1-yl)carbonyl]-1H-pyrrol-2-yl}methylene)-2-oxoindoline-5-carboxamide |
| II.13 | 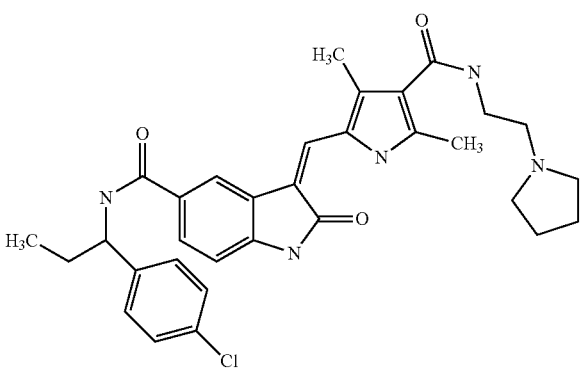 [SMILES: CCC(NC(=O)c1ccc2c(c1)/C(=C/c1[nH]c(C)c(C(=O)NCCN3CCCC3)c1C)C(=O)N2)c1ccc(Cl)cc1]<br>(3Z)-N-[1-(4-chlorophenyl)propyl]-3-({3,5-dimethyl-4-[(2-pyrrolidin-1-ylethyl)carbamoyl]-1H-pyrrol-2-yl}methylene)-2-oxoindoline-5-carboxamide |
| II.14 | 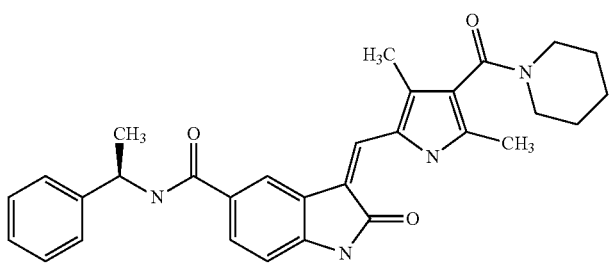 [SMILES: Cc1[nH]c(/C=C2\C(=O)Nc3ccc(C(=O)N[C@H](C)c4ccccc4)cc32)c(C)c1C(=O)N1CCCCC1]<br>(3Z)-3-{[3,5-dimethyl-4-(piperidin-1-ylcarbonyl)-1H-pyrrol-2-yl]methylene}-2-oxo-N-[(1R)-1-phenylethyl]indoline-5-carboxamide |

TABLE 3-continued

| No. | Compound |
|---|---|
| II.15 | 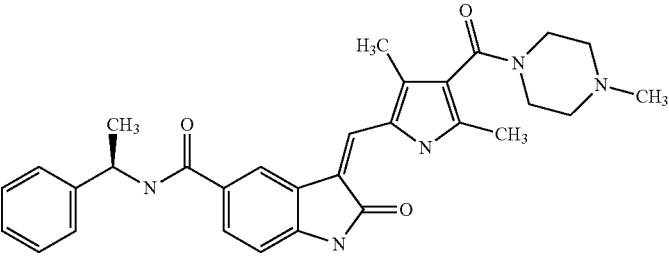 [SMILES: Cc1[nH]c(/C=C2\C(=O)Nc3ccc(C(=O)N[C@H](C)c4ccccc4)cc32)c(C)c1C(=O)N1CCN(C)CC1]
(3Z)-3-({3,5-dimethyl-4-[(4-methylpiperazin-1-yl)carbonyl]-1H-pyrrol-2-yl}methylene)-2-oxo-N-[(1R)-1-phenylethyl]indoline-5-carboxamide |
| II.16 | 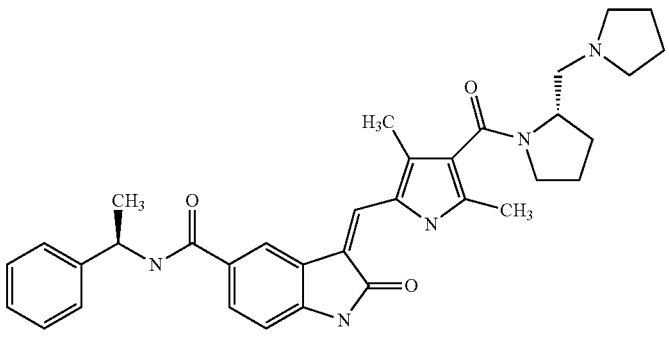 [SMILES: Cc1[nH]c(/C=C2\C(=O)Nc3ccc(C(=O)N[C@H](C)c4ccccc4)cc32)c(C)c1C(=O)N1CCC[C@H]1CN1CCCC1]
(3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1R)-1-phenylethyl]indoline-5-carboxamide |
| II.17 | 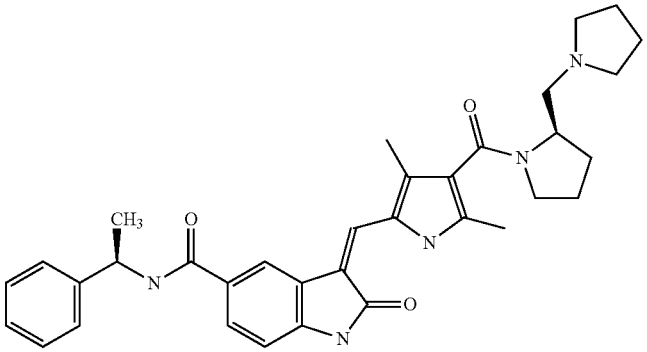 [SMILES: Cc1[nH]c(/C=C2\C(=O)Nc3ccc(C(=O)N[C@H](C)c4ccccc4)cc32)c(C)c1C(=O)N1CCC[C@@H]1CN1CCCC1]
(3Z)-3-[(3,5-dimethyl-4-{[(2R)-2-(pyrrolidin-1-ylmethyl)pyrrolidin-1-yl]carbonyl}-1H-pyrrol-2-yl)methylene]-2-oxo-N-[(1R)-1-phenylethyl]indoline-5-carboxamide |

TABLE 3-continued

| No. | Compound |
|---|---|
| II.18 | 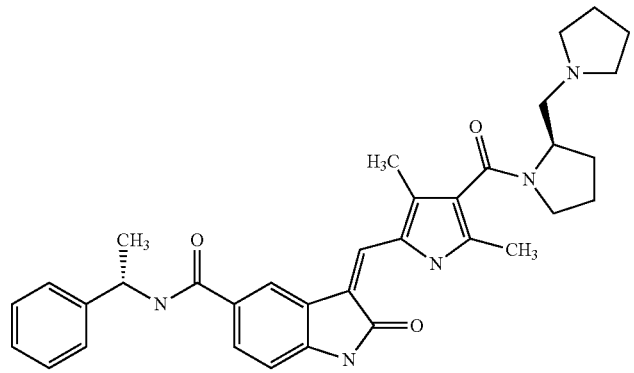 [SMILES: Cc1[nH]c(/C=C2\C(=O)Nc3ccc(C(=O)N[C@@H](C)c4ccccc4)cc32)c(C)c1C(=O)N1CCC[C@@H]1CN1CCCC1]<br>(3Z)-3-[(3,5-dimethyl-4-{[(2R)-2-(pyrrolidin-1-ylmethyl)pyrrolidin-1-yl]carbonyl}-1H-pyrrol-2-yl)methylene]-2-oxo-N-[(1S)-1-phenylethyl]indoline-5-carboxamide |
| II.19 | 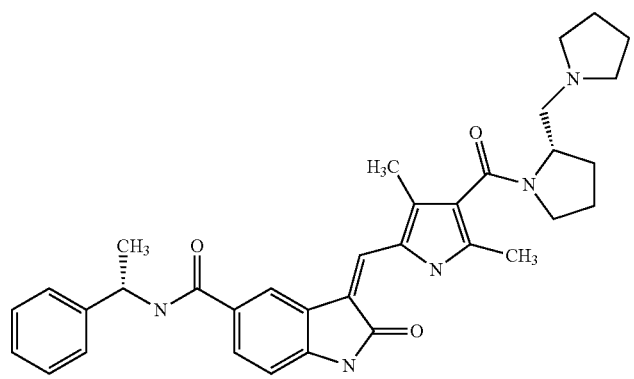 [SMILES: Cc1[nH]c(/C=C2\C(=O)Nc3ccc(C(=O)N[C@@H](C)c4ccccc4)cc32)c(C)c1C(=O)N1CCC[C@H]1CN1CCCC1]<br>(3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1S)-1-phenylethyl]indoline-5-carboxamide |
| II.20 | 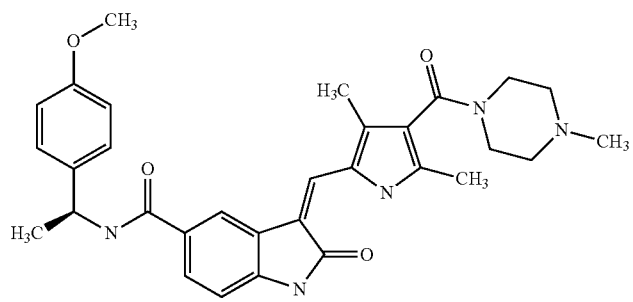 [SMILES: COc1ccc([C@H](C)NC(=O)c2ccc3c(c2)/C(=C/c2[nH]c(C)c(C(=O)N4CCN(C)CC4)c2C)C(=O)N3)cc1]<br>(3Z)-3-({3,5-dimethyl-4-[(4-methylpiperazin-1-yl)carbonyl]-1H-pyrrol-2-yl}methylene)-N-[(1S)-1-(4-methoxyphenyl)ethyl]-2-oxoindoline-5-carboxamide |

TABLE 3-continued

| No. | Compound |
|---|---|
| II.21 | 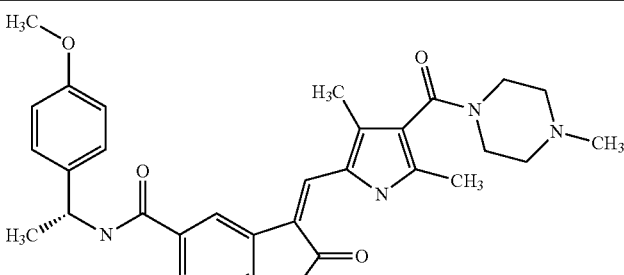(3Z)-3-({3,5-dimethyl-4-[(4-methylpiperazin-1-yl)carbonyl]-1H-pyrrol-2-yl}methylene)-N-[(1R)-1-(4-methoxyphenyl)ethyl]-2-oxoindoline-5-carboxamide |
| II.22 | 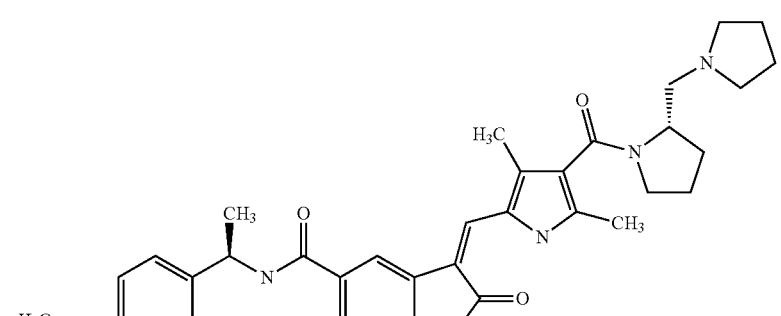(3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1R)-1-(4-methoxyphenyl)ethyl]-2-oxoindoline-5-carboxamide |
| II.23 | 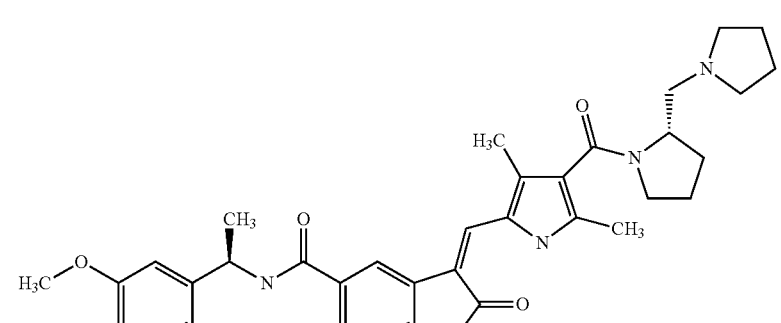(3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1R)-1-(3-methoxyphenyl)ethyl]-2-oxoindoline-5-carboxamide |
| II.24 | 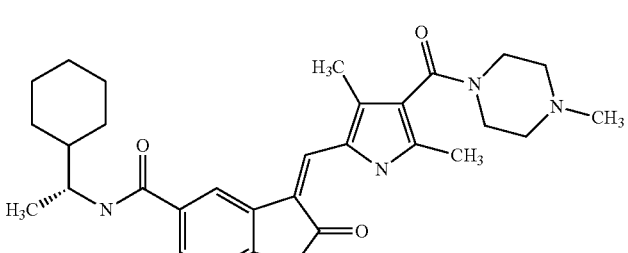(3Z)-N-[(1R)-1-cyclohexylethyl]-3-({3,5-dimethyl-4-[(4-methylpiperazin-1-yl)carbonyl]-1H-pyrrol-2-yl}methylene)-2-oxoindoline-5-carboxamide |

| No. | Compound |
|---|---|
| II.25 | 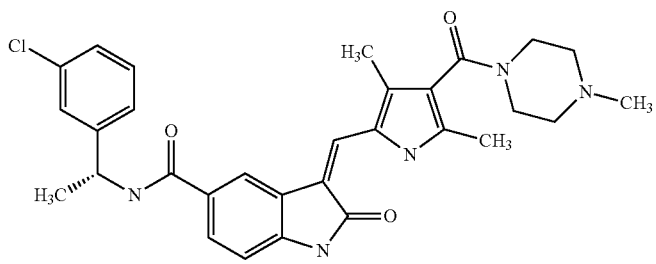 [SMILES: Cc1[nH]c(/C=C2\C(=O)Nc3ccc(C(=O)N[C@H](C)c4cccc(Cl)c4)cc32)c(C)c1C(=O)N1CCN(C)CC1]<br>(3Z)-N-[(1R)-1-(3-chlorophenyl)ethyl]-3-({3,5-dimethyl-4-[(4-methylpiperazin-1-yl)carbonyl]-1H-pyrrol-2-yl}methylene)-2-oxoindoline-5-carboxamide |
| II.26 | 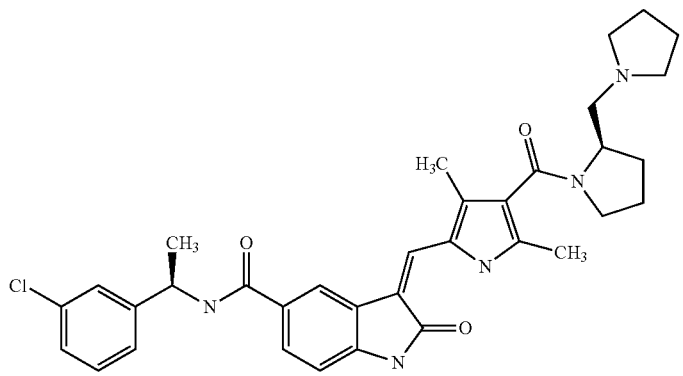 [SMILES: Cc1[nH]c(/C=C2\C(=O)Nc3ccc(C(=O)N[C@H](C)c4cccc(Cl)c4)cc32)c(C)c1C(=O)N1CCC[C@@H]1CN1CCCC1]<br>(3Z)-N-[(1R)-1-(3-chlorophenyl)ethyl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide |
| II.27 | 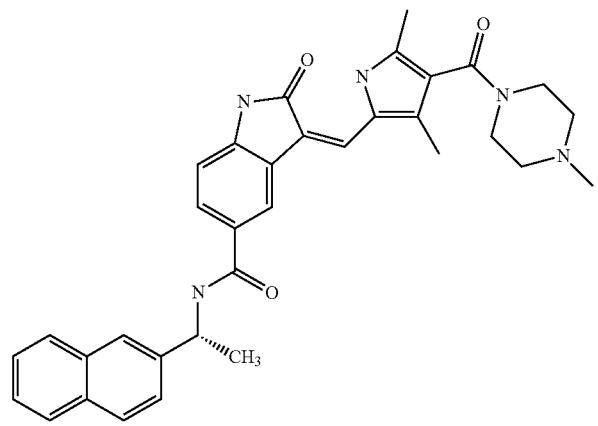 [SMILES: Cc1[nH]c(/C=C2\C(=O)Nc3ccc(C(=O)N[C@H](C)c4ccc5ccccc5c4)cc32)c(C)c1C(=O)N1CCN(C)CC1]<br>(3Z)-3-({3,5-dimethyl-4-[(4-methylpiperazin-1-yl)carbonyl]-1H-pyrrol-2-yl}methylene)-N-[(1R)-1-(2-naphthyl)ethyl]-2-oxoindoline-5-carboxamide |

TABLE 3-continued

| No. | Compound |
|---|---|
| II.28 | 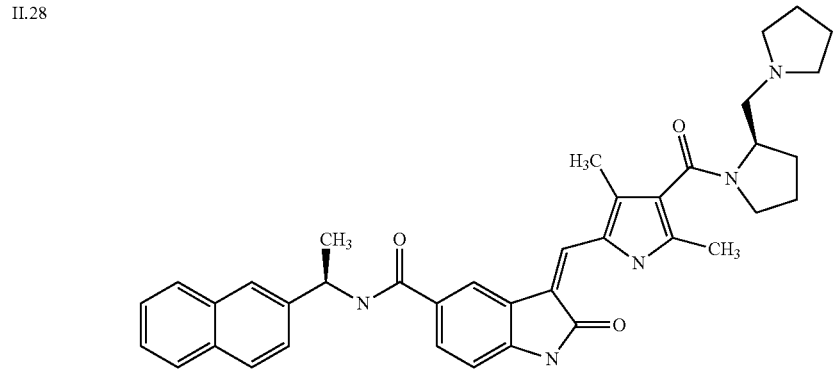<br>(3Z)-3-[(3,5-dimethyl-4-{[(2R)-2-(pyrrolidin-1-ylmethyl)pyrrolidin-1-yl]carbonyl}-1H-pyrrol-2-yl)methylene]-N-[(1R)-1-(2-naphthyl)ethyl]-2-oxoindoline-5-carboxamide |
| II.29 | 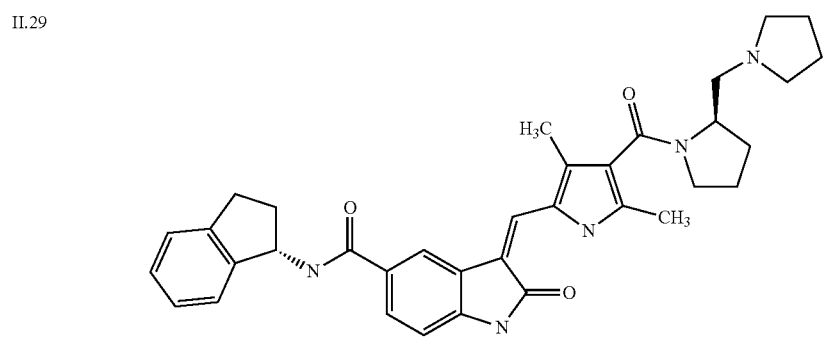<br>(3Z)-N-[(1S)-2,3-dihydro-1H-inden-1-yl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide |
| II.30 | 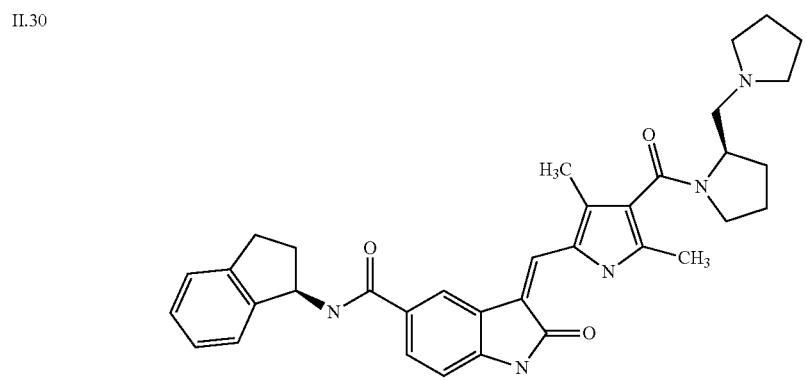<br>(3Z)-N-[(1R)-2,3-dihydro-1H-inden-1-yl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide |

TABLE 3-continued

| No. | Compound |
| --- | --- |
| II.31 | 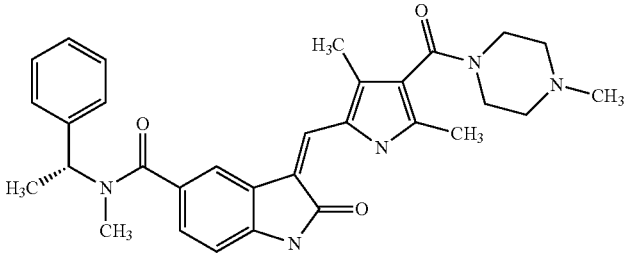 [SMILES: Cc1[nH]c(/C=C2\C(=O)Nc3ccc(C(=O)N(C)[C@H](C)c4ccccc4)cc32)c(C)c1C(=O)N1CCN(C)CC1]
(3Z)-3-({3,5-dimethyl-4-[(4-methylpiperazin-1-yl)carbonyl]-1H-pyrrol-2-yl}methylene)-N-methyl-2-oxo-N-[(1R)-1-phenylethyl]indoline-5-carboxamide |
| II.32 | 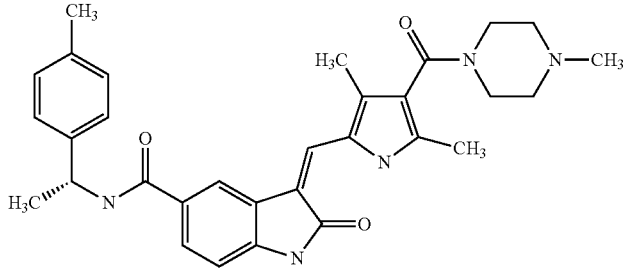 [SMILES: Cc1ccc([C@@H](C)NC(=O)c2ccc3c(c2)/C(=C/c2[nH]c(C)c(C(=O)N4CCN(C)CC4)c2C)C(=O)N3)cc1]
(3Z)-3-({3,5-dimethyl-4-[(4-methylpiperazin-1-yl)carbonyl]-1H-pyrrol-2-yl}methylene)-N-[(1R)-1-(4-methylphenyl)ethyl]-2-oxoindoline-5-carboxamide |
| II.33 | 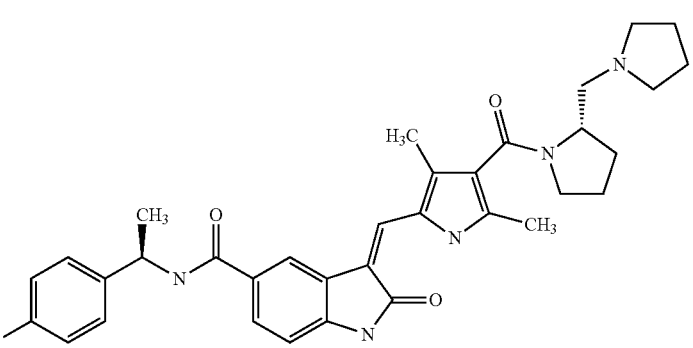
(3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1R)-1-(4-methylphenyl)ethyl]-2-oxoindoline-5-carboxamide |
| II.34 | 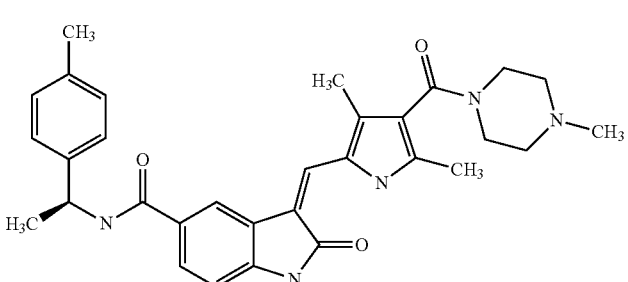
(3Z)-3-({3,5-dimethyl-4-[(4-methylpiperazin-1-yl)carbonyl]-1H-pyrrol-2-yl}methylene)-N-[(1R)-1-(4-methylphenyl)ethyl]-2-oxoindoline-5-carboxamide |

TABLE 3-continued

| No. | Compound |
|---|---|
| II.35 | 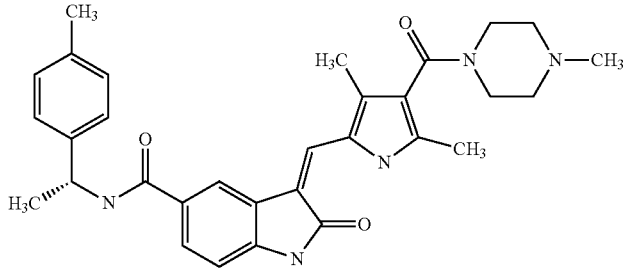 [SMILES: Cc1ccc([C@@H](C)NC(=O)c2ccc3c(c2)/C(=C/c2[nH]c(C)c(C(=O)N4CCN(C)CC4)c2C)C(=O)N3)cc1]<br>(3Z)-N-[(1R)-1-(4-chlorophenyl)ethyl]-3-({3,5-dimethyl-4-[(4-methylpiperazin-1-yl)carbonyl]-1H-pyrrol-2-yl}methylene)-2-oxoindoline-5-carboxamide |
| II.36 | 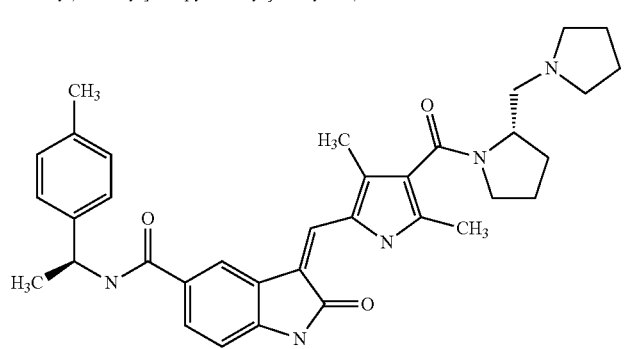<br>(3Z)-N-[(1S)-1-(4-chlorophenyl)ethyl]-3-[(3,5-dimethyl-4-{[(2S)-2-(pyrrolidin-1-ylmethyl)pyrrolidin-1-yl]carbonyl}-1H-pyrrol-2-yl)methylene]-2-oxoindoline-5-carboxamide |
| II.37 | 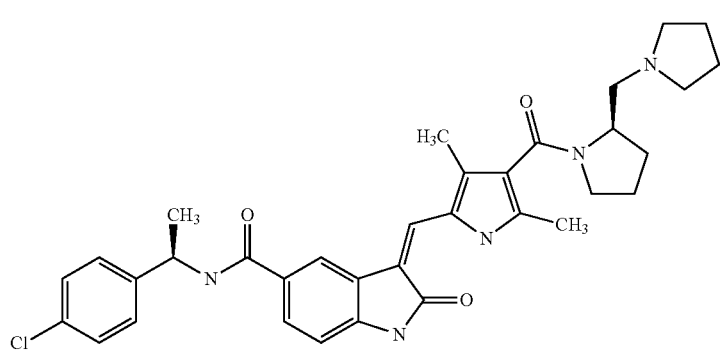 [SMILES: Cc1[nH]c(/C=C2\C(=O)Nc3ccc(C(=O)N[C@H](C)c4ccc(Cl)cc4)cc32)c(C)c1C(=O)N1CCC[C@@H]1CN1CCCC1]<br>(3Z)-N-[(1R)-1-(4-chlorophenyl)ethyl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide |
| II.38 | 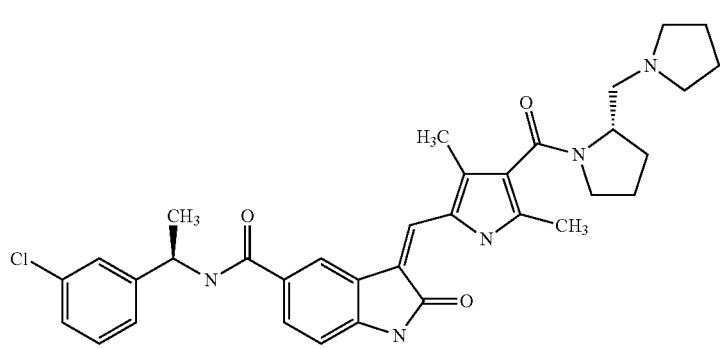 [SMILES: Cc1[nH]c(/C=C2\C(=O)Nc3ccc(C(=O)N[C@H](C)c4cccc(Cl)c4)cc32)c(C)c1C(=O)N1CCC[C@H]1CN1CCCC1]<br>(3Z)-N-[(1R)-1-(3-chlorophenyl)ethyl]-3-[(3,5-dimethyl-4-{[(2S)-2-(pyrrolidin-1-ylmethyl)pyrrolidin-1-yl]carbonyl}-1H-pyrrol-2-yl)methylene]-2-oxoindoline-5-carboxamide |

TABLE 3-continued

| No. | Compound |
|---|---|
| II.39 | 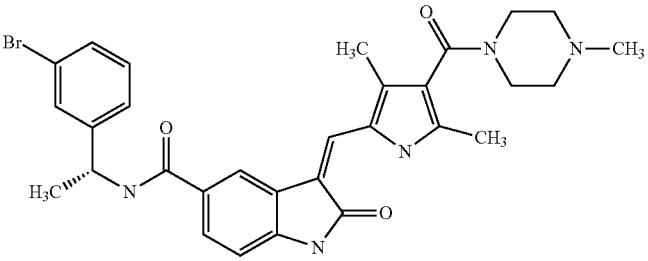 [SMILES: Cc1[nH]c(/C=C2\C(=O)Nc3ccc(C(=O)N[C@H](C)c4cccc(Br)c4)cc32)c(C)c1C(=O)N1CCN(C)CC1] (3Z)-N-[(1R)-1-(3-bromophenyl)ethyl]-3-({3,5-dimethyl-4-[(4-methylpiperazin-1-yl)carbonyl]-1H-pyrrol-2-yl}methylene)-2-oxoindoline-5-carboxamide |
| II.40 | 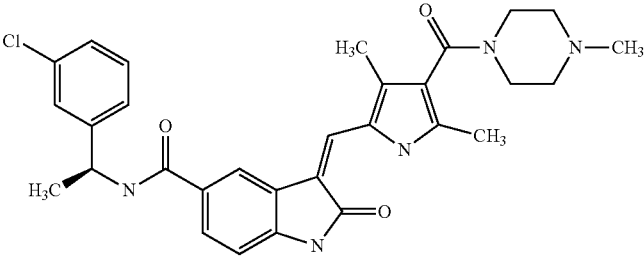 [SMILES: Cc1[nH]c(/C=C2\C(=O)Nc3ccc(C(=O)N[C@@H](C)c4cccc(Cl)c4)cc32)c(C)c1C(=O)N1CCN(C)CC1] (3Z)-N-[(1S)-1-(3-chlorophenyl)ethyl]-3-({3,5-dimethyl-4-[(4-methylpiperazin-1-yl)carbonyl]-1H-pyrrol-2-yl}methylene)-2-oxoindoline-5-carboxamide |
| II.41 | 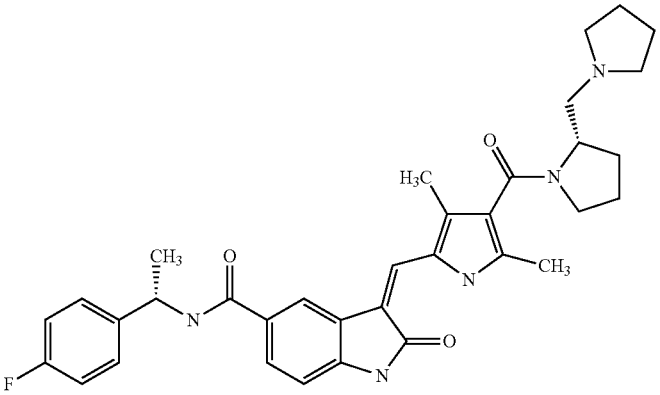 [SMILES: Cc1[nH]c(/C=C2\C(=O)Nc3ccc(C(=O)N[C@@H](C)c4ccc(F)cc4)cc32)c(C)c1C(=O)N1CCC[C@H]1CN1CCCC1] (3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1S)-1-(4-fluorophenyl)ethyl]-2-oxoindoline-5-carboxamide |

TABLE 3-continued

| No. | Compound |
|---|---|
| II.42 | 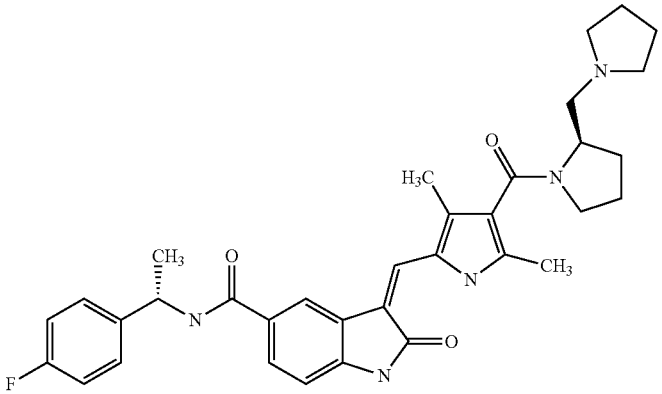 [SMILES: Cc1[nH]c(/C=C2\C(=O)Nc3ccc(C(=O)N[C@@H](C)c4ccc(F)cc4)cc32)c(C)c1C(=O)N1CCC[C@@H]1CN1CCCC1]
(3Z)-3-[(3,5-dimethyl-4-{[(2R)-2-(pyrrolidin-1-ylmethyl)pyrrolidin-1-yl]carbonyl}-1H-pyrrol-2-yl)methylene]-N-[(1S)-1-(4-fluorophenyl)ethyl]-2-oxoindoline-5-carboxamide |
| II.43 | 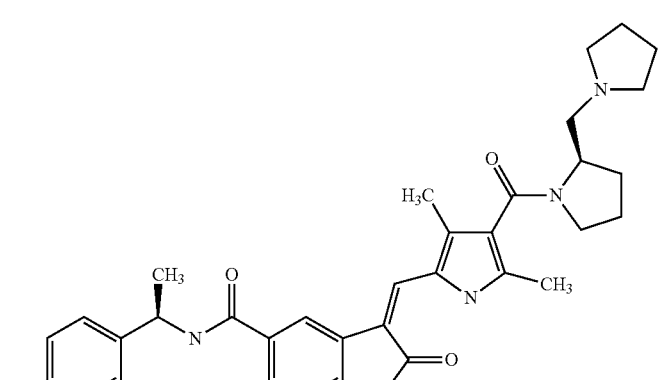
(3Z)-3-[(3,5-dimethyl-4-{[(2R)-2-(pyrrolidin-1-ylmethyl)pyrrolidin-1-yl]carbonyl}-1H-pyrrol-2-yl)methylene]-N-[(1R)-1-(4-fluorophenyl)ethyl]-2-oxoindoline-5-carboxamide |
| II.44 | 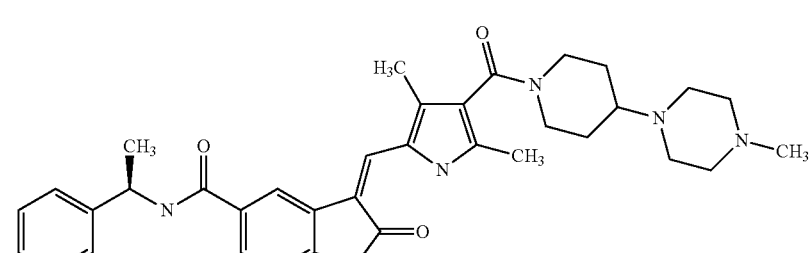
(3Z)-3-[(3,5-dimethyl-4-{[4-(4-methylpiperazin-1-yl)piperidin-1-yl]carbonyl}-1H-pyrrol-2-yl)methylene]-2-oxo-N-[(1R)-1-phenylethyl]indoline-5-carboxamide |

TABLE 3-continued

| No. | Compound |
|---|---|
| II.45 | 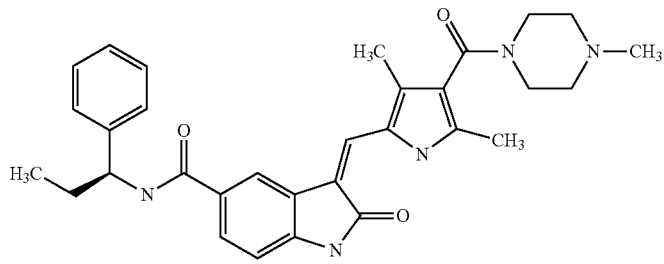 [SMILES: CC[C@H](NC(=O)c1ccc2c(c1)/C(=C/c1[nH]c(C)c(C(=O)N3CCN(C)CC3)c1C)C(=O)N2)c1ccccc1]<br>(3Z)-3-({3,5-dimethyl-4-[(4-methylpiperazin-1-yl)carbonyl]-1H-pyrrol-2-yl}methylene)-2-oxo-N-[(1S)-1-phenylpropyl]indoline-5-carboxamide |
| II.46 | 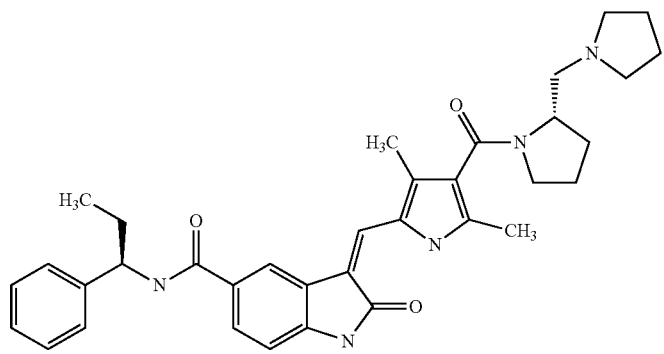 [SMILES: CC[C@@H](NC(=O)c1ccc2c(c1)/C(=C/c1[nH]c(C)c(C(=O)N3CCC[C@H]3CN3CCCC3)c1C)C(=O)N2)c1ccccc1]<br>(3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1R)-1-phenylpropyl]indoline-5-carboxamide |
| II.47 | 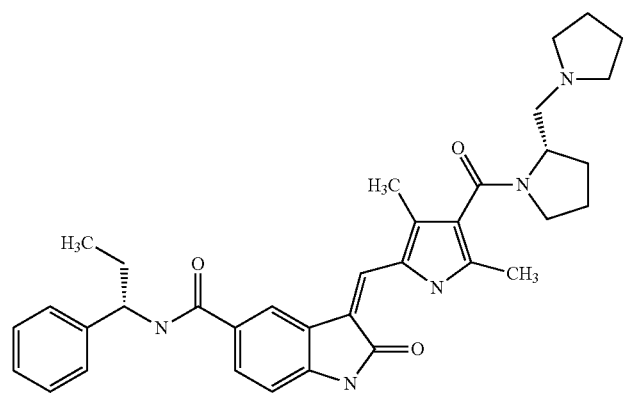 [SMILES: CC[C@H](NC(=O)c1ccc2c(c1)/C(=C/c1[nH]c(C)c(C(=O)N3CCC[C@H]3CN3CCCC3)c1C)C(=O)N2)c1ccccc1]<br>(3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1S)-1-phenylpropyl]indoline-5-carboxamide |

TABLE 3-continued

| No. | Compound |
|---|---|
| II.48 | 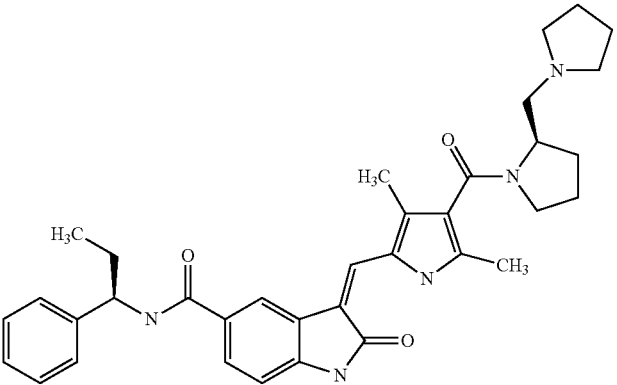 [SMILES: CC[C@@H](NC(=O)c1ccc2c(c1)/C(=C/c1[nH]c(C)c(C(=O)N3CCC[C@@H]3CN3CCCC3)c1C)C(=O)N2)c1ccccc1]<br>(3Z)-3-[(3,5-dimethyl-4-{[(2R)-2-(pyrrolidin-1-ylmethyl)pyrrolidin-1-yl]carbonyl}-1H-pyrrol-2-yl)methylene]-2-oxo-N-[(1R)-1-phenylpropyl]indoline-5-carboxamide |
| II.49 | 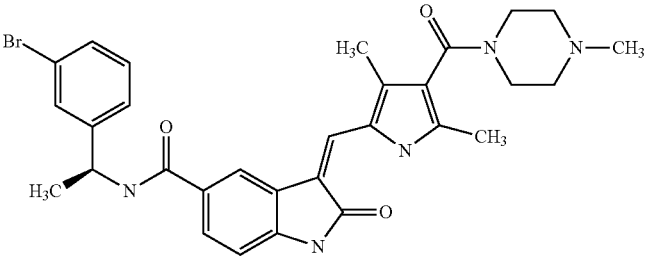<br>(3Z)-N-[(1S)-1-(3-bromophenyl)ethyl]-3-({3,5-dimethyl-4-[(4-methylpiperazin-1-yl)carbonyl]-1H-pyrrol-2-yl}methylene)-2-oxoindoline-5-carboxamide |
| II.50 | 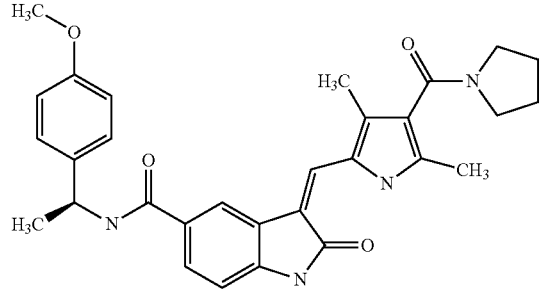 [SMILES: COc1ccc([C@H](C)NC(=O)c2ccc3c(c2)/C(=C/c2[nH]c(C)c(C(=O)N4CCCC4)c2C)C(=O)N3)cc1]<br>(3Z)-3-{[3,5-dimethyl-4-(pyrrolidin-1-ylcarbonyl)-1H-pyrrol-2-yl]methylene}-N-[(1S)-1-(4-methoxyphenyl)ethyl]-2-oxoindoline-5-carboxamide |

TABLE 3-continued

| No. | Compound |
|---|---|
| II.51 | 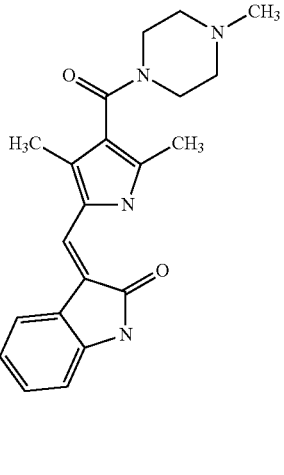<br>(3Z)-3-({3,5-dimethyl-4-[(4-methylpiperazin-1-yl)carbonyl]-1H-pyrrol-2-yl}methylene)-N-[1-(3-methylphenyl)ethyl]-2-oxoindoline-5-carboxamide |
| II.52 | 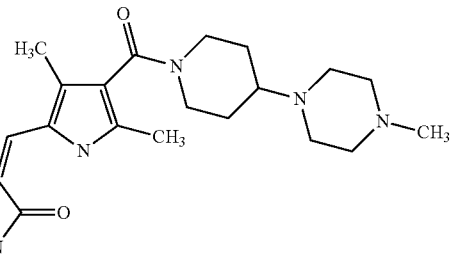<br>(3Z)-3-[(3,5-dimethyl-4-{[4-(4-methylpiperazin-1-yl)piperidin-1-yl]carbonyl}-1H-pyrrol-2-yl)methylene]-2-oxo-N-[(1S)-1-phenylpropyl]indoline-5-carboxamide |
| II.53 | 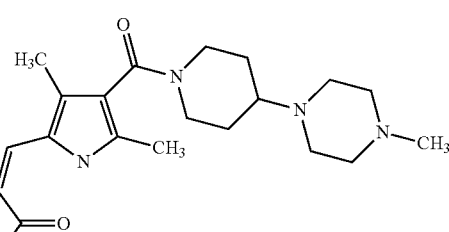<br>(3Z)-3-[(3,5-dimethyl-4-{[4-(4-methylpiperazin-1-yl)piperidin-1-yl]carbonyl}-1H-pyrrol-2-yl)methylene]-2-oxo-N-[(1R)-1-phenylpropyl]indoline-5-carboxamide |
| II.54 | 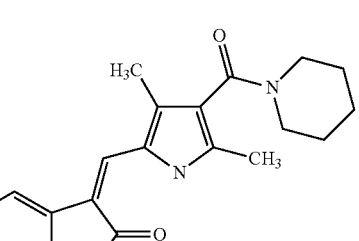<br>(3Z)-3-{[3,5-dimethyl-4-(piperidin-1-ylcarbonyl)-1H-pyrrol-2-yl]methylene}-2-oxo-N-[(1S)-1-phenylethyl]indoline-5-carboxamide |

TABLE 3-continued

| No. | Compound |
|---|---|
| II.55 | 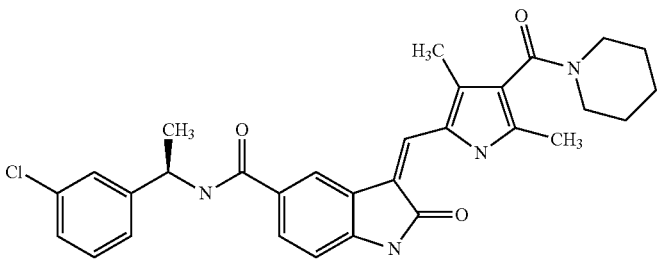 [SMILES: Cc1[nH]c(/C=C2\C(=O)Nc3ccc(C(=O)N[C@H](C)c4cccc(Cl)c4)cc32)c(C)c1C(=O)N1CCCCC1]<br>(3Z)-N-[(1R)-1-(3-chlorophenyl)ethyl]-3-{[3,5-dimethyl-4-(piperidin-1-ylcarbonyl)-1H-pyrrol-2-yl]methylene}-2-oxoindoline-5-carboxamide |
| II.56 | 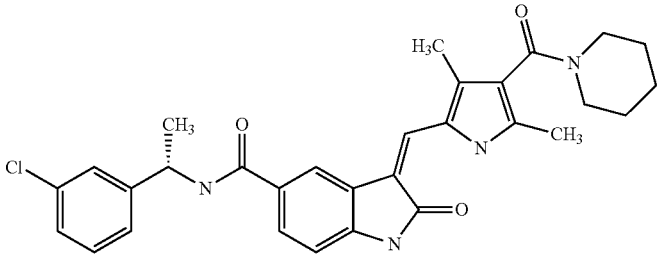 [SMILES: Cc1[nH]c(/C=C2\C(=O)Nc3ccc(C(=O)N[C@@H](C)c4cccc(Cl)c4)cc32)c(C)c1C(=O)N1CCCCC1]<br>(3Z)-N-[(1S)-1-(3-chlorophenyl)ethyl]-3-{[3,5-dimethyl-4-(piperidin-1-ylcarbonyl)-1H-pyrrol-2-yl]methylene}-2-oxoindoline-5-carboxamide |
| II.57 | 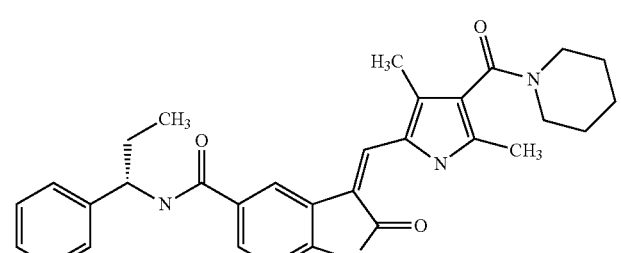<br>(3Z)-3-{[3,5-dimethyl-4-(piperidin-1-ylcarbonyl)-1H-pyrrol-2-yl]methylene}-2-oxo-N-[(1S)-1-phenylpropyl]indoline-5-carboxamide |
| II.58 | 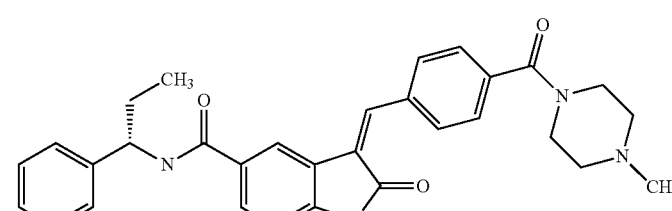<br>(3Z)-3-{4-[(4-methylpiperazin-1-yl)carbonyl]benzylidene}-2-oxo-N-[(1S)-1-phenylpropyl]indoline-5-carboxamide |

TABLE 3-continued

| No. | Compound |
|---|---|
| II.59 | 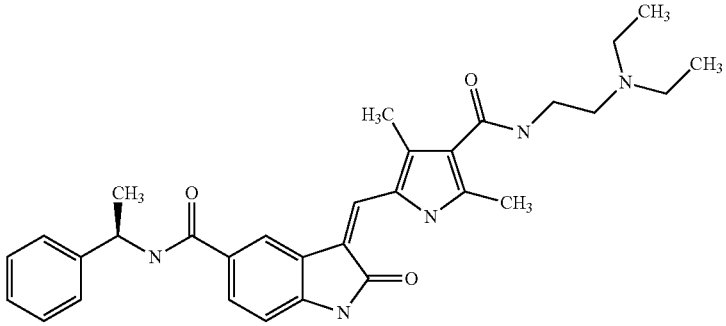 [SMILES: CCN(CC)CCNC(=O)c1c(C)[nH]c(/C=C2\C(=O)Nc3ccc(C(=O)N[C@H](C)c4ccccc4)cc32)c1C]<br>(3Z)-3-[(4-{[2-(diethylamino)ethyl]carbamoyl}-3,5-dimethyl-1H-pyrrol-2-yl)methylene]-2-oxo-N-[(1R)-1-phenylethyl]indoline-5-carboxamide |
| II.60 | 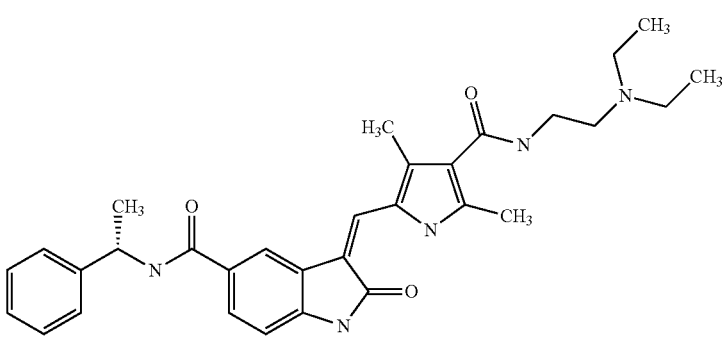 [SMILES: CCN(CC)CCNC(=O)c1c(C)[nH]c(/C=C2\C(=O)Nc3ccc(C(=O)N[C@@H](C)c4ccccc4)cc32)c1C]<br>(3Z)-3-[(4-{[2-(diethylamino)ethyl]carbamoyl}-3,5-dimethyl-1H-pyrrol-2-yl)methylene]-2-oxo-N-[(1S)-1-phenylethyl]indoline-5-carboxamide |
| II.61 | 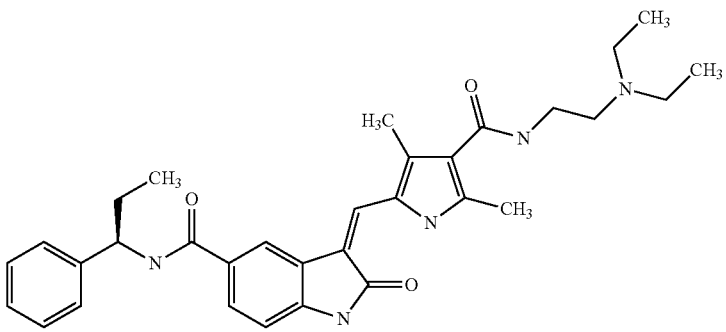 [SMILES: CC[C@@H](NC(=O)c1ccc2c(c1)/C(=C/c1[nH]c(C)c(C(=O)NCCN(CC)CC)c1C)C(=O)N2)c1ccccc1]<br>(3Z)-3-[(4-{[2-(diethylamino)ethyl]carbamoyl}-3,5-dimethyl-1H-pyrrol-2-yl)methylene]-2-oxo-N-[(1R)-1-phenylpropyl]indoline-5-carboxamide |
| II.62 | 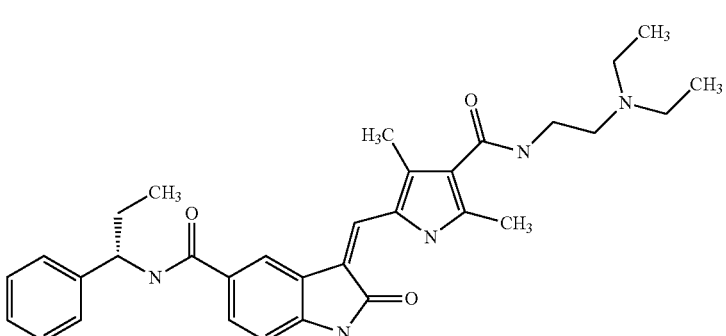<br>(3Z)-3-[(4-{[2-(diethylamino)ethyl]carbamoyl}-3,5-dimethyl-1H-pyrrol-2-yl)methylene]-2-oxo-N-[(1S)-1-phenylpropyl]indoline-5-carboxamide |

TABLE 3-continued

| No. | Compound |
|---|---|
| II.63 | 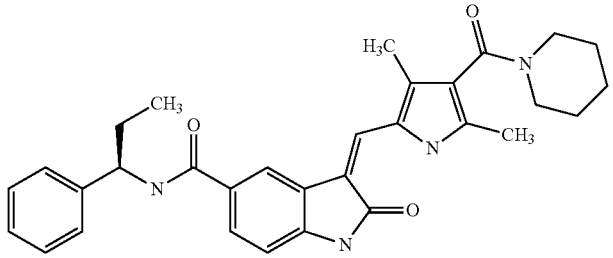 [SMILES: CC[C@@H](NC(=O)c1ccc2c(c1)/C(=C/c1[nH]c(C)c(C(=O)N3CCCCC3)c1C)C(=O)N2)c1ccccc1]<br>(3Z)-3-{[3,5-dimethyl-4-(piperidin-1-ylcarbonyl)-1H-pyrrol-2-yl]methylene)-2-oxo-N-[(1R)-1-phenylpropyl]indoline-5-carboxamide |
| II.64 | 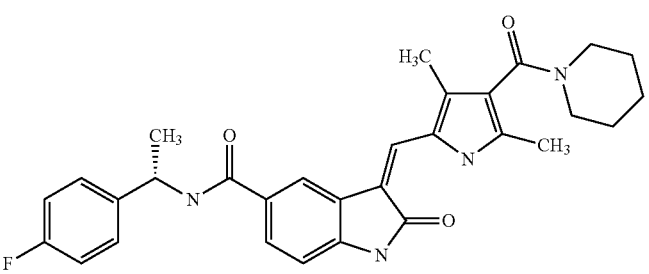 [SMILES: Cc1[nH]c(/C=C2\C(=O)Nc3ccc(C(=O)N[C@@H](C)c4ccc(F)cc4)cc32)c(C)c1C(=O)N1CCCCC1]<br>(3Z)-3-{[3,5-dimethyl-4-(piperidin-1-ylcarbonyl)-1H-pyrrol-2-yl]methylene}-N-[(1S)-1-(4-fluorophenyl)ethyl]-2-oxoindoline-5-carboxamide |
| II.65 | 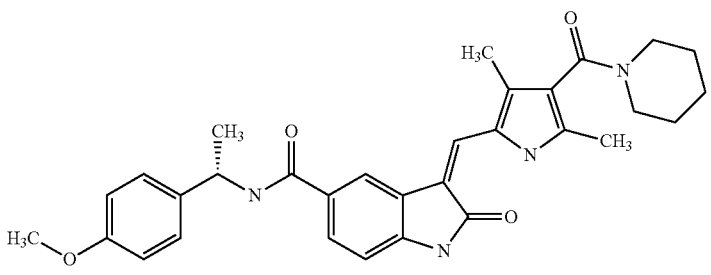 [SMILES: COc1ccc([C@H](C)NC(=O)c2ccc3c(c2)/C(=C/c2[nH]c(C)c(C(=O)N4CCCCC4)c2C)C(=O)N3)cc1]<br>(3Z)-3-{[3,5-dimethyl-4-(piperidin-1-ylcarbonyl)-1H-pyrrol-2-yl]methylene}-N-[(1S)-1-(4-methoxyphenyl)ethyl]-2-oxoindoline-5-carboxamide |
| II.66 | 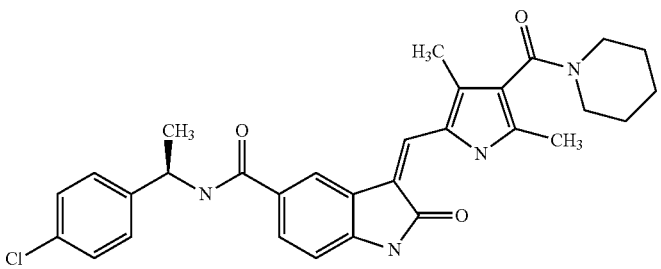 [SMILES: Cc1[nH]c(/C=C2\C(=O)Nc3ccc(C(=O)N[C@H](C)c4ccc(Cl)cc4)cc32)c(C)c1C(=O)N1CCCCC1]<br>(3Z)-N-[(1R)-1-(4-chlorophenyl)ethyl]-3-{[3,5-dimethyl-4-(piperidin-1-ylcarbonyl)-1H-pyrrol-2-yl]methylene}-2-oxoindoline-5-carboxamide |

TABLE 3-continued
| No. | Compound |
|---|---|
| II.67 | 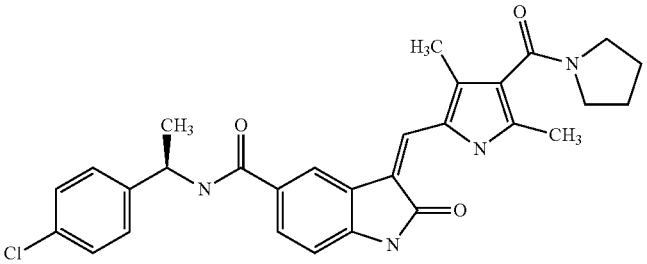 [SMILES: Cc1[nH]c(/C=C2\C(=O)Nc3ccc(C(=O)N[C@H](C)c4ccc(Cl)cc4)cc32)c(C)c1C(=O)N1CCCC1]<br>(3Z)-N-[(1R)-1-(4-chlorophenyl)ethyl]-3-{[3,5-dimethyl-4-(pyrrolidin-1-ylcarbonyl)-1H-pyrrol-2-yl]methylene}-2-oxoindoline-5-carboxamide |
| II.68 | 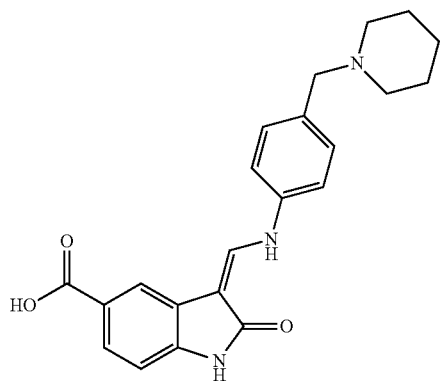 [SMILES: O=C1Nc2ccc(C(=O)O)cc2/C1=C/Nc1ccc(CN2CCCCC2)cc1]<br>(3Z)-2-oxo-3-({[4-(piperidin-1-ylmethyl)phenyl]amino}methylene)indoline-5-carboxylic acid |
| II.69 | 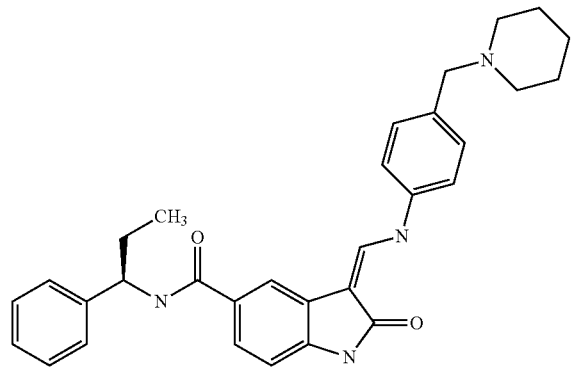 [SMILES: CC[C@@H](NC(=O)c1ccc2c(c1)/C(=C/Nc1ccc(CN3CCCCC3)cc1)C(=O)N2)c1ccccc1]<br>(3Z)-2-oxo-N-[(1R)-1-phenylpropyl]-3-({[4-(piperidin-1-ylmethyl)phenyl]amino}methylene)-indoline-5-carboxamide |

| No. | Compound |
|---|---|
| II.70 | 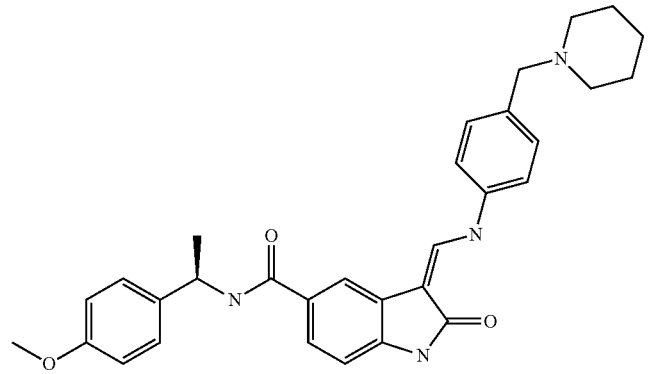 [SMILES: COc1ccc([C@@H](C)NC(=O)c2ccc3c(c2)/C(=C/Nc2ccc(CN4CCCCC4)cc2)C(=O)N3)cc1]<br>(3Z)-N-[(1R)-1-(4-methoxyphenyl)ethyl]-2-oxo-3-({[4-(piperidin-1-ylmethyl)phenyl]amino}methylene)indoline-5-carboxamide |
| II.71 | 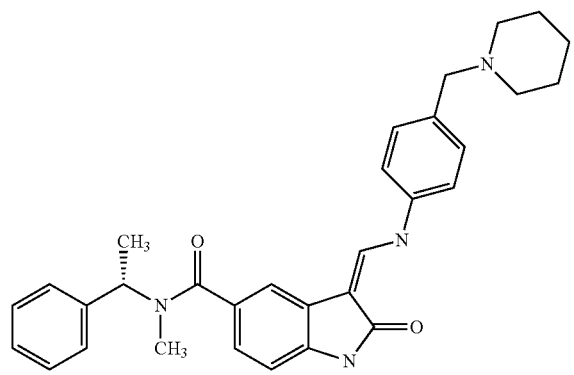 [SMILES: C[C@@H](c1ccccc1)N(C)C(=O)c1ccc2c(c1)/C(=C/Nc1ccc(CN3CCCCC3)cc1)C(=O)N2]<br>(3Z)-N-methyl-2-oxo-N-[(1S)-1-phenylethyl]-3-({[4-(piperidin-1-ylmethyl)phenyl]amino}methylene)indoline-5-carboxamide |
| II.72 | 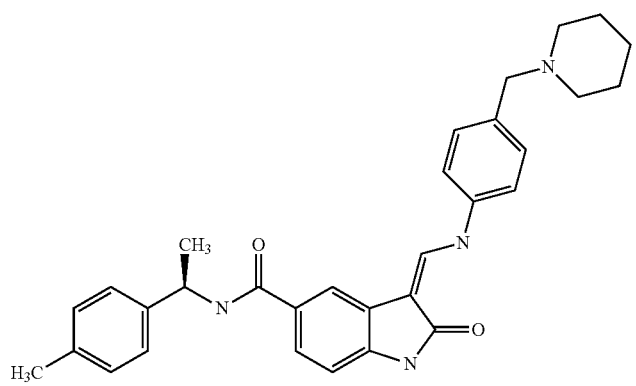 [SMILES: Cc1ccc([C@@H](C)NC(=O)c2ccc3c(c2)/C(=C/Nc2ccc(CN4CCCCC4)cc2)C(=O)N3)cc1]<br>(3Z)-N-[(1R)-1-(4-methylphenyl)ethyl]-2-oxo-3-({[4-(piperidin-1-ylmethyl)phenyl]amino}methylene)indoline-5-carboxamide |

TABLE 3-continued
| No. | Compound |
|---|---|
| II.73 | 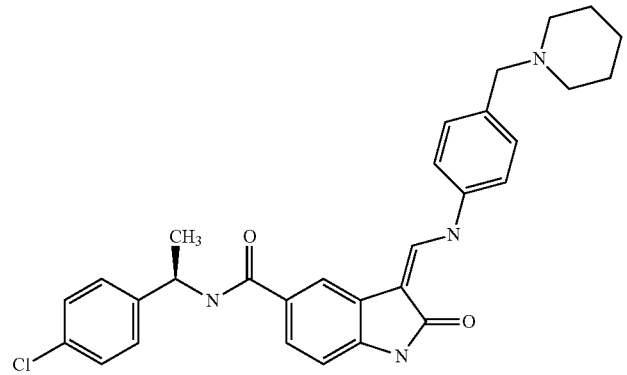 [SMILES: C[C@@H](NC(=O)c1ccc2c(c1)/C(=C/Nc1ccc(CN3CCCCC3)cc1)C(=O)N2)c1ccc(Cl)cc1]<br>(3Z)-N-[(1R)-1-(4-chlorophenyl)ethyl]-2-oxo-3-({[4-(piperidin-1-ylmethyl)phenyl]amino}methylene)indoline-5-carboxamide |
| II.74 | 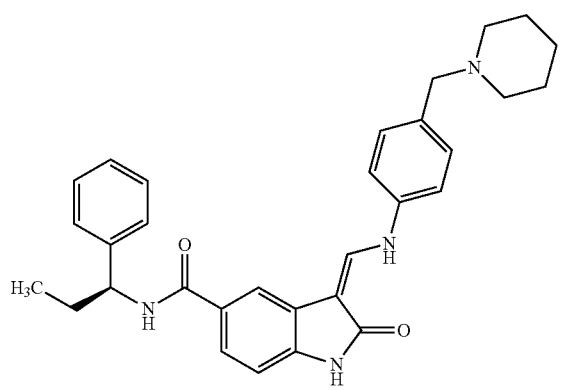 [SMILES: CC[C@H](NC(=O)c1ccc2c(c1)/C(=C/Nc1ccc(CN3CCCCC3)cc1)C(=O)N2)c1ccccc1]<br>(3Z)-2-oxo-N-[(1S)-1-phenylpropyl]-3-({[4-(piperidin-1-ylmethyl)phenyl]amino}methylene)indoline-5-carboxamide |
| II.75 | 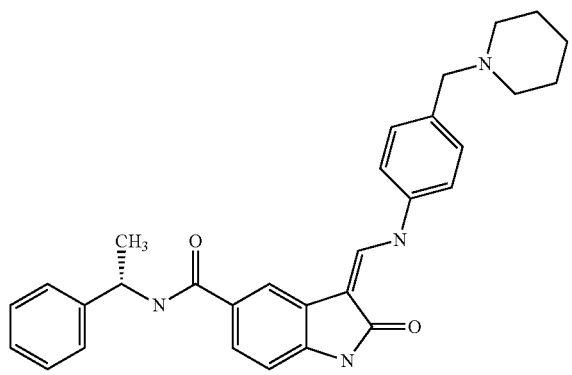 [SMILES: C[C@H](NC(=O)c1ccc2c(c1)/C(=C/Nc1ccc(CN3CCCCC3)cc1)C(=O)N2)c1ccccc1]<br>(3Z)-2-oxo-N-[(1S)-1-phenylethyl]-3-({[4-(piperidin-1-ylmethyl)phenyl]amino}methylene)indoline-5-carboxamide |

| No. | Compound |
|---|---|
| II.76 | 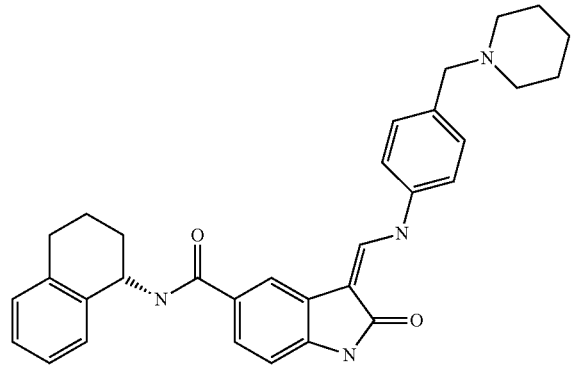
(3Z)-2-oxo-3-({[4-(piperidin-1-ylmethyl)phenyl]amino}methylene)-N-[(1S)-1,2,3,4-tetrahydronaphthalen-1-yl]indoline-5-carboxamide |
| II.77 | 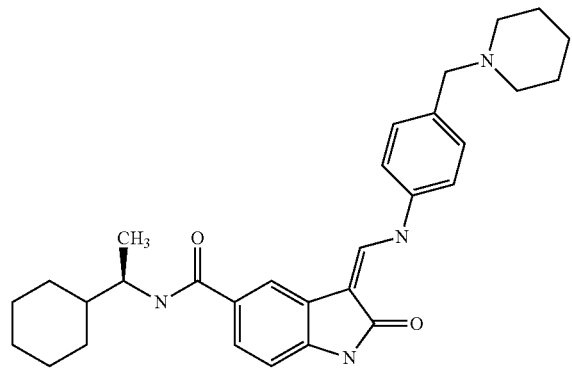 [SMILES: C[C@@H](NC(=O)c1ccc2c(c1)/C(=C/Nc1ccc(CN3CCCCC3)cc1)C(=O)N2)C1CCCCC1]
(3Z)-N-[(1R)-1-cyclohexylethyl]-2-oxo-3-({[4-(piperidin-1-ylmethyl)phenyl]amino}methylene)indoline-5-carboxamide |
| II.78 | 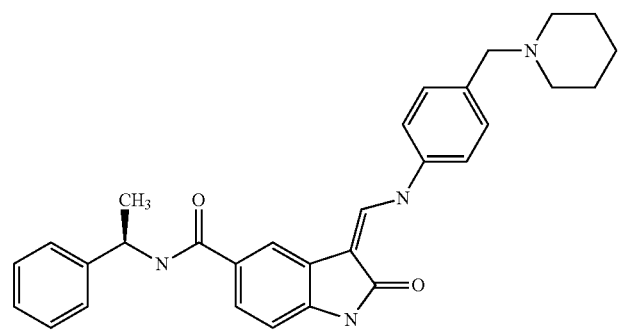 [SMILES: C[C@@H](NC(=O)c1ccc2c(c1)/C(=C/Nc1ccc(CN3CCCCC3)cc1)C(=O)N2)c1ccccc1]
(3Z)-2-oxo-N-[(1R)-1-phenylethyl]-3-({[4-(piperidin-1-ylmethyl)phenyl]amino}methylene)indoline-5-carboxamide |

| No. | Compound |
|---|---|
| II.79 | 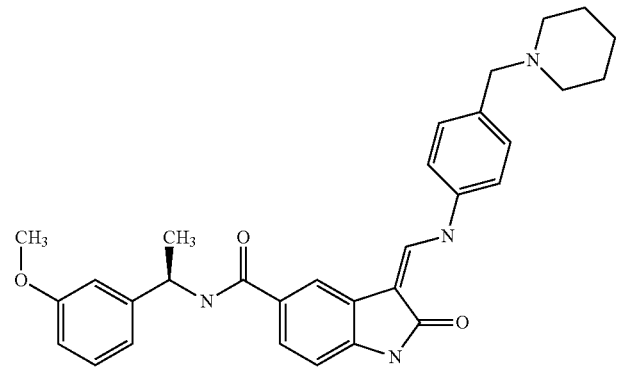 [SMILES: COc1cccc([C@@H](C)NC(=O)c2ccc3c(c2)/C(=C/Nc2ccc(CN4CCCCC4)cc2)C(=O)N3)c1]<br>(3Z)-N-[(1R)-1-(3-methoxyphenyl)ethyl]-2-oxo-3-({[4-(piperidin-1-ylmethyl)phenyl]amino}methylene)indoline-5-carboxamide |
| II.80 | 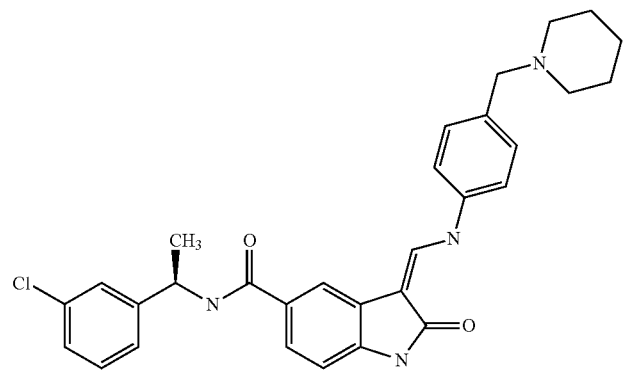 [SMILES: C[C@@H](NC(=O)c1ccc2c(c1)/C(=C/Nc1ccc(CN3CCCCC3)cc1)C(=O)N2)c1cccc(Cl)c1]<br>(3Z)-N-[(1R)-1-(3-chlorophenyl)ethyl]-2-oxo-3-({[4-(piperidin-1-ylmethyl)phenyl]amino}methylene)indoline-5-carboxamide |
| II.81 | 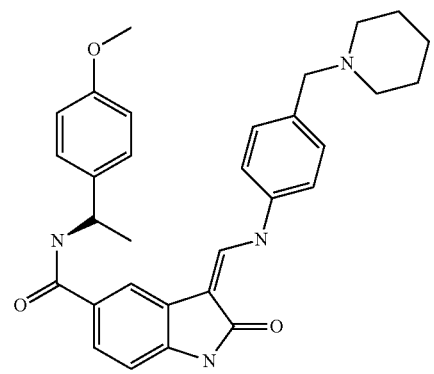<br>(3Z)-N-[(1R)-1-(4-methoxyphenyl)ethyl]-2-oxo-3-({[4-(piperidin-1-ylmethyl)phenyl]amino}methylene)indoline-5-carboxamide |

| No. | Compound |
|---|---|
| II.82 | 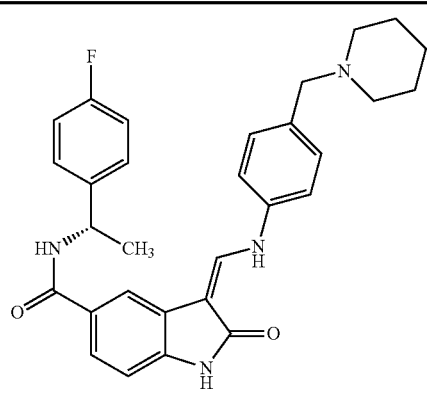<br>(3Z)-N-[(1S)-1-(4-fluorophenyl)ethyl]-2-oxo-3-({[4-(piperidin-1-ylmethyl)phenyl]amino}methylene)indoline-5-carboxamide |
| II.83 | 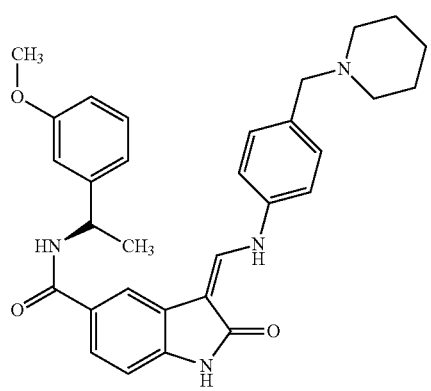<br>(3Z)-N-[(1R)-1-(3-methoxyphenyl)ethyl]-2-oxo-3-({[4-(piperidin-1-ylmethyl)phenyl]amino}methylene)indoline-5-carboxamide |
| II.84 | 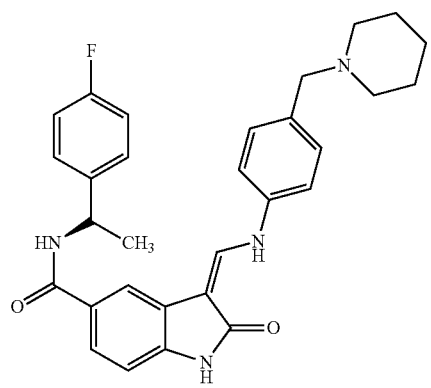<br>(3Z)-N-[(1R)-1-(4-fluorophenyl)ethyl]-2-oxo-3-({[4-(piperidin-1-ylmethyl)phenyl]amino}methylene)indoline-5-carboxamide |

TABLE 3-continued

| No. | Compound |
|---|---|
| II.85 | 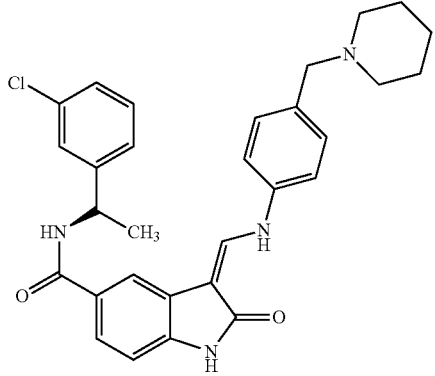<br>(3Z)-N-[(1R)-1-(3-chlorophenyl)ethyl]-2-oxo-3-({[4-(piperidin-1-ylmethyl)phenyl]amino}methylene)indoline-5-carboxamide |
| II.86 | 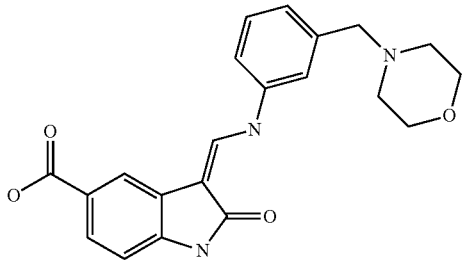 [SMILES: O=C1Nc2ccc(C(=O)O)cc2/C1=C/Nc1cccc(CN2CCOCC2)c1]<br>(3Z)-3-({[3-(morpholin-4-ylmethyl)phenyl]amino}methylene)-2-oxoindoline-5-carboxylic acid |
| II.87 | 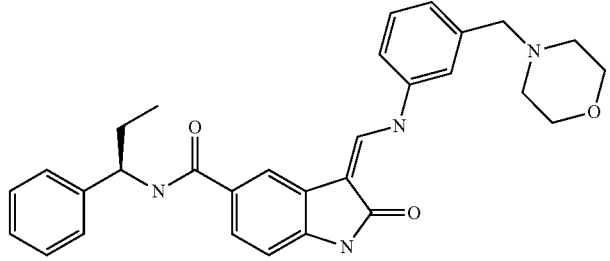 [SMILES: CC[C@@H](NC(=O)c1ccc2c(c1)/C(=C/Nc1cccc(CN3CCOCC3)c1)C(=O)N2)c1ccccc1]<br>(3Z)-3-({[3-(morpholin-4-ylmethyl)phenyl]amino}methylene)-2-oxo-N-[(1R)-1-phenylpropyl]indoline-5-carboxamide |
| II.88 | 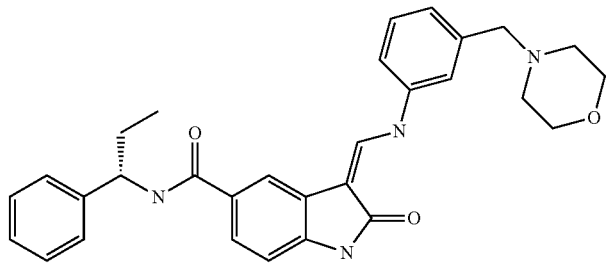 [SMILES: CC[C@H](NC(=O)c1ccc2c(c1)/C(=C/Nc1cccc(CN3CCOCC3)c1)C(=O)N2)c1ccccc1]<br>(3Z)-3-({[3-(morpholin-4-ylmethyl)phenyl]amino}methylene)-2-oxo-N-[(1S)-1-phenylpropyl]indoline-5-carboxamide |

TABLE 3-continued

| No. | Compound |
|---|---|
| II.89 | 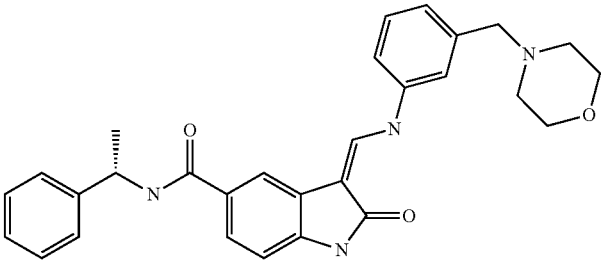 [SMILES: C[C@H](NC(=O)c1ccc2c(c1)/C(=C/Nc1cccc(CN3CCOCC3)c1)C(=O)N2)c1ccccc1]
(3Z)-3-({[3-(morpholin-4-ylmethyl)phenyl]amino}methylene)-2-oxo-N-[(1S)-1-phenylethyl]indoline-5-carboxamide |
| II.90 | 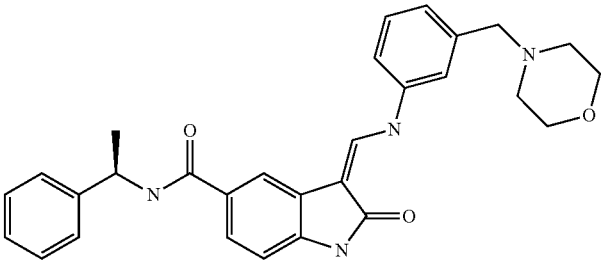 [SMILES: C[C@@H](NC(=O)c1ccc2c(c1)/C(=C/Nc1cccc(CN3CCOCC3)c1)C(=O)N2)c1ccccc1]
(3Z)-3-({[3-(morpholin-4-ylmethyl)phenyl]amino}methylene)-2-oxo-N-[(1R)-1-phenylethyl]indoline-5-carboxamide |
| II.91 | 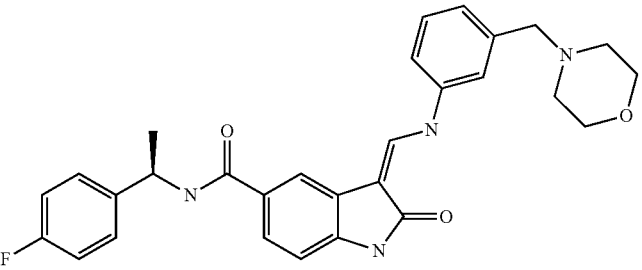 [SMILES: C[C@@H](NC(=O)c1ccc2c(c1)/C(=C/Nc1cccc(CN3CCOCC3)c1)C(=O)N2)c1ccc(F)cc1]
(3Z)-N-[(1R)-1-(4-fluorophenyl)ethyl]-3-({[3-(morpholin-4-ylmethyl)phenyl]amino}methylene)-2-oxoindoline-5-carboxamide |
| II.92 | 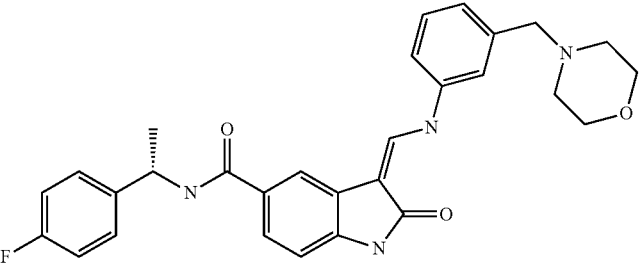 [SMILES: C[C@H](NC(=O)c1ccc2c(c1)/C(=C/Nc1cccc(CN3CCOCC3)c1)C(=O)N2)c1ccc(F)cc1]
(3Z)-N-[(1S)-1-(4-fluorophenyl)ethyl]-3-({[3-(morpholin-4-ylmethyl)phenyl]amino}methylene)-2-oxoindoline-5-carboxamide |

TABLE 3-continued
| No. | Compound |
|---|---|
| II.93 | 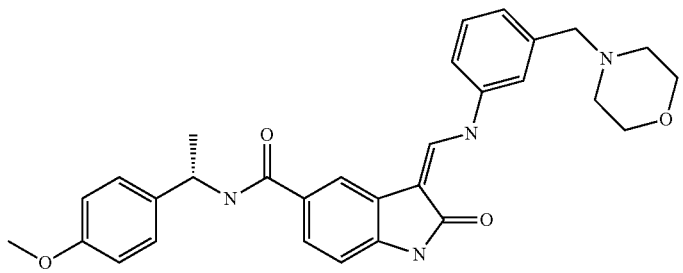 [SMILES: COc1ccc([C@H](C)NC(=O)c2ccc3c(c2)/C(=C/Nc2cccc(CN4CCOCC4)c2)C(=O)N3)cc1]<br>(3Z)-N-[(1S)-1-(4-methoxyphenyl)ethyl]-3-({[3-(morpholin-4-ylmethyl)phenyl]amino}methylene)-2-oxoindoline-5-carboxamide |
| II.94 | 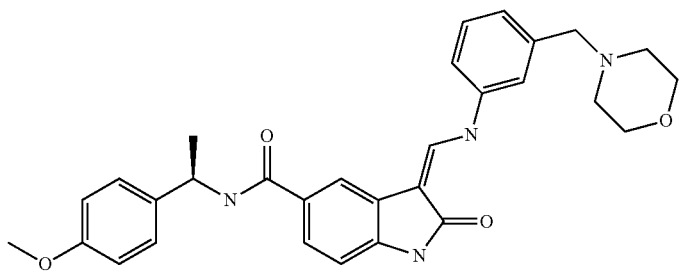 [SMILES: COc1ccc([C@@H](C)NC(=O)c2ccc3c(c2)/C(=C/Nc2cccc(CN4CCOCC4)c2)C(=O)N3)cc1]<br>3Z)-N-[(1R)-1-(4-methoxyphenyl)ethyl]-3-({[3-(morpholin-4-ylmethyl)phenyl]amino}methylene)-2-oxoindoline-5-carboxamide |
| II.95 | 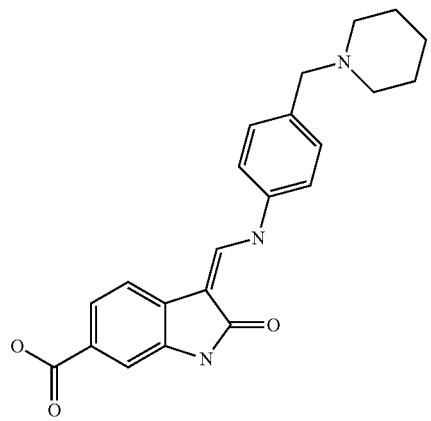 [SMILES: O=C1Nc2cc(C(=O)O)ccc2/C1=C/Nc1ccc(CN2CCCCC2)cc1]<br>(3Z)-2-oxo-3-({[4-(piperidin-1-ylmethyl)phenyl]amino}methylene)indoline-6-carboxylic acid |

| No. | Compound |
|---|---|
| II.96 | 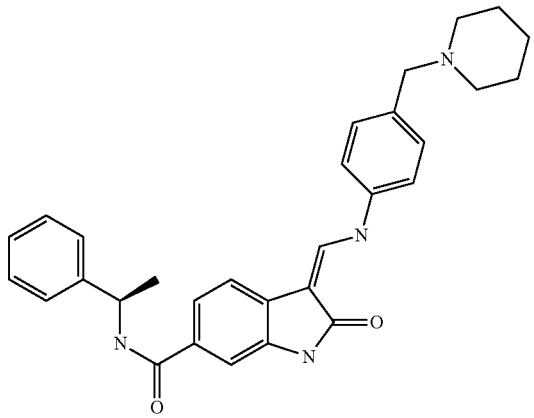 [SMILES: C[C@@H](NC(=O)c1ccc2c(c1)NC(=O)/C2=C\Nc1ccc(CN2CCCCC2)cc1)c1ccccc1]<br>(3Z)-2-oxo-N-[(1R)-1-phenylethyl]-3-({[4-(piperidin-1-ylmethyl)phenyl]amino}methylene)indoline-6-carboxamide |
| II.97 | 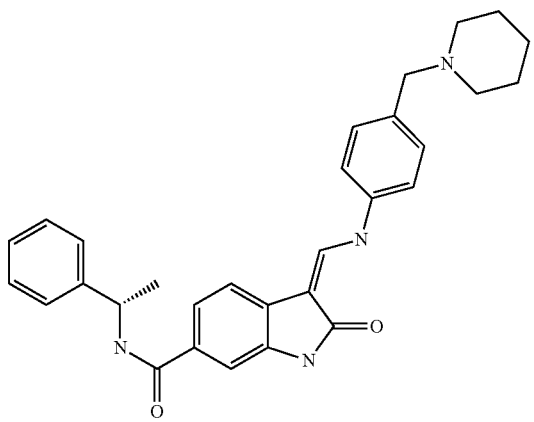 [SMILES: C[C@H](NC(=O)c1ccc2c(c1)NC(=O)/C2=C\Nc1ccc(CN2CCCCC2)cc1)c1ccccc1]<br>(3Z)-2-oxo-N-[(1S)-1-phenylethyl]-3-({[4-(piperidin-1-ylmethyl)phenyl]amino}methylene)indoline-6-carboxamide |
| II.98 | 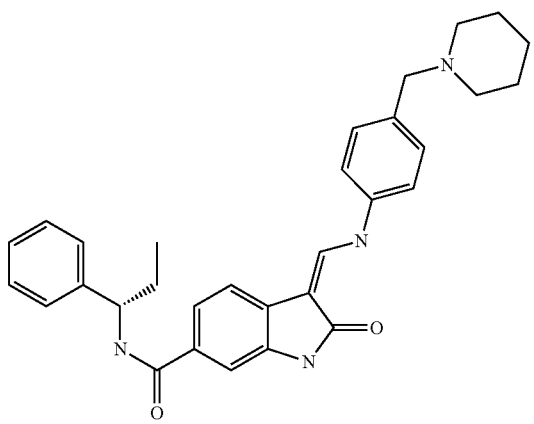 [SMILES: CC[C@H](NC(=O)c1ccc2c(c1)NC(=O)/C2=C\Nc1ccc(CN2CCCCC2)cc1)c1ccccc1]<br>(3Z)-2-oxo-N-[(1S)-1-phenylpropyl]-3-({[4-(piperidin-1-ylmethyl)phenyl]amino}methylene)indoline-6-carboxamide |

| No. | Compound |
|---|---|
| II.99 | 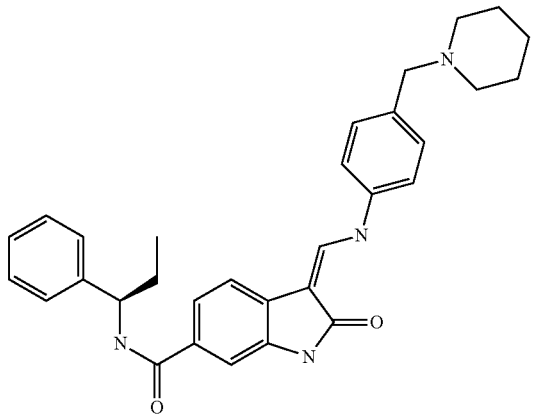 [SMILES: CC[C@@H](NC(=O)c1ccc2c(c1)NC(=O)/C2=C\Nc1ccc(CN2CCCCC2)cc1)c1ccccc1]<br>(3Z)-2-oxo-N-[(1R)-1-phenylpropyl]-3-({[4-(piperidin-1-ylmethyl)phenyl]amino}methylene)indoline-6-carboxamide |
| II.100 | 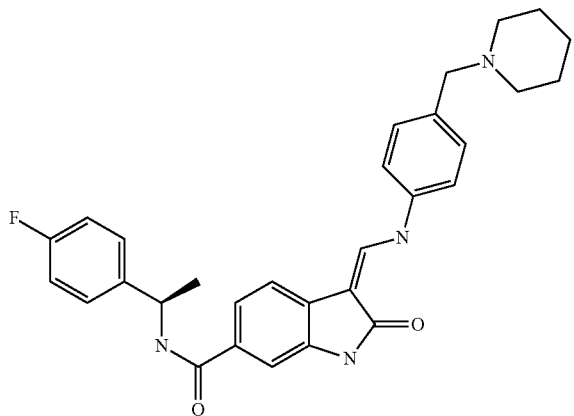 [SMILES: C[C@@H](NC(=O)c1ccc2c(c1)NC(=O)/C2=C\Nc1ccc(CN2CCCCC2)cc1)c1ccc(F)cc1]<br>(3Z)-N-[(1R)-1-(4-fluorophenyl)ethyl]-2-oxo-3-({[4-(piperidin-1-ylmethyl)phenyl]amino}methylene)indoline-6-carboxamide |
| II.101 | 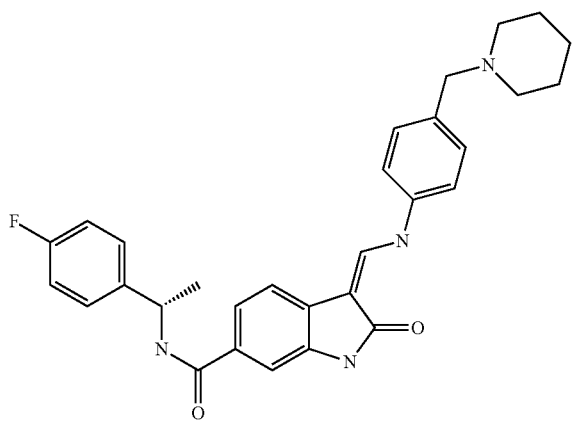 [SMILES: C[C@H](NC(=O)c1ccc2c(c1)NC(=O)/C2=C\Nc1ccc(CN2CCCCC2)cc1)c1ccc(F)cc1]<br>(3Z)-N-[(1S)-1-(4-fluorophenyl)ethyl]-2-oxo-3-({[4-(piperidin-1-ylmethyl)phenyl]amino}methylene)indoline-6-carboxamide |

| No. | Compound |
|---|---|
| II.102 | 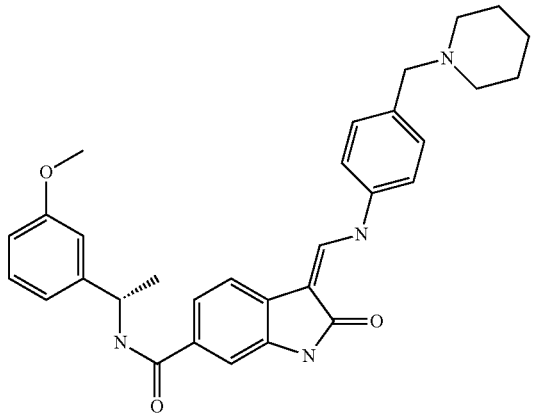 [SMILES: COc1cccc([C@H](C)NC(=O)c2ccc3c(c2)NC(=O)/C3=C\Nc2ccc(CN3CCCCC3)cc2)c1]
(3Z)-N-[(1S)-1-(3-methoxyphenyl)ethyl]-2-oxo-3-({[4-(piperidin-1-ylmethyl)phenyl]amino}methylene)indoline-6-carboxamide |
| II.103 | 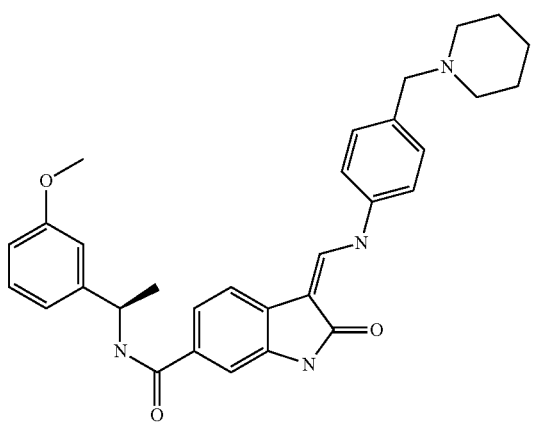 [SMILES: COc1cccc([C@@H](C)NC(=O)c2ccc3c(c2)NC(=O)/C3=C\Nc2ccc(CN3CCCCC3)cc2)c1]
(3Z)-N-[(1R)-1-(3-methoxyphenyl)ethyl]-2-oxo-3-({[4-(piperidin-1-ylmethyl)phenyl]amino}methylene)indoline-6-carboxamide |
| II.104 | 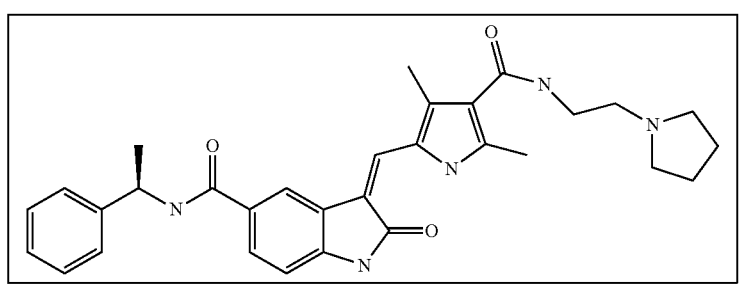 [SMILES: Cc1[nH]c(/C=C2\C(=O)Nc3ccc(C(=O)N[C@H](C)c4ccccc4)cc32)c(C)c1C(=O)NCCN1CCCC1]
(3Z)-3-({3,5-dimethyl-4-[(2-pyrrolidin-1-ylethyl)carbamoyl]-1H-pyrrol-2-yl}methylene)-2-oxo-N-[(1R)-1-phenylethyl]indoline-5-carboxamide |

TABLE 3-continued

| No. | Compound |
|---|---|
| II.105 | 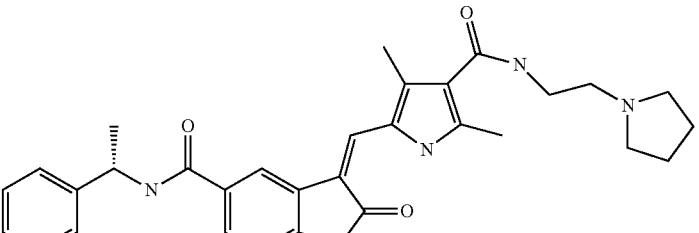<br>(3Z)-3-({3,5-dimethyl-4-[(2-pyrrolidin-1-ylethyl)carbamoyl]-1H-pyrrol-2-yl}methylene)-2-oxo-N-[(1S)-1-phenylethyl]indoline-5-carboxamide |
| II.106 | 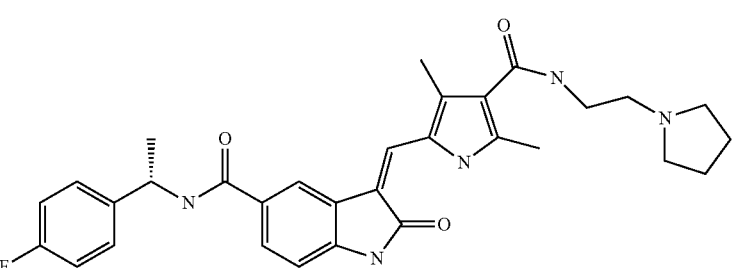<br>(3Z)-3-({3,5-dimethyl-4-[(2-pyrrolidin-1-ylethyl)carbamoyl]-1H-pyrrol-2-yl}methylene)-N-[(1S)-1-(4-fluorophenyl)ethyl]-2-oxoindoline-5-carboxamide |
| II.107 | 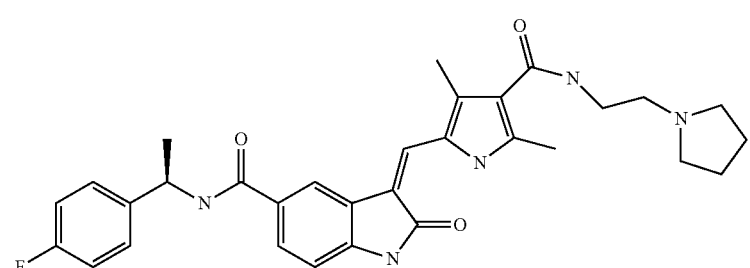<br>(3Z)-3-({3,5-dimethyl-4-[(2-pyrrolidin-1-ylethyl)carbamoyl]-1H-pyrrol-2-yl}methylene)-N-[(1R)-1-(4-fluorophenyl)ethyl]-2-oxoindoline-5-carboxamide |
| II.108 | 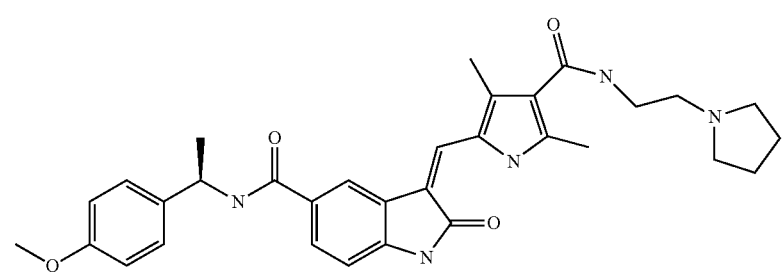 [SMILES: COc1ccc([C@@H](C)NC(=O)c2ccc3c(c2)/C(=C/c2[nH]c(C)c(C(=O)NCCN4CCCC4)c2C)C(=O)N3)cc1]<br>(3Z)-3-({3,5-dimethyl-4-[(2-pyrrolidin-1-ylethyl)carbamoyl]-1H-pyrrol-2-yl}methylene)-N-[(1S)-1-(4-methoxyphenyl)ethyl]-2-oxoindoline-5-carboxamide |

| No. | Compound |
|---|---|
| II.109 | 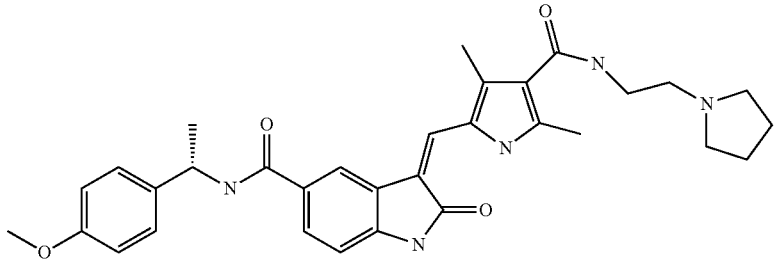 [SMILES: COc1ccc([C@H](C)NC(=O)c2ccc3c(c2)/C(=C/c2[nH]c(C)c(C(=O)NCCN4CCCC4)c2C)C(=O)N3)cc1]<br>(3Z)-3-({3,5-dimethyl-4-[(2-pyrrolidin-1-ylethyl)carbamoyl]-1H-pyrrol-2-yl}methylene)-N-[(1S)-1-(4-methoxyphenyl)ethyl]-2-oxoindoline-5-carboxamid |
| II.110 | 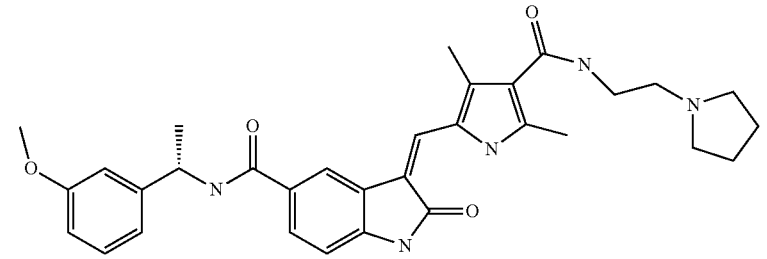 [SMILES: COc1cccc([C@H](C)NC(=O)c2ccc3c(c2)/C(=C/c2[nH]c(C)c(C(=O)NCCN4CCCC4)c2C)C(=O)N3)c1]<br>(3Z)-3-({3,5-dimethyl-4-[(2-pyrrolidin-1-ylethyl)carbamoyl]-1H-pyrrol-2-yl}methylene)-N-[(1S)-1-(3-methoxyphenyl)ethyl]-2-oxoindoline-5-carboxamide |
| II.111 | 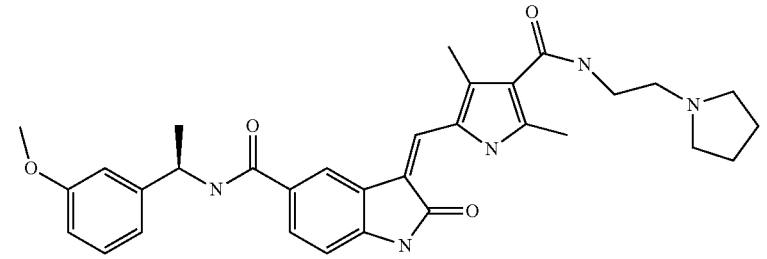 [SMILES: COc1cccc([C@@H](C)NC(=O)c2ccc3c(c2)/C(=C/c2[nH]c(C)c(C(=O)NCCN4CCCC4)c2C)C(=O)N3)c1]<br>(3Z)-3-({3,5-dimethyl-4-[(2-pyrrolidin-1-ylethyl)carbamoyl]-1H-pyrrol-2-yl}methylene)-N-[(1R)-1-(3-methoxyphenyl)ethyl]-2-oxoindoline-5-carboxamide |
| II.112 | 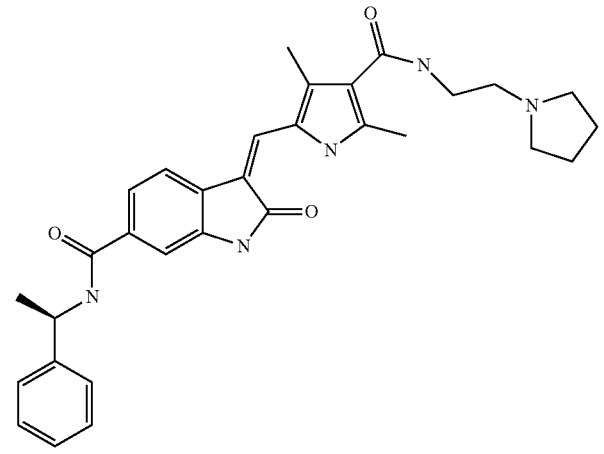 [SMILES: Cc1[nH]c(/C=C2\C(=O)Nc3cc(C(=O)N[C@H](C)c4ccccc4)ccc32)c(C)c1C(=O)NCCN1CCCC1]<br>(3Z)-3-({3,5-dimethyl-4-[(2-pyrrolidin-1-ylethyl)carbamoyl]-1H-pyrrol-2-yl}methylene)-2-oxo-N-[(1R)-1-phenylethyl]indoline-6-carboxamide |

TABLE 3-continued

| No. | Compound |
|---|---|
| II.113 | 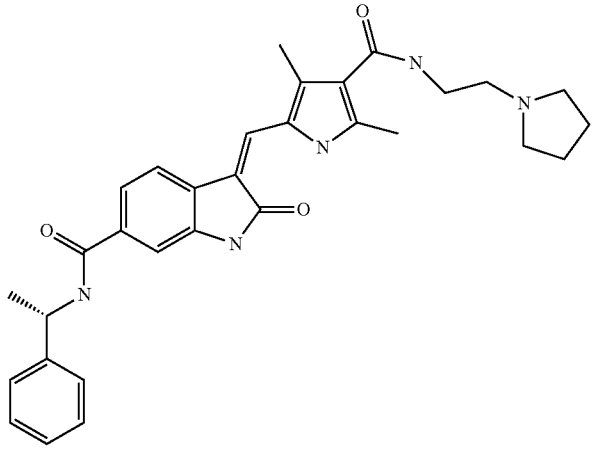 [SMILES: Cc1[nH]c(/C=C2\C(=O)Nc3cc(C(=O)N[C@@H](C)c4ccccc4)ccc32)c(C)c1C(=O)NCCN1CCCC1]<br>(3Z)-3-({3,5-dimethyl-4-[(2-pyrrolidin-1-ylethyl)carbamoyl]-1H-pyrrol-2-yl}methylene)-2-oxo-N-[(1S)-1-phenylethyl]indoline-6-carboxamide |
| II.114 | 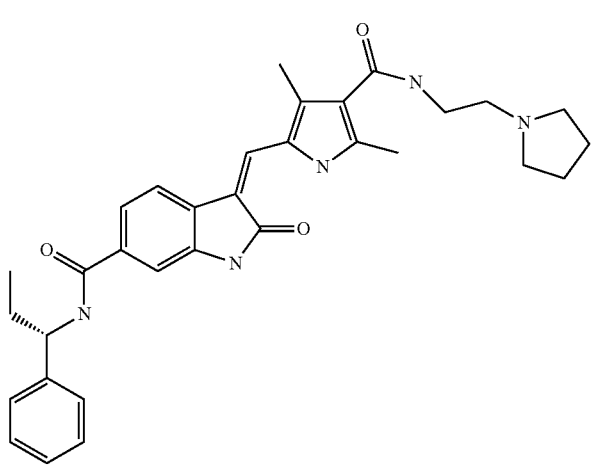 [SMILES: CC[C@H](NC(=O)c1ccc2c(c1)NC(=O)/C2=C\c1[nH]c(C)c(C(=O)NCCN2CCCC2)c1C)c1ccccc1]<br>(3Z)-3-({3,5-dimethyl-4-[(2-pyrrolidin-1-ylethyl)carbamoyl]-1H-pyrrol-2-yl}methylene)-2-oxo-N-[(1S)-1-phenylpropyl]indoline-6-carboxamide |
| II.115 | 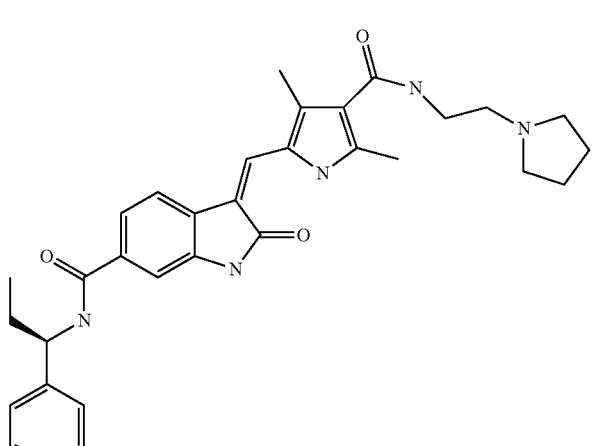<br>(3Z)-3-({3,5-dimethyl-4-[(2-pyrrolidin-1-ylethyl)carbamoyl]-1H-pyrrol-2-yl}methylene)-2-oxo-N-[(1R)-1-phenylpropyl]indoline-6-carboxamide |

TABLE 3-continued
| No. | Compound |
|---|---|
| II.116 | 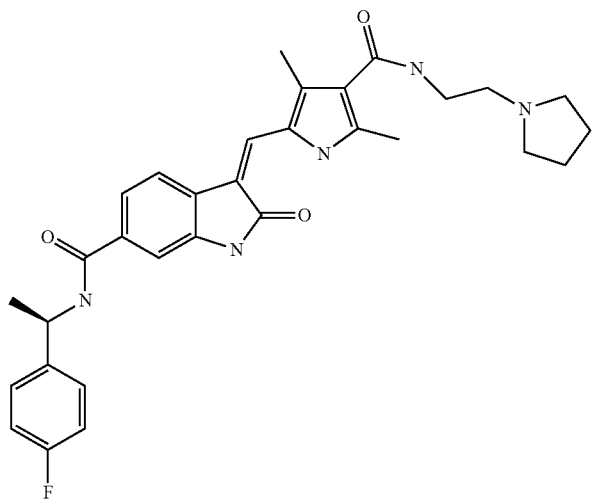 [SMILES: Cc1[nH]c(/C=C2\C(=O)Nc3cc(C(=O)N[C@H](C)c4ccc(F)cc4)ccc32)c(C)c1C(=O)NCCN1CCCC1]<br>(3Z)-3-({3,5-dimethyl-4-[(2-pyrrolidin-1-ylethyl)carbamoyl]-1H-pyrrol-2-yl}methylene)-N-[(1R)-1-(4-fluorophenyl)ethyl]-2-oxoindoline-6-carboxamide |
| II.117 | 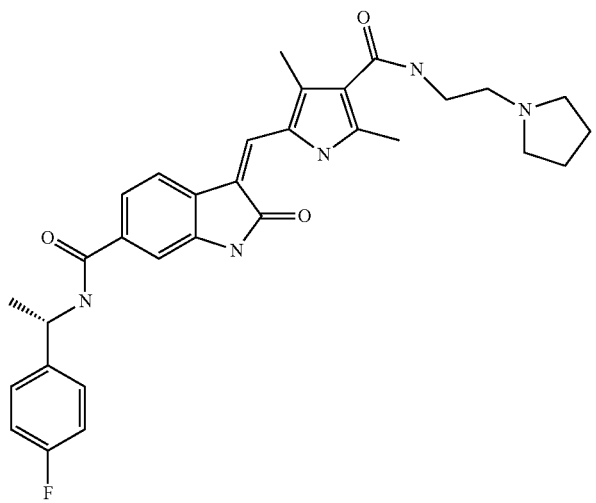 [SMILES: Cc1[nH]c(/C=C2\C(=O)Nc3cc(C(=O)N[C@@H](C)c4ccc(F)cc4)ccc32)c(C)c1C(=O)NCCN1CCCC1]<br>(3Z)-3-({3,5-dimethyl-4-[(2-pyrrolidin-1-ylethyl)carbamoyl]-1H-pyrrol-2-yl}methylene)-N-[(1S)-1-(4-fluorophenyl)ethyl]-2-oxoindoline-6-carboxamide |

| No. | Compound |
|---|---|
| II.118 | 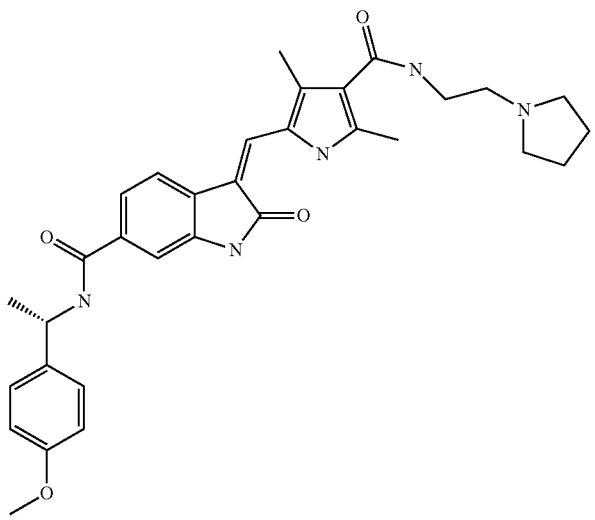 [SMILES: COc1ccc([C@H](C)NC(=O)c2ccc3c(c2)NC(=O)/C3=C\c2[nH]c(C)c(C(=O)NCCN3CCCC3)c2C)cc1]<br>(3Z)-3-({3,5-dimethyl-4-[(2-pyrrolidin-1-ylethyl)carbamoyl]-1H-pyrrol-2-yl}methylene)-N-[(1S)-1-(4-methoxyphenyl)ethyl]-2-oxoindoline-6-carboxamide |
| II.119 | 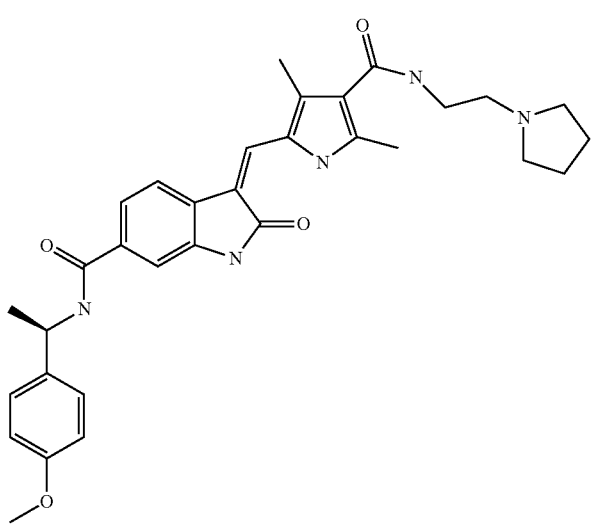 [SMILES: COc1ccc([C@@H](C)NC(=O)c2ccc3c(c2)NC(=O)/C3=C\c2[nH]c(C)c(C(=O)NCCN3CCCC3)c2C)cc1]<br>(3Z)-3-({3,5-dimethyl-4-[(2-pyrrolidin-1-ylethyl)carbamoyl]-1H-pyrrol-2-yl}methylene)-N-[(1R)-1-(4-methoxyphenyl)ethyl]-2-oxoindoline-6-carboxamide |
| II.120 | 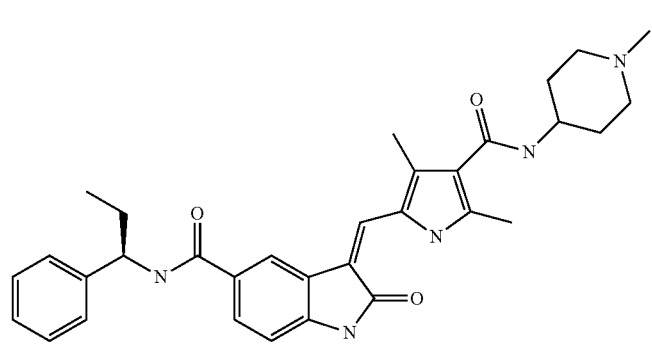 [SMILES: CC[C@@H](NC(=O)c1ccc2c(c1)/C(=C/c1[nH]c(C)c(C(=O)NC3CCN(C)CC3)c1C)C(=O)N2)c1ccccc1]<br>(3Z)-3-({3,5-dimethyl-4-[(1-methylpiperidin-4-yl)carbamoyl]-1H-pyrrol-2-yl}methylene)-2-oxo-N-[(1R)-1-phenylpropyl]indoline-5-carboxamide |

TABLE 3-continued

| No. | Compound |
|---|---|
| II.121 | 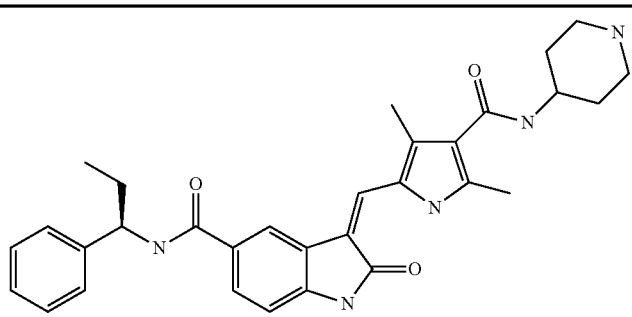<br>(3Z)-3-{[3,5-dimethyl-4-(piperidin-4-ylcarbamoyl)-1H-pyrrol-2-yl]methylene}-2-oxo-N-[(1R)-1-phenylpropyl]indoline-5-carboxamide |
| II.122 | 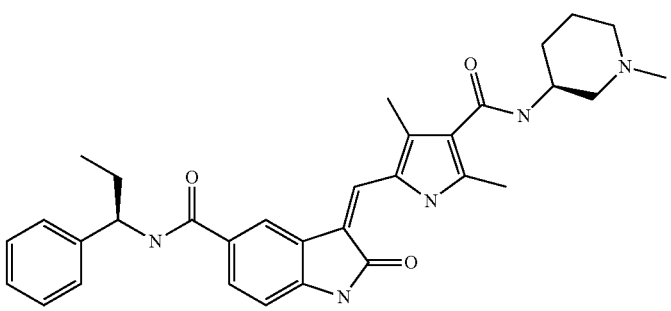 [SMILES: CC[C@@H](NC(=O)c1ccc2c(c1)/C(=C/c1[nH]c(C)c(C(=O)N[C@H]3CCCN(C)C3)c1C)C(=O)N2)c1ccccc1]<br>(3Z)-3-[(3,5-dimethy[-4-{[(3S)-1-methylpiperidin-3-yl]carbamoyl}-1H-pyrrol-2-yl)methylene]-2-oxo-N-[(1R)-1-phenylpropyl]indoline-5-carboxamide |
| II.123 | 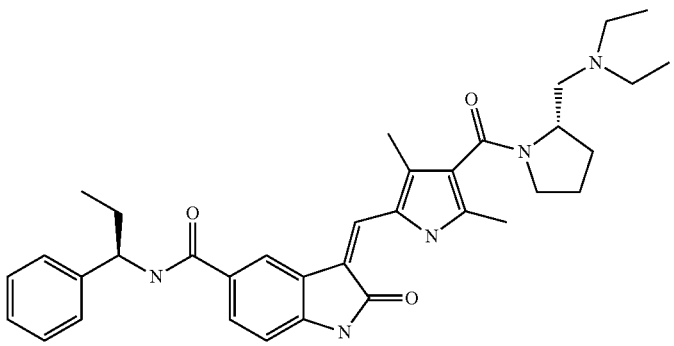 [SMILES: CC[C@@H](NC(=O)c1ccc2c(c1)/C(=C/c1[nH]c(C)c(C(=O)N3CCC[C@H]3CN(CC)CC)c1C)C(=O)N2)c1ccccc1]<br>(3Z)-3-{[4-({(2S)-2-[(diethylamino)methyl]pyrrolidin-1-yl}carbonyl)-3,5-dimethyl-1H-pyrrol-2-yl]methylene}-2-oxo-N-[(1R)-1-phenylpropyl]indoline-5-carboxamide |
| II.124 | 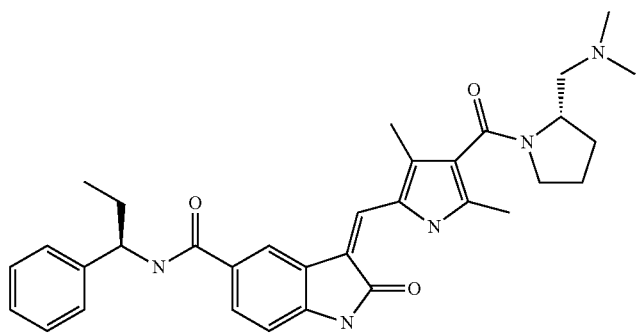 [SMILES: CC[C@@H](NC(=O)c1ccc2c(c1)/C(=C/c1[nH]c(C)c(C(=O)N3CCC[C@H]3CN(C)C)c1C)C(=O)N2)c1ccccc1]<br>(3Z)-3-{[4-({(2S)-2-[(dimethylamino)methyl]pyrrolidin-1-yl}carbonyl)-3,5-dimethyl-1H-pyrrol-2-yl]methylene}-2-oxo-N-[(1R)-1-phenylpropyl]indoline-5-carboxamide |

TABLE 3-continued

| No. | Compound |
|---|---|
| II.125 | 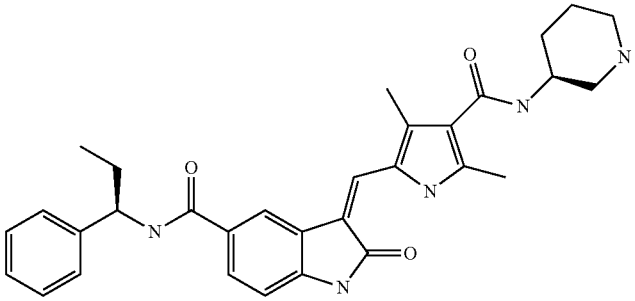 [SMILES: CC[C@@H](NC(=O)c1ccc2c(c1)/C(=C/c1[nH]c(C)c(C(=O)N[C@H]3CCCNC3)c1C)C(=O)N2)c1ccccc1]<br>(3Z)-3-({3,5-dimethyl-4-[(3S)-piperidin-3-ylcarbamoyl]-1H-pyrrol-2-yl}methylene)-2-oxo-N-[(1R)-1-phenylpropyl]indoline-5-carboxamide |
| II.126 | 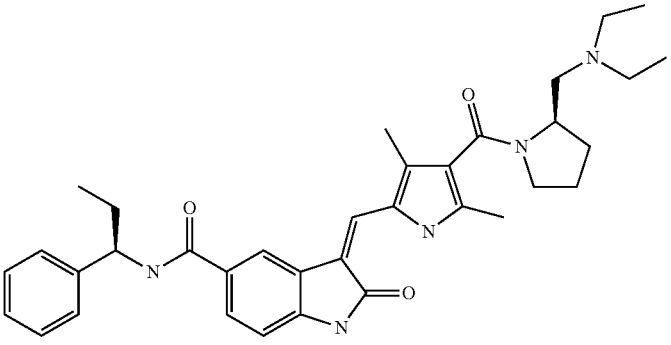 [SMILES: CC[C@@H](NC(=O)c1ccc2c(c1)/C(=C/c1[nH]c(C)c(C(=O)N3CCC[C@@H]3CN(CC)CC)c1C)C(=O)N2)c1ccccc1]<br>(3Z)-3-{[4-({(2R)-2-[(diethylamino)methyl]pyrrolidin-1-yl}carbonyl)-3,5-dimethyl-1H-pyrrol-2-yl]methylene}-2-oxo-N-[(1R)-1-phenylpropyl]indoline-5-carboxamide |
| II.127 | 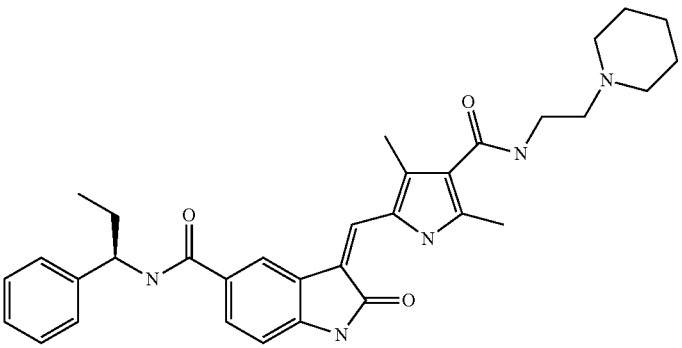 [SMILES: CC[C@@H](NC(=O)c1ccc2c(c1)/C(=C/c1[nH]c(C)c(C(=O)NCCN3CCCCC3)c1C)C(=O)N2)c1ccccc1]<br>(3Z)-3-({3,5-dimethyl-4-[(2-piperidin-1-ylethyl)carbamoyl]-1H-pyrrol-2-yl}methylene)-2-oxo-N-[(1R)-1-phenylpropyl]indoline-5-carboxamide |

TABLE 3-continued

| No. | Compound |
| --- | --- |
| II.128 | 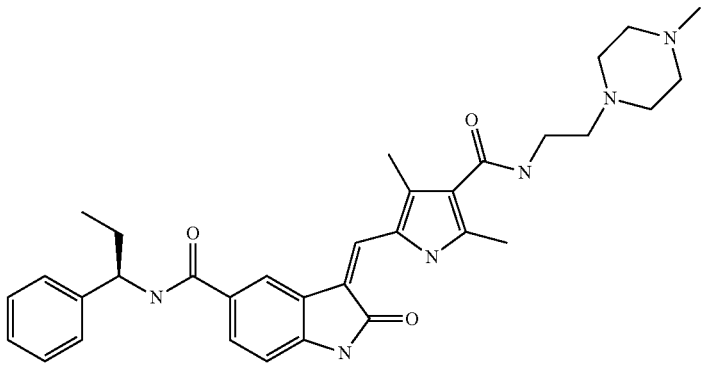 [SMILES: CC[C@@H](NC(=O)c1ccc2c(c1)/C(=C/c1[nH]c(C)c(C(=O)NCCN3CCN(C)CC3)c1C)C(=O)N2)c1ccccc1]<br>(3Z)-3-[(3,5-dimethyl-4-{[2-(4-methylpiperazin-1-yl)ethyl]carbamoyl}-1H-pyrrol-2-yl)methylene]-2-oxo-N-[(1R)-1-phenylpropyl]indoline-5-carboxamide |
| II.129 | 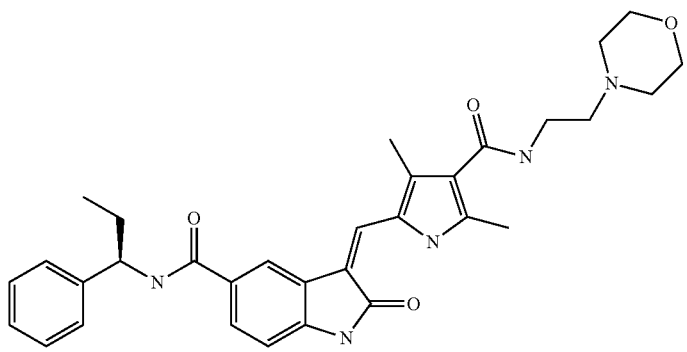 [SMILES: CC[C@@H](NC(=O)c1ccc2c(c1)/C(=C/c1[nH]c(C)c(C(=O)NCCN3CCOCC3)c1C)C(=O)N2)c1ccccc1]<br>(3Z)-3-({3,5-dimethyl-4-[(2-morpholin-4-ylethyl)carbamoyl]-1H-pyrrol-2-yl}methylene)-2-oxo-N-[(1R)-1-phenylpropyl]indoline-5-carboxamide |
| II.130 | 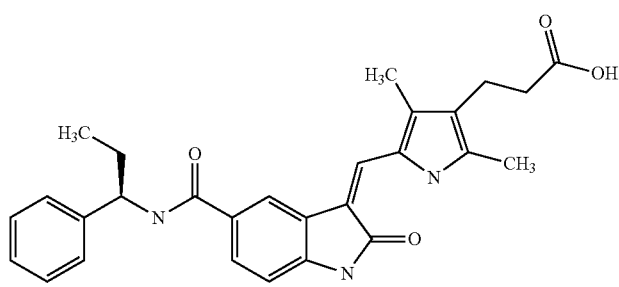 [SMILES: CC[C@@H](NC(=O)c1ccc2c(c1)/C(=C/c1[nH]c(C)c(CCC(=O)O)c1C)C(=O)N2)c1ccccc1]<br>(3Z)-3-{2,4-dimethyl-5-[2-oxo-5-(1R)-(1-phenyl-propylcarbamoyl)-1,2-dihydro-indol-3-ylidenemethyl]-1H-pyrrol-3-yl}-propionic acid |

| No. | Compound |
|---|---|
| II.131 | 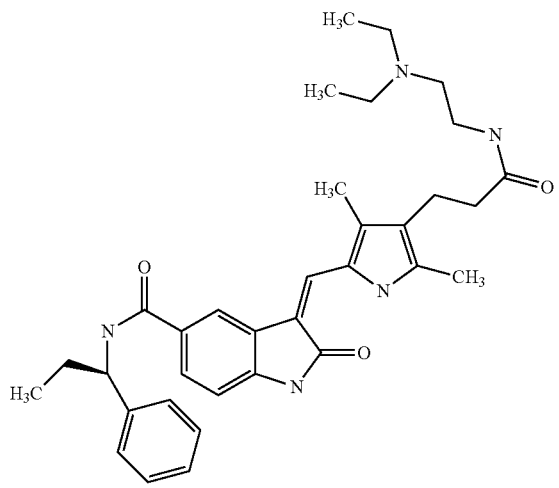 [SMILES: CC[C@@H](NC(=O)c1ccc2c(c1)/C(=C/c1[nH]c(C)c(CCC(=O)NCCN(CC)CC)c1C)C(=O)N2)c1ccccc1]
(3Z)-3-{4-[2-(2-diethylamino-ethylcarbamoyl)-ethyl]-3,5-dimethyl-1H-pyrrol-2-ylmethylene}-2-oxo-2,3-dihydro-1H-indole-5-carboxylic acid (1-phenyl-propyl)-amide |
| II.132 | 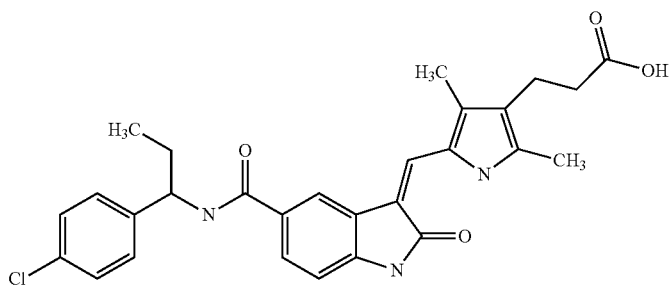 [SMILES: CCC(NC(=O)c1ccc2c(c1)/C(=C/c1[nH]c(C)c(CCC(=O)O)c1C)C(=O)N2)c1ccc(Cl)cc1]
(3Z)-3-(5-{5-[1-(4-chloro-phenyl)-propylcarbamoyl]-2-oxo-1,2-dihydro-indol-3-ylidenemethyl}-2,4-dimethyl-1H-pyrrol-3-yl)-propionic acid |
| II.133 | 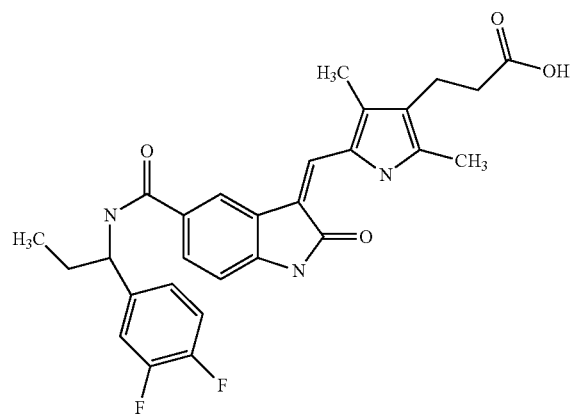 [SMILES: CCC(NC(=O)c1ccc2c(c1)/C(=C/c1[nH]c(C)c(CCC(=O)O)c1C)C(=O)N2)c1ccc(F)c(F)c1]
(3Z)-3-(5-{5-[1-(3,4-difluoro-phenyl)-propylcarbamoyl]-2-oxo-1,2-dihydro-indol-3-ylidenemethyl}-2,4-dimethyl-1H-pyrrol-3-yl)-propionic acid |

TABLE 3-continued

| No. | Compound |
|---|---|
| II.134 | 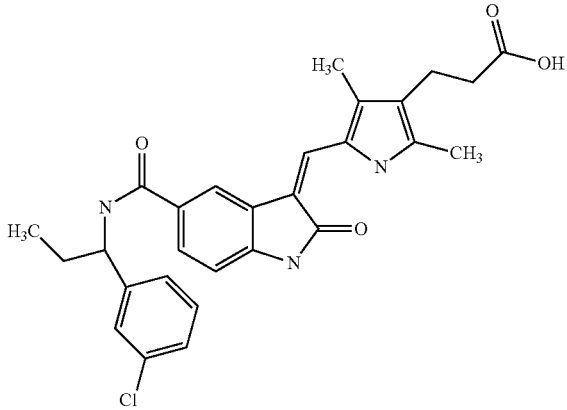 [SMILES: CCC(NC(=O)c1ccc2c(c1)/C(=C/c1[nH]c(C)c(CCC(=O)O)c1C)C(=O)N2)c1cccc(Cl)c1] (3Z)-3-(5-{5-[1-(3-chloro-phenyl)-propylcarbamoyl]-2-oxo-1,2-dihydro-indol-3-ylidenemethyl}-2,4-dimethyl-1H-pyrrol-3-yl)-propionic acid |
| II.135 | 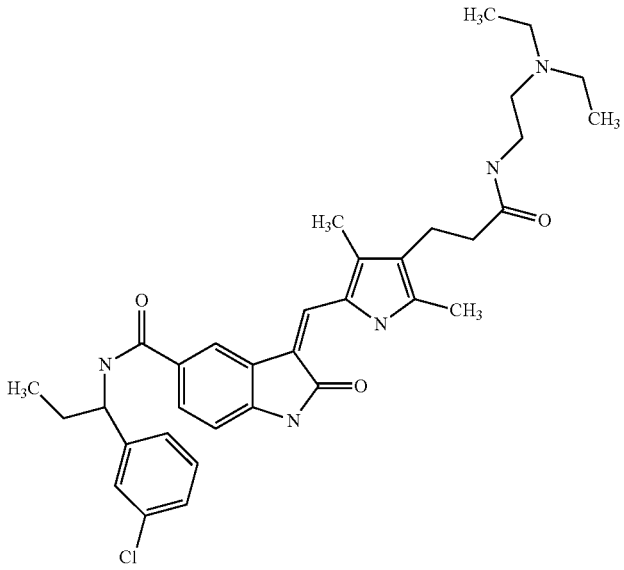 [SMILES: CCC(NC(=O)c1ccc2c(c1)/C(=C/c1[nH]c(C)c(CCC(=O)NCCN(CC)CC)c1C)C(=O)N2)c1cccc(Cl)c1] (3Z)-3-{4-[2-(2-diethylamino-ethylcarbamoyl)-ethyl]-3,5-dimethyl-1H-pyrrol-2-ylmethyiene}-2-oxo-2,3-dihydro-1H-indole-5-carboxylic acid [1-(3-chloro-phenyl)-propyl]-amide |
| II.136 | 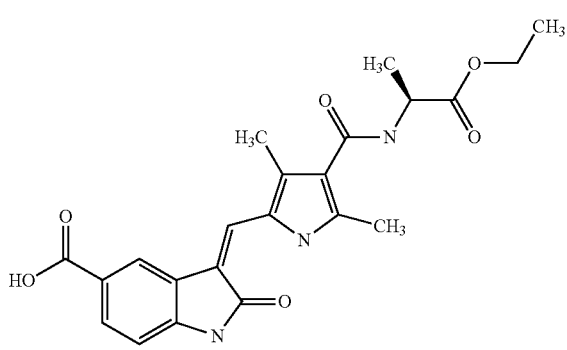 [SMILES: CCOC(=O)[C@H](C)NC(=O)c1c(C)[nH]c(/C=C2\C(=O)Nc3ccc(C(=O)O)cc32)c1C] (3Z)-3-[4-(1S)-1-ethoxycarbonyl-ethylcarbamoyl)-3,5-dimethyl-1H-pyrrol-2-ylmethylene]-2-oxo-2,3-dihydro-1H-indole-5-carboxylic acid |

| No. | Compound |
|---|---|
| II.137 | 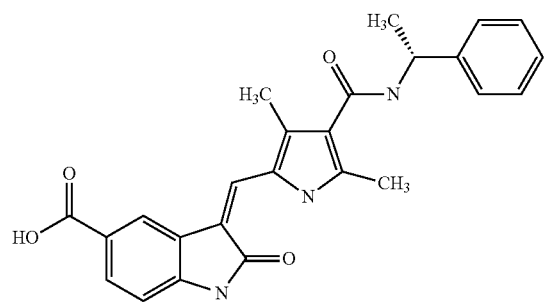 [SMILES: Cc1[nH]c(/C=C2\C(=O)Nc3ccc(C(=O)O)cc32)c(C)c1C(=O)N[C@H](C)c1ccccc1] (3Z)-3-[3,5-dimethyl-4-((1R)-1-phenyl-ethylcarbamoyl)-1H-pyrrol-2-ylmethylene]-2-oxo-2,3-dihydro-1H-indole-5-carboxylic acid |
| II.138 | 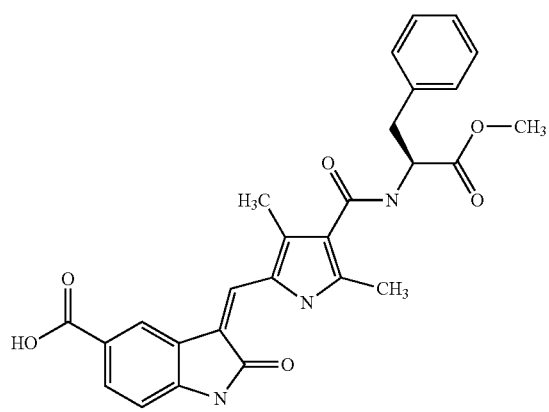 [SMILES: COC(=O)[C@H](Cc1ccccc1)NC(=O)c1c(C)[nH]c(/C=C2\C(=O)Nc3ccc(C(=O)O)cc32)c1C] (3Z)-3-[3,5-dimethyl-4-((1R)-1-phenyl-ethylcarbamoyl)-1H-pyrrol-2-ylmethylene]-2-oxo-2,3-dihydro-1H-indole-5-carboxylic acid |
| II.139 | 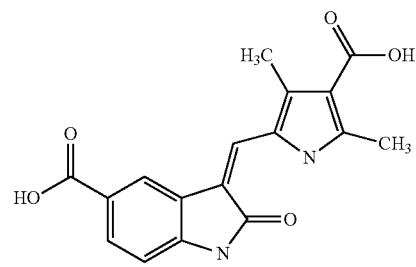 [SMILES: Cc1[nH]c(/C=C2\C(=O)Nc3ccc(C(=O)O)cc32)c(C)c1C(=O)O] (3Z)-3-(4-carboxy-3,5-dimethyl-1H-pyrrol-2-ylmethylene)-2-oxo-2,3-dihydro-1H-indole-5-carboxylic acid |

TABLE 3-continued

| No. | Compound |
| --- | --- |
| II.140 | 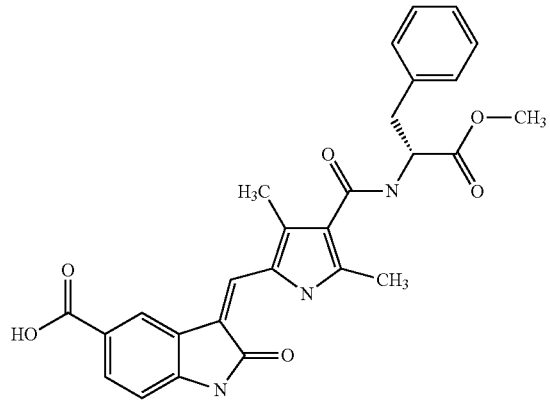 [SMILES: COC(=O)[C@@H](Cc1ccccc1)NC(=O)c1c(C)[nH]c(/C=C2\C(=O)Nc3ccc(C(=O)O)cc32)c1C]
(3Z)-3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5-carboxylic acid |
| II.141 | 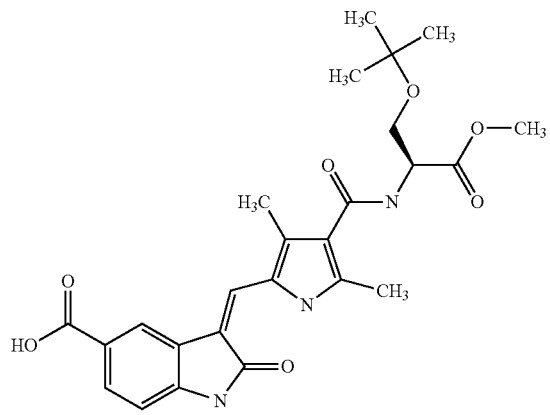 [SMILES: COC(=O)[C@H](COC(C)(C)C)NC(=O)c1c(C)[nH]c(/C=C2\C(=O)Nc3ccc(C(=O)O)cc32)c1C]
(3Z)-3-[4-(2-tert-butoxy-(1S)-1-methoxycarbonyl-ethylcarbamoyl)-3,5-dimethyl-1H-pyrrol-2-ylmethylene]-2-oxo-2,3-dihydro-1H-indole-5-carboxylic acid |
| II.142 | 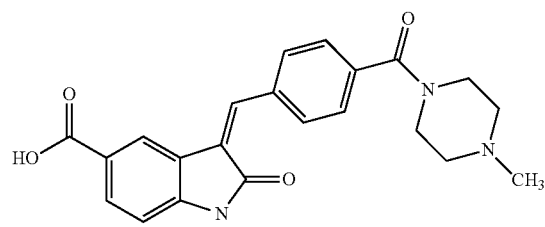 [SMILES: CN1CCN(C(=O)c2ccc(/C=C3\C(=O)Nc4ccc(C(=O)O)cc43)cc2)CC1]
(3Z)-3-[4-(4-methyl-piperazine-1-carbonyl)-benzylidene]-2-oxo-2,3-dihydro-1H-indole-5-carboxylic acid |
| II.143 | 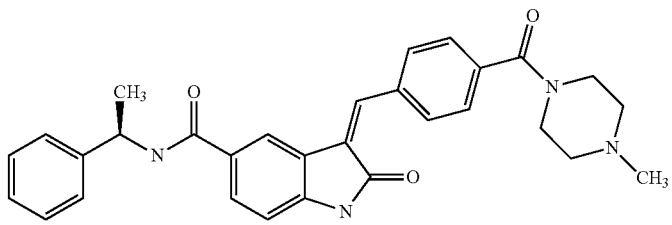 [SMILES: C[C@@H](NC(=O)c1ccc2c(c1)/C(=C/c1ccc(C(=O)N3CCN(C)CC3)cc1)C(=O)N2)c1ccccc1]
(3Z)-3-[4-(4-methyl-piperazine-1-carbonyl)-benzylidene]-2-oxo-2,3-dihydro-1H-indole-5-carboxylic acid (1R)-(1-phenyl-ethyl)-amide |

TABLE 3-continued

| No. | Compound |
|---|---|
| II.144 | 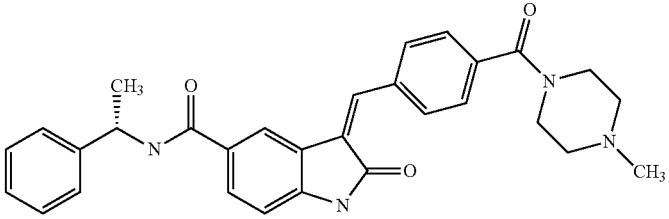 [SMILES: C[C@H](NC(=O)c1ccc2c(c1)/C(=C/c1ccc(C(=O)N3CCN(C)CC3)cc1)C(=O)N2)c1ccccc1]<br>(3Z)-3-[4-(4-methyl-piperazine-1-carbonyl)-benzylidene]-2-oxo-2,3-dihydro-1H-indole-5-carboxylic acid (1S)-(1-phenyl-ethyl)-amide |
| II.145 | 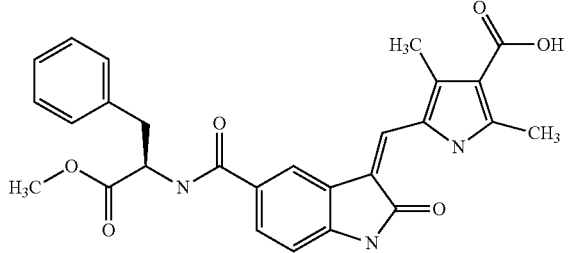 [SMILES: COC(=O)[C@@H](Cc1ccccc1)NC(=O)c1ccc2c(c1)/C(=C/c1[nH]c(C)c(C(=O)O)c1C)C(=O)N2]<br>(3Z)-5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carboxylic acid |
| II.146 | 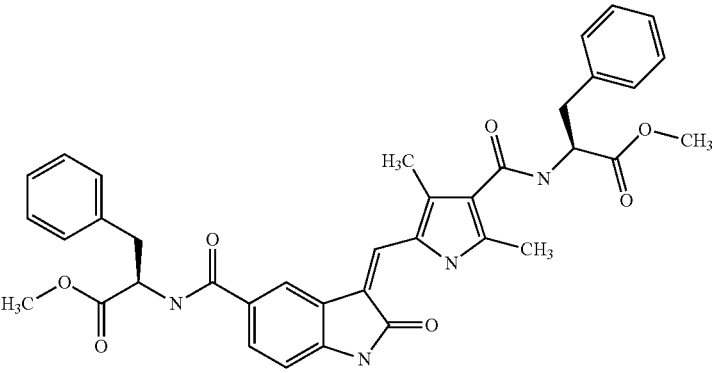<br>(3Z)-2-({3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2R)-3-phenyl-propionic acid methyl ester |
| II.147 | 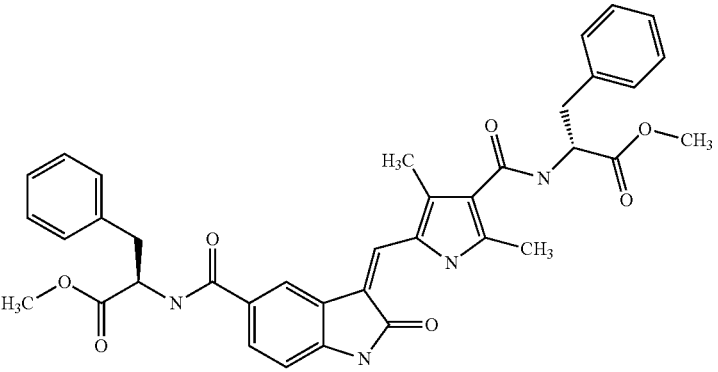<br>(3Z)-2-({3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2R)-3-phenyl-propionic acid methyl ester |

| No. | Compound |
|---|---|
| II.148 | 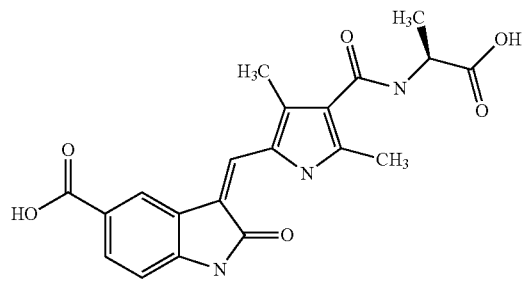 [SMILES: Cc1[nH]c(/C=C2\C(=O)Nc3ccc(C(=O)O)cc32)c(C)c1C(=O)N[C@@H](C)C(=O)O]<br>(3Z)-3-[4-(1-carboxy-(1R)-ethylcarbamoyl)-3,5-dimethyl-1H-pyrrol-2-ylmethylene]-2-oxo-2,3-dihydro-1H-indole-5-carboxylic acid |
| II.149 | 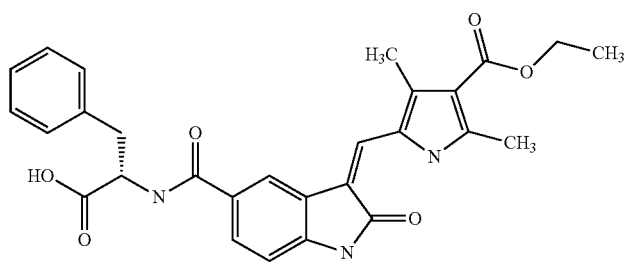 [SMILES: CCOC(=O)c1c(C)[nH]c(/C=C2\C(=O)Nc3ccc(C(=O)N[C@@H](Cc4ccccc4)C(=O)O)cc32)c1C]<br>(3Z)-5-[5-((1S)-1-carboxy-2-phenyl-ethylcarbamoyl)-2-oxo-1,2-dihydro-indol-3-ylidenemethyl]-2,4-dimethyl-1H-pyrrole-3-carboxylic acid ethyl ester |
| II.150 | 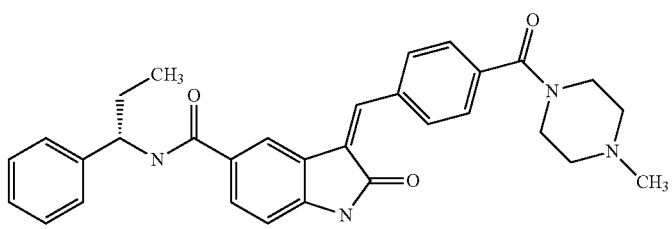 [SMILES: CC[C@H](NC(=O)c1ccc2c(c1)/C(=C/c1ccc(C(=O)N3CCN(C)CC3)cc1)C(=O)N2)c1ccccc1]<br>(3Z)-3-[4-(4-methyl-piperazine-1-carbonyl)-benzylidene]-2-oxo-2,3-dihydro-1H-indole-5-carboxylic acid ((1S)-1-phenyl-propyl)-amide |
| II.151 | 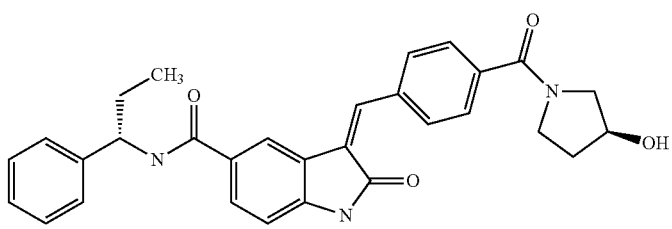 [SMILES: CC[C@H](NC(=O)c1ccc2c(c1)/C(=C/c1ccc(C(=O)N3CC[C@H](O)C3)cc1)C(=O)N2)c1ccccc1]<br>(3Z)-3-[4-((3S)-3-hydroxy-pyrrolidine-1-carbonyl)-benzylidene]-2-oxo-2,3-dihydro-1H-indole-5-carboxylic acid ((1S)-1-phenyl-propyl)-amide |

| No. | Compound |
| --- | --- |
| II.152 | 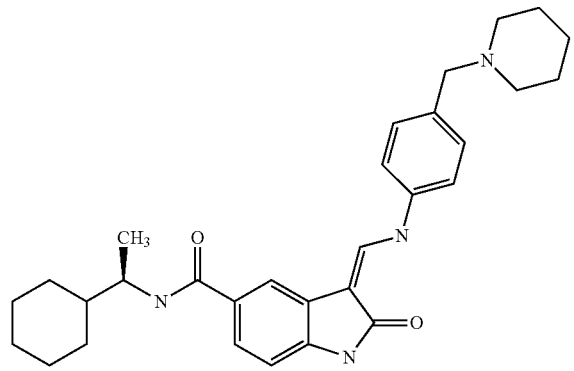 [SMILES: C[C@@H](NC(=O)c1ccc2c(c1)/C(=C/Nc1ccc(CN3CCCCC3)cc1)C(=O)N2)C1CCCCC1]
(3Z)-2-oxo-3-[(4-piperidin-1-ylmethyl-phenylamino)-methylene]-2,3-dihydro-1H-indole-5-carboxylic acid ((1R)-1-cyclohexyl-ethyl)-amide |
| II.153 | 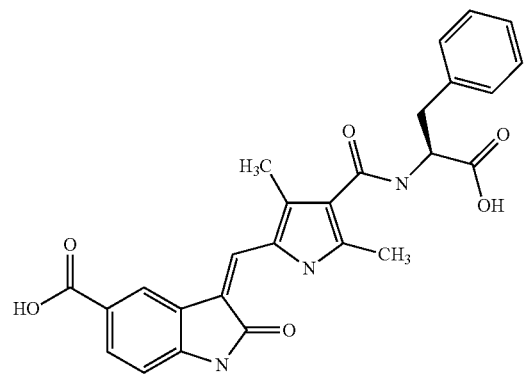 [SMILES: Cc1[nH]c(/C=C2\C(=O)Nc3ccc(C(=O)O)cc32)c(C)c1C(=O)N[C@@H](Cc1ccccc1)C(=O)O]
(3Z)-3-[4-((1R)-1-carboxy-2-phenyl-ethylcarbamoyl)-3,5-dimethyl-1H-pyrrol-2-ylmethylene]-2-oxo-2,3-dihydro-1H-indole-5-carboxylic acid |
| II.154 | 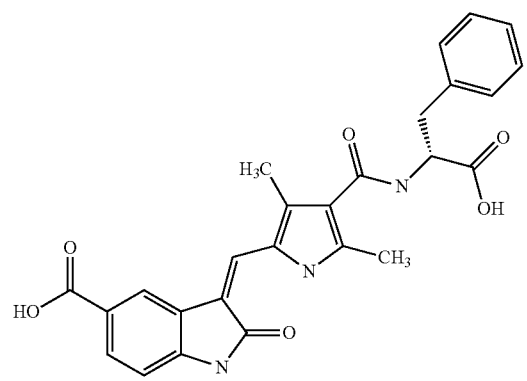 [SMILES: Cc1[nH]c(/C=C2\C(=O)Nc3ccc(C(=O)O)cc32)c(C)c1C(=O)N[C@H](Cc1ccccc1)C(=O)O]
(3Z)-3-[4-((1S)-1-carboxy-2-phenyl-ethylcarbamoyl)-3,5-dimethyl-1H-pyrrol-2-ylmethylene]-2-oxo-2,3-dihydro-1H-indole-5-carboxylic acid |

TABLE 3-continued

| No. | Compound |
|---|---|
| II.155 | 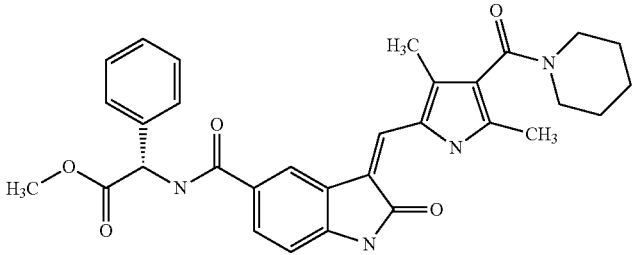 [SMILES: COC(=O)[C@@H](NC(=O)c1ccc2c(c1)/C(=C/c1[nH]c(C)c(C(=O)N3CCCCC3)c1C)C(=O)N2)c1ccccc1]<br>(3Z)-({3-[3,5-dimethyl-4-(piperidine-1-carbonyl)-1H-pyrrol-2-ylmethylene]-2-oxo-2,3-dihydro-1H-indole-5-carbonyl}-amino)-(S)-phenyl-acetic acid methyl ester |
| II.156 | 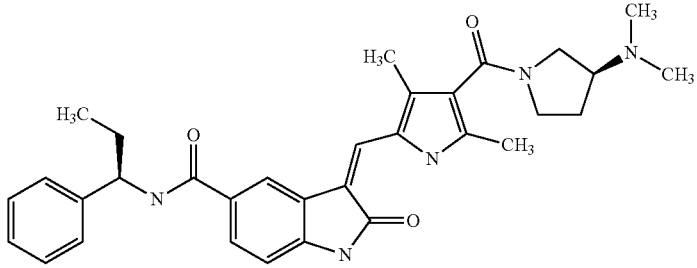 [SMILES: CC[C@@H](NC(=O)c1ccc2c(c1)/C(=C/c1[nH]c(C)c(C(=O)N3CC[C@H](N(C)C)C3)c1C)C(=O)N2)c1ccccc1]<br>(3Z)-3-[4-((3S)-3-dimethylamino-pyrrolidine-1-carbonyl)-3,5-dimethyl-1H-pyrrol-2-ylmethylene]-2-oxo-2,3-dihydro-1H-indole-5-carboxylic acid ((S)-1-phenyl-propyl)-amide |
| II.157 | 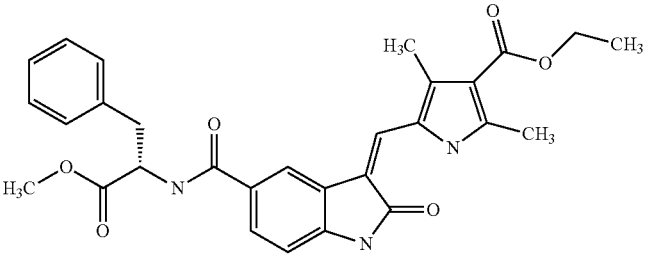 [SMILES: CCOC(=O)c1c(C)[nH]c(/C=C2\C(=O)Nc3ccc(C(=O)N[C@@H](Cc4ccccc4)C(=O)OC)cc32)c1C]<br>(3Z)-5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carboxylic II. acid ester ethyl |
| II.158 | 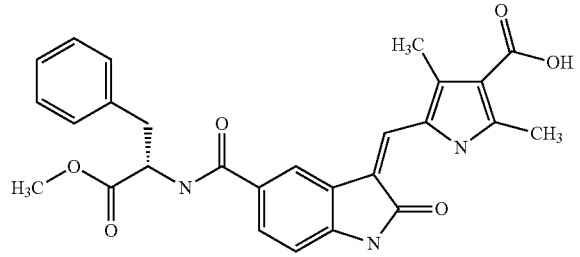 [SMILES: COC(=O)[C@H](Cc1ccccc1)NC(=O)c1ccc2c(c1)/C(=C/c1[nH]c(C)c(C(=O)O)c1C)C(=O)N2]<br>(3Z)-5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carboxylic acid |

TABLE 3-continued

| No. | Compound |
|---|---|
| II.159 | 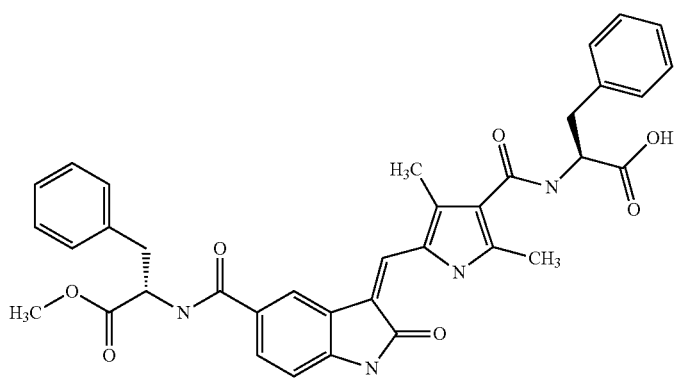 [SMILES: COC(=O)[C@H](Cc1ccccc1)NC(=O)c1ccc2c(c1)/C(=C/c1[nH]c(C)c(C(=O)N[C@@H](Cc3ccccc3)C(=O)O)c1C)C(=O)N2]

(3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-3-phenyl-(2S)-propionic acid |
| II.160 | 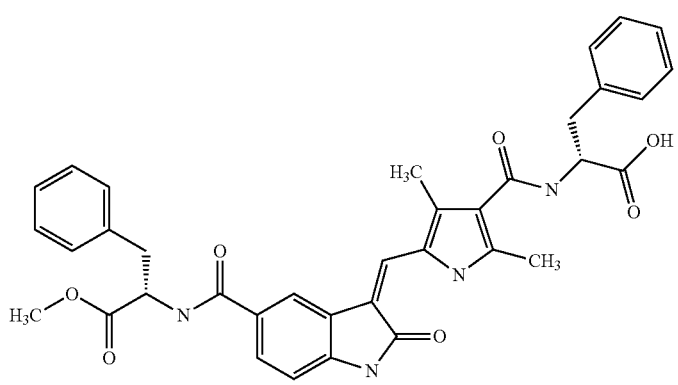 [SMILES: COC(=O)[C@H](Cc1ccccc1)NC(=O)c1ccc2c(c1)/C(=C/c1[nH]c(C)c(C(=O)N[C@H](Cc3ccccc3)C(=O)O)c1C)C(=O)N2]

(3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-3-phenyl-(2R)-propionic acid |
| II.161 | 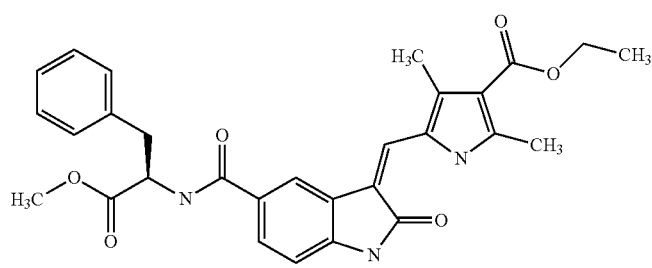 [SMILES: CCOC(=O)c1c(C)[nH]c(/C=C2\C(=O)Nc3ccc(C(=O)N[C@H](Cc4ccccc4)C(=O)OC)cc32)c1C]

(3Z)-5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carboxylic acid ethyl ester |

TABLE 3-continued

| No. | Compound |
|---|---|
| II.162 | 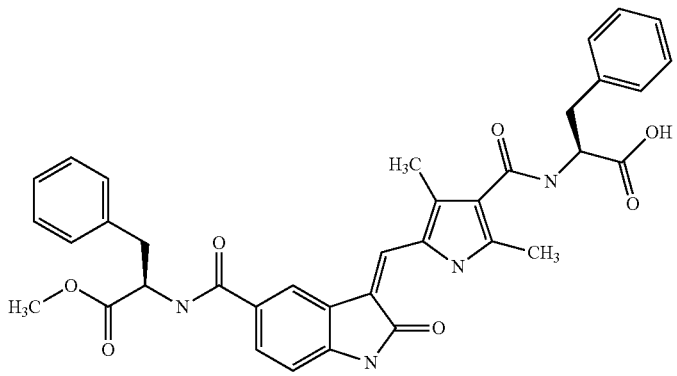 [SMILES: COC(=O)[C@@H](Cc1ccccc1)NC(=O)c1ccc2c(c1)/C(=C/c1[nH]c(C)c(C(=O)N[C@@H](Cc3ccccc3)C(=O)O)c1C)C(=O)N2]<br>(3Z)-2-({5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-(2S)-3-phenyl-propionic acid |
| II.163 | 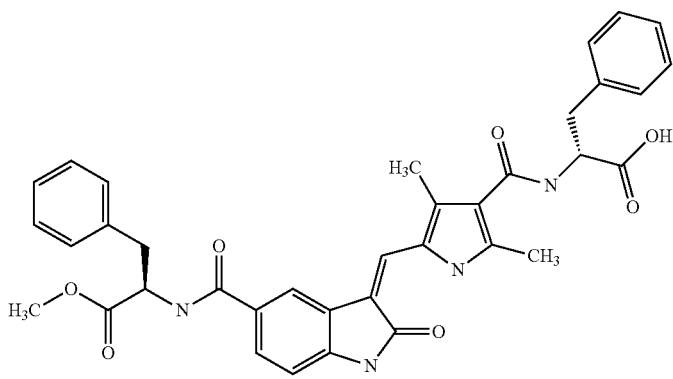 [SMILES: COC(=O)[C@@H](Cc1ccccc1)NC(=O)c1ccc2c(c1)/C(=C/c1[nH]c(C)c(C(=O)N[C@H](Cc3ccccc3)C(=O)O)c1C)C(=O)N2]<br>(3Z)-2-({5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carbonyl)-amino)-(2R)-3-phenyl-propionic acid |
| II.164 | 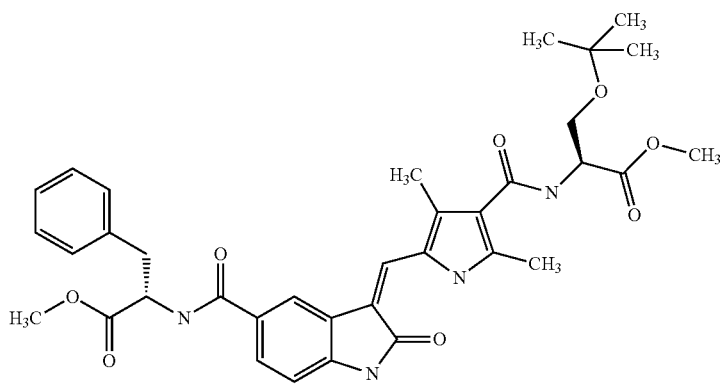<br>(3Z)-2-({3-[4-((1S)-2-tert-butoxy-1-methoxycarbonyl-ethylcarbamoyl)-3,5-dimethyl-1H-pyrrol-2-ylmethylene]-2-oxo-2,3-dihydro-1H-indole-5-carbonyl}-amino)-(2S)-3-phenyl-propionic acid methyl ester |

TABLE 3-continued

| No. | Compound |
|---|---|
| II.165 | 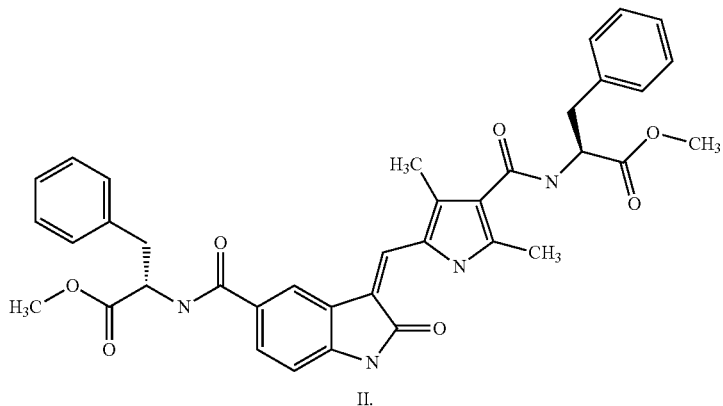<br>(3Z)-2-({3-[4-((1S)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2S)-3-phenyl-propionic acid methyl ester |
| II.166 | 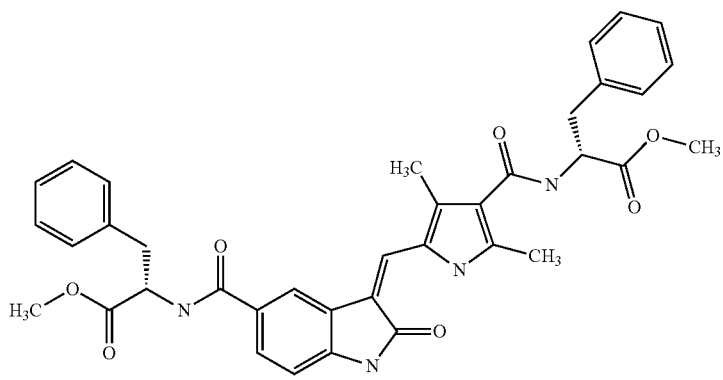<br>(3Z)-2-({3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2S)-3-phenyl-propionic acid methyl ester |
| II.167 | 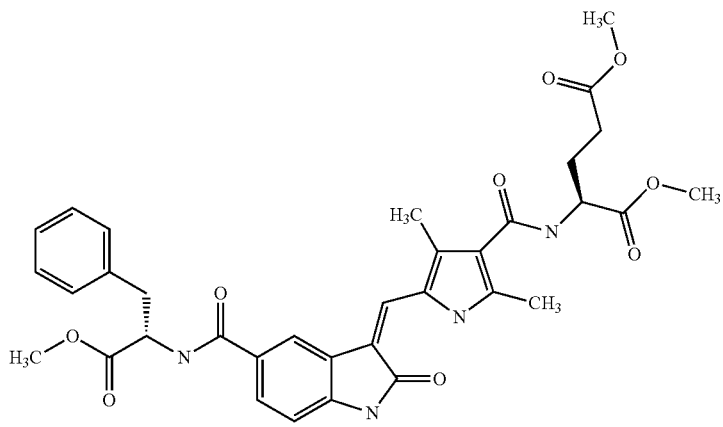<br>(3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-(S)-pentanedioic acid dimethyl ester |

TABLE 3-continued

| No. | Compound |
|---|---|
| II.168 | 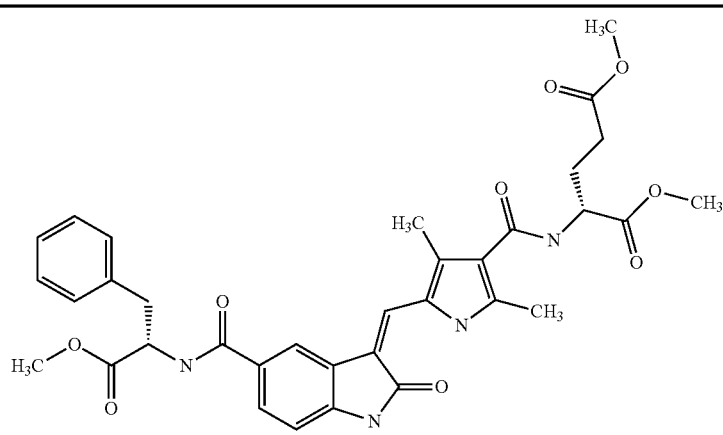<br>(3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-(R)-pentanedioic acid dimethyl ester |
| II.169 | 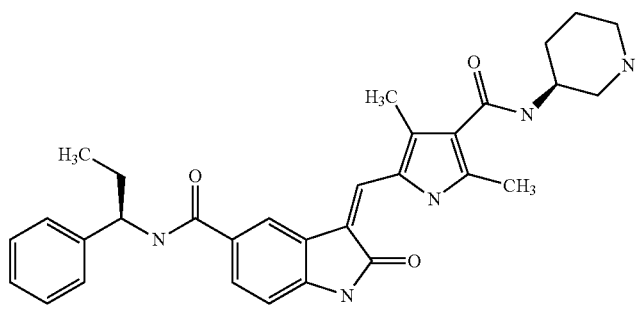 [SMILES: CC[C@@H](NC(=O)c1ccc2c(c1)/C(=C/c1[nH]c(C)c(C(=O)N[C@H]3CCCNC3)c1C)C(=O)N2)c1ccccc1]<br>(3Z)-3-[3,5-dimethyl-4-((3R)-piperidin-3-ylcarbamoyl)-1H-pyrrol-2-ylmethylene]-2-oxo-2,3-dihydro-1H-indole-5-carboxylic acid ((1R)-1-phenyl-propyl)-amide |
| II.170 | 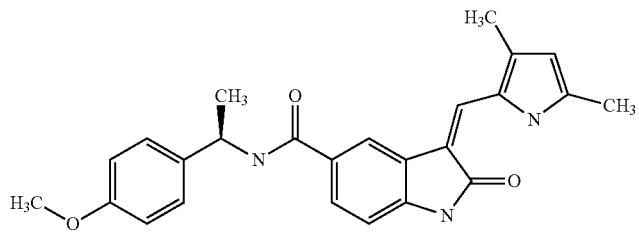<br>(3Z)-3-(3,5-dimethyl-1H-pyrrol-2-ylmethylene)-2-oxo-2,3-dihydro-1H-indole-5-carboxylic acid [(1R)-1-(4-methoxy-phenyl)-ethyl]-amide |
| II.171 | 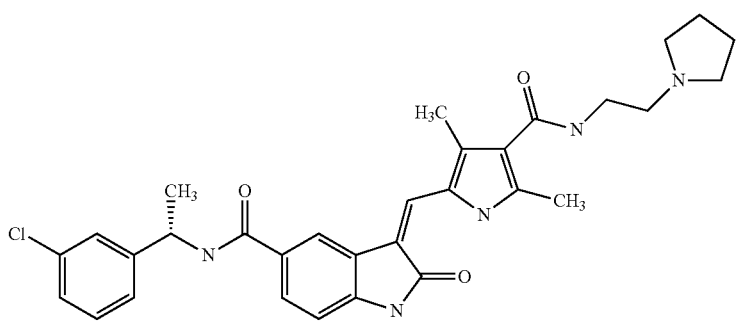 [SMILES: Cc1[nH]c(/C=C2\C(=O)Nc3ccc(C(=O)N[C@@H](C)c4cccc(Cl)c4)cc32)c(C)c1C(=O)NCCN1CCCC1]<br>(3Z)-3-[3,5-dimethyl-4-(2-pyrrolidin-1-yl-ethylcarbamoyl)-1H-pyrrol-2-ylmethylene]-2-oxo-2,3-dihydro-1H-indole-5-carboxylic acid [(1S)-1-(3-chloro-phenyl)-ethyl]-amide |

TABLE 3-continued

| No. | Compound |
|---|---|
| II.172 | 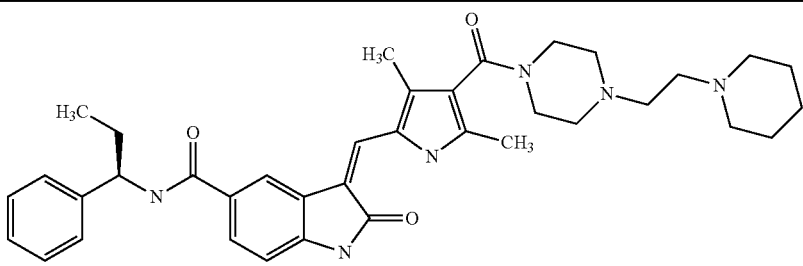<br>(3Z)-3-{3,5-dimethyl-4-[4-(2-piperidin-1-yl-ethyl)-piperazine-1-carbonyl]-1H-pyrrol-2-ylmethylene}-2-oxo-2,3-dihydro-1H-indole-5-carboxylic acid ((1R)-1-phenyl-propyl)-amide |
| II.173 | 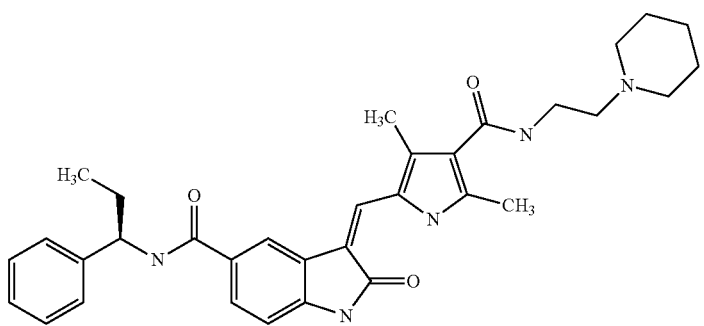 [SMILES: CC[C@@H](NC(=O)c1ccc2c(c1)/C(=C/c1[nH]c(C)c(C(=O)NCCN3CCCCC3)c1C)C(=O)N2)c1ccccc1]<br>(3Z)-3-[3,5-dimethyl-4-(2-piperidin-1-yl-ethylcarbamoyl)-1H-pyrrol-2-ylmethylene]-2-oxo-2,3-dihydro-1H-indole-5-carboxylic acid ((1R)-1-phenyl-propyl)-amide |
| II.174 | 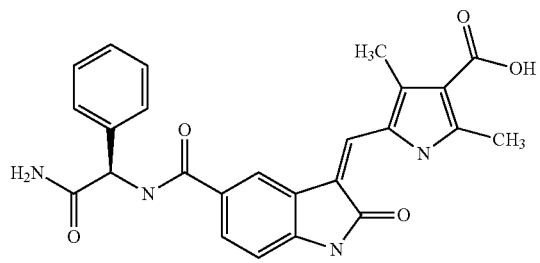 [SMILES: Cc1[nH]c(/C=C2\C(=O)Nc3ccc(C(=O)N[C@@H](C(N)=O)c4ccccc4)cc32)c(C)c1C(=O)O]<br>5-{5-[(R)-(carbamoyl-phenyl-methyl)-carbamoyl]-2-oxo-1,2-dihydro-indol-3-ylidenemethyl}-2,4-dimethyl-1H-pyrrole-3-carboxylic acid |
| II.175 | 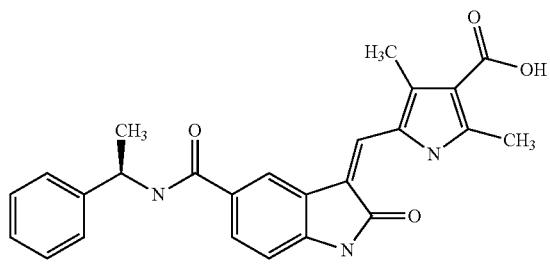 [SMILES: Cc1[nH]c(/C=C2\C(=O)Nc3ccc(C(=O)N[C@H](C)c4ccccc4)cc32)c(C)c1C(=O)O]<br>(3Z)-2,4-dimethyl-5-[2-oxo-5-((1R)-1-phenyl-ethylcarbamoyl)-1,2-dihydro-indol-3-ylidenemethyl]-1H-pyrrole-3-carboxylic acid |

| No. | Compound |
|---|---|
| II.176 | 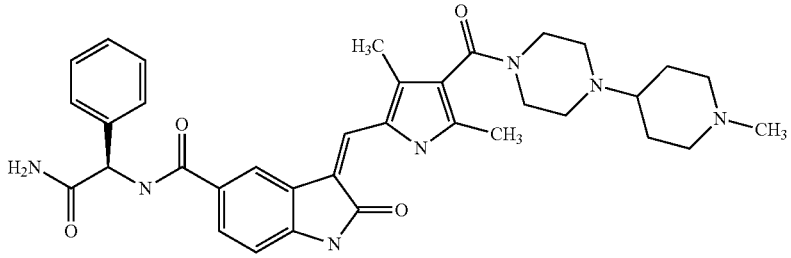 [SMILES: Cc1[nH]c(/C=C2\C(=O)Nc3ccc(C(=O)N[C@@H](C(N)=O)c4ccccc4)cc32)c(C)c1C(=O)N1CCN(C2CCN(C)CC2)CC1]
(3Z)-3-{3,5-dimethyl-4-[4-(1-methyl-piperidin-4-yl)-piperazine-1-carbonyl]-
1H-pyrrol-2-ylmethylene}-2-oxo-2,3-dihydro-1H-indole-5-carboxylic acid
(R)-(carbamoyl-phenyl-methyl)-amide |
| II.177 | 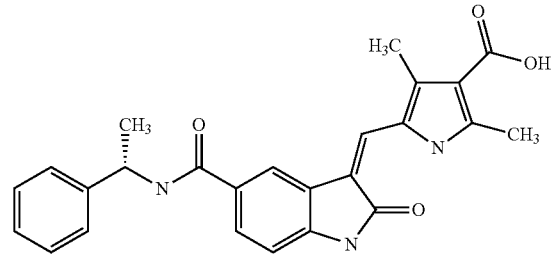 [SMILES: Cc1[nH]c(/C=C2\C(=O)Nc3ccc(C(=O)N[C@@H](C)c4ccccc4)cc32)c(C)c1C(=O)O]
(3Z)-2,4-dimethyl-5-[2-oxo-5-((1S)-1-phenyl-ethylcarbamoyl)-1,2-dihydro-
indol-3-ylidenemethyl]-1H-pyrrole-3-carboxylic acid |
| II.178 | 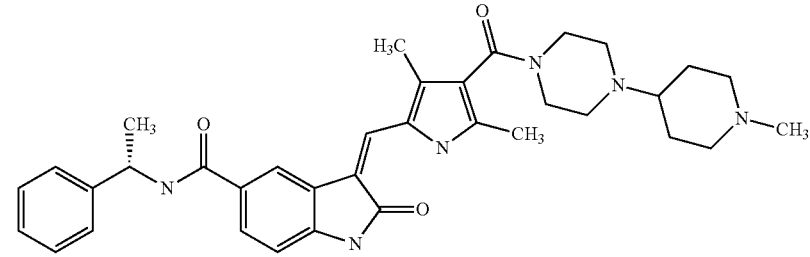 [SMILES: Cc1[nH]c(/C=C2\C(=O)Nc3ccc(C(=O)N[C@@H](C)c4ccccc4)cc32)c(C)c1C(=O)N1CCN(C2CCN(C)CC2)CC1]
(3Z)-3-{3,5-dimethyl-4-[4-(1-methyl-piperidin-4-yl)-piperazine-1-carbonyl]-
1H-pyrrol-2-ylmethylene}-2-oxo-2,3-dihydro-1H-indole-5-carboxylic acid
((1S)-1-phenyl-ethyl)-amide |
| II.179 | 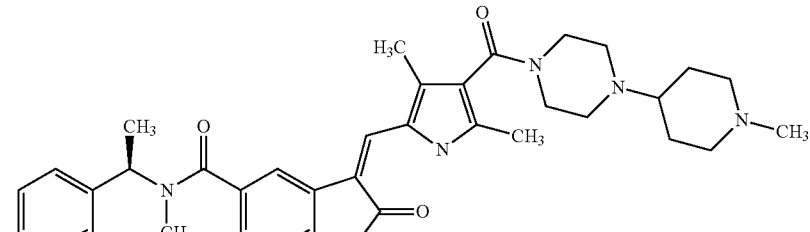
(3Z)-3-{3,5-dimethyl-4-[4-(1-methyl-piperidin-4-yl)-piperazine-1-carbonyl]-
1H-pyrrol-2-ylmethylene}-2-oxo-2,3-dihydro-1H-indole-5-carboxylic acid
methyl-((1R)-1-phenyl-ethyl)-amide |

TABLE 3-continued

| No. | Compound |
|---|---|
| II.180 | 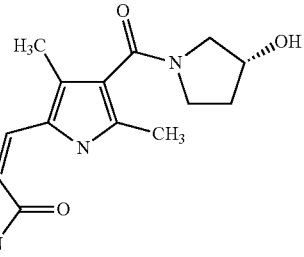<br>(3Z)-3-[4-((3R)-3-hydroxy-pyrrolidine-1-carbonyl)-3,5-dimethyl-1H-pyrrol-2-ylmethylene]-2-oxo-2,3-dihydro-1H-indole-5-carboxylic acid ((1R)-1-p-tolyl-ethyl)-amide |
| II.181 | 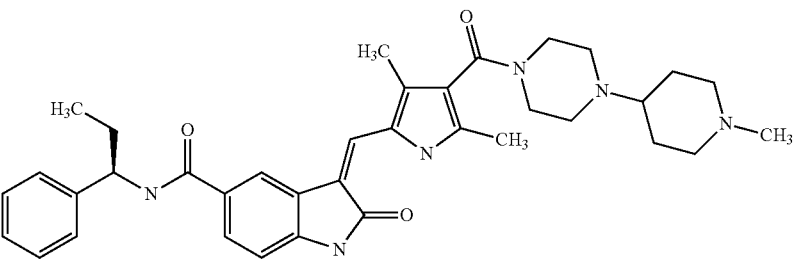 [SMILES: CC[C@@H](NC(=O)c1ccc2c(c1)/C(=C/c1[nH]c(C)c(C(=O)N3CCN(C4CCN(C)CC4)CC3)c1C)C(=O)N2)c1ccccc1]<br>(3Z)-3-{3,5-dimethyl-4-[4-(1-methyl-piperidin-4-yl)-piperazine-1-carbonyyl]-1H-pyrrol-2-ylmethylene}-2-oxo-2,3-dihydro-1H-indole-5-carboxylic acid ((1R)-1-phenyl-propyl)-amide |
| II.182 | 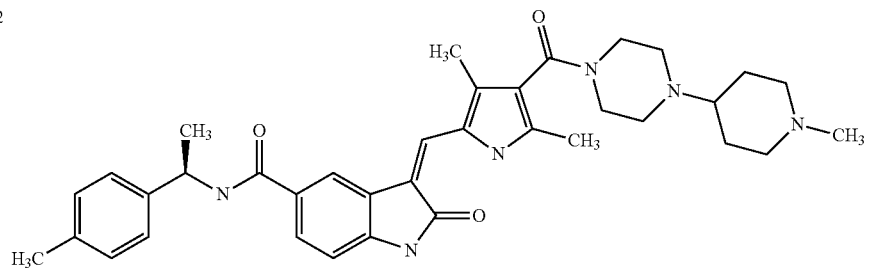<br>(3Z)-3-{3,5-dimethyl-4-[4-(1-methyl-piperidin-4-yl)-piperazine-1-carbonyyl]-1H-pyrrol-2-ylmethylene}-2-oxo-2,3-dihydro-1H-indole-5-carboxylic acid ((1R)-1-p-tolyl-ethyl)-amide |
| II.183 | 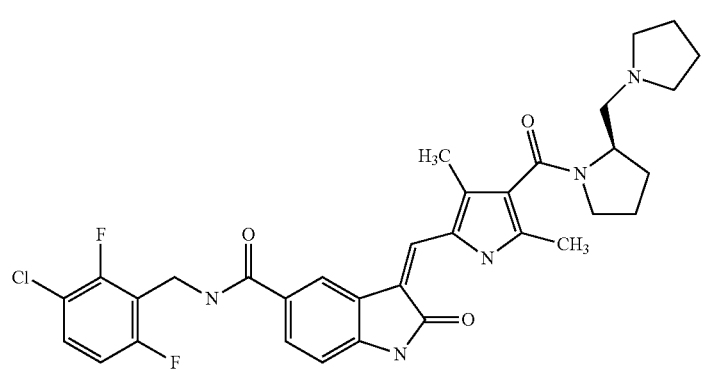 [SMILES: Cc1[nH]c(/C=C2\C(=O)Nc3ccc(C(=O)NCc4c(F)ccc(Cl)c4F)cc32)c(C)c1C(=O)N1CCC[C@@H]1CN1CCCC1]<br>(3Z)-3-[3,5-dimethyl-4-((2R)-2-pyrrolidin-1-ylmethyl-pyrrolidine-1-carbonyl)-1H-pyrrol-2-ylmethylene]-2-oxo-2,3-dihydro-1H-indole-5-carboxylic acid 3-chloro-2,6-difluoro-benzylamide |

TABLE 3-continued

| No. | Compound |
|---|---|
| II.184 | 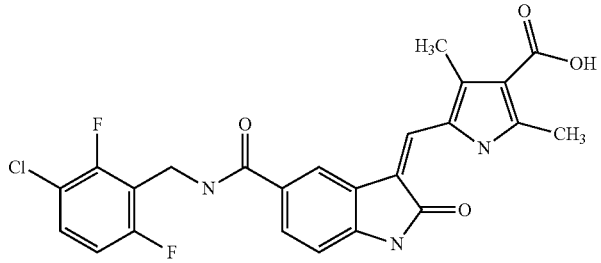 [SMILES: Cc1[nH]c(/C=C2\C(=O)Nc3ccc(C(=O)NCc4c(F)ccc(Cl)c4F)cc32)c(C)c1C(=O)O]<br>(3Z)-5-[5-(3-chloro-2,6-difluoro-benzylcarbamoyl)-2-oxo-1,2-dihydro-indol-3-ylidenemethyl]-2,4-dimethyl-1H-pyrrole-3-carboxylic acid |
| II.185 | 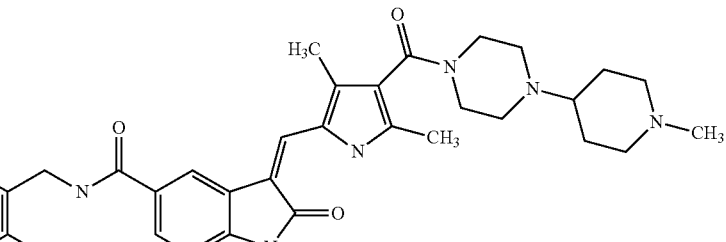<br>(3Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid 3-chloro-2,6-difluoro-benzylamide |
| II.186 | 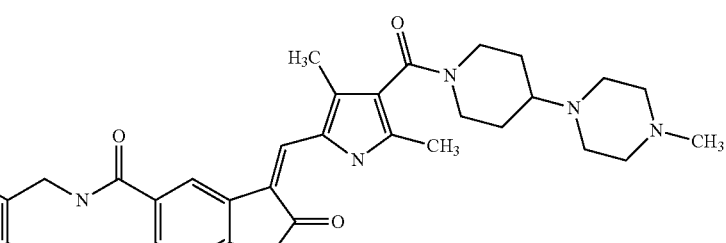<br>(3Z)-3-[3,5-dimethy l-4-(1'-methyl-[4,4']bipiperidinyl-1 -carbonyl)-1H-pyrrol-2-ylmethylene]-2-oxo-2,3-dihydro-1H-indole-5-carboxylic acid 3-chloro-2,6-difluoro-benzylamide |
| II.187 | 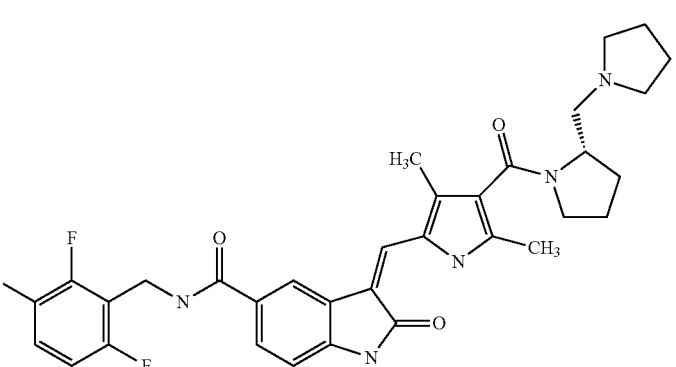<br>(3Z)-3-[3,5-dimethyl-4-((2S)-2-pyrrolidin-1-ylmethyl-pyrrolidine-1-carbonyl)-1H-pyrrol-2-ylmethylene]-2-oxo-2,3-dihydro-1H-indole-5-carboxylic acid 3-chloro-2,6-difluoro-benzylamide |

| No. | Compound |
|---|---|
| II.188 | 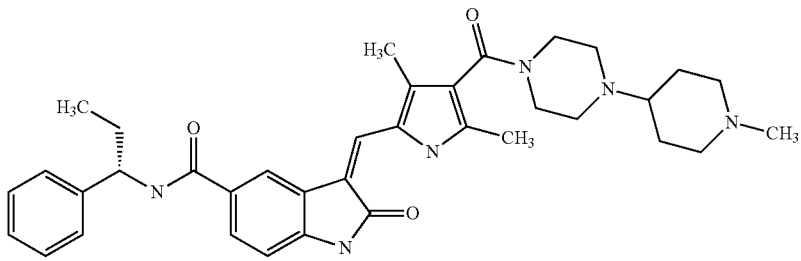 [SMILES: CC[C@H](NC(=O)c1ccc2c(c1)/C(=C/c1[nH]c(C)c(C(=O)N3CCN(C4CCN(C)CC4)CC3)c1C)C(=O)N2)c1ccccc1]

(3Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid ((1S)-1-phenyl-propyl)-amide |
| II.189 | 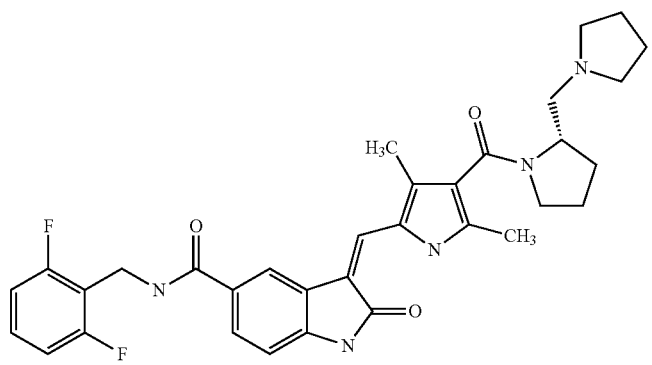 [SMILES: Cc1[nH]c(/C=C2\C(=O)Nc3ccc(C(=O)NCc4c(F)cccc4F)cc32)c(C)c1C(=O)N1CCC[C@H]1CN1CCCC1]

(3Z)-3-[3,5-dimethyl-4-((2S)-2-pyrrolidin-1-ylmethyl-pyrrolidine-1-carbonyl)-1H-pyrrol-2-ylmethylene]-2-oxo-2,3-dihydro-1H-indole-5-carboxylic acid 2,6-difluoro-benzylamide |
| II.190 | 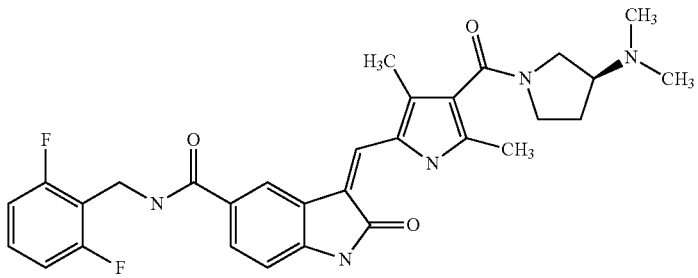 [SMILES: Cc1[nH]c(/C=C2\C(=O)Nc3ccc(C(=O)NCc4c(F)cccc4F)cc32)c(C)c1C(=O)N1CC[C@H](N(C)C)C1]

(3Z)-3-[4-((3S)-3-dimethylamino-pyrrolidine-1-carbonyl)-3,5-dimethyl-1H-pyrrol-2-ylmethylene]-2-oxo-2,3-dihydro-1H-indole-5-carboxylic acid 2,6-difluoro-benzylamide |
| II.191 | 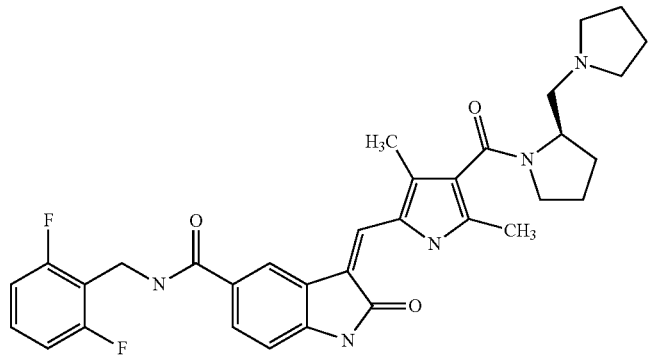 [SMILES: Cc1[nH]c(/C=C2\C(=O)Nc3ccc(C(=O)NCc4c(F)cccc4F)cc32)c(C)c1C(=O)N1CCC[C@@H]1CN1CCCC1]

(3Z)-3-[3,5-dimethyl-4-((2R)-2-pyrrolidin-1-ylmethyl-pyrrolidine-1-carbonyl)-1H-pyrrol-2-ylmethylene]-2-oxo-2,3-dihydro-1H-indole-5-carboxylic acid 2,6-difluoro-benzylamide |

TABLE 3-continued

| No. | Compound |
|---|---|
| II.192 | 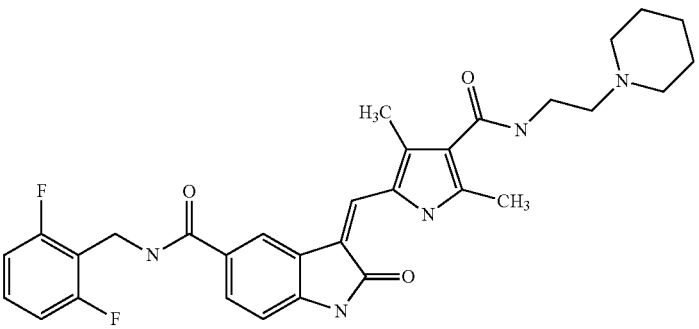 [SMILES: Cc1[nH]c(/C=C2\C(=O)Nc3ccc(C(=O)NCc4c(F)cccc4F)cc32)c(C)c1C(=O)NCCN1CCCCC1]<br>(3Z)-3-[3,5-dimethyl-4-(2-piperidin-1-yl-ethylcarbamoyl)-1H-pyrrol-2-ylmethylene]-2-oxo-2,3-dihydro-1H-indole-5-carboxylic acid 2,6-difluoro-benzylamide |
| II.193 | 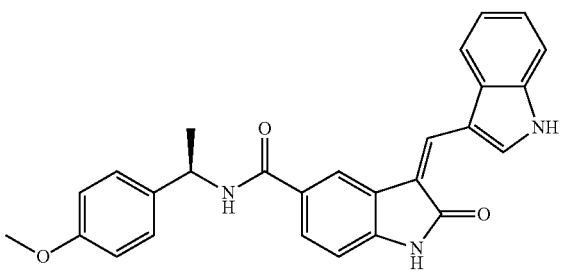 [SMILES: COc1ccc([C@@H](C)NC(=O)c2ccc3c(c2)/C(=C/c2c[nH]c4ccccc24)C(=O)N3)cc1]<br>(3Z)-3-(1H-indol-3-ylmethylene)-2-oxo-2,3-dihydro-1H-indole-5-carboxylic acid [(1R)-1-(4-methoxy-phenyl)-ethyl]-amide |

Further small molecules inhibiting GRK5 consist of the group III.

Wherein group III comprises
Compounds of the General Formula (X)

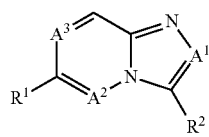

wherein
A$^1$, A$^2$ and A$^3$ represent independently of each other C—H or N, wherein one of A$^1$, A$^2$ and A$^3$ represents N;
R$^1$ represents —(CH$_2$)$_n$—R$^3$ or —NH—(CH$_2$)$_n$—R$^3$;
R$^2$ represents —(CH$_2$)$_m$—R$^4$ or —NHCO—(CH$_2$)$_m$—R$^4$;
R$^3$ and R$^4$ are independently of each other
—H, —F, —Cl, —Br, —I, —CN, —NO$_2$, —NHCH$_3$, —N(CH$_3$)$_2$, —CH═CH—C$_4$H$_9$, —CH═CH—C$_5$H$_{11}$, —CH═CH-Ph, —CH═CH—C$_6$H$_{13}$, —CH$_2$—OH; —C$_2$H$_4$—OH; —C$_3$H$_6$—OH, —C$_4$H$_9$—OH, —C$_5$H$_{10}$—OH, —C$_6$H$_{12}$—OH, —C$_7$H$_{14}$—OH, —C$_8$H$_{16}$—OH, —CH═CH—C$_3$H$_6$—OH, —CH═CH—C$_4$H$_8$—OH, —CH(CH$_2$OH)$_2$, —CH(C$_2$H$_5$)—CH$_2$—OH, —CH(CH$_3$)—C$_2$H$_4$—OH, —C(CH$_3$)$_2$—OH, —C(CH$_3$)$_2$—CH$_2$—OH, —CH(CH$_3$)OH, —CH$_2$—CH(CH$_3$)OH, —C(OH)(CH$_3$)—C$_2$H$_5$, —C(OH)(CH$_3$)—C$_3$H$_7$, —CH$_2$—C(OH)(CH$_3$)—C$_2$H$_5$, —CH(CH$_3$)—CH(CH$_3$)OH, —C(CH$_3$)$_2$—C$_2$H$_4$OH, —CH$_2$—C(CH$_3$)$_2$OH, —C(OH)(C$_2$H$_5$)$_2$, —C$_2$H$_4$—C(OH)(CH$_3$)$_2$, —C(CH(CH$_3$)$_2$)CH$_2$OH, —C$_3$H$_6$—C(OH)(CH$_3$)$_2$, —CH(CH(CH$_3$)$_2$)CH$_2$—OH, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —OCF$_3$, —CH$_2$—OCF$_3$, —C$_2$H$_4$—OCF$_3$, —C$_3$H$_6$—OCF$_3$, —OC$_2$F$_5$, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —C≡C—R$^5$, —R$^{11}$, —R$^{12}$;

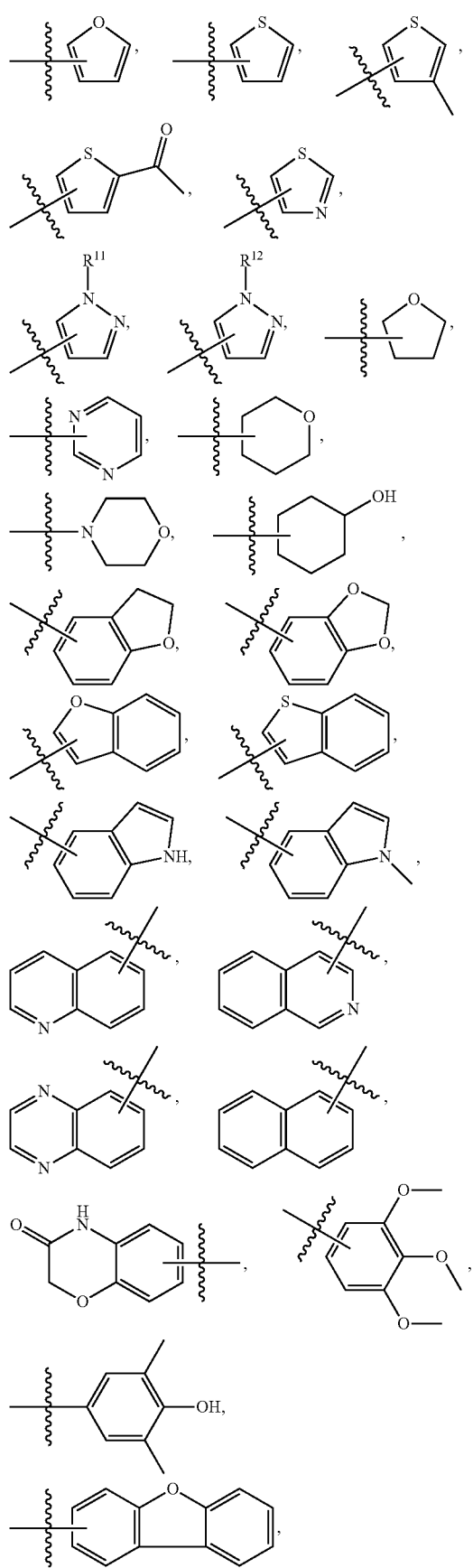
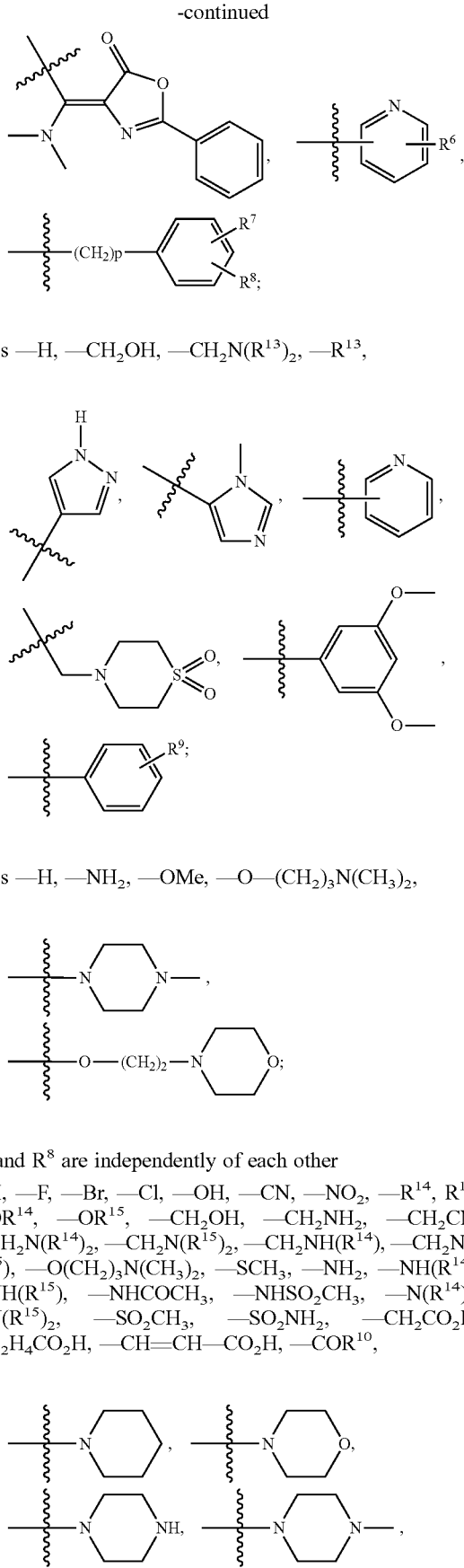
R[5] is —H, —CH$_2$OH, —CH$_2$N(R[13])$_2$, —R[13],
R[6] is —H, —NH$_2$, —OMe, —O—(CH$_2$)$_3$N(CH$_3$)$_2$,
R[7] and R[8] are independently of each other
—H, —F, —Br, —Cl, —OH, —CN, —NO$_2$, —R[14], R[15], —OR[14], —OR[15], —CH$_2$OH, —CH$_2$NH$_2$, —CH$_2$CN, —CH$_2$N(R[14])$_2$, —CH$_2$N(R[15])$_2$, —CH$_2$NH(R[14]), —CH$_2$NH (R[15]), —O(CH$_2$)$_3$N(CH$_3$)$_2$, —SCH$_3$, —NH$_2$, —NH(R[14]), —NH(R[15]), —NHCOCH$_3$, —NHSO$_2$CH$_3$, —N(R[14])$_2$, —N(R[15])$_2$, —SO$_2$CH$_3$, —SO$_2$NH$_2$, —CH$_2$CO$_2$H, —C$_2$H$_4$CO$_2$H, —CH=CH—CO$_2$H, —COR[10], -continued

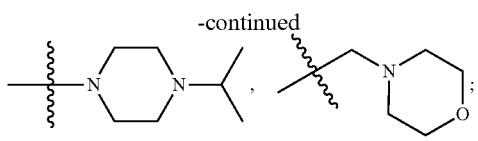

R⁹ is —H, —F, —Br, —Cl, —OH, —CN, —R¹⁶, —OR¹⁶, —NHCOCH₃, or —CON(CH₃)₂;

R¹⁰ is —OH, —R¹⁷, —OR¹⁷, —NH₂, —NHR¹⁷, —N(R¹⁷)₂, —NHC₂H₄OH, —NH(CH₂)$_q$N(R¹⁷)₂,

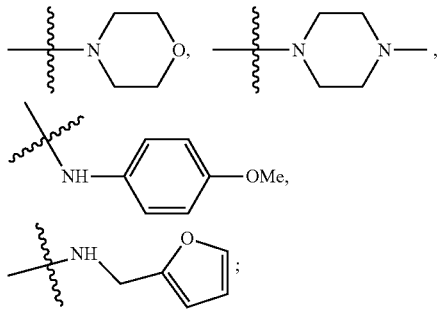

R¹¹, R¹², R¹³, R¹⁴, R¹⁵, R¹⁶, and R¹⁷ are independently of each other

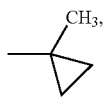

cyclo-C₃H₅, cyclo-C₄H₇, cyclo-C₅H₉, cyclo-C₆H₁₁, cyclo-C₇H₁₃,
—H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C≡CH, —C≡C—CH₃, —CH₂—C≡CH, —C₂H₄—C≡CH, —CH₂—C≡C—CH₃, —C≡C—C₂H₅, —CH(CH₃)Ph, or —C(CH₃)₂Ph;

m, n, p and q are independently of each other an integer from 0 to 3;

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

---

Wherein the compound according to group III. Can be selected from the group consisting of 4-[6-[(4-fluorophenyl)methyl]imidazo[1,2-b]pyridazin-3-yl]benzamide,
4-(6-benzylimidazo[1,2-b]pyridazin-3-yl)benzamide,
6-(1-methylpyrazol-4-yl)-3-(2-thienyl)imidazo[1,2-b]pyridazine,
N-(2-dimethylaminoethyl)-3-[6-(4-hydroxy-3-methoxy-phenyl)imidazo[1,2-b]pyridazin-3-yl]benzamide,
(2S)-2-[[3-(4-aminophenyl)imidazo[1,2-b]pyridazin-6-yl]amino]-3-methyl-butan-1-ol,
3-(2,4-dimethoxyphenyl)-N-(2-thienylmethyl)imidazo[1,2-b]pyridazin-6-amine,
4-[6-(2-methoxyethylamino)imidazo[1,2-b]pyridazin-3-yl]-N-(4-methoxyphenyl)benzamide,
2-[[3-[(E)-hex-1-enyl]imidazo[1,2-b]pyridazin-6-yl]amino]butan-1-ol,
2-[[3-(2-chlorophenyl)imidazo[1,2-b]pyridazin-6-yl]amino]butan-1-ol,
3-(3-pyridyl)-6-(3,4,5-trimethoxyphenyl)imidazo[1,2-b]pyridazine,
6-(3,4-dimethoxyphenyl)-3-(4-pyridyl)imidazo[1,2-b]pyridazine,
N-[3-[3-(3-acetamidophenyl)imidazo[1,2-b]pyridazin-6-yl]phenyl]acetamide,
2-methoxy-4-[6-(3,4,5-trimethoxyphenyl)imidazo[1,2-b]pyridazin-3-yl]phenol,
N-(2-dimethylaminoethyl)-3-[6-[3-(methanesulfonamido)phenyl]imidazo[1,2-b]pyridazin-3-yl]benzamide,
N-[(3-chlorophenyl)methyl]-3-[4-(trifluoromethoxy)phenyl]imidazo[1,2-b]pyridazin-6-amine,
4-[6-[(3-chlorophenyl)methylamino]imidazo[1,2-b]pyridazin-3-yl]-2-methoxy-phenol,
methyl 4-[6-[(3-chlorophenyl)methylamino]imidazo[1,2-b]pyridazin-3-yl]benzoate,
N-[(4-fluorophenyl)methyl]-3-(3-thienyl)imidazo[1,2-b]pyridazin-6-amine,
N-[3-[6-[(4-fluorophenyl)methylamino]imidazo[1,2-b]pyridazin-3-yl]phenyl]acetamide, -continued 4-[6-(propylamino)imidazo[1,2-b]pyridazin-3-yl]benzoic acid,
(E)-3-[3-[6-(propylamino)imidazo[1,2-b]pyridazin-3-yl]phenyl]prop-2-enoic acid,
3-(3-aminophenyl)-N-[(3,4-dichlorophenyl)methyl]imidazo[1,2-b]pyridazin-6-amine,
3-(4-fluorophenyl)-N-(2-methoxyethyl)imidazo[1,2-b]pyridazin-6-amine,
3-(4-morpholinophenyl)-N-[2-(3-pyridyl)ethyl]imidazo[1,2-b]pyridazin-6-amine,
3-(2-naphthyl)-N-[2-(3-pyridyl)ethyl]imidazo[1,2-b]pyridazin-6-amine,
N-(1,3-benzodioxol-5-ylmethyl)-3-(4-morpholinophenyl)imidazo[1,2-b]pyridazin-6-amine,
N-(1,3-benzodioxol-5-ylmethyl)-3-(8-quinolyl)imidazo[1,2-b]pyridazin-6-amine,
N-(1,3-benzodioxol-5-ylmethyl)-3-(4-chlorophenyl)imidazo[1,2-b]pyridazin-6-amine,
3-(2-fluorophenyl)-N-(2-methoxyethyl)imidazo[1,2-b]pyridazin-6-amine,
(E)-3-[3-[6-(1,3-benzodioxol-5-ylmethylamino)imidazo[1,2-b]pyridazin-3-yl]phenyl]prop-2-enoic acid,
3-(2-phenoxyphenyl)-N-(4-pyridylmethyl)imidazo[1,2-b]pyridazin-6-amine,
4-[(3-bromoimidazo[1,2-b]pyridazin-6-yl)amino]cyclohexanol,
3-(3-aminophenyl)-N-tetrahydropyran-4-yl-imidazo[1,2-b]pyridazin-6-amine,
3-(4-phenoxyphenyl)-N-tetrahydropyran-4-yl-imidazo[1,2-b]pyridazin-6-amine,
3-(benzofuran-2-yl)-N-[(4-methoxyphenyl)methyl]imidazo[1,2-b]pyridazin-6-amine,
4-[6-[(4-methoxyphenyl)methylamino]imidazo[1,2-b]pyridazin-3-yl]phenol,
3-(1H-indol-5-yl)-N-[(4-methoxyphenyl)methyl]imidazo[1,2-b]pyridazin-6-amine,
3-(1-naphthyl)-N-[2-(2-pyridyl)ethyl]imidazo[1,2-b]pyridazin-6-amine,
3-(2,4-dimethoxyphenyl)-N-[(4-methoxyphenyl)methyl]imidazo[1,2-b]pyridazin-6-amine,
3-[[3-(2-furyl)imidazo[1,2-b]pyridazin-6-yl]amino]propan-1-ol,
3-[[3-(4-methoxyphenyl)imidazo[1,2-b]pyridazin-6-yl]amino]propan-1-ol,
3-[[3-(2,4-dimethoxyphenyl)imidazo[1,2-b]pyridazin-6-yl]amino]propan-1-ol,
N-(3-morpholinopropyl)-3-(3,4,5-trimethoxyphenyl)imidazo[1,2-b]pyridazin-6-amine,
3-bromo-N-(3-morpholinopropyl)imidazo[1,2-b]pyridazin-6-amine
(2S)-3-methyl-2-[[3-(2-naphthyl)imidazo[1,2-b]pyridazin-6-yl]amino]butan-1-ol,
(2S)-2-[[3-(2,4-dimethoxyphenyl)imidazo[1,2-b]pyridazin-6-yl]amino]-3-methyl-butan-1-ol,
3-(3,4-dimethoxyphenyl)-N-(2-pyridylmethyl)imidazo[1,2-b]pyridazin-6-amine,
3-(5-isopropyl-2-methoxy-phenyl)-N-(2-pyridylmethyl)imidazo[1,2-b]pyridazin-6-amine,
3-(4-dimethylaminophenyl)-N-[(3,4,5-trimethoxyphenyl)methyl]imidazo[1,2-b]pyridazin-6-amine,
N',N'-dimethyl-N-[3-(p-tolyl)imidazo[1,2-b]pyridazin-6-yl]ethane-1,2-diamine,
N-(cyclopropylmethyl)-3-(6-methoxy-3-pyridyl)imidazo[1,2-b]pyridazin-6-amine,
4-[6-[(2,4-dimethylphenyl)methylamino]imidazo[1,2-b]pyridazin-3-yl]phenol,
3-[4-[6-[(2,4-dimethylphenyl)methylamino]imidazo[1,2-b]pyridazin-3-yl]phenyl]propanoic acid,
N-(2-dimethylaminoethyl)-4-[6-[(2,4-dimethylphenyl)methylamino]imidazo[1,2-b]pyridazin-3-yl]benzamide,
N-[(2,4-dimethylphenyl)methyl]-3-(3-methoxyphenyl)imidazo[1,2-b]pyridazin-6-amine,
4-[[[3-(1,3-benzodioxol-5-yl)imidazo[1,2-b]pyridazin-6-yl]amino]methyl]benzenesulfonamide,
4-[[[3-(1-benzylpyrazol-4-yl)imidazo[1,2-b]pyridazin-6-yl]amino]methyl]benzenesulfonamide,
4-[6-[[4-(4-methylpiperazin-1-yl)phenyl]methylamino]imidazo[1,2-b]pyridazin-3-yl]benzonitrile,
(Z)-5-[6-(methylamino)imidazo[1,2-b]pyridazin-3-yl]pent-4-en-1-ol,
2-[6-(methylamino)imidazo[1,2-b]pyridazin-3-yl]phenol,
N,N-dimethyl-3-[6-(methylamino)imidazo[1,2-b]pyridazin-3-yl]benzamide,
1-[2-[6-(methylamino)imidazo[1,2-b]pyridazin-3-yl]phenyl]ethanone,
3-[4-(dimethylaminomethyl)phenyl]-N-methyl-imidazo[1,2-b]pyridazin-6-amine,
3-(3,3-dimethylbut-1-ynyl)-N-methyl-imidazo[1,2-b]pyridazin-6-amine,
N-[2-[6-(methylamino)imidazo[1,2-b]pyridazin-3-yl]phenyl]acetamide,
3-methyl-4-[6-(methylamino)imidazo[1,2-b]pyridazin-3-yl]phenol,
3-[(5-imidazo[1,2-b]pyridazin-3-yl-2-pyridyl)oxy]-N,N-dimethyl-propan-1-amine,
1-(2-imidazo[1,2-b]pyridazin-3-ylphenyl)-N,N-dimethyl-methanamine, 3-[6-(4-methylpiperazin-1-yl)-3-pyridyl]imidazo[1,2-b]pyridazine,
3-(benzothiophen-2-yl)-N-[(3,4,5-trimethoxyphenyl)methyl]imidazo[1,2-b]pyridazin-6-amine,
3-dibenzofuran-4-ylimidazo[1,2-b]pyridazine,
3-(4-methylsulfanylphenyl)imidazo[1,2-b]pyridazine,
3-(4-chlorophenyl)imidazo[1,2-b]pyridazine,
3-[(E)-styryl]imidazo[1,2-b]pyridazine,
2-imidazo[1,2-b]pyridazin-3-ylbenzoic acid,
3-(3-ethoxyphenyl)imidazo[1,2-b]pyridazine,
4-imidazo[1,2-b]pyridazin-3-yl-2,6-dimethyl-phenol,
N-(2-hydroxyethyl)-4-imidazo[1,2-b]pyridazin-3-yl-benzamide,
(4-imidazo[1,2-b]pyridazin-3-ylphenyl)-(4-methylpiperazin-1-yl)methanone,
3-(2,3-dihydrobenzofuran-5-yl)imidazo[1,2-b]pyridazine,
3-(3-fluoro-4-methyl-phenyl)imidazo[1,2-b]pyridazine,
3-imidazo[1,2-b]pyridazin-3-ylbenzonitrile,
3-(3,4-difluorophenyl)imidazo[1,2-b]pyridazine,
3-(m-tolyl)imidazo[1,2-b]pyridazine,
3-(4-ethoxyphenyl)imidazo[1,2-b]pyridazine,
3-(2-methylsulfanylphenyl)imidazo[1,2-b]pyridazine,
1-(4-imidazo[1,2-b]pyridazin-3-ylphenyl)ethanone,
5-imidazo[1,2-b]pyridazin-3-ylquinoline,
N-cyclopropyl-4-imidazo[1,2-b]pyridazin-3-yl-benzamide,
4-imidazo[1,2-b]pyridazin-3-ylisoquinoline,
(2-imidazo[1,2-b]pyridazin-3-ylphenyl)methanol,
3-(2-fluoro-3-methoxy-phenyl)imidazo[1,2-b]pyridazine,
(3-imidazo[1,2-b]pyridazin-3-ylphenyl)-morpholino-methanone,
2-(4-imidazo[1,2-b]pyridazin-3-ylphenyl)acetonitrile,
N-(2-furylmethyl)-3-imidazo[1,2-b]pyridazin-3-yl-benzamide,
N-(4-imidazo[1,2-b]pyridazin-3-ylphenyl)methanesulfonamide,
4-[(4-imidazo[1,2-b]pyridazin-3-ylphenyl)methyl]morpholine,
3-(1-isobutylpyrazol-4-yl)imidazo[1,2-b]pyridazine,
N-cyclopropyl-3-imidazo[1,2-b]pyridazin-3-yl-benzamide,
4-(3-phenylimidazo[1,2-b]pyridazin-6-yl)benzamide,
3-(1,3-benzodioxol-5-yl)-6-phenyl-imidazo[1,2-b]pyridazine,
3-(1,3-benzodioxol-5-yl)-6-[3-(trifluoromethyl)phenyl]imidazo[1,2-b]pyridazine,
3-(3,4-dimethylphenyl)-N-[(3,4,5-trimethoxyphenyl)methyl]imidazo[1,2-b]pyridazin-6-amine,
3-(1,3-benzodioxol-5-yl)-6-(3-fluorophenyl)imidazo[1,2-b]pyridazine,
N-[3-[3-(4-pyridyl)imidazo[1,2-b]pyridazin-6-yl]phenyl]methanesulfonamide,
[4-[3-(3-pyridyl)imidazo[1,2-b]pyridazin-6-yl]phenyl]methanol,
6-(3-furyl)-3-(3-pyridyl)imidazo[1,2-b]pyridazine,
3-(3-pyridyl)-6-(2-thienyl)imidazo[1,2-b]pyridazine,
N-[3-[6-(3-pyridyl)imidazo[1,2-b]pyridazin-3-yl]phenyl]acetamide,
N-[3-[6-(3-acetylphenyl)imidazo[1,2-b]pyridazin-3-yl]phenyl]acetamide,
N-[3-[6-[(3,4-difluorophenyl)methyl]imidazo[1,2-b]pyridazin-3-yl]phenyl]acetamide,
3-[3-(3-acetamidophenyl)imidazo[1,2-b]pyridazin-6-yl]-N-methyl-benzamide,
3-(3-chloro-4-fluoro-phenyl)-6-(2-methoxyphenyl)imidazo[1,2-b]pyridazine,
3-(3-chloro-4-fluoro-phenyl)-6-(3,4,5-trimethoxyphenyl)imidazo[1,2-b]pyridazine,
6-(2-methoxyphenyl)-3-[3-(trifluoromethoxy)phenyl]imidazo[1,2-b]pyridazine,
N-(2-dimethylaminoethyl)-3-[3-[3-(trifluoromethoxy)phenyl]imidazo[1,2-b]pyridazin-6-yl]benzamide,
4-[3-[3-(trifluoromethoxy)phenyl]imidazo[1,2-b]pyridazin-6-yl]benzamide,
3-(4-methyl-2-thienyl)-N-[(3,4,5-trimethoxyphenyl)methyl]imidazo[1,2-b]pyridazin-6-amine,
6-benzyl-3-(4-methylsulfonylphenyl)imidazo[1,2-b]pyridazine,
3-[6-(3-chlorophenyl)imidazo[1,2-b]pyridazin-3-yl]-N-(2-dimethylaminoethyl)benzamide,
N-(2-dimethylaminoethyl)-3-[6-[3-(hydroxymethyl)phenyl]imidazo[1,2-b]pyridazin-3-yl]benzamide,
6-[(4-fluorophenyl)methyl]-3-(5-methoxy-3-pyridyl)imidazo[1,2-b]pyridazine,
3-[3-(3-chlorophenyl)imidazo[1,2-b]pyridazin-6-yl]aniline,
3-(3-chlorophenyl)-6-(3,4-dimethoxyphenyl)imidazo[1,2-b]pyridazine,
3-(3-chlorophenyl)-6-(4-methoxy-2-methyl-phenyl)imidazo[1,2-b]pyridazine,
3-(3-chlorophenyl)-6-(3-methoxyphenyl)imidazo[1,2-b]pyridazine,
3-[6-(4-fluorophenyl)imidazo[1,2-b]pyridazin-3-yl]phenol,
3-[6-(5-quinolyl)imidazo[1,2-b]pyridazin-3-yl]phenol,
[4-[6-(4-dimethylaminophenyl)imidazo[1,2-b]pyridazin-3-yl]phenyl]methanol,
[4-(6-pyrimidin-5-ylimidazo[1,2-b]pyridazin-3-yl)phenyl]methanol,

[4-[6-(1-methylpyrazol-4-yl)imidazo[1,2-b]pyridazin-3-yl]phenyl]methanol,
N-(2-hydroxyethyl)-3-[3-[3-(hydroxymethyl)phenyl]imidazo[1,2-b]pyridazin-6-yl]benzamide,
[3-[6-(3-phenoxyphenyl)imidazo[1,2-b]pyridazin-3-yl]phenyl]methanol,
6-(4-pyridyl)-3-[3-(trifluoromethyl)phenyl]imidazo[1,2-b]pyridazine,
3-[3-[3-(trifluoromethyl)phenyl]imidazo[1,2-b]pyridazin-6-yl]phenol,
6-cyclopropyl-3-[3-(trifluoromethyl)phenyl]imidazo[1,2-b]pyridazine,
3-(3-fluorophenyl)-6-[(4-fluorophenyl)methyl]imidazo[1,2-b]pyridazine,
2-methoxy-4-[6-[3-(trifluoromethoxy)phenyl]imidazo[1,2-b]pyridazin-3-yl]phenol,
3-[3-(dimethylamino)phenyl]-N-(2-furylmethyl)imidazo[1,2-b]pyridazin-6-amine,
4-[6-(2-furylmethylamino)imidazo[1,2-b]pyridazin-3-yl]benzoic acid,
N-[3-[3-(3-furyl)imidazo[1,2-b]pyridazin-6-yl]phenyl]acetamide,
3-[3-(3-furyl)imidazo[1,2-b]pyridazin-6-yl]benzoic acid,
3-(3-furyl)-6-(5-methoxy-3-pyridyl)imidazo[1,2-b]pyridazine,
N-[4-[3-(3-furyl)imidazo[1,2-b]pyridazin-6-yl]phenyl]acetamide,
4-[6-[(3,4-difluorophenyl)methyl]imidazo[1,2-b]pyridazin-3-yl]benzamide,
4-[6-(m-tolylmethyl)imidazo[1,2-b]pyridazin-3-yl]benzamide,
N-[4-[6-(4-morpholinophenyl)imidazo[1,2-b]pyridazin-3-yl]phenyl]acetamide,
N-[4-[6-(1,3-benzodioxol-5-yl)imidazo[1,2-b]pyridazin-3-yl]phenyl]acetamide,
N-[4-[6-(4-methylsulfonylphenyl)imidazo[1,2-b]pyridazin-3-yl]phenyl]acetamide,
6-benzyl-3-pyrimidin-5-yl-imidazo[1,2-b]pyridazine,
6-[(4-fluorophenyl)methyl]-3-(4-methoxy-2-methyl-phenyl)imidazo[1,2-b]pyridazine,
6-[(4-fluorophenyl)methyl]-3-(3-phenoxyphenyl)imidazo[1,2-b]pyridazine,
1-[3-[6-(6-amino-3-pyridyl)imidazo[1,2-b]pyridazin-3-yl]phenyl]ethanone,
3-[3,5-bis(trifluoromethyl)phenyl]-N-(2-thienylmethyl)imidazo[1,2-b]pyridazin-6-amine,
N,N-dimethyl-3-[3-(2-thienyl)imidazo[1,2-b]pyridazin-6-yl]aniline,
6-(3-chloro-4-fluoro-phenyl)-3-(2-thienyl)imidazo[1,2-b]pyridazine,
2-methoxy-4-[3-(2-thienyl)imidazo[1,2-b]pyridazin-6-yl]phenol,
6-(2-chlorophenyl)-3-(2-thienyl)imidazo[1,2-b]pyridazine,
N-[3-[6-[(4-fluorophenyl)methyl]imidazo[1,2-b]pyridazin-3-yl]phenyl]methanesulfonamide,
3-(1-methylpyrazol-4-yl)-6-(m-tolylmethyl)imidazo[1,2-b]pyridazine,
5-(6-benzylimidazo[1,2-b]pyridazin-3-yl)pyridin-2-amine,
(4Z)-4-[dimethylamino(imidazo[1,2-b]pyridazin-3-yl)methylene]-2-phenyl-oxazol-5-one,
3-(3-bromophenyl)-N-(2-thienylmethyl)imidazo[1,2-b]pyridazin-6-amine,
6-(1,3-benzodioxol-5-yl)-3-phenyl-[1,2,4]triazolo[4,3-a]pyridine,
N-[3-(3-phenyl-[1,2,4]triazolo[4,3-a]pyridin-6-yl)phenyl]acetamide,
6-(4-methoxy-2-methyl-phenyl)-3-phenyl-[1,2,4]triazolo[4,3-a]pyridine,
3-phenyl-6-[2-(2-pyridyl)ethynyl]-[1,2,4]triazolo[4,3-a]pyridine,
N,N-dimethyl-3-(3-phenyl-[1,2,4]triazolo[4,3-a]pyridin-6-yl)prop-2-yn-1-amine,
N-[3-(3-phenyl-[1,2,4]triazolo[4,3-a]pyridin-6-yl)phenyl]methanesulfonamide,
3-(1,3-benzodioxol-5-yl)-6-(3-chlorophenyl)-[1,2,4]triazolo[4,3-a]pyridine,
3-(1,3-benzodioxol-5-yl)-6-(3-furyl)-[1,2,4]triazolo[4,3-a]pyridine,
3-(1,3-benzodioxol-5-yl)-6-[2-(3-methylimidazol-4-yl)ethynyl]-[1,2,4]triazolo[4,3-a]pyridine,
3-[3-(1,3-benzodioxol-5-yl)-[1,2,4]triazolo[4,3-a]pyridin-6-yl]prop-2-yn-1-ol,
3-(1,3-benzodioxol-5-yl)-6-(1-methylpyrazol-4-yl)-[1,2,4]triazolo[4,3-a]pyridine,
3-[3-(1,3-benzodioxol-5-yl)-[1,2,4]triazolo[4,3-a]pyridin-6-yl]-N-methyl-benzamide,
4-[4-[3-(4-pyridyl)-[1,2,4]triazolo[4,3-a]pyridin-6-yl]phenyl]morpholine,
6-(3,4-dimethoxyphenyl)-3-(4-pyridyl)-[1,2,4]triazolo[4,3-a]pyridine,
3-(4-pyridyl)-6-[3-(trifluoromethoxy)phenyl]-[1,2,4]triazolo[4,3-a]pyridine,
[4-[3-(4-pyridyl)-[1,2,4]triazolo[4,3-a]pyridin-6-yl]phenyl]methanol,
3-(4-pyridyl)-6-[2-[3-(trifluoromethyl)phenyl]ethynyl]-[1,2,4]triazolo[4,3-a]pyridine,
6-(3-phenoxyphenyl)-3-(4-pyridyl)-[1,2,4]triazolo[4,3-a]pyridine,
N,N-dimethyl-4-[3-(3-pyridyl)-[1,2,4]triazolo[4,3-a]pyridin-6-yl]aniline,
6-(3-isopropylphenyl)-3-(3-pyridyl)-[1,2,4]triazolo[4,3-a]pyridine,
6-(2-chlorophenyl)-3-(3-pyridyl)-[1,2,4]triazolo[4,3-a]pyridine,
3-[3-(3,4-dimethoxyphenyl)-[1,2,4]triazolo[4,3-a]pyridin-6-yl]-N,N-dimethyl-aniline,
3-(3,4-dimethoxyphenyl)-6-(4-methylsulfonylphenyl)-[1,2,4]triazolo[4,3-a]pyridine,
3-(3,4-dimethoxyphenyl)-6-(3-fluorophenyl)-[1,2,4]triazolo[4,3-a]pyridine,
3-[3-(3,4-dimethoxyphenyl)-[1,2,4]triazolo[4,3-a]pyridin-6-yl]-N,N-dimethyl-benzamide,
3-(3,4-dimethoxyphenyl)-6-[2-(3-pyridyl)ethynyl]-[1,2,4]triazolo[4,3-a]pyridine, 3-(3,4-dimethoxyphenyl)-6-[2-(4-pyridyl)ethynyl]-[1,2,4]triazolo[4,3-a]pyridine,
3-(3,4-dimethoxyphenyl)-6-(2-thienyl)-[1,2,4]triazolo[4,3-a]pyridine,
6-(5-methoxy-3-pyridyl)-3-[3-(trifluoromethoxy)phenyl]-[1,2,4]triazolo[4,3-a]pyridine,
6-(3-methylsulfonylphenyl)-3-[3-(trifluoromethoxy)phenyl]-[1,2,4]triazolo[4,3-a]pyridine,
6-[2-(3-methoxyphenyl)ethynyl]-3-[3-(trifluoromethoxy)phenyl]-[1,2,4]triazolo[4,3-a]pyridine,
6-(2-thienyl)-3-[3-(trifluoromethoxy)phenyl]-[1,2,4]triazolo[4,3-a]pyridine,
6-(2-phenylethynyl)-3-[3-(trifluoromethoxy)phenyl]-[1,2,4]triazolo[4,3-a]pyridine,
3-[3-(3-chlorophenyl)-[1,2,4]triazolo[4,3-a]pyridin-6-yl]aniline,
6-(1,3-benzodioxol-5-yl)-3-(3-chlorophenyl)-[1,2,4]triazolo[4,3-a]pyridine,
3-(3-chlorophenyl)-6-(4-pyridyl)-[1,2,4]triazolo[4,3-a]pyridine,
3-(3-chlorophenyl)-6-(3-pyridyl)-[1,2,4]triazolo[4,3-a]pyridine,
3-(3-chlorophenyl)-6-(3-furyl)-[1,2,4]triazolo[4,3-a]pyridine,
N-[4-[3-(3-chlorophenyl)-[1,2,4]triazolo[4,3-a]pyridin-6-yl]phenyl]acetamide,
3-(3-chlorophenyl)-6-pyrimidin-5-yl-[1,2,4]triazolo[4,3-a]pyridine,
3-(3-chlorophenyl)-6-pyrimidin-2-yl-[1,2,4]triazolo[4,3-a]pyridine,
4-[3-(3-chlorophenyl)-[1,2,4]triazolo[4,3-a]pyridin-6-yl]isoquinoline,
4-[3-(3-hydroxyphenyl)-[1,2,4]triazolo[4,3-a]pyridin-6-yl]benzonitrile,
3-[6-(4-isopropylphenyl)-[1,2,4]triazolo[4,3-a]pyridin-3-yl]phenol,
3-[6-(4-fluorophenyl)-[1,2,4]triazolo[4,3-a]pyridin-3-yl]phenol,
3-[6-(5-quinolyl)-[1,2,4]triazolo[4,3-a]pyridin-3-yl]phenol,
3-[3-(trifluoromethyl)phenyl]-6-(3,4,5-trimethoxyphenyl)-[1,2,4]triazolo[4,3-a]pyridine,
N-[3-(dimethylamino)propyl]-4-[3-[3-(trifluoromethyl)phenyl]-[1,2,4]triazolo[4,3-a]pyridin-6-yl]benzamide,
morpholino-[4-[3-[3-(trifluoromethyl)phenyl]-[1,2,4]triazolo[4,3-a]pyridin-6-yl]phenyl]methanone,
N,N-dimethyl-4-[3-[3-(trifluoromethyl)phenyl]-[1,2,4]triazolo[4,3-a]pyridin-6-yl]benzamide,
5-[3-[3-(trifluoromethyl)phenyl]-[1,2,4]triazolo[4,3-a]pyridin-6-yl]pyridin-2-amine,
2-methoxy-4-[6-[4-(4-methylpiperazin-1-yl)phenyl]-[1,2,4]triazolo[4,3-a]pyridin-3-yl]phenol,
2-methoxy-4-[6-(6-methoxy-3-pyridyl)-[1,2,4]triazolo[4,3-a]pyridin-3-yl]phenol,
4-[6-(3-fluorophenyl)-[1,2,4]triazolo[4,3-a]pyridin-3-yl]-2-methoxy-phenol,
2-methoxy-4-[6-(o-tolyl)-[1,2,4]triazolo[4,3-a]pyridin-3-yl]phenol,
3-(3-furyl)-6-(3,4,5-trimethoxyphenyl)-[1,2,4]triazolo[4,3-a]pyridine,
3-(3-furyl)-6-(4-methoxyphenyl)-[1,2,4]triazolo[4,3-a]pyridine,
3-(3-furyl)-6-(2-thienyl)-[1,2,4]triazolo[4,3-a]pyridine,
3-[6-(2-pyridyl)-[1,2,4]triazolo[4,3-a]pyridin-3-yl]benzonitrile,
6-(3,4-dimethoxyphenyl)-3-(o-tolyl)-[1,2,4]triazolo[4,3-a]pyridine,
N-(2-hydroxyethyl)-3-[3-(o-tolyl)-[1,2,4]triazolo[4,3-a]pyridin-6-yl]benzamide,
4-[3-(o-tolyl)-[1,2,4]triazolo[4,3-a]pyridin-6-yl]benzamide,
4-[4-(3-thiazol-4-yl-[1,2,4]triazolo[4,3-a]pyridin-6-yl)phenyl]morpholine,
N,N-dimethyl-3-(3-thiazol-4-yl-[1,2,4]triazolo[4,3-a]pyridin-6-yl)aniline,
4-[6-(3-chloro-4-fluoro-phenyl)-[1,2,4]triazolo[4,3-a]pyridin-3-yl]thiazole,
4-[6-(1H-indol-5-yl)-[1,2,4]triazolo[4,3-a]pyridin-3-yl]thiazole,
3-thiazol-4-yl-[1,2,4]triazolo[4,3-a]pyridin-6-yl)benzamide,
4-[6-(4-methoxy-2-methyl-phenyl)-[1,2,4]triazolo[4,3-a]pyridin-3-yl]thiazole,
4-[3-(3-thiazol-4-yl-[1,2,4]triazolo[4,3-a]pyridin-6-yl)prop-2-ynyl]-1,4-thiazinane 1,1-dioxide,
4-[6-(2-chlorophenyl)-[1,2,4]triazolo[4,3-a]pyridin-3-yl]thiazole,
4-[6-(3-methoxyphenyl)-[1,2,4]triazolo[4,3-a]pyridin-3-yl]thiazole,
4-[6-(6-quinolyl)-[1,2,4]triazolo[4,3-a]pyridin-3-yl]thiazole,
3-[4-[6-(3,4-dimethoxyphenyl)-[1,2,4]triazolo[4,3-a]pyridin-3-yl]phenoxy]-N,N-dimethyl-propan-1-amine,
3-[4-[6-(4-chlorophenyl)-[1,2,4]triazolo[4,3-a]pyridin-3-yl]phenoxy]-N,N-dimethyl-propan-1-amine,
4-[2-[3-[4-[3-(dimethylamino)propoxy]phenyl]-[1,2,4]triazolo[4,3-a]pyridin-6-yl]ethynyl]-N,N-dimethyl-benzamide,
3-[4-[6-[2-(3,5-dimethoxyphenyl)ethynyl]-[1,2,4]triazolo[4,3-a]pyridin-3-yl]phenoxy]-N,N-dimethyl-propan-1-amine,
4-[3-[4-[3-(dimethylamino)propoxy]phenyl]-[1,2,4]triazolo[4,3-a]pyridin-6-yl]-N-methyl-benzamide,
N-[3-(3-quinoxalin-6-yl-[1,2,4]triazolo[4,3-a]pyridin-6-yl)phenyl]acetamide,
N-(2-dimethylaminoethyl)-3-(3-quinoxalin-6-yl-[1,2,4]triazolo[4,3-a]pyridin-6-yl)benzamide,
(4-methylpiperazin-1-yl)-[3-(3-quinoxalin-6-yl-[1,2,4]triazolo[4,3-a]pyridin-6-yl)phenyl]methanone,
2-methoxy-4-(3-quinoxalin-6-yl-[1,2,4]triazolo[4,3-a]pyridin-6-yl)phenol,
6-[6-(3-furyl)-[1,2,4]triazolo[4,3-a]pyridin-3-yl]quinoxaline, -continued N,N-dimethyl-3-(3-quinoxalin-6-yl-[1,2,4]triazolo[4,3-a]pyridin-6-yl)benzamide,
3-[3-(2-pyridyl)-[1,2,4]triazolo[4,3-a]pyridin-6-yl]phenol,
[3-[3-(2-pyridyl)-[1,2,4]triazolo[4,3-a]pyridin-6-yl]phenyl]methanol,
6-(3-methylsulfonylphenyl)-3-(2-pyridyl)-[1,2,4]triazolo[4,3-a]pyridine,
N-[6-(2,3-dichlorophenyl)imidazo[1,2-a]pyrazin-3-yl]-2-(2-methoxyphenyl)acetamide,
N-[6-(4-isopropylphenyl)imidazo[1,2-a]pyrazin-3-yl]-2-(2-methoxyphenyl)acetamide,
N-[6-[2-(dimethylaminomethyl)phenyl]imidazo[1,2-a]pyrazin-3-yl]-2-(3-methoxyphenyl)acetamide,
N-[6-[(E)-hex-1-enyl]imidazo[1,2-a]pyrazin-3-yl]-2-(3-methoxyphenyl)acetamide,
N-[6-(1H-indol-5-yl)imidazo[1,2-a]pyrazin-3-yl]-2-(3-methoxyphenyl)acetamide,
N-[6-[3-(hydroxymethyl)phenyl]imidazo[1,2-a]pyrazin-3-yl]-2-(3-methoxyphenyl)acetamide,
2-(3-methoxyphenyl)-N-[6-[3-(trifluoromethyl)phenyl]imidazo[1,2-a]pyrazin-3-yl]acetamide,
N-[6-(4-fluorophenyl)imidazo[1,2-a]pyrazin-3-yl]-2-(3-methoxyphenyl)acetamide,
N-[6-(3-furyl)imidazo[1,2-a]pyrazin-3-yl]-2-(3-methoxyphenyl)acetamide,
2-(3-methoxyphenyl)-N-[6-(4-phenoxyphenyl)imidazo[1,2-a]pyrazin-3-yl]acetamide,
2-(3-methoxyphenyl)-N-[6-(2-thienyl)imidazo[1,2-a]pyrazin-3-yl]acetamide,
2-(3-methoxyphenyl)-N-[6-(1-methylpyrazol-4-yl)imidazo[1,2-a]pyrazin-3-yl]acetamide,
N-[6-[(E)-hex-1-enyl]imidazo[1,2-a]pyrazin-3-yl]pyridine-4-carboxamide,
N-[6-(3-thienyl)imidazo[1,2-a]pyrazin-3-yl]thiophene-2-carboxamide,
N-[6-(4-isopropylphenyl)imidazo[1,2-a]pyrazin-3-yl]acetamide,
N-[6-[3-(2-dimethylaminoethylcarbamoyl)phenyl]imidazo[1,2-a]pyrazin-3-yl]furan-2-carboxamide,
N-[6-(1-benzylpyrazol-4-yl)imidazo[1,2-a]pyrazin-3-yl]-2-methyl-propanamide,
N-[6-(2-methoxyphenyl)imidazo[1,2-a]pyrazin-3-yl]benzamide,
N-[6-[3-(dimethylamino)phenyl]imidazo[1,2-a]pyrazin-3-yl]benzamide,
N-[6-(4-aminophenyl)imidazo[1,2-a]pyrazin-3-yl]benzamide,
N-[6-(1,3-benzodioxol-5-yl)imidazo[1,2-a]pyrazin-3-yl]-2-phenyl-propanamide,
N-[6-(3-nitrophenyl)imidazo[1,2-a]pyrazin-3-yl]-2-phenyl-propanamide,
2-(o-tolyl)-N-[6-(1H-pyrazol-4-yl)imidazo[1,2-a]pyrazin-3-yl]acetamide,
N-[6-(1-benzylpyrazol-4-yl)imidazo[1,2-a]pyrazin-3-yl]cyclobutanecarboxamide,
N-[6-(3-acetylphenyl)imidazo[1,2-a]pyrazin-3-yl]-2-cyclopropyl-acetamide,
N-[6-(2-naphthyl)imidazo[1,2-a]pyrazin-3-yl]tetrahydrofuran-3-carboxamide,
N-[6-(4-methoxyphenyl)imidazo[1,2-a]pyrazin-3-yl]tetrahydrofuran-3-carboxamide,
N-[6-(3-aminophenyl)imidazo[1,2-a]pyrazin-3-yl]-2-(3,4-difluorophenyl)acetamide,
N-[6-(2-fluorophenyl)imidazo[1,2-a]pyrazin-3-yl]-2-(3-thienyl)acetamide,
N-[6-(3-methoxyphenyl)imidazo[1,2-a]pyrazin-3-yl]-2-(3-thienyl)acetamide,
N-[6-(2,4-dimethoxyphenyl)imidazo[1,2-a]pyrazin-3-yl]-2-(3-thienyl)acetamide,
4-[6-[6-[3-(dimethylamino)propoxy]-3-pyridyl]imidazo[1,2-a]pyrazin-3-yl]-N,N-dimethyl-aniline,
5-[3-(4-dimethylaminophenyl)imidazo[1,2-a]pyrazin-6-yl]-N-(2-morpholinoethyl)pyridin-2-amine,
2-[3-(4-dimethylaminophenyl)imidazo[1,2-a]pyrazin-6-yl]-N,N-dimethyl-aniline,
4-[3-(4-dimethylaminophenyl)imidazo[1,2-a]pyrazin-6-yl]phenol,
4-[3-(4-dimethylaminophenyl)imidazo[1,2-a]pyrazin-6-yl]-N-[3-(dimethylamino)propyl]benzamide,
3-[3-(4-dimethylaminophenyl)imidazo[1,2-a]pyrazin-6-yl]-N-(2-hydroxyethyl)benzamide,
[4-[3-(4-dimethylaminophenyl)imidazo[1,2-a]pyrazin-6-yl]phenyl]methanol,
4-[6-(6-methoxy-3-pyridyl)imidazo[1,2-a]pyrazin-3-yl]-N,N-dimethyl-aniline,
N-(2-dimethylaminoethyl)-4-[3-(4-dimethylaminophenyl)imidazo[1,2-a]pyrazin-6-yl]benzamide,
4-[3-(4-dimethylaminophenyl)imidazo[1,2-a]pyrazin-6-yl]-N-(2-hydroxyethyl)benzamide,
[4-[3-(4-dimethylaminophenyl)imidazo[1,2-a]pyrazin-6-yl]phenyl]-morpholino-methanone,
3-[3-(4-dimethylaminophenyl)imidazo[1,2-a]pyrazin-6-yl]benzamide,
3-[3-(4-dimethylaminophenyl)imidazo[1,2-a]pyrazin-6-yl]-N,N-dimethyl-benzamide, -continued 4-[6-(2-chlorophenyl)imidazo[1,2-a]pyrazin-3-yl]-N,N-dimethyl-aniline,
N-[3-[3-(4-dimethylaminophenyl)imidazo[1,2-a]pyrazin-6-yl]phenyl]methanesulfonamide,
3-phenyl-6-(3-thienyl)imidazo[1,2-a]pyrazine,
6-(3-fluorophenyl)-3-phenyl-imidazo[1,2-a]pyrazine,
3-phenyl-6-(2-thienyl)imidazo[1,2-a]pyrazine,
N-cyclopropyl-4-(3-phenylimidazo[1,2-a]pyrazin-6-yl)benzamide,
3-(1,3-benzodioxol-5-yl)-6-phenyl-imidazo[1,2-a]pyrazine,
3-(1,3-benzodioxol-5-yl)-6-(3-thienyl)imidazo[1,2-a]pyrazine,
3-(1,3-benzodioxol-5-yl)-6-(3-ethoxyphenyl)imidazo[1,2-a]pyrazine,
3-(1,3-benzodioxol-5-yl)-6-(3-chlorophenyl)imidazo[1,2-a]pyrazine,
3-(1,3-benzodioxol-5-yl)-6-(3-fluorophenyl)imidazo[1,2-a]pyrazine,
3-(1,3-benzodioxol-5-yl)-6-(o-tolyl)imidazo[1,2-a]pyrazine,
3-(1,3-benzodioxol-5-yl)-6-(2-thienyl)imidazo[1,2-a]pyrazine,
3-(1,3-benzodioxol-5-yl)-6-(1-benzylpyrazol-4-yl)imidazo[1,2-a]pyrazine,
3-(1,3-benzodioxol-5-yl)-6-(3,5-dimethoxyphenyl)imidazo[1,2-a]pyrazine,
5-[3-(1,3-benzodioxol-5-yl)imidazo[1,2-a]pyrazin-6-yl]pyridin-2-amine,
3-(1,3-benzodioxol-5-yl)-6-(3-isopropoxyphenyl)imidazo[1,2-a]pyrazine,
6-(2-phenoxyphenyl)-3-(4-pyridyl)imidazo[1,2-a]pyrazine,
2,6-dimethyl-4-[3-(4-pyridyl)imidazo[1,2-a]pyrazin-6-yl]phenol,
morpholino-[4-[3-(4-pyridyl)imidazo[1,2-a]pyrazin-6-yl]phenyl]methanone,
3-(4-pyridyl)-6-(2-thienyl)imidazo[1,2-a]pyrazine,
4-[4-[3-(3-pyridyl)imidazo[1,2-a]pyrazin-6-yl]phenyl]morpholine,
6-(benzothiophen-2-yl)-3-(3-pyridyl)imidazo[1,2-a]pyrazine,
6-(4-methylsulfanylphenyl)-3-(3-pyridyl)imidazo[1,2-a]pyrazine,
N-[3-[3-(3-pyridyl)imidazo[1,2-a]pyrazin-6-yl]phenyl]methanesulfonamide,
6-(2-furyl)-3-(3-thienyl)imidazo[1,2-a]pyrazine,
6-(3-chloro-4-fluoro-phenyl)-3-(3-thienyl)imidazo[1,2-a]pyrazine,
N-(2-hydroxyethyl)-4-[3-(3-thienyl)imidazo[1,2-a]pyrazin-6-yl]benzamide,
6-(2-thienyl)-3-(3-thienyl)imidazo[1,2-a]pyrazine,
6-(3,5-dimethoxyphenyl)-3-(3-thienyl)imidazo[1,2-a]pyrazine,
4-[6-(4-chlorophenyl)imidazo[1,2-a]pyrazin-3-yl]phenol,
4-[6-[4-(4-isopropylpiperazin-1-yl)phenyl]imidazo[1,2-a]pyrazin-3-yl]phenol,
N-cyclopropyl-4-[3-(4-hydroxyphenyl)imidazo[1,2-a]pyrazin-6-yl]benzamide,
4-[6-(1-methylpyrazol-4-yl)imidazo[1,2-a]pyrazin-3-yl]phenol,
3-[4-[6-(3-ethoxyphenyl)imidazo[1,2-a]pyrazin-3-yl]phenyl]propanoic acid,
3-[4-[6-(3-chlorophenyl)imidazo[1,2-a]pyrazin-3-yl]phenyl]propanoic acid,
3-[4-[6-(o-tolyl)imidazo[1,2-a]pyrazin-3-yl]phenyl]propanoic acid,
3-[4-[6-(2-chlorophenyl)imidazo[1,2-a]pyrazin-3-yl]phenyl]propanoic acid,
3-[4-[6-(2-thienyl)imidazo[1,2-a]pyrazin-3-yl]phenyl]propanoic acid,
3-[4-[6-[2-(hydroxymethyl)phenyl]imidazo[1,2-a]pyrazin-3-yl]phenyl]propanoic acid,
3-[4-[6-(2,3-dimethylphenyl)imidazo[1,2-a]pyrazin-3-yl]phenyl]propanoic acid,
4-(6-phenylimidazo[1,2-a]pyrazin-3-yl)benzonitrile,
4-[6-(3-thienyl)imidazo[1,2-a]pyrazin-3-yl]benzonitrile,
4-[6-(4-chlorophenyl)imidazo[1,2-a]pyrazin-3-yl]benzonitrile,
4-[6-[4-(hydroxymethyl)phenyl]imidazo[1,2-a]pyrazin-3-yl]benzonitrile,
4-[6-(2-thienyl)imidazo[1,2-a]pyrazin-3-yl]benzonitrile,
6-[6-(4-methylpiperazin-1-yl)-3-pyridyl]-3-(3,4,5-trimethoxyphenyl)imidazo[1,2-a]pyrazine,
3-[6-[6-[3-(dimethylamino)propoxy]-3-pyridyl]imidazo[1,2-a]pyrazin-3-yl]-N,N-dimethyl-aniline,
N,N-dimethyl-3-[6-(4-pyridyl)imidazo[1,2-a]pyrazin-3-yl]aniline,
N,N-dimethyl-3-[6-(3-thienyl)imidazo[1,2-a]pyrazin-3-yl]aniline,
[4-[3-[3-(dimethylamino)phenyl]imidazo[1,2-a]pyrazin-6-yl]phenyl]methanol,
N,N-dimethyl-3-[6-(2-thienyl)imidazo[1,2-a]pyrazin-3-yl]aniline,
3-[6-(3,5-dimethoxyphenyl)imidazo[1,2-a]pyrazin-3-yl]-N,N-dimethyl-aniline,
3-(4-chlorophenyl)-6-(4-pyridyl)imidazo[1,2-a]pyrazine,
3-(4-chlorophenyl)-6-(3-thienyl)imidazo[1,2-a]pyrazine,
3-(4-chlorophenyl)-6-(2-thienyl)imidazo[1,2-a]pyrazine,
N-[3-[3-(3-chloro-4-fluoro-phenyl)imidazo[1,2-a]pyrazin-6-yl]phenyl]acetamide,
3-(3-chloro-4-fluoro-phenyl)-6-(2-furyl)imidazo[1,2-a]pyrazine,
6-(3-pyridyl)-3-[3-(trifluoromethoxy)phenyl]imidazo[1,2-a]pyrazine,
N-(2-hydroxyethyl)-3-[3-[3-(trifluoromethoxy)phenyl]imidazo[1,2-a]pyrazin-6-yl]benzamide,
(4-methylpiperazin-1-yl)-[3-[6-(2-phenoxyphenyl)imidazo[1,2-a]pyrazin-3-yl]phenyl]methanone,
[3-[6-(1,3-benzodioxol-5-yl)imidazo[1,2-a]pyrazin-3-yl]phenyl]-(4-methylpiperazin-1-yl)methanone,
(4-methylpiperazin-1-yl)-[3-[6-[4-(trifluoromethoxy)phenyl]imidazo[1,2-a]pyrazin-3-yl]phenyl]methanone,
[3-[6-(3-chlorophenyl)imidazo[1,2-a]pyrazin-3-yl]phenyl]-(4-methylpiperazin-1-yl)methanone,

[3-[6-(1-methylindol-5-yl)imidazo[1,2-a]pyrazin-3-yl]phenyl]-(4-methylpiperazin-1-yl)methanone,
[3-[6-[4-(anilinomethyl)phenyl]imidazo[1,2-a]pyrazin-3-yl]phenyl]-(4-methylpiperazin-1-yl)methanone,
[4-[3-(3-chlorophenyl)imidazo[1,2-a]pyrazin-6-yl]phenyl]methanol,
[4-[3-(4-methoxyphenyl)imidazo[1,2-a]pyrazin-6-yl]phenyl]methanol,
3-(4-methoxyphenyl)-6-(2-thienyl)imidazo[1,2-a]pyrazine,
5-[3-(4-methoxyphenyl)imidazo[1,2-a]pyrazin-6-yl]pyridin-2-amine,
3-[6-(benzothiophen-2-yl)imidazo[1,2-a]pyrazin-3-yl]phenol,
3-[6-(4-chlorophenyl)imidazo[1,2-a]pyrazin-3-yl]phenol,
3-[6-[(E)-styryl]imidazo[1,2-a]pyrazin-3-yl]phenol,
3-[6-[4-(4-methylpiperazin-1-yl)phenyl]imidazo[1,2-a]pyrazin-3-yl]phenol,
3-[6-(3-chlorophenyl)imidazo[1,2-a]pyrazin-3-yl]phenol,
3-[6-(6-methoxy-3-pyridyl)imidazo[1,2-a]pyrazin-3-yl]phenol,
3-[6-(2-thienyl)imidazo[1,2-a]pyrazin-3-yl]phenol,
3-[6-(3,5-dimethoxyphenyl)imidazo[1,2-a]pyrazin-3-yl]phenol,
3-[6-(2-fluoro-3-methoxy-phenyl)imidazo[1,2-a]pyrazin-3-yl]phenol,
[4-[6-(2-furyl)imidazo[1,2-a]pyrazin-3-yl]phenyl]methanol,
[4-[6-(2,4-dichlorophenyl)imidazo[1,2-a]pyrazin-3-yl]phenyl]methanol,
N-cyclopentyl-4-[3-[4-(hydroxymethyl)phenyl]imidazo[1,2-a]pyrazin-6-yl]benzamide,
[3-(6-phenylimidazo[1,2-a]pyrazin-3-yl)phenyl]methanol,
[3-[6-(4-methylsulfanylphenyl)imidazo[1,2-a]pyrazin-3-yl]phenyl]methanol,
[3-[6-(3-ethoxyphenyl)imidazo[1,2-a]pyrazin-3-yl]phenyl]methanol,
[3-[6-(2-thienyl)imidazo[1,2-a]pyrazin-3-yl]phenyl]methanol,
[3-[6-(3-isopropoxyphenyl)imidazo[1,2-a]pyrazin-3-yl]phenyl]methanol,
3-(6-methoxy-3-pyridyl)-6-[4-(4-methylpiperazin-1-yl)phenyl]imidazo[1,2-a]pyrazine,
3,6-bis(6-methoxy-3-pyridyl)imidazo[1,2-a]pyrazine,
3-[6-(6-methoxy-3-pyridyl)imidazo[1,2-a]pyrazin-6-yl]benzamide,
3-[3-(3-fluorophenyl)imidazo[1,2-a]pyrazin-6-yl]aniline,
3-(3-fluorophenyl)-6-phenyl-imidazo[1,2-a]pyrazine,
6-(1,3-benzodioxol-5-yl)-3-(3-fluorophenyl)imidazo[1,2-a]pyrazine,
3-(3-fluorophenyl)-6-(4-piperazin-1-ylphenyl)imidazo[1,2-a]pyrazine,
6-(4-chlorophenyl)-3-(3-fluorophenyl)imidazo[1,2-a]pyrazine,
[4-[3-(3-fluorophenyl)imidazo[1,2-a]pyrazin-6-yl]phenyl]methanol,
3-(3-fluorophenyl)-6-(2-thienyl)imidazo[1,2-a]pyrazine,
4-[6-[6-[3-(dimethylamino)propoxy]-3-pyridyl]imidazo[1,2-a]pyrazin-3-yl]-2-methoxy-phenol,
2-methoxy-4-[6-[6-(2-morpholinoethylamino)-3-pyridyl]imidazo[1,2-a]pyrazin-3-yl]phenol,
2-methoxy-4-[6-[6-(4-methylpiperazin-1-yl)-3-pyridyl]imidazo[1,2-a]pyrazin-3-yl]phenol,
4-[6-(1,3-benzodioxol-5-yl)imidazo[1,2-a]pyrazin-3-yl]-2-methoxy-phenol,
4-[6-(3-ethoxyphenyl)imidazo[1,2-a]pyrazin-3-yl]-2-methoxy-phenol,
4-[6-(6-amino-3-pyridyl)imidazo[1,2-a]pyrazin-3-yl]-2-methoxy-phenol,
2-methoxy-4-[6-(1-methylpyrazol-4-yl)imidazo[1,2-a]pyrazin-3-yl]phenol,
N-[3-(dimethylamino)propyl]-4-[3-(1-methylindol-5-yl)imidazo[1,2-a]pyrazin-6-yl]benzamide,
N-(2-hydroxyethyl)-3-[3-(1-methylindol-5-yl)imidazo[1,2-a]pyrazin-6-yl]benzamide,
2-methoxy-4-[3-(1-methylindol-5-yl)imidazo[1,2-a]pyrazin-6-yl]phenol,
3-[3-(1-methylindol-5-yl)imidazo[1,2-a]pyrazin-6-yl]benzamide,
(4-methylpiperazin-1-yl)-[4-[6-[(E)-styryl]imidazo[1,2-a]pyrazin-3-yl]phenyl]methanone,
N-[3-[3-(4-phenoxyphenyl)imidazo[1,2-a]pyrazin-6-yl]phenyl]methanesulfonamide,
6-(3-fluorophenyl)-3-(o-tolyl)imidazo[1,2-a]pyrazine,
3-(o-tolyl)-6-(2-thienyl)imidazo[1,2-a]pyrazine,
4-[3-(2-chlorophenyl)imidazo[1,2-a]pyrazin-6-yl]-2-methoxy-phenol,
3-[3-(4-tert-butylphenyl)imidazo[1,2-a]pyrazin-6-yl]-N,N-dimethyl-benzamide,
5-[3-(4-tert-butylphenyl)imidazo[1,2-a]pyrazin-6-yl]pyridin-2-amine,
1-[3-[6-(3-pyridyl)imidazo[1,2-a]pyrazin-3-yl]phenyl]ethanone,
1-[3-[6-(3-fluorophenyl)imidazo[1,2-a]pyrazin-3-yl]phenyl]ethanone,
4-[3-(3-acetylphenyl)imidazo[1,2-a]pyrazin-6-yl]-N-(2-dimethylaminoethyl)benzamide,
1-[3-[6-(2-thienyl)imidazo[1,2-a]pyrazin-3-yl]phenyl]ethanone,
N,N-dimethyl-2-[3-(2-thienyl)imidazo[1,2-a]pyrazin-6-yl]aniline,
6-(4-pyridyl)-3-(2-thienyl)imidazo[1,2-a]pyrazine,
3-(2-thienyl)-6-(3-thienyl)imidazo[1,2-a]pyrazine,
6-(benzothiophen-2-yl)-3-(2-thienyl)imidazo[1,2-a]pyrazine,
4-[3-(2-thienyl)imidazo[1,2-a]pyrazin-6-yl]phenol,
3-(2-thienyl)-6-[4-(trifluoromethoxy)phenyl]imidazo[1,2-a]pyrazine,
6-[(E)-styryl]-3-(2-thienyl)imidazo[1,2-a]pyrazine,
N-(2-hydroxyethyl)-3-[3-(2-thienyl)imidazo[1,2-a]pyrazin-6-yl]benzamide,
6-(3-chlorophenyl)-3-(2-thienyl)imidazo[1,2-a]pyrazine,
[4-[3-(2-thienyl)imidazo[1,2-a]pyrazin-6-yl]phenyl]methanol,
N-(2-hydroxyethyl)-4-[3-(2-thienyl)imidazo[1,2-a]pyrazin-6-yl] benzamide, -continued 3,6-bis(2-thienyl)imidazo[1,2-a]pyrazine,
N-[3-[3-(2-thienyl)imidazo[1,2-a]pyrazin-6-yl]phenyl] methanesulfonamide,
6-(3,5-dimethoxyphenyl)-3-(2-thienyl)imidazo[1,2-a]pyrazine,
5-[3-(2-thienyl)imidazo[1,2-a]pyrazin-6-yl]pyridin-2-amine,
6-(3-isopropoxyphenyl)-3-(2-thienyl)imidazo[1,2-a]pyrazine,
N,N-dimethyl-4-[6-[6-(4-methylpiperazin-1-yl)-3-pyridyl]imidazo[1,2-a]pyrazin-3-yl] benzamide,
N,N-dimethyl-4-[6-(2-phenoxyphenyl)imidazo[1,2-a]pyrazin-3-yl] benzamide,
N,N-dimethyl-4-[6-(3-thienyl)imidazo[1,2-a]pyrazin-3-yl]benzamide,
4-[6-(3-acetamidophenyl)imidazo[1,2-a]pyrazin-3-yl]-N,N-dimethyl-benzamide,
N,N-dimethyl-4-[6-(1-methylindol-5-yl)imidazo[1,2-a]pyrazin-3-yl] benzamide,
4-[6-(5-acetyl-2-thienyl)imidazo[1,2-a]pyrazin-3-yl]-N-cyclopropyl-benzamide,
N-cyclopropyl-4-[6-[4-(4-isopropylpiperazin-1-yl)phenyl]imidazo[1,2-a]pyrazin-3-yl]benzamide,
2-[3-(3,5-dimethoxyphenyl)imidazo[1,2-a]pyrazin-6-yl]-N,N-dimethyl-aniline,
3-(3,5-dimethoxyphenyl)-6-(3-isopropoxyphenyl)imidazo[1,2-a] pyrazine,
3-(1-methylpyrazol-4-yl)-6-(4-pyridyl)imidazo[1,2-a]pyrazine,
6-(benzothiophen-2-yl)-3-(1-methylpyrazol-4-yl)imidazo[1,2-a] pyrazine,
6-[6-(3,4,5-trimethoxyphenyl)imidazo[1,2-a]pyrazin-3-yl]quinoline,
2-methoxy-4-[3-(6-quinolyl)imidazo[1,2-a]pyrazin-6-yl]phenol,
2,6-dimethyl-4-[3-(6-quinolyl)imidazo[1,2-a]pyrazin-6-yl]phenol,
6-[6-(1-methylindol-5-yl)imidazo[1,2-a]pyrazin-3-yl]quinoline, and
N-[3-[3-(6-quinolyl)imidazo[1,2-a]pyrazin-6-yl]phenyl] methanesulfonamide,
4-[3-[6-(2-thienyl)imidazo[1,2-a]pyrazin-3-yl]phenyl]morpholine,
N-[3-[6-(2-thienyl)imidazo[1,2-a]pyrazin-3-yl]phenyl]methanesulfonamide,
3-(benzothiophen-2-yl)-6-(2-thienyl)imidazo[1,2-a]pyrazine,
3-[6-(2-thienyl)imidazo[1,2-a]pyrazin-3-yl]aniline,
5-[6-(2-thienyl)imidazo[1,2-a]pyrazin-3-yl]pyridin-2-amine,
3-(3-isopropoxyphenyl)-6-(2-thienyl)imidazo[1,2-a]pyrazine,
3-[4-(1-piperidyl)phenyl]-6-(2-thienyl)imidazo[1,2-a]pyrazine,
(2S)-3-methyl-2-[[3-[4-(1-piperidyl)phenyl]imidazo[1,2-b]pyridazin-6-yl]amino]butan-1-ol,
(2S)-2-[[3-[3-(dimethylamino)phenyl]imidazo[1,2-b]pyridazin-6-yl]amino]-3-methyl-butan-1-ol,
(2S)-3-methyl-2-[[3-(3-morpholinophenyl)imidazo[1,2-b]pyridazin-6-yl]amino]butan-1-ol,
(2S)-2-[[3-(6-amino-3-pyridyl)imidazo[1,2-b]pyridazin-6-yl]amino]-3-methyl-butan-1-ol,
(2S)-2-[[3-(3-isopropoxyphenyl)imidazo[1,2-b]pyridazin-6-yl]amino]-3-methyl-butan-1-ol,
N,N-dimethyl-3-(3-thiazol-4-ylimidazo[1,2-a]pyrazin-6-yl)aniline,
4-[3-(3-thiazol-4-ylimidazo[1,2-a]pyrazin-6-yl)phenyl]morpholine,
5-(3-thiazol-4-ylimidazo[1,2-a]pyrazin-6-yl)pyridin-2-amine,
4-[6-(3-isopropoxyphenyl)imidazo[1,2-a]pyrazin-3-yl]thiazole,
N-[3-(3-thiazol-4-ylimidazo[1,2-a]pyrazin-6-yl)phenyl]methanesulfonamide,
3-(3-thiazol-4-ylimidazo[1,2-a]pyrazin-6-yl)aniline.

Further preferred small molecules according to group III for GRK5 inhibition are of the general formula (XI)

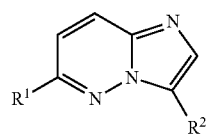

(XI)

$R^1$ represents —$(CH_2)_n$—$R^3$ or —NH—$(CH_2)_n$—$R^3$;
$R^2$ represents —$(CH_2)_m$—$R^4$;
$R^3$ and $R^4$ are independently of each other
—H, —F, —Br, —Cl, —CN, —OH, —OCH$_3$, —OC$_2$H$_5$, —NHCH$_3$, —N(CH$_3$)$_2$, —CH$_3$, —C$_2$H$_5$, -cyclo-C$_3$H$_5$, —C$_3$H$_7$, —CH(CH$_3$)$_2$, -cyclo-C$_4$H$_7$, —C$_4$H$_9$, —CH$_2$—CH(CH$_3$)$_2$, —CH(CH$_3$)—C$_2$H$_5$, —C(CH$_3$)$_3$, -cyclo-C$_5$H$_9$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, -cyclo-C$_6$H$_{11}$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH(CH$_3$)Ph, —CH=CH—C$_4$H$_9$, —CH=CH—C$_5$H$_{11}$, —CH=CH-Ph, —CH=CH—C$_6$H$_{13}$, —C≡C—C(CH$_3$)$_3$, —CH$_2$—OH; —C$_2$H$_4$—OH; —C$_3$H$_6$—OH, —C$_4$H$_9$—OH, —C$_5$H$_{10}$—OH, —C$_6$H$_{12}$—OH, —C$_7$H$_{14}$—OH, —C$_8$H$_{16}$—OH, —CH=CH—C$_3$H$_6$—OH, —CH=CH—C$_4$H$_8$—OH, —CH(CH$_2$OH)$_2$, —CH(C$_2$H$_5$)—CH$_2$—OH, —CH(CH$_3$)—C$_2$H$_4$—OH, —C(CH$_3$)$_2$—OH, —C(CH$_3$)$_2$—CH$_2$—OH, —CH(CH$_3$)OH, —CH$_2$—CH(CH$_3$)OH, —C(OH)(CH$_3$)—C$_2$H$_5$, —C(OH)(CH$_3$)—C$_3$H$_7$, —CH$_2$—C(OH)(CH$_3$)—C$_2$H$_5$, —CH(CH$_3$)—CH(CH$_3$)OH, —C(CH$_3$)$_2$—C$_2$H$_4$OH, —CH$_2$—C(CH$_3$)$_2$ OH, —C(OH)(C₂H₅)₂, —C₂H₄—C(OH)(CH₃)₂,
—C(CH(CH₃)₂)CH₂OH, —C₃H₅—C(OH)(CH₃)₂,
—CH(CH(CH₃)₂)CH₂—OH,

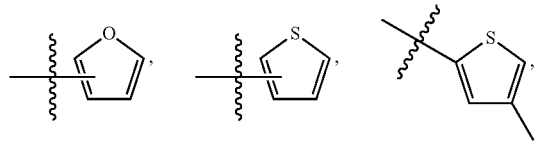

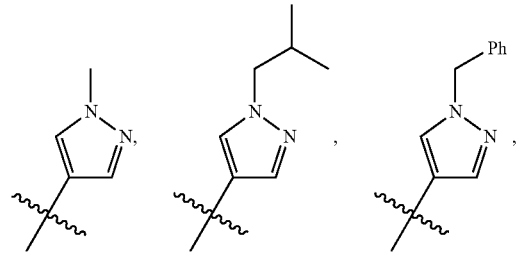

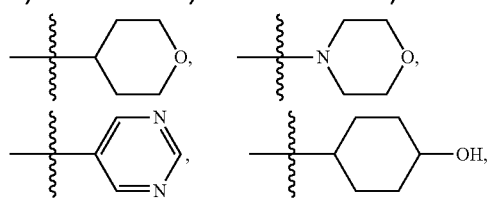

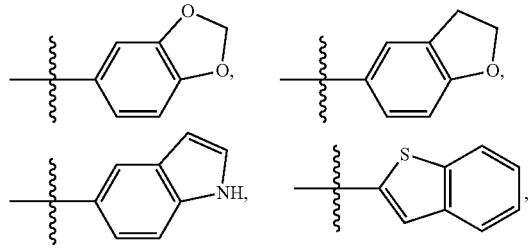

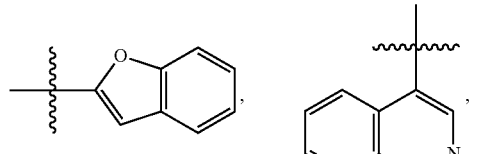

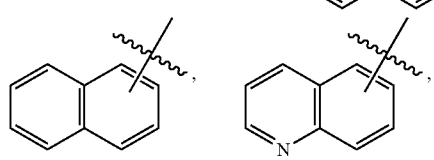

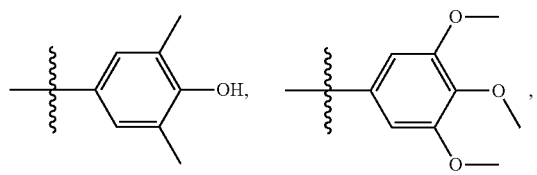

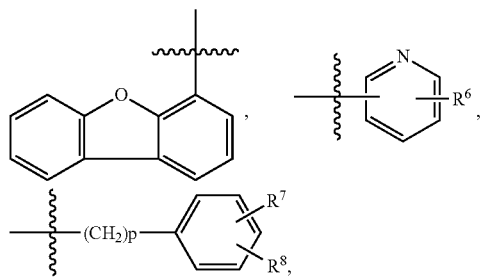

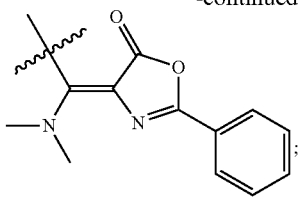

R⁶ is —H, —NH₂, —OMe, —O—(CH₂)₃N(CH₃)₂, or

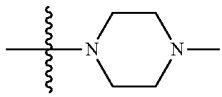

R⁷ and R⁸ are independently of each other
—H, —F, —Br, —Cl, —OH, —CN, —NO₂, —CH₃,
—CH(CH₃)₂, —OCH₃, —OC₂H₅, —CF₃, —OCF₃,
—CH₂OH, —CH₂NH₂, —CH₂CN, —CH₂N(CH₃)₂,
—OPh, —SCH₃, —NH₂, —NHCH₃, —NHCOCH₃,
—NHSO₂CH₃, —N(CH₃)₂, —SO₂CH₃, —SO₂NH₂,
—C₂H₄CO₂H, —CH=CH—CO₂H, —COR¹⁰,

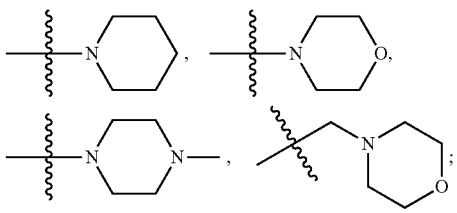

R¹⁰ is —OH, —CH₃, —OCH₃, —NH₂, —NHCH₃,
—NHC₂H₄OH, —NHC₂H₄N(CH₃)₂, —NH(CH₂)₃N(CH₃)₂,

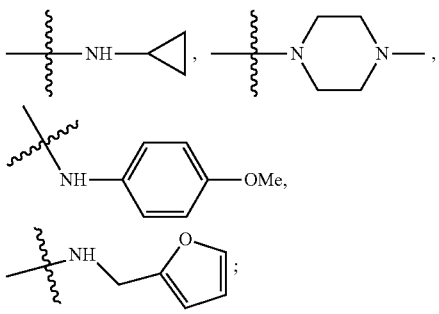

m, n and p are independently of each other an integer from 0 to 3;

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

Further preferred small molecules for GRK5 inhibition of group III are of the general formula (XII)

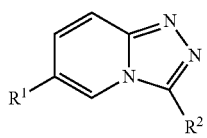
(XII)

wherein
R¹ represents —(CH₂)ₙ—R³;
R² represents —(CH₂)ₘ—R⁴;
R³ and R⁴ are independently of each other
—H, —F, —Br, —Cl, —CN, —OH, —OCH₃, —OC₂H₅, —NHCH₃, —N(CH₃)₂, —CH₃, —C₂H₅, -cyclo-C₃H₅, —C₃H₇, —CH(CH₃)₂, -cyclo-C₄H₇, —C₄H₉, —CH₂—CH(CH₃)₂, —CH(CH₃)—C₂H₅, —C(CH₃)₃, -cyclo-C₅H₉, —C₅H₁₁, —CH(CH₃)—C₃H₇, —CH₂—CH(CH₃)—C₂H₅, —CH(CH₃)—CH(CH₃)₂, —C(CH₃)—C₂H₅, —CH₂—C(CH₃)₃, —CH(C₂H₅)₂, —C₂H₄—CH(CH₃)₂, -cyclo-C₆H₁₁, —C₆H₁₃, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH(CH₃)Ph, —CH=CH—C₄H₉, —CH=CH—C₅H₁₁, —CH=CH-Ph, —CH=CH—C₆H₁₃, —CH₂—OH; —C₂H₄—OH; —C₃H₆—OH, —C₄H₉—OH, —C₅H₁₀—OH, —C₆H₁₂—OH, —C₇H₁₄—OH, —C₈H₁₆—OH, —CH=CH—C₃H₆—OH, —CH=CH—C₄H₈—OH, —CH(CH₂OH)₂, —CH(C₂H₅)—CH₂—OH, —CH(CH₃)—C₂H₄—OH, —C(CH₃)₂—OH, —C(CH₃)₂—CH₂—OH, —CH(CH₃)OH, —CH₂—CH(CH₃)OH, —C(OH)(CH₃)—C₂H₅, —C(OH)(CH₃)—C₃H₇, —CH₂—C(OH)(CH₃)—C₂H₅, —CH(CH₃)—CH(CH₃)OH, —C(CH₃)₂—C₂H₄OH, —CH₂—C(CH₃)₂OH, —C(OH)(C₂H₅)₂, —C₂H₄—C(OH)(CH₃)₂, —C(CH(CH₃)₂)CH₂OH, —C₃H₆—C(OH)(CH₃)₂, —CH(CH(CH₃)₂)CH₂—OH, —C≡C—R⁵,

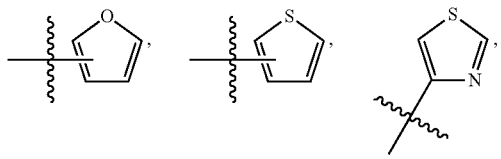

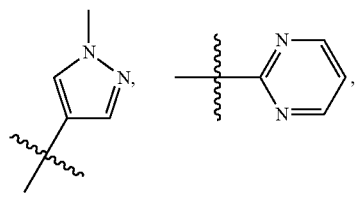

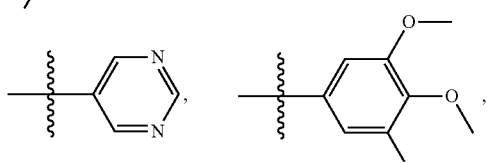

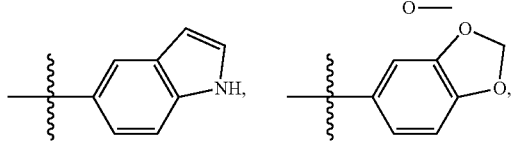

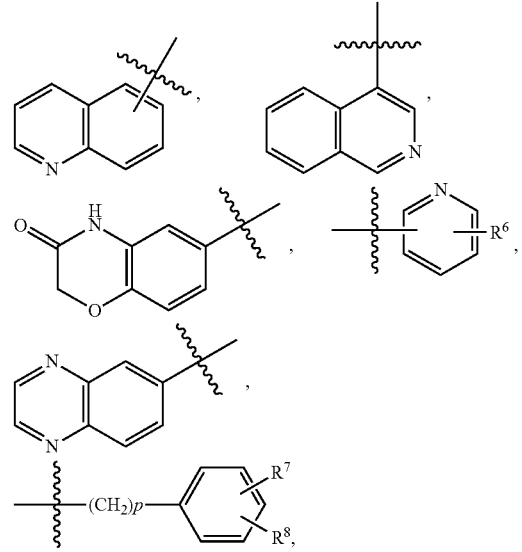

R⁵ is selected from —H, —CH₂OH, —CH₂N(CH₃)₂,

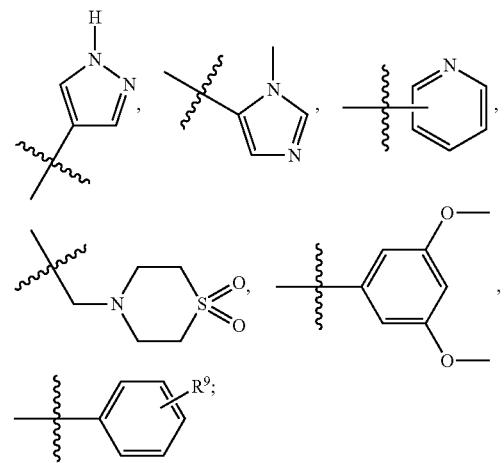

R⁶ is selected from —H, —NH₂, or —OMe;
R⁷ and R⁸ are independently of each other
—H, —F, —Cl, —OH, —CN, —NO₂, —CH₃, —CH(CH₃)₂, —OCH₃, —CF₃, —OCF₃, —CH₂OH, —CH₂N(CH₃)₂, —CH₂NHPh, —O(CH₂)₃N(CH₃)₂, —OPh, —SCH₃, —NH₂, —NHCOCH₃, —NHSO₂CH₃, —N(CH₃)₂, —SO₂CH₃, —COR¹⁰,

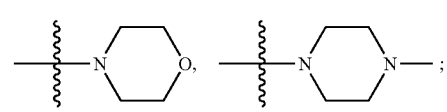

R⁹ is —H, —F, —Br, —Cl, —OH, —CN, —CH₃, —CH(CH₃)₂, —OCH₃, —OC₂H₅, —CF₃, —OCF₃, —NHCOCH₃, or —CON(CH₃)₂;
R¹⁰ is —OH, —CH₃, —NH₂, —NHCH₃, —N(CH₃)₂, —NHC₂H₄OH,
—NHC₂H₄N(CH₃)₂, —NH(CH₂)₃N(CH₃)₂,

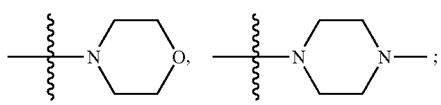

m, n and p are independently of each other 0 or 1;

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

Further preferred small molecules for GRK5 inhibition according to group III are of general formula (XIII)

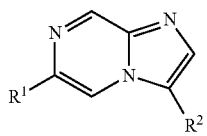
(XIII)

wherein $R^1$ represents —$(CH_2)_n$—$R^3$;

$R^2$ represents —$(CH_2)_m$—$R^4$ or —NHCO—$(CH_2)_m$—$R^4$;

$R^3$ and $R^4$ are independently of each other

—H, —F, —Br, —Cl, —CN, —OH, —OCH$_3$, —OC$_2$H$_5$, —NHCH$_3$, —N(CH$_3$)$_2$, —CH$_3$, —C$_2$H$_5$, -cyclo-C$_3$H$_5$, —C$_3$H$_7$, —CH(CH$_3$)$_2$, -cyclo-C$_4$H$_7$, —C$_4$H$_9$, —CH$_2$—CH(CH$_3$)$_2$, —CH(CH$_3$)—C$_2$H$_5$, —C(CH$_3$)$_3$, -cyclo-C$_5$H$_9$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, -cyclo-C$_6$H$_{11}$, —C$_6$H$_{13}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH(CH$_3$)Ph, —CH=CH—C$_4$H$_9$, —CH=CH—C$_5$H$_{11}$, —CH=CH-Ph, —CH=CH—C$_6$H$_{13}$, —CH$_2$—OH; —C$_2$H$_4$—OH; —C$_3$H$_6$—OH, —C$_4$H$_9$—OH, —C$_5$H$_{10}$—OH, —C$_6$H$_{12}$—OH, —C$_7$H$_{14}$—OH, —C$_8$H$_{16}$—OH, —CH=CH—C$_3$H$_6$—OH, —CH=CH—C$_4$H$_8$—OH, —CH(CH$_2$OH)$_2$, —CH(C$_2$H$_5$)—CH$_2$—OH, —CH(CH$_3$)—C$_2$H$_4$—OH, —C(CH$_3$)$_2$—OH, —C(CH$_3$)$_2$—CH$_2$—OH, —CH(CH$_3$)OH, —CH$_2$—CH(CH$_3$)OH, —C(OH)(CH$_3$)—C$_2$H$_5$, —C(OH)(CH$_3$)—C$_3$H$_7$, —CH$_2$—C(OH)(CH$_3$)—C$_2$H$_5$, —CH(CH$_3$)—CH(CH$_3$)OH, —C(CH$_3$)$_2$—C$_2$H$_4$OH, —CH$_2$—C(CH$_3$)$_2$OH, —C(OH)(C$_2$H$_5$)$_2$, —C$_2$H$_4$—C(OH)(CH$_3$)$_2$, —C(CH(CH$_3$)$_2$)CH$_2$OH, —C$_3$H$_6$—C(OH)(CH$_3$)$_2$, —CH(CH(CH$_3$)$_2$)CH$_2$—OH,

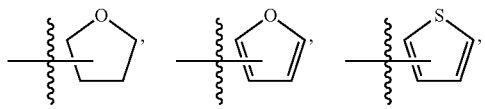

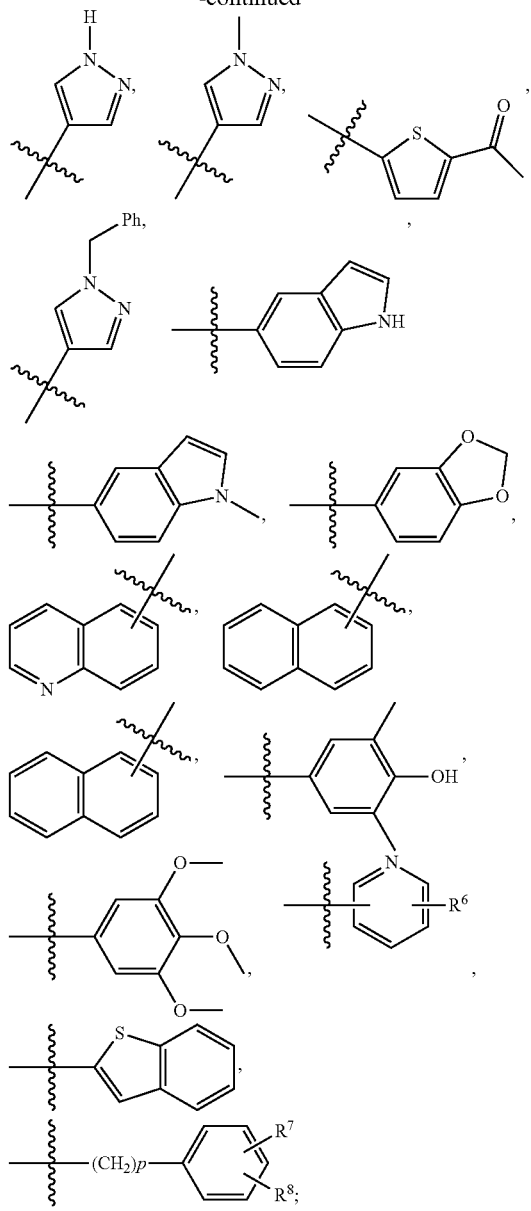

$R^6$ is selected from —H, —NH$_2$, —OMe, or —O—(CH$_2$)$_3$—N(CH$_3$)$_2$,

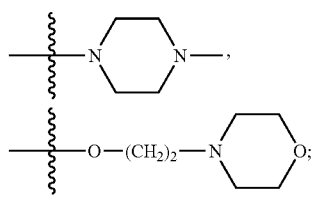

$R^7$ and $R^8$ are independently of each other

—H, —F, —Br, —Cl, —OH, —CN, —NO$_2$, —CH$_3$, —CH(CH$_3$)$_2$, —C(CH$_3$)$_3$, —OCH$_3$, —OC$_2$H$_5$, —OCH(CH$_3$)$_2$, —CF$_3$, —OCF$_3$, —CH$_2$OH, —CH$_2$N(CH$_3$)$_2$, —CH$_2$NHPh, —OPh, —O(CH$_2$)$_3$N(CH$_3$)$_2$, —SCH$_3$, —NH$_2$, —NHCH$_3$, —NHCOCH$_3$, —NHSO$_2$CH$_3$, —N(CH$_3$)$_2$, —C$_2$H$_4$CO$_2$H, —COR$^{10}$,

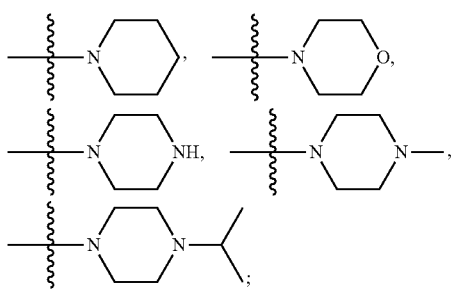

R$^{10}$ is selected from —CH$_3$, —NH$_2$, —N(CH$_3$)$_2$, —NHC$_2$H$_4$N(CH$_3$)$_2$, —NHC$_2$H$_4$OH, —NH(CH$_2$)$_3$N(CH$_3$)$_2$,

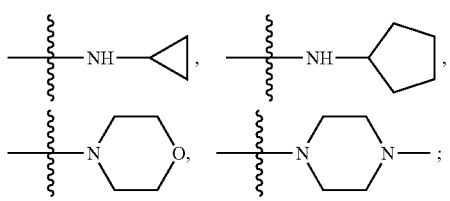

m, n and p are independently of each other 0 or 1;
and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

EXAMPLES

General Cell Culture Techniques

Cell lines were routinely assayed for *mycoplasma* contamination and cultured at 95% air, 5% CO$_2$ and 37° C. in a Hera-Cell-150 incubator. Before seeding, the cell amount was determined using a Coulter Counter system (Coulter Electronics) and the corresponding cell amount for seeding was calculated. All cells were cultured according to the appropriate recommendations of ATCC protocols.

For analysis using the following assays, cells were seeded at different plate size and suitable cell-density. After 24 h the cells were washed with PBS and fresh media containing DMSO respectively the appropriate treatment with TKIs, peptides or chemicals, was replaced. Starving for insulin dependent examinations was performed in glucose- and FCS-free DMEM media for 4 h.

TABLE 4

| Condition for the used cell lines: | | |
|---|---|---|
| Cell line | Culture media | Initial cell amount 96-/12-/6-well |
| 3T3-L1 | DMEM 1.0 g/L glucose, 10% (v/v) NCS, 2 mM L-glutamine, 1x Pen/Strep | 5 × 103/5 × 104/1 × 105 |
| Beta TC-6 | DMEM 4.5 g/L glucose, 15% (v/v) FCS, 2 mM L-glutamine, 1x Pen/Strep | 3 × 104/3 × 105/6 × 105 |

TABLE 4-continued

| Condition for the used cell lines: | | |
|---|---|---|
| Cell line | Culture media | Initial cell amount 96-/12-/6-well |
| C2C12 | DMEM 4.5 g/L glucose, 10% (v/v) FCS, 2 mM L-glutamine, 1x Pen/Strep | 3 × 103/3 × 104/6 × 104 |
| RIN-5AH-T2B | RPMI-1640 4.5 g/L glucose, 10% (v/v) FCS, 2 mM L-glutamine, 1x Pen/Strep | 3 × 104/3 × 105/6 × 105 |

Example 1

Cytotoxicity Assays

Using a MTT (3-(4,5-dimethylthiazol-2-yl)-2,5-diphenyl tetrazolium bromide) approach, the potential citotoxic effect of the small molecules on the viability and proliferation of the beta-TC6 and C2C12 cells was determined in vitro after a 72 h treatment.

For MTT transformation, ⅕ of total volume of a 5 mg/mL MTT stock solution was added to the cells as well as control wells and incubated at 37° C., 5% CO$_2$ (v/v) for 1 h. Then ½ of total volume of MTT-stop solution was added and plates were incubated overnight in the dark at 25° C. The optical density (OD) was measured using a multiwell spectrophotometer at a wavelength of 570 nm.

TABLE 5

| Control compounds: | |
|---|---|
| Compound | Structure |
| D1 | (structure shown) |
| D3 | (structure shown) |

TABLE 5-continued

Control compounds:

| Compound | Structure |
|---|---|
| D2 | (structure image) |
| D4 | (structure image) |
| Sunitinib (Sut, Sutent) | (structure image) |
| Akt1 | (structure image) |
| Exendin-4 | His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ |
| GLP-1 | His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-NH$_2$ |
| MEK | (structure image) |

In order to determine the IC$_{50}$ values for all compounds 35% inhibition, triplicates at 12 different concentrations with a dilution factor of three were used. The maximal compound assay concentration was set to 100 µM, representing the compound assay concentration used in the primary screen. For all assay plates, z-factor values were found to be significantly larger than 0.5, proving statistical relevance of the data.

Experimental Data for Small Molecules According to Group I

Example 2

High Throughput Screening Based on GRK5 Kinase Activity Assay

Screening for possible inhibitory compounds of GRK5 was performed using the ADP Glo™ Kinase Assay technology (Promega) according to the protocol as describe below. As suitable substrate for full length GRK5 casein was identified. Increasing concentrations of GRK5 are incubated together with 100 µM ATP in the absence and presence of 10 µM casein in a reaction buffer. Within this incubation non-phosphorylated casein is converted into phosphorylated casein and ATP is converted into ADP. Thereafter nonconverted ATP is digested into AMP by addition of the ADP-Glo™ Reagent. Subsequently the ADP that is produced by GRK5 activity is phosphorylated back to ATP by addition of Promega Kinase Detection Reagent. These ATP levels serve as measure for the GRK5 activity and are quantified by a luciferase/luciferin reaction. A linear dependence between GRK5 concentration and luminescence signal can be observed. In the absence of casein increasing GRK5 concentration result only in a minor increase of luminescence demonstrating the specificity of the luminescence signal for GRK5 activity.

Km(ATP) was determined by measuring the GRK5 activity at increasing ATP concentrations. Km(ATP) was quantified to be 18.7 µM by fitting the GRK5 activity to the Michaelis Menten equation:

$$v(GRK5 \text{ activity}) = (V\max \times [ATP])/(Km(ATP) + [ATP])$$

For GRK5 kinase activity assay, the following protocol was used:

The assay was performed in: 384 well U bottom, PP, black, low volume (Corning, 3676) assay plates at reaction temperature of 25° C. The reaction buffer used was composed of: 20 mM MES pH 6.0, 1 mM DTT, 10 mM MgCl$_2$, 0.01% Tween20 and the reaction volume was 6 µL.

Firstly 4 µL 6/4 fold concentrated substrate and 6/4 fold concentrated ATP in 1 fold concentrated reaction buffer are added to each well of the assay plate. Subsequently 67 nL 1000 fold concentrated test compound in 100% DMSO are added to each well except to C− and C+ wells using pin tool. Then 67 nL 100% DMSO are pipetted to C− (no kinase, no compound) and C+ (no compound) wells using pin-tool and 2 µL reaction buffer are added to C− wells. 2 µL 6/2 fold concentrated full length GRK5 (Millipore, #14-714) in reaction buffer is added to each well except C− wells. After incubation for 120 min. at room temperature 6 µL ADP-Glo™ Reagent (ADP Glo™ Kinase Assay Kit: Promega, V9101) are added to each well to stop the kinase reaction and deplete the unconsumed ATP. After a second incubation for 40 min. at room temperature 12 µL of Kinase Detection Reagent are added to convert ADP to ATP and start luciferase/luciferin reaction for detection of ATP. The final assay concentrations are 20 nM GRK5, 18.7 µM ATP and 10 µM of the substrate casein. Finally, after incubation for 40 min at room temperature the luminescence intensity was measured.

Example 3.1

$IC_{50}$ Determination of Compounds Inhibiting GRK5 by ADP Glo™ Kinase Assay Technology (Promega)

The activity of the compounds was classified according to $IC_{50}$ for binding sites of Grk5 into the following ranges:

| | |
|---|---|
| $IC_{50} \leq 5\ \mu M$ | ++++ |
| $5\ \mu M < IC_{50} \leq 20\ \mu M$ | +++ |
| $20\ \mu M < IC_{50} \leq 80\ \mu M$ | ++ |
| $80\ \mu M < IC_{50} \leq 120\ \mu M$ | + |

Example 3.2

$IC_{50}$ Determination of Compounds Inhibiting GRK5 by Millipore KinaseProfiler™

As alternative, $IC_{50}$ values are determined by a radiometric based filtration binding assay, namely Millipore KinaseProfiler™. GRK5 is incubated with 8 mM MOPS pH7.0, 0.2 mM EDTA, 2 mg/mL casein, 10 mM MgAcetate and [$\gamma$-$^{33}$P-APT] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

The activity of the compounds was classified according to $IC_{50}$ for binding sites of GRK5 into the following ranges:

| | |
|---|---|
| $IC_{50} \leq 5\ \mu M$ | ++++ |
| $5\ \mu M < IC_{50} \leq 20\ \mu M$ | +++ |
| $20\ \mu M < IC_{50} \leq 80\ \mu M$ | ++ |
| $80\ \mu M < IC_{50} \leq 120\ \mu M$ | + |

Example 4

Release of Insulin after Treatment with the Compounds of the Example 2

After having identified the most promising compounds acting as GRK5 inhibitors and determined the $IC_{50}$ values, the effect of the compounds of the example 2 on the release of insulin by beta-TC6 was determined. Cells were cultured overnight, washed with PBS and then treated with 5 μM of test compounds as well as non-inhibitor controls and Sunitinib as positive control, for 2 h in a high glucose (4.5 g/L) DMEM at 37° C. and 5% (v/v) $CO_2$. Release of insulin was detected using a rat/mouse insulin ELISA.

In order to measure the insulin released by beta-TC6 insulinoma (mouse) cells upon treatment with the small molecules, beta-TC6 insulinoma (mouse)cells were washed and incubated for 2 h in high (4.5 g/L) or low (1.125 g/L) glucose media at 37° C. After incubation, the supernatant of the beta-TC6 insulinoma cells was diluted 1:20. The insulin release was measured with rat/mouse insulin ELISA (Merck Millipore Darmstadt, Cat. # EZRMI-13K) by following the manufacture protocol. The enzyme activity of the horseradish peroxidase of the immobilized biotinylated antibodies was monitored spectrophotometrically by the increased absorbency at 490 nm, and corrected by the absorbency at 610 nm. The results are summarized in Table 6 and show that compound 243 has a better effect on the insulin release by beta-TC6 cells than the positive control Sunitinib. Moreover, compound 6 induces a level similar to Sunitinib on the insulin release by beta-TC6 cells.

TABLE 6

Insulin release by beta-TC6 cells treated with the small molecules of group I (the % values are in regard to the DMSO control, thus 30% means an increase of insulin release of 30% in regard to the physiological conditions where the insulin release is set at 0%)

| Compound group I | Insulin release by beta-TC6 cells at 5 μM [%] |
|---|---|
| 392 | 30.52% |
| 305 | 20.24% |
| 6 | 81.25% |
| 3 | 15.43% |
| 475 | 48.72% |
| 243 | 142.26% |

Example 5

Glucose Uptake after Treatment of C2C12 Cells with Compounds of the Example 2

To investigate the impact of the GRK5 inhibitors on glucose uptake, the fluorescent D-glucose analog 2-[4N-(7-nitrobenz-2-oxa-1,3-diazol-4-yl)-amino]-2-deoxy-D-glucose (2-NBDG) was used. 2-NBDG is a fluorescently-labeled deoxyglucose analog that is commonly used to directly monitor glucose uptake by living cells. For 2-NBDG detection, cells were cultured for 1 h together with 5 μM of a small molecule in glucose free media supplied with 100 μM 2-NBDG at 37° C. before collecting. Furthermore, as internal controls, samples of glucose free media, rFc4espectively glucose free media with test compound, were tested. Subsequently, cells were washed, trypsinized and harvested in ice-cold PBS before centrifuged at 1.6×10³ rpm at 4° C. Cells were analyzed by flow cytometry (FACS Calibur, BD Bioscience, respectively a BD Accuri® C6 Flow Cytometer). For evaluation, cells were gated using the side- and forward scatter SSC/FSC and quantified by excited at 488 nm and collected at 533 nM (RA). The results are summarized in Table 7.

TABLE 7

2-NBDG glucose uptake (%) by cells treated with the small molecules

| Compound of group I | 2-NBDG Glucose Uptake [%] |
|---|---|
| 305 | 50.81% |
| 6 | 45.35% |
| 3 | 38.51% |
| 137 | 69.73% |
| 243 | 48.87% |

Example 6

Glucose Mediated Effect on Insulin Release by Treatment of Beta-TC6 Cells with Compounds of the Example 2

Hypoglycemia can cause impairment of cognitive function, motoric control or even consciousness. For safety reasons, it is important that the inventive compounds are glucose dependent and do not enhance the insulin release in low glucose environment. Therefore, the glucose dependent insulin release in beta-TC6 cells using media with 1.125 mM (20 mg/dL) glucose was verified. Cells were cultured for 24 h in a 96-well plate, washed with PBS and then appropriate media was replaced for 2 h at 37° C. and 5% (v/v) $CO_2$. Afterwards, the supernatant was used to detect the amount of insulin released in a rat/mouse insulin ELISA (Merck Millipore Darmstadt, Cat. # EZRMI-13K) by following the manufacture protocol. The enzyme activity of the horseradish peroxidase of the immobilized biotinylated antibodies was monitored spectrophotometrically by the increased absorbency at 490 nm, and corrected by the absorbency at 610 nm.

Treatment of beta-TC6 cells with compounds of the invention did not lead to increased insulin release like observed in high glucose media. Sunitinib seemed to decrease the insulin release (0.77±0.03), whereas all the small molecules ranged close to the DMSO control.

Example 7

Evaluation of Insulin Dependence of the Small Molecules

To investigate if the 2-NBDG uptake of the small molecule inhibitors of GRK5 are insulin dependent, 3T3-L pre-adipocytes were differentiated to matured adipocytes. Afterwards, cells were starved for 4 h before they were washed and glucose free media supplied with 100 μM 2-NBDG, in the presence and absence of 10 μg/ml insulin the test compound was added for 1 h at 37° C. Furthermore, as internal controls, samples of glucose free media or glucose free media with compound were measured (data not shown). Fluorescence was analyzed by flow cytometer (FACS Calibur, BD Bioscience, respectively a BD Accuri® C6 Flow Cytometer). For evaluation, cells were gated using the side- and forward scatter SSC/FSC and quantified by excited at 488 and detected at 533 nm (FL1).

Example 8

Comparison of the Influence on Insulin Release of the Small Molecules and Commercially Available Kinase Inhibitors Based on literature references, several commercially available inhibitors were compared with compounds according to the invention. For comparison we chose the Akt1-Inhibitor II (Calbiochem #124008), which should lead to decreased insulin release, as well as the Map2K3-Inhibitor II (Calbiochem #444938), Exendin-4 (Sigma #E7144) and GLP-1 (Sigma #G8147), which should lead to an increased insulin release. Cells were cultured for 24 h before treated with the inventive compounds and control inhibitors for 2 h at 37° C. and 5% (v/v) $CO_2$. Insulin in the supernatant was detected by mouse/rat insulin ELISA.

Example 9

Insulin HTRF Assay Principle

For further screening of compounds derived from compounds described above for their ability to regulate insulin release an insulin HTRF® (Homogeneous Time-Resolved Fluorescence; Cisbio International, France) was used. This assay is based on two antibodies against insulin binding to different epitopes of insulin. One of these antibodies is coupled to Europium (Ab-Eu-Cryptate) and the other one to the fluorophore XL665 (Ab-XL665). If the insulin is secreted into the supernatant of cell culture, both antibodies can bind to insulin and come therefore into close proximity, which allows upon excitation that energy transfer between (FRET) the long-life fluorescent donor Europium (cryptate) and the acceptors XL665. FRET increases proportionally with insulin concentration.

The automated assay protocol is as follows:

On day 1, 15 k beta-TC6 cells per well were seeded for 24 or 48 h in 50 μL complete medium. On day 2 or respective on day 3, the medium is removed and cells are washed with 60 μL 1×PBS and 20 μL induction buffer is added using BioTek washer. Subsequently, 10 μL Sunitininb (5-μM f.c.) or the test compound in induction buffer; 0.5% f.c. DMSO (CyBi-well) is transferred to the cells. The cells are then incubated at 37° C. for 2, 3, 4 h.

The HTRF assay is carried out using Greiner 384-well 784075 assay plates.

First 10 μL supernatant is transferred from the cell plates in HTRF plates (CyBi-well). 10 μL of 0, 1, 2, and 4 ng/ml insulin standard controls in assay medium is used as a control. To each well 10 μL of combined 1:25 Ab-XL665 (Acc) and 1:20 Ab-Eu-Cryptate (WellMate) are added and incubated for 120 min at RT in the dark. Finally HTRF is measured on ViewLux ultra high throughput microplate imager (PerkinElmer).

The evaluation software DataFactory derives relative activities Ar according to the following equation:

$$Ar = \frac{V - R_{(0\% \, control)}}{R_{(100\% \, control)} - R_{(0\% \, control)}} \times 100$$

| | |
|---|---|
| Ar | relative activity in % |
| V | Raw data value of test well |
| $R_{(0\% \, control)}$ | Median raw data value of 0% control wells |
| $R_{(100\% \, control)}$ | Median raw data value of 100% control wells |

The activity of the compounds was classified according to their $A_r$ (relative activity) into the following ranges:

| | |
|---|---|
| $A_r \geq 100\%$ | ++++ |
| $50\% \leq A_r < 100\%$ | +++ |
| $30\% \leq A_r < 50\%$ | ++ |
| $0\% < A_r < 30\%$ | + |

The relative activity values of the compounds of the present application are summarized in Table 8.

TABLE 8

$A_r$ (relative activity) values of the small molecules of group I

| Compound | $A_r$ | Compound | $A_r$ |
|---|---|---|---|
| 1 | +++ | 14 | ++ |
| 2 | ++ | 15 | ++ |
| 3 | ++++ | 16 | ++ |
| 4 | ++ | 17 | +++ |
| 5 | + | 18 | +++ |
| 6 | +++ | 19 | +++ |
| 7 | +++ | 21 | +++ |
| 8 | ++ | 22 | ++++ |
| 9 | + | 23 | ++ |

TABLE 8-continued $A_r$ (relative activity) values of the small molecules of group I

| Compound | $A_r$ | Compound | $A_r$ |
|---|---|---|---|
| 10 | +++ | 24 | +++ |
| 11 | ++ | 25 | + |
| 12 | ++++ | 26 | +++ |
| 13 | +++ | 64 | +++ |
| 27 | +++ | 65 | ++++ |
| 28 | +++ | 66 | ++ |
| 29 | ++ | 67 | ++ |
| 30 | +++ | 68 | +++ |
| 31 | ++++ | 69 | ++ |
| 32 | ++ | 70 | ++++ |
| 33 | ++ | 71 | +++ |
| 34 | + | 72 | ++++ |
| 35 | + | 73 | +++ |
| 36 | + | 74 | ++++ |
| 38 | + | 75 | ++++ |
| 39 | +++ | 76 | ++ |
| 40 | ++++ | 77 | +++ |
| 41 | ++++ | 80 | ++++ |
| 42 | +++ | 81 | ++ |
| 43 | +++ | 82 | +++ |
| 44 | ++ | 84 | +++ |
| 45 | ++ | 85 | +++ |
| 46 | +++ | 86 | +++ |
| 47 | +++ | 87 | +++ |
| 48 | +++ | 88 | ++ |
| 49 | +++ | 89 | +++ |
| 50 | +++ | 90 | ++ |
| 51 | ++ | 91 | +++ |
| 52 | ++ | 92 | + |
| 53 | +++ | 93 | +++ |
| 54 | +++ | 94 | ++ |
| 55 | +++ | 95 | +++ |
| 56 | +++ | 96 | +++ |
| 57 | ++ | 97 | ++ |
| 58 | ++ | 98 | ++ |
| 59 | + | 99 | ++ |
| 60 | + | 100 | ++++ |
| 61 | + | 139 | +++ |
| 62 | ++++ | 140 | ++ |
| 101 | +++ | 141 | +++ |
| 103 | ++ | 143 | ++++ |
| 104 | +++ | 144 | ++++ |
| 105 | +++ | 145 | ++++ |
| 107 | +++ | 147 | +++ |
| 109 | +++ | 149 | ++++ |
| 110 | ++++ | 150 | +++ |
| 112 | +++ | 152 | ++++ |
| 113 | +++ | 153 | ++ |
| 115 | ++++ | 155 | +++ |
| 116 | + | 156 | ++ |
| 117 | ++++ | 157 | +++ |
| 118 | ++++ | 158 | +++ |
| 119 | +++ | 159 | +++ |
| 120 | ++++ | 160 | +++ |
| 121 | ++++ | 161 | +++ |
| 122 | ++ | 162 | +++ |
| 124 | ++++ | 164 | +++ |
| 125 | ++++ | 165 | ++++ |
| 126 | +++ | 166 | ++ |
| 127 | +++ | 167 | ++ |
| 128 | +++ | 168 | ++ |
| 130 | ++++ | 170 | +++ |
| 131 | ++++ | 171 | +++ |
| 132 | +++ | 172 | +++ |
| 133 | +++ | 173 | ++ |
| 134 | +++ | 174 | +++ |
| 135 | +++ | 212 | ++ |
| 136 | +++ | 213 | +++ |
| 175 | +++ | 215 | +++ |
| 176 | +++ | 216 | +++ |
| 177 | +++ | 217 | + |
| 178 | ++ | 218 | +++ |
| 179 | ++ | 219 | ++ |
| 180 | +++ | 220 | + |
| 181 | ++++ | 221 | ++ |
| 182 | +++ | 222 | + |
| 183 | +++ | 223 | + |
| 184 | ++ | 224 | + |
| 185 | + | 225 | ++ |
| 186 | ++ | 226 | +++ |
| 187 | ++ | 227 | ++ |
| 188 | + | 228 | +++ |
| 189 | ++++ | 229 | ++++ |
| 190 | +++ | 230 | ++ |
| 191 | +++ | 231 | ++++ |
| 192 | + | 232 | +++ |
| 193 | +++ | 233 | +++ |
| 194 | + | 234 | +++ |
| 195 | ++ | 235 | +++ |
| 196 | +++ | 236 | +++ |
| 197 | ++ | 237 | ++++ |
| 198 | +++ | 238 | ++ |
| 199 | +++ | 239 | ++ |
| 200 | ++ | 240 | + |
| 201 | ++ | 241 | + |
| 202 | ++ | 242 | + |
| 203 | ++ | 243 | + |
| 204 | +++ | 244 | +++ |
| 205 | +++ | 245 | +++ |
| 206 | +++ | 246 | ++++ |
| 207 | +++ | 247 | ++++ |
| 208 | ++ | 248 | + |
| 209 | +++ | 294 | +++ |
| 210 | ++ | 295 | +++ |
| 211 | ++ | 296 | ++ |
| 249 | ++++ | 297 | ++ |
| 250 | +++ | 298 | +++ |
| 251 | ++ | 299 | +++ |
| 252 | +++ | 300 | +++ |
| 253 | +++ | 301 | +++ |
| 254 | +++ | 302 | +++ |
| 255 | +++ | 303 | ++ |
| 256 | +++ | 304 | ++ |
| 257 | ++ | 305 | ++ |
| 258 | ++++ | 306 | +++ |
| 259 | +++ | 307 | +++ |
| 260 | +++ | 308 | +++ |
| 261 | + | 309 | ++ |
| 262 | +++ | 310 | +++ |
| 263 | +++ | 311 | +++ |
| 264 | ++ | 312 | +++ |
| 265 | +++ | 313 | ++++ |
| 266 | +++ | 315 | ++ |
| 267 | +++ | 316 | ++ |
| 268 | +++ | 317 | +++ |
| 269 | + | 318 | ++++ |
| 270 | +++ | 319 | +++ |
| 271 | +++ | 320 | ++ |
| 272 | +++ | 321 | ++ |
| 273 | ++ | 322 | ++++ |
| 274 | ++ | 323 | +++ |
| 275 | +++ | 324 | +++ |
| 276 | ++ | 325 | ++ |
| 277 | ++ | 326 | ++ |
| 278 | +++ | 327 | +++ |
| 279 | ++ | 328 | ++ |
| 280 | ++ | | |
| 281 | + | | |
| 282 | ++ | | |
| 283 | ++ | | |
| 284 | +++ | | |
| 285 | +++ | | |
| 286 | +++ | | |
| 287 | +++ | | |
| 288 | ++ | | |
| 289 | ++ | | |
| 290 | +++ | | |
| 291 | +++ | | |
| 292 | ++ | | |
| 293 | +++ | | |

N.D. (not determined)

Experimental Data for Small Molecules According to Group II

The small molecules efficiently inhibit the GRK5 activity at a concentration of 5 μM (the final assay concentration in tested compound is 5 μM) (Table 9-A).

| Compound group II | GRK5 inhibition [%] at 5 μM |
|---|---|
| II.58 | 96% |
| II.66 | 76% |
| II.77 | 98% |
| II.148 | 48% |
| II.150 | 96% |
| II.152 | 98% |
| II.153 | 56% |
| II.157 | 74% |
| II.167 | 81% |
| II.170 | 58% |
| II.181 | 49% |
| II.187 | 76% |
| II.189 | 98% |
| II.190 | 61% |
| II.191 | 66% |
| II.192 | 86% |
| II.193 | 88% |

Example 10.1

$IC_{50}$ Determination of Compounds Inhibiting GRK5 by ADP Glo™ Kinase Assay Technology (Promega) (Table 9-B)

The activity of the compounds was classified according to $IC_{50}$ for binding sites of Grk5 into the following ranges:

| | |
|---|---|
| $IC_{50} \leq 0.1$ μM | ++++ |
| 0.1 μM < $IC_{50} \leq 1.0$ μM | +++ |
| 1.0 μM < $IC_{50} \leq 2.0$ μM | ++ |
| 2.0 μM < $IC_{50} \leq 10.0$ μM | + |

TABLE 9-B

| Compound group II | GRK5 $IC_{50}$ [μM] |
|---|---|
| II.2 | ++ |
| II.6 | +++ |
| II.7 | + |
| II.10 | +++ |
| II.11 | +++ |
| II.12 | +++ |
| II.13 | +++ |
| II.14 | +++ |
| II.15 | ++ |
| II.21 | + |
| II.30 | + |
| II.32 | ++ |
| II.46 | ++++ |
| II.47 | + |
| II.48 | +++ |
| II.51 | + |
| II.53 | +++ |
| II.55 | +++ |
| II.59 | ++++ |
| II.60 | + |
| II.61 | ++++ |
| II.63 | +++ |
| II.67 | +++ |
| II.69 | ++++ |
| II.70 | +++ |
| II.71 | + |
| II.72 | +++ |
| II.73 | +++ |
| II.78 | ++++ |
| II.79 | ++++ |
| II.80 | ++++ |
| II.130 | +++ |
| II.131 | +++ |
| II.132 | +++ |
| II.133 | +++ |
| II.134 | ++ |
| II.135 | ++++ |
| II.136 | +++ |
| II.137 | +++ |
| II.138 | ++ |
| II.139 | ++ |
| II.140 | ++ |
| II.141 | + |

Example 10.2

$IC_{50}$ Determination of Compounds Inhibiting GRK5 by Millipore KinaseProfiler™ (Table 10)

$IC_{50}$ values are determined by a radiometric based filtration binding assay, namely Millipore KinaseProfiler™. GRK5 is incubated with 8 mM MOPS pH 7.0, 0.2 mM EDTA, 2 mg/mL casein, 10 mM MgAcetate and [γ-$^{33}$P-APT] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

The activity of the compounds was classified according to $IC_{50}$ for binding sites of GRK5 into the following ranges:

| | |
|---|---|
| $IC_{50} \leq 0.1$ μM | ++++ |
| 0.1 μM < $IC_{50} \leq 1.0$ μM | +++ |
| 1.0 μM < $IC_{50} \leq 2.0$ μM | ++ |
| 2.0 μM < $IC_{50} \leq 10.0$ μM | + |

TABLE 10

| Compound | GRK5 $IC_{50}$ [μM] |
|---|---|
| II.12 | +++ |
| II.16 | +++ |
| II.30 | + |
| II.46 | ++++ |
| II.47 | + |
| II.48 | +++ |
| II.53 | +++ |
| II.55 | +++ |
| II.59 | ++++ |
| II.63 | +++ |
| II.70 | +++ |
| II.71 | + |
| II.72 | +++ |
| II.73 | +++ |
| Sunitib | 169 μM |

Example 11

Release of Insulin after Treatment with the Small Molecules According to Group II After having identified the most promising compounds acting as GRK5 inhibitors and determined the $IC_{50}$ values, the effect of said compounds on the release of insulin by beta-TC6 was determined. Cells were cultured overnight, washed with PBS and then treated with 5 μM of test compounds as well as non-inhibitor controls and Sunitinib as positive control, for 2 h in a high glucose (4.5 g/L) DMEM at 37° C. and 5% (v/v) $CO_2$. Release of insulin was detected using a rat/mouse insulin ELISA.

To measure the insulin released by beta-TC6 insulinoma (mouse) cells upon treatment with the compounds according to II., beta-TC6 insulinoma (mouse) cells were washed and incubated for 2 h in high (4.5 g/L) or low (1.125 g/L) glucose media at 37° C. After incubation, the supernatant of the beta-TC6 insulinoma cells was diluted 1:20. The insulin release was measured with rat/mouse insulin ELISA (Merck Millipore Darmstadt, Cat. # EZRMI-13K) by following the manufacture protocol. The enzyme activity of the horseradish peroxidase of the immobilized biotinylated antibodies was monitored spectrophotometrically by the increased absorbency at 490 nm, and corrected by the absorbency at 610 nm. The results are summarized in Table 11.

TABLE 11

Insulin release by beta-TC6 cells treated with the small molecules according to group II. (the % values are in regard to the DMSO control, thus 30% means an increase of insulin release of 30% in regard to the physiological conditions where the insulin release is set at 0%)

| Compound group II | Insulin release by beta-TC6 cells at 5 μM [%] |
| --- | --- |
| II.51 | 252% |
| II.11 | 96% |
| II.131 | 134% |
| II.13 | 221% |
| II.12 | 214% |
| II.10 | 164% |
| II.67 | 159% |
| II.32 | 143% |
| II.133 | 131% |
| II.132 | 117% |
| II.130 | 103% |
| II.13 | 93% |
| Sunitinib | 80% |

Example 12

Glucose Uptake after Treatment of C2C12 Cells with Small Molecules According to Group II To investigate the impact of the GRK5 inhibitors on glucose uptake, the fluorescent D-glucose analog 2-[4N-(7-nitrobenz-2-oxa-1,3-diazol-4-yl)-amino]-2-deoxy-D-glucose (2-NBDG) was used. 2-NBDG is a fluorescently-labeled deoxyglucose analog that is commonly used to directly monitor glucose uptake by living cells. For 2-NBDG detection, cells were cultured for 1 h together with 5 μM of an inventive compound in glucose free media supplied with 100 μM 2-NBDG at 37° C. before collecting. Furthermore, as internal controls, samples of glucose free media, glucose free media with test compound, respectively glucose free media supplied with 100 μM 2-NBDG were tested. Subsequently, cells were washed, trypsinized and harvested in ice-cold PBS before centrifuged at $1.6 \times 10^3$ rpm at 4° C. Cells were analyzed by flow cytometry (FACS Calibur, BD Bioscience, respectively a BD Accuri® C6 Flow Cytometer). For evaluation, cells were gated using the side- and forward scatter SSC/FSC and quantified by excited at 488 nm and collected at 533 nM (FL1). The results are summarized in Table 12.

TABLE 12

2-NBDG glucose uptake (%) by cells treated with small molecules according to group II. at 5 μM

| Compound | 2-NBDG Glucose Uptake [%] |
| --- | --- |
| II.143 | 72% |
| II.73 | 127% |

Example 13

Glucose Mediated Effect on Insulin Release by Treatment of Beta-TC6 Cells with Small Molecules According to Group II Hypoglycemia can cause impairment of cognitive function, motoric control or even consciousness. For safety reasons, it is important that the small molecules are glucose dependent and do not enhance the insulin release in low glucose environment. Therefore, the glucose dependent insulin release in beta-TC6 cells using media with 1.125 mM (20 mg/dL) glucose was verified. Cells were cultured for 24 h in a 96-well plate, washed with PBS and then appropriate media was replaced for 2 h at 37° C. and 5% (v/v) $CO_2$. Afterwards, the supernatant was used to detect the amount of insulin released in a rat/mouse insulin ELISA (Merck Millipore Darmstadt, Cat. # EZRMI-13K) by following the manufacture protocol. The enzyme activity of the horseradish peroxidase of the immobilized biotinylated antibodies was monitored spectrophotometrically by the increased absorbency at 490 nm, and corrected by the absorbency at 610 nm.

Treatment of beta-TC6 cells with small molecules according to group II. did not lead to increased insulin release like observed in high glucose media. Sunitinib seemed to decrease the insulin release (0.77±0.03), whereas all the small molecules according to group II. ranged close to the DMSO control.

Example 14

Evaluation of Insulin Dependence of the Small Molecules According to Group II To investigate if the 2-NBDG uptake of the small molecule inhibitors of GRK5 are insulin dependent, 3T3-L pre-adipocytes were differentiated to matured adipocytes. Afterwards, cells were starved for 4 h before they were washed and glucose free media supplied with 100 μM 2-NBDG, in the presence and absence of 10 μg/ml insulin the small molecules according to group II. were added for 1 h at 37° C. Furthermore, as internal controls, samples of glucose free media or glucose free media with compound were measured (data not shown). Fluorescence was analyzed by flow cytometer (FACS Calibur, BD Bioscience, respectively a BD Accuri® C6 Flow Cytometer). For evaluation, cells were gated using the side- and forward scatter SSC/FSC and quantified by excited at 488 and detected at 533 nm (FL1).

Example 15

Comparison of the Influence on Insulin Release of the Small Molecules According to Group II. and Commercially Available Kinase Inhibitors Based on literature references, several commercially available inhibitors were compared with small molecules according to group II. For comparison we chose the Akt1-Inhibitor II (Calbiochem #124008), which should lead to decreased insulin release, as well as the Map2K3-Inhibitor II (Calbiochem #444938), Exendin-4 (Sigma #E7144) and GLP-1 (Sigma #G8147), which should lead to an increased insulin release. Cells were cultured for 24 h before treated with the small molecules according to group II. and control inhibitors for 2 h at 37° C. and 5% (v/v) $CO_2$. Insulin in the supernatant was detected by mouse/rat insulin ELISA.

Example 16

Insulin HTRF Assay Principle

For further screening of compounds derived from compounds described above for their ability to regulate insulin release an insulin HTRF® (Homogeneous Time-Resolved Fluorescence; Cisbio International, France) was used. This assay is based on two antibodies against insulin binding to different epitopes of insulin. One of these antibodies is coupled to Europium (Ab-Eu-Cryptate) and the other one to the fluorophore XL665 (Ab-XL665). If the insulin is secreted into the supernatant of cell culture, both antibodies can bind to insulin and come therefore into close proximity, which allows upon excitation that energy transfer between (FRET) the long-life fluorescent donor Europium (cryptate) and the acceptors XL665. FRET increases proportionally with insulin concentration.

The automated assay protocol is as follows:

On day 1, 15 k beta-TC6 cells per well were seeded for 24 or 48 h in 50 µL complete medium. On day 2 or respective on day 3, the medium is removed and cells are washed with 60 µL 1×PBS and 20 µL induction buffer is added using BioTek washer. Subsequently, 10 µL Sunitininb (5-µM f.c.) or the test compound in induction buffer; 0.5% f.c. DMSO (CyBi-well) is transferred to the cells. The cells are then incubated at 37° C. for 2, 3, 4 h.

The HTRF assay is carried out using Greiner 384-well 784075 assay plates.

First 10 µL supernatant is transferred from the cell plates in HTRF plates (CyBi-well). 10 µL of 0, 1, 2, and 4 ng/ml insulin standard controls in assay medium is used as a control. To each well 10 µL of combined 1:25 Ab-XL665 (Acc) and 1:20 Ab-Eu-Cryptate (WellMate) are added and incubated for 120 min at RT in the dark. Finally HTRF is measured on ViewLux ultra high throughput microplate imager (PerkinElmer).

Example 17

Cells Viability Assays

CellTiter-Glo®

Luminescent cell viability assay. For the detection of cell viability, the CellTiter-Glo® Luminescent Cell Viability Assay was used. This test is based on a luciferase reaction to measure the amount of ATP in cells. This correlates directly with the number of cells and their viability because cells lose the ability to synthesize ATP directly after e.g. loss of membrane integrity or a cytotoxic event. The protocol was adapted to 24 well plates and to the different culture conditions resulting in a standardized protocol which is described below. Cell lysis, inhibition of endogenous ATPases and detection of ATP was performed by adding the CellTiter-Glo® Reagent to the culture wells. Per well, 100 µl reagent were mixed with the same volume of proper Medium. Lysing of the cells took place by 10 min incubation at RT and moderate shaking. Three times 50 µl cell lysate was transferred into a white 96 well plate to eliminate stray light, and the bioluminescence was measured.

Automated Determination of Cell Number and Percentage Apoptosis

In a 96 well dish 10000 cells per well (100 µl) were seed and treated for 72 h. At the end of the treatment, cells were fixed with 4% paraformaldehyde in PBS for 15 minutes, permeabilized with 0.1% triton-X 100 in PBS for 15 minutes and stained with Hoechst 33342 (20 µg/ml in PBS; dilute from 20 mg/ml stock) directly to cells in 100 µl medium in PBS for 30 minutes at 37° C. Stained cells were imaged with a Cellomics ArrayScan VT I automated microscope. Images were analyzed with vHCS Scan Target Activation software v5.1.2 to identify apoptotic cells. Six fields per well of a 96 well plate we re-imaged at 10× magnification. First, cells were identified by their nuclei staining in channel 1 of Cellomics and their amount. Staining intensity was plotted and compared between NT controls and compound treated cells. Finally, data was obtained using vHCS View software v 5.1.2 and the numbers of cells present in the 96 well were identified as "Valid Object Count" whereas the percentage of infection was determined as "% selected". IC50 values have been calculated accordingly.

TABLE 13

Inhibition of cell viability in 3T3-L1, beta TC6, C2C12 and HepG2 cells by the small molecules according to group II.. All $IC_{50}$ (inhibitory concentration at 50% of maximal effect) values are indicated in µM.

| Compound | II.130 | II.15 | II.67 | II.6 | II.51 | II.10 | II.11 |
| --- | --- | --- | --- | --- | --- | --- | --- |
| 3T3-L1 | >10 | 1.12 | 1.52 | 1.70 | 1.36 | >10 | >10 |
| beta TC6 | 8.52 | 1.68 | 1.94 | 0.42 | 1.97 | 0.67 | 0.96 |
| C2C12 | >10 | 2.37 | 3.94 | 1.49 | 3.34 | 3.23 | 3.37 |
| HepG2 | 1.58 | 0.54 | 1.47 | 0.27 | 1.11 | 0.63 | 0.80 |

TABLE 13-continued

Inhibition of cell viability in 3T3-L1, beta TC6, C2C12 and HepG2 cells by the small molecules according to group II.. All $IC_{50}$ (inhibitory concentration at 50% of maximal effect) values are indicated in µM.

| Compound | II.7 | II.131 | II.13 | II.32 | II.21 | II.14 | II.59 |
|---|---|---|---|---|---|---|---|
| 3T3-L1 | 1.07 | >10 | >10 | 0.70 | 1.31 | 0.75 | 0.63 |
| beta TC6 | 1.19 | 3.47 | 1.63 | 1.60 | 4.07 | 1.19 | 0.71 |
| C2C12 | 1.31 | >10 | 4.61 | 4.25 | 9.83 | 1.42 | 1.11 |
| HepG2 | 0.69 | 1.49 | 1.59 | 1.23 | 1.61 | 0.72 | 0.37 |

| Compound | II.71 | II.73 | II.63 | II.60 | II.61 | II.55 | II.70 |
|---|---|---|---|---|---|---|---|
| 3T3-L1 | 3.10 | 2.73 | 0.94 | 2.00 | 0.60 | 0.86 | 2.16 |
| beta TC6 | 2.75 | 0.73 | 1.26 | 2.21 | 0.44 | 1.10 | 1.48 |
| C2C12 | 4.26 | 2.33 | 1.72 | 4.06 | 1.49 | 1.41 | >10 |
| HepG2 | 2.53 | 0.89 | 1.25 | 2.29 | 0.33 | 0.79 | 1.81 |

| Compound | II.72 | II.139 | II.136 | II.138 | II.140 | II.141 | II.135 |
|---|---|---|---|---|---|---|---|
| 3T3-L1 | 1.54 | 1.34 | 2.69 | 2.26 | 4.00 | 3.41 | 1.35 |
| beta TC6 | 1.27 | >10 | >10 | >10 | >10 | >10 | 1.55 |
| C2C12 | >10 | >10 | >10 | >10 | >10 | >10 | >10 |
| HepG2 | 2.07 | >10 | >10 | >10 | >10 | >10 | 1.85 |

| Compound | II.46 | II.48 | II.47 | II.30 | II.53 | II.69 | II.78 |
|---|---|---|---|---|---|---|---|
| 3T3-L1 | 0.32 | 0.60 | 1.34 | 0.81 | 1.14 | >10 | >10 |
| beta TC6 | 0.22 | 1.08 | 2.21 | 1.69 | 1.55 | >10 | >10 |
| C2C12 | 8.86 | >10 | >10 | >10 | >10 | 5.63 | >10 |
| HepG2 | 0.78 | 1.43 | 3.25 | 2.84 | 1.30 | 4.51 | 5.73 |

| Compound | II.79 | II.80 |
|---|---|---|
| 3T3-L1 | >10 | >10 |
| beta TC6 | 2.05 | 0.47 |
| C2C12 | >10 | >10 |
| HepG2 | 2.08 | 3.90 |

Example 18 siRNA Screen in the Pancreatic Beta Cell Line Beta-TC6

To identify the kinases, which might be responsible for the elevated insulin release after Sunitinib treatment, we performed a kinome wide siRNA knock-down screen. The effect on the insulin release of each kinase depletion was monitored by using a rat/mouse insulin ELISA. The resulting data were compared to Sunitinib treatment (5 µM) as positive control and correlated to a non-targeting siRNA. Candidate genes were limited by using hierarchical clustering and by proposing a significant in-/decrease of the insulin release by 15%. Depletion of SCY1-like 1 (SCYL1), aarF-containing kinase 1 (ADCK1), and G protein-coupled receptor kinase 5 (GRK5), resulted in an increase of the insulin release in beta-TC6 cells compared to the control siRNA, rendering those kinases as potential negative modulators of insulin release (FIG. 1).

Example 19

Validation of the Negative Modulators

Figure 3:
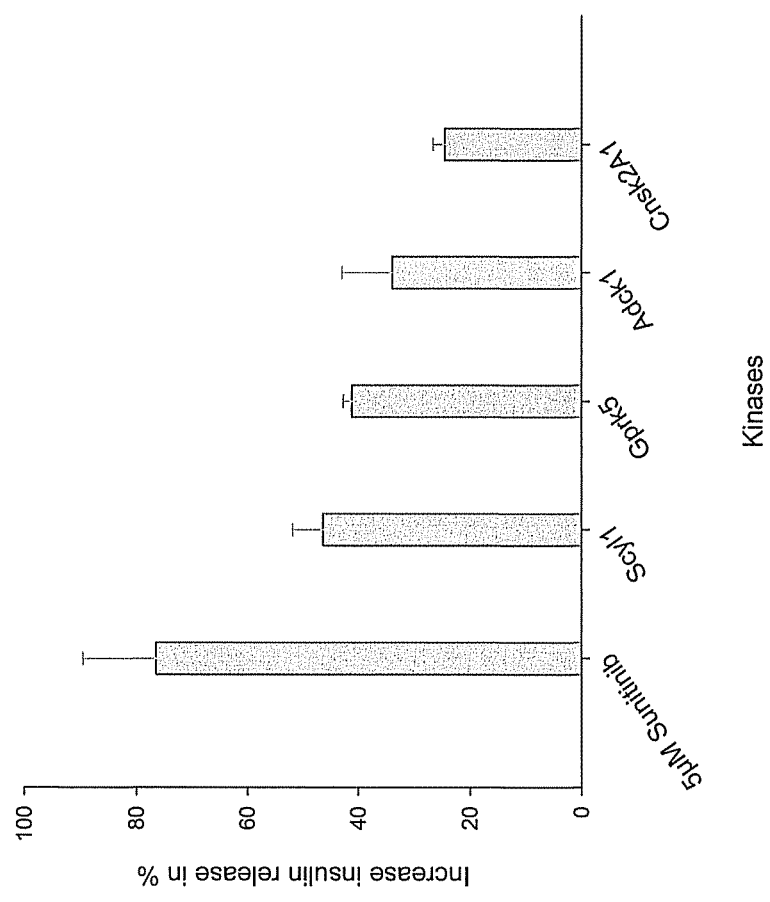
FIG. 3: Validation of insulin release increase for kinases SCYL1, GRK5 and ADCK1. SCYL1 showed the most reliable increase in insulin release after gene-depletion with about 46.38±5.51%, followed by GRK5 (41.23±1.53%), and ADCK1 (33.95±9.02%). The control Sunitinib resulted in 76.52±13%.

For the validation of the negative modulating kinases SCYL1, GRK5, and ADCK1, the target genes were depleted using four different siRNA-sequences each (FIG. 2A-D). The gene-depletion was measured via mRNA-levels after 72 hours while the insulin release was measured using a rat/mouse insulin ELISA after two hours incubation. The depletion of the residual kinases SCYL1, GRK5, and ADCK1 led to an increased insulin release with different efficiencies. Furthermore, the insulin release for the kinases inversely correlated with the respective knock-down efficiency of SCYL1 and ADCK1 which ranged from 50 to nearly 100% as estimated by RT-PCR and scanning densitometry. In case of GRK5 where all sequences lead to equal knock-down efficiency, this correlation could not be observed. The increase was highest for the depletion of SCYL1 (46.38±5.51%), followed by GRK5 (41.23±1.53%), and ADCK1 (33.95±9.02%). Sunitinib was included as a control (FIG. 3). This enhances the role of those kinases in triggering the insulin release.

TABLE 14

Sequences of the primers used in RT-PCR for target validation

| SeqIdNo | Gene-Symbol | Primer | Gene-Accession | Sequence 5'- 3' |
|---|---|---|---|---|
| 1 | SCYL1 | Fwd | NM_023912 | CGGCGGCGACGATGTGGTTCTTT |
| 2 | SCYL1 | Rev | NM_023912 | CGGCGTTGCCCTGTGCCGAGTA |
| 3 | ADCK1 | Fwd | NM_028105 | CTGACACGGGCAAGGCTGAGATT |
| 4 | ADCK1 | Rev | NM_028105 | GCGCCCTGATACAACACCGAGAC |
| 5 | GRK5 | Fwd | NM_018869 | GCCGGGTGCTGGAGACTGAGGA |

TABLE 14 -continued

Sequences of the primers used in RT-PCR
for target validation

| SeqIdNo | Gene-Symbol | Primer | Gene-Accession | Sequence 5'- 3' |
|---|---|---|---|---|
| 6 | GRK5 | Rev | NM_018869 | TGGCGGTTCTGGAGGC TGACTTCT |

Example 20

Results Double Knock-Down of the Validated Kinase

Compared to the Sunitinib treatment, the effect of the single knock-downs was less pronounced suggesting the involvement of multiple kinases in triggering the insulin release. The candidate kinases are widespread in various signaling pathways. To investigate whether the kinases have a redundant or additive effect on insulin release, we performed double-knock-downs for each possible kinase pair. The insulin increase due to the double knock-down was correlated to the single knock-downs as well as to the non-targeting siRNA. Out of 16 kinase pairs, SCYL1 and ADCK1 depletion resulted in the highest insulin release (90.64±17.32%), which was equal to the Sunitinib induced insulin release (FIG. 4). For the other kinase pairs, no increased insulin release compared to the single-knock-downs was observed (data not shown).

Example 21

Figure 5:
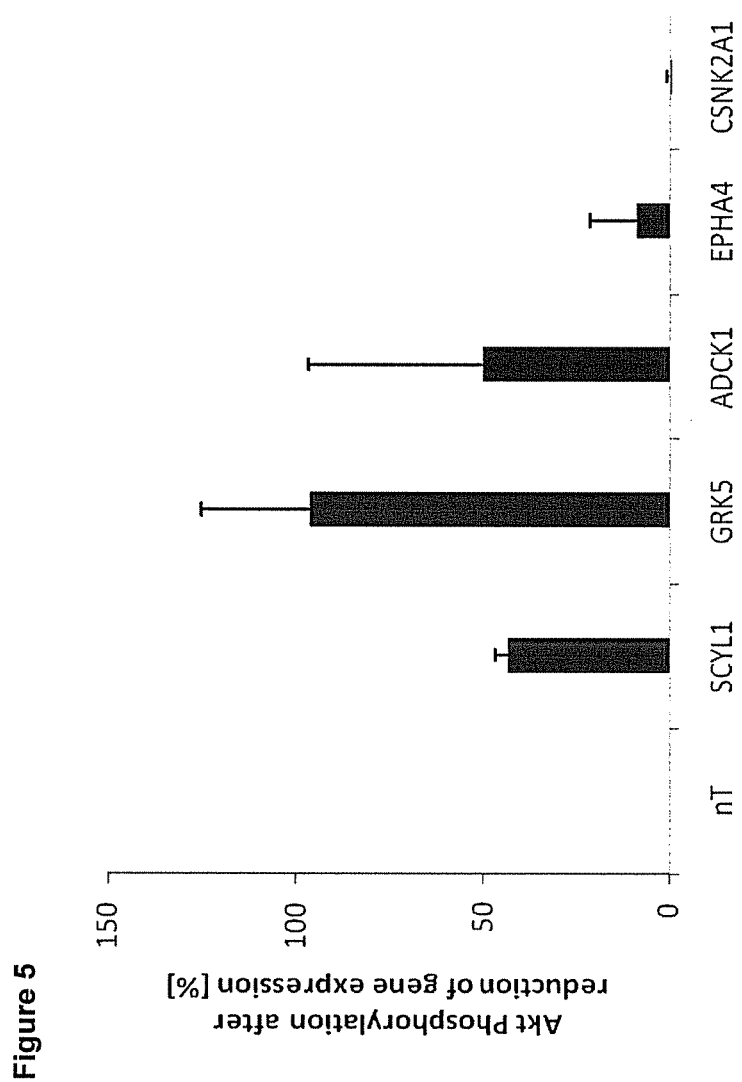
FIG. 5: Phosphorylation of AKT1 upon reduction of gene expression of SCYL1, GRK5 and ADCK1.

Phosphorylation of AKT1 Upon Reduction of Kinase C Candidate Gene Expression in Beta-TC6 Cells The gene expression of SCYL1, GRK5, and ADCK1 was inhibited by siRNA. Downregulation of SCYL1, GRK5 as well as ADCK1 increased phosphorylation of AKT with a tolerable standard deviation (SCYL1: 43.73±3.37%; GRK5: 96.53±28.87%; ADCK1:) (FIG. 5). It can be concluded that the siRNA mediated reduction of the gene expression results in increased AKT1 phosphorylation. As already mentioned, this increase seems to be connected to insulin release according to the publication by Leibiger B. and colleagues (Leibiger et al. FASEB J, 2010, 24; 1824-1837).

Example 22

Measurement of SCYL1, GRK5, and ADCK1 mRNA Levels Upon 24 h Sunitinib Treatment

Figure 6:
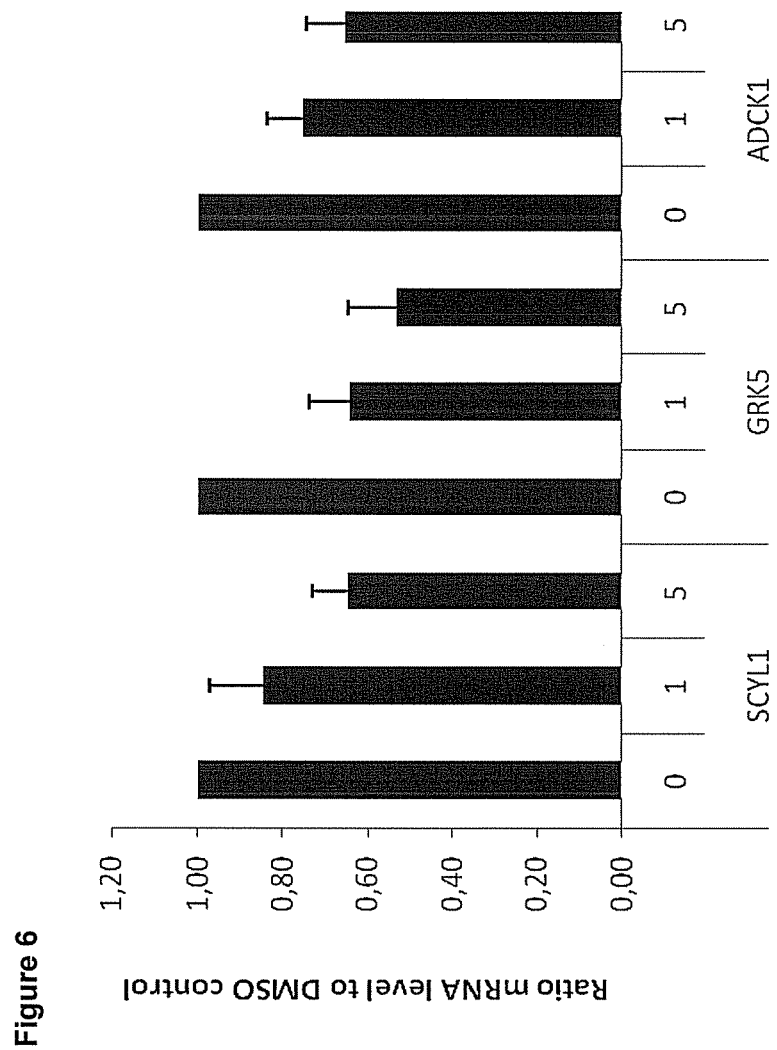
FIG. 6: Measurement of SCYL1, GRK5 and ADCK1 mRNA levels upon Sunitinib treatment of 24 h.

Beta TC6 cells were treated with 1 µM and 5 µM, respectively, Sunitinib for 24 h. The inhibition of gene expression was estimated by measurement of mRNA levels. Sunitinib treatment negatively influences mRNA levels of candidate kinases (FIG. 6). This observation might represent a further explanation for the positive effect of Sunitinib on diabetes patients in clinics where Sunitinib is applied for a longer period of time.

Example 23

Figure 7:
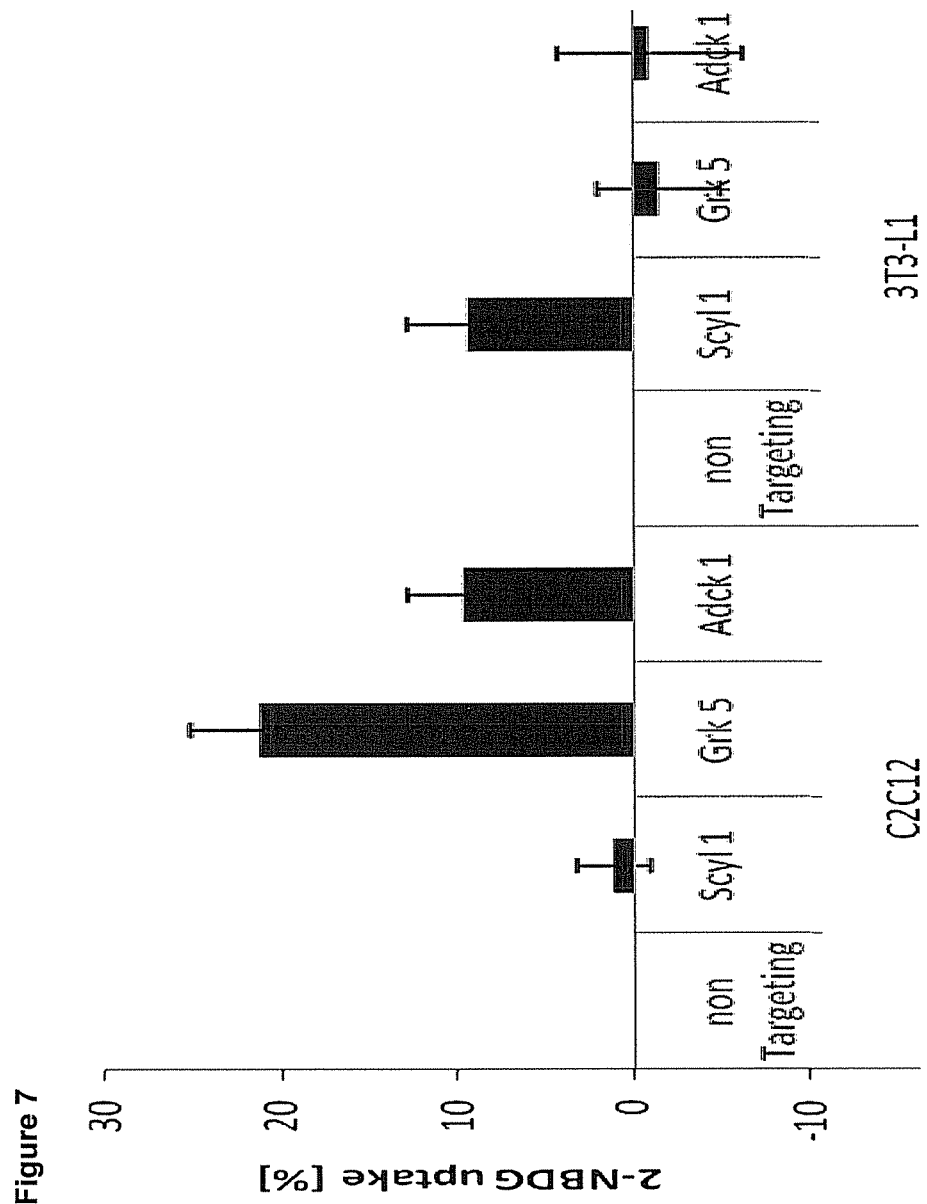
FIG. 7: Uptake of the fluorescent glucose analogue 2-NBDG upon candidate kinase gene knock-down in beta C2C12 and 3T3-L1 cells.

Uptake of the Fluorescent Glucose Analogue 2-NBDG Upon Candidate Kinase Knock-Down in Beta C2C12 and 3T3-L1 Cells The glucose uptake of cells was investigated in response to reduction of candidate gene expression. Down-regulation of GRK5 remarkably affects uptake of 2-NBDG in C2C12 (GRK5: 21.24±3.96%) whereas ADCK1 showed an increase of 9.72±3.81%. In 3T3-L1 cells the reduction of gene expression for SCYL1 gene reduction shows an impact on glucose uptake (9.45±3.45%) (FIG. 7). All data are presented as mean values (±SEM). It can be concluded that the reduction of the G protein-coupled receptor kinase 5 (GRK5) and ADCK1 expression seems to enhance uptake of the glucose analogue 2-NBDG (21.24±3.96%) in mouse myoblast cells (C2C12) without need of insulin stimulation, thus GRK5 seems to trigger the insulin sensitivity and/or insulin independent glucose uptake.

Example 24

Figure 8:
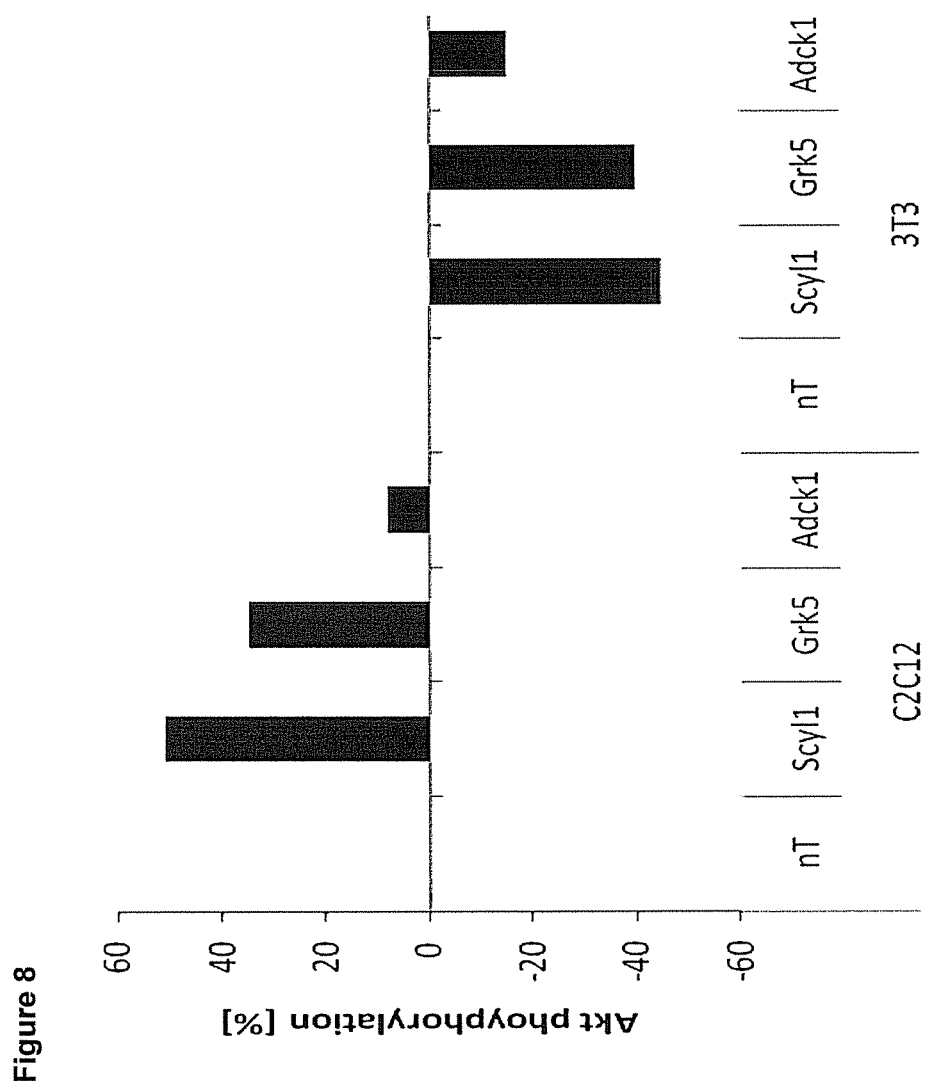
FIG. 8: Phosphorylation of AKT1 upon candidate target knock-down in C2C12 and 3T3-L1 cells.

Phosphorylation of AKT1 Upon Candidate Target Knock-Down in C2C12 and 3T3-L1 Cells The phosphorylation of AKT1 was investigated upon the reduction of gene expression of SCYL1, GRK5, and ADCK1. As illustrated, downregulation of SCYL1 as well as GRK5 increases phosphorylation of AKT1 in C2C12 cells. In the 3T3-L1 model system we detected a decrease of AKT1 phosphorylation for all candidate kinases (FIG. 8). It can be concluded that in peripheral tissues AKT1 phosphorylation is connected to GLUT4 translocation and therefore to glucose uptake. In the beta-TC6 cell line, the knock-down of SCYL1 and GRK5 increases phosphorylation of AKT1. Furthermore, the results of the 2-NBDG uptake assay in C2C12 cells as well as the observed increase in AKT1 phosphorylation in the beta-TC6 upon reduction of candidate gene expression might explain the functional role of GRK5 in regard to an elevated release of insulin.

Example 25

Figure 9:
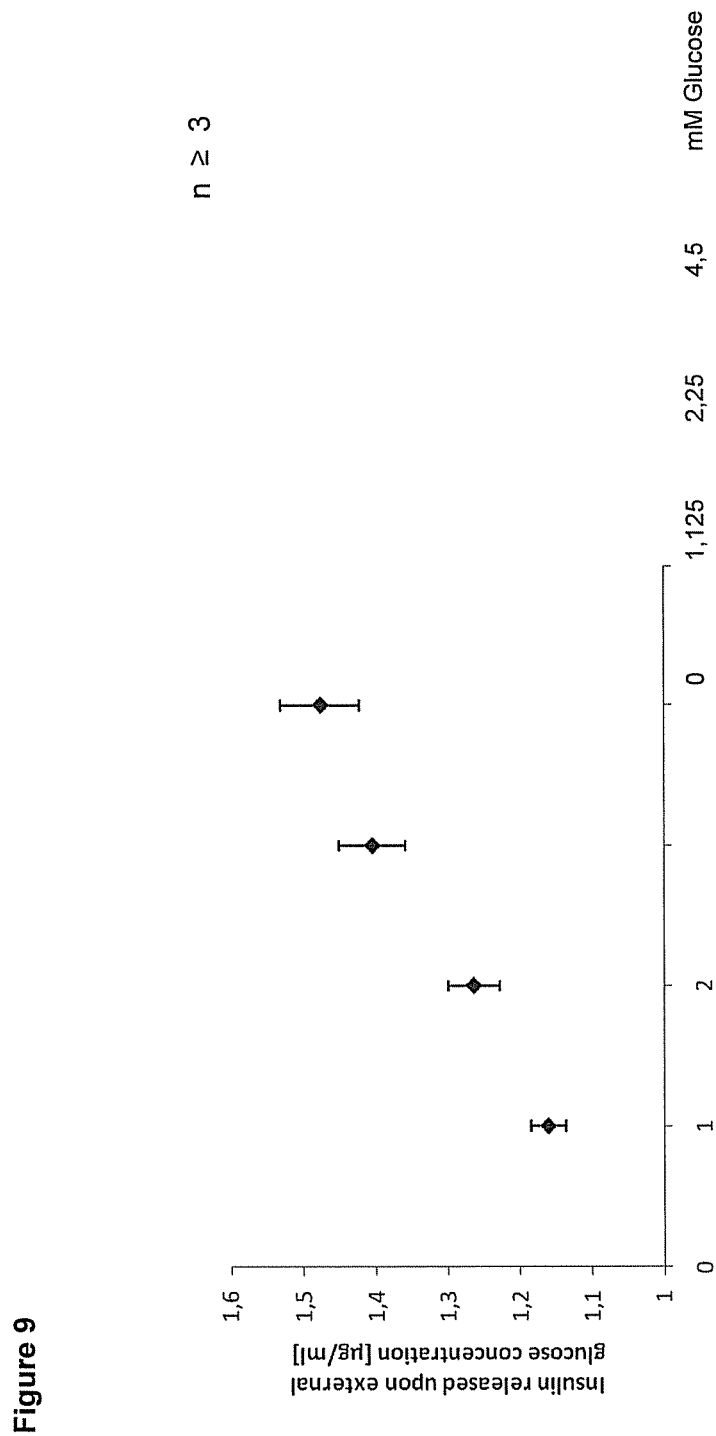
FIG. 9: Analysis of a potential glucose-mediated effect on insulin released by beta TC6 cells (1.125 to 4.5 mM Glucose).

Analysis of a Potential Glucose Mediated Effect on Insulin Released by Beta TC6 Cells The influence of external glucose was investigated at glucose concentrations ranging from 1.125 to 4.5 mM relative to glucose free control (FIG. 9). The addition of different glucose concentrations ranging from physiological to pathophysiological concentrations (ranging from 1 g/L (5.5 mM) up to 4.5 g/L (25.5 mM)) to media of beta-TC6 cells does not results in a concentration dependent increase in insulin release. However, using concentrations under 0.8 g/L (4.5 mM) glucose displayed a glucose dependent release of insulin (Poitout et al., Diabetes, 1995, 4; 306-313). Thus a glucose concentration of 0.2 g/L (1.125 mM) was chosen for further experiments with a low glucose environment.

Example 26

Figure 10:
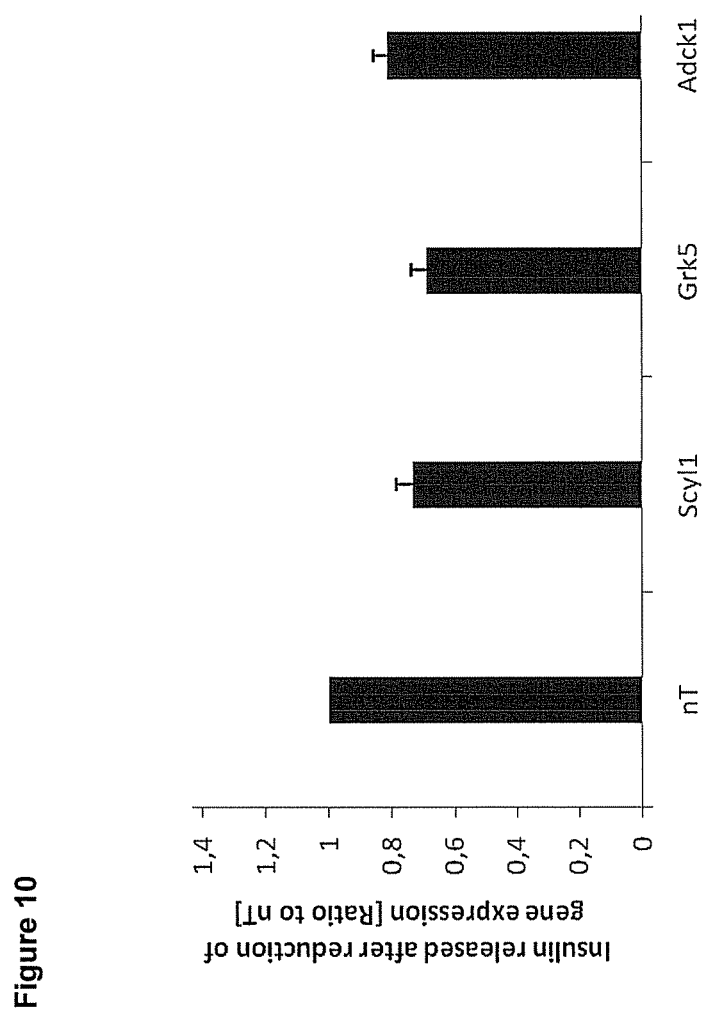
FIG. 10: Insulin released by beta TC6 cells after reduction of gene expression in low glucose media.

Insulin Released by Beta T6 Cells after Reduction of Gene Expression in Low Glucose Media The insulin release was mediated by reduction of gene expression in a low glucose environment of 0.2 g/L (1.125 mM) (FIG. 10). It can be concluded that knock-down of SCYL1, GRK5, and ADCK1 seems to decrease the insulin release in a low glucose environment. A performed MTT-assay displayed no impaired cell viability.

Example 27

GRK5 as Anti-Diabetic Target for Drug Development

8800 Customer compounds were screened for their ability to inhibit the enzymatic activity of GRK5. Screening was performed using the ADP Glo™ Kinase Assay technology (Promega). The small molecular weight compounds were delivered at 10 mM stock concentration and were tested at a final assay concentration of 100 µM. A narrow hit distribution was observed with an average inhibition of 3.2% and a standard deviation of 11%. In consequence compounds with an inhibition value above 36.1% (=inhav+(3×inhstdev)) are recommended to be considered as hit. The top candidate compounds are summarized in table 5. All five compounds identified by the screen have a molecular weight in the range of 200 to 450 g per mol.

TABLE 15

Top candidates revealed by the screen

| Compound | Inhibition of Grk5 [%] |
|---|---|
| C1 | 68.0 |
| C2 | 60.0 |
| C3 | 56.0 |
| C4 | 52.0 |
| C5 | 51.0 |

Figure 11:
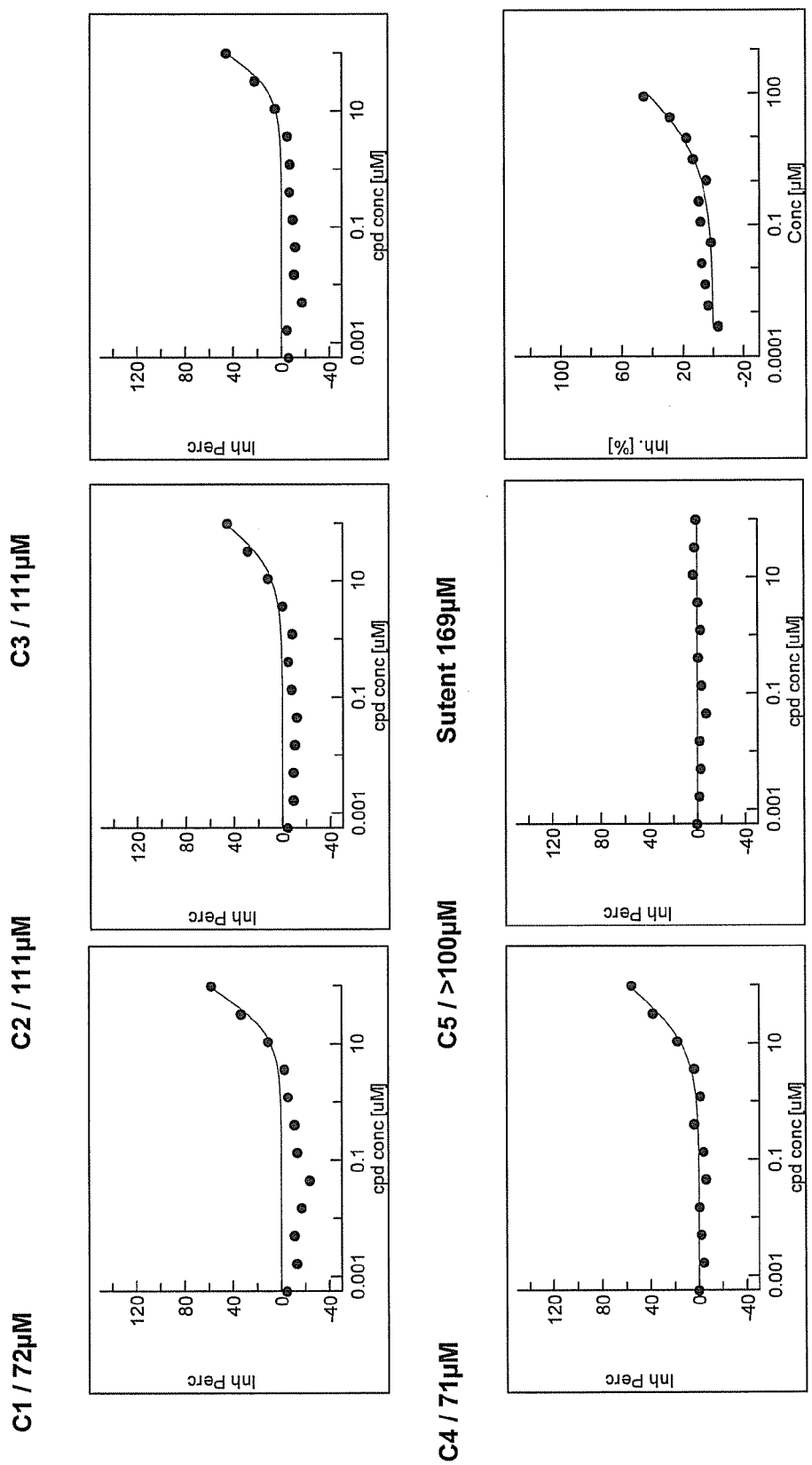
FIG. 11: $IC_{50}$ graphs of GRK5 primary hit compounds.

$IC_{50}$ values were determined in triplicates at 12 concentrations with a dilution factor of three. Triplicates were measured on three different assay plates. The maximal compound assay concentration was set to 100 µM representing the compound assay concentration used in the primary screen. A larger maximal compound assay concentration could not be achieved since the maximal compound concentration on the compound plates was 10 mM (>1% DMSO concentration in the assay). For all assay plates z prime values were found to be significantly larger than 0.5 proving statistical relevance of the data (see Table 16). Since the majority of all primary screening hits showed less than 50% GRK5 inhibition at 100 µM primary screening concentration, also the majority of all $IC_{50}$ graphs did not reach 50% inhibition at the maximal compound concentration of 100 µM. For these compounds the $IC_{50}$ values were extrapolated if the at least 30% GRK5 inhibition was observed at the maximal compound concentration of 100 µM. For 62% of the examined compounds a valid $IC_{50}$ value could be determined. The remaining 38% of the compounds had less than 30% inhibition at the highest compound concentration of 100 µM (FIG. 11, Table 16).

TABLE 16

IC50 values of the 5 top candidates

| Copound_ID | IC50 [µM] | ZPRIME (assay plate 1/2/3) | Comment |
|---|---|---|---|
| C1 | 72 | 0.87/0.90/0.92 | |
| C2 | 111 | 0.87/0.90/0.92 | * |
| C3 | 111 | 0.87/0.90/0.92 | * |
| C4 | 71 | 0.87/0.90/0.92 | |
| C5 | >100 | 0.87/0.90/0.92 | |
| Sutent | 169 | 0.87/0.90/0.92 | * |

Example 28

Figure 12:
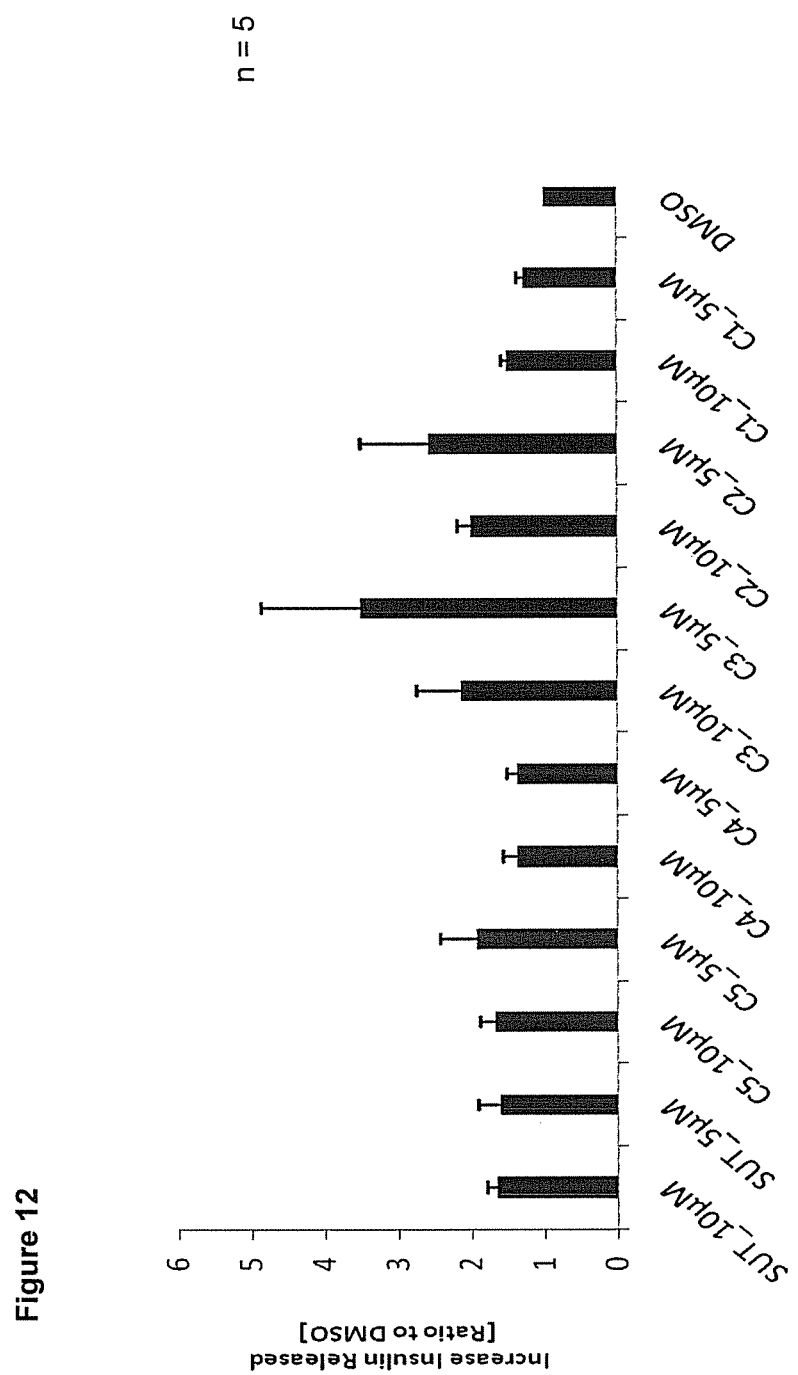
FIG. 12: Release of Insulin after inhibition of GRK5 by compounds 1-5 in a beta TC6-cell system.

Release of Insulin after Inhibition of GRK5 by Compounds 1-5 in a Beta TC6-Cell System Insulin release in beta-TC6 cells was increased by GRK5 inhibitor treatment. The inhibition by compound two (C2), three (C3) and five (C5) led to the most remarkable effect of elevating insulin release by doubling the effect of Sunitinib (SUT) in our system (C2: 2.58±0.94 at 5 µM and 2.01±0.19 at 10 µM; C3: 3.52±1.35 at 5 µM and 2.15±0.59 at 10 µM; C5: 1.93±0.5 at 5 µM and 1.69±0.19 at 10 µM) (FIG. 12). The values are also displayed in table 17.

TABLE 17

Averages and SEM of FIG. 12

| SUT_10 µM | SUT_5 µM | C5_10 µM | C5_5 µM | C4_10 µM | C4_5 µM |
|---|---|---|---|---|---|
| 1.65 | 1.61 | 1.69 | 1.93 | 1.38 | 1.37 |
| 0.14 | 0.31 | 0.19 | 0.50 | 0.18 | 0.14 |

| C3_10 µM | C3_5 µM | C2_10 µM | C2_5 µM | C1_10 µM | C1_5 µM | DMSO |
|---|---|---|---|---|---|---|
| 2.15 | 3.52 | 2.01 | 2.58 | 1.52 | 1.29 | 1 |
| 0.59 | 1.35 | 0.19 | 0.94 | 0.06 | 0.08 | 0 |

It was shown that all of the GRK5-screen based inhibitors stimulate insulin release in the beta TC6 cell system. Thus the target GRK5 has been validated as important regulator of insulin secretion. Furthermore, the inhibition by compounds two, three and five led to the most remarkable effect of elevating insulin release by doubling the effect of Sunitinib in our system (C2: 2.58±0.94 at 5 µM and 2.01±0.19 at 10 µM; C3: 3.52±1.35 at 5 µM and 2.15±0.59 at 10 µM; C5: 1.93±0.5 at 5 µM and 1.69±0.19 at 10 µM).

Example 29

Figure 13:
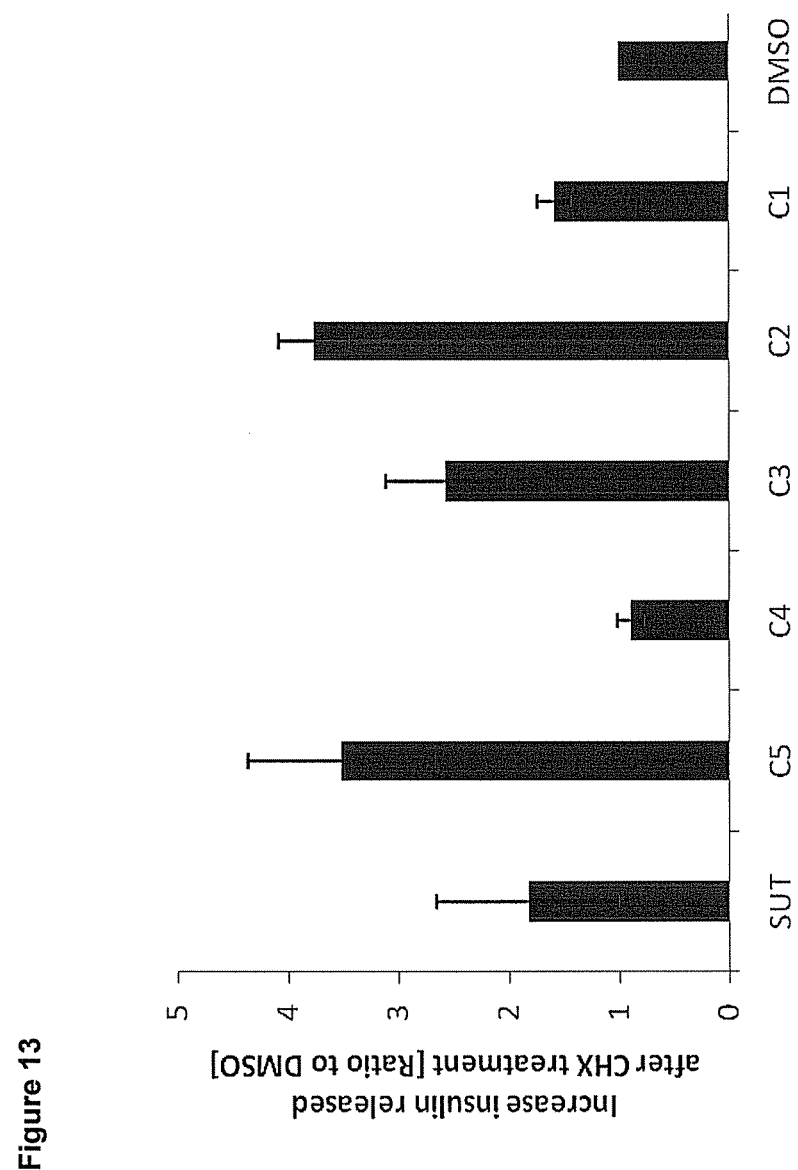
FIG. 13: Insulin released after blocking of protein biosynthesis with cyclohexamid and GRK5 inhibitor treatment.

Insulin Released after Blocking of Protein Biosynthesis with Cycloheximid and GRK5 Inhibitor Treatment It was found that the impact of GRK5 inhibitor on insulin release is not based on intensified insulin synthesis. The insulin release was measured upon cycloheximid (CHX) and appropriate 5 µM compound treatment compared to control treated with cycloheximid and DMSO in mean values (±SEM) (FIG. 13). It can be concluded that blocking of the protein transcription and thus of renewing insulin by protein biosynthesis does not affect insulin release upon exposure to the GRK5 inhibitor compounds.

Example 30

Phosphorylation of AKT1 in Beta-TC6 Cells by GRK5 Inhibitor

Figure 14:
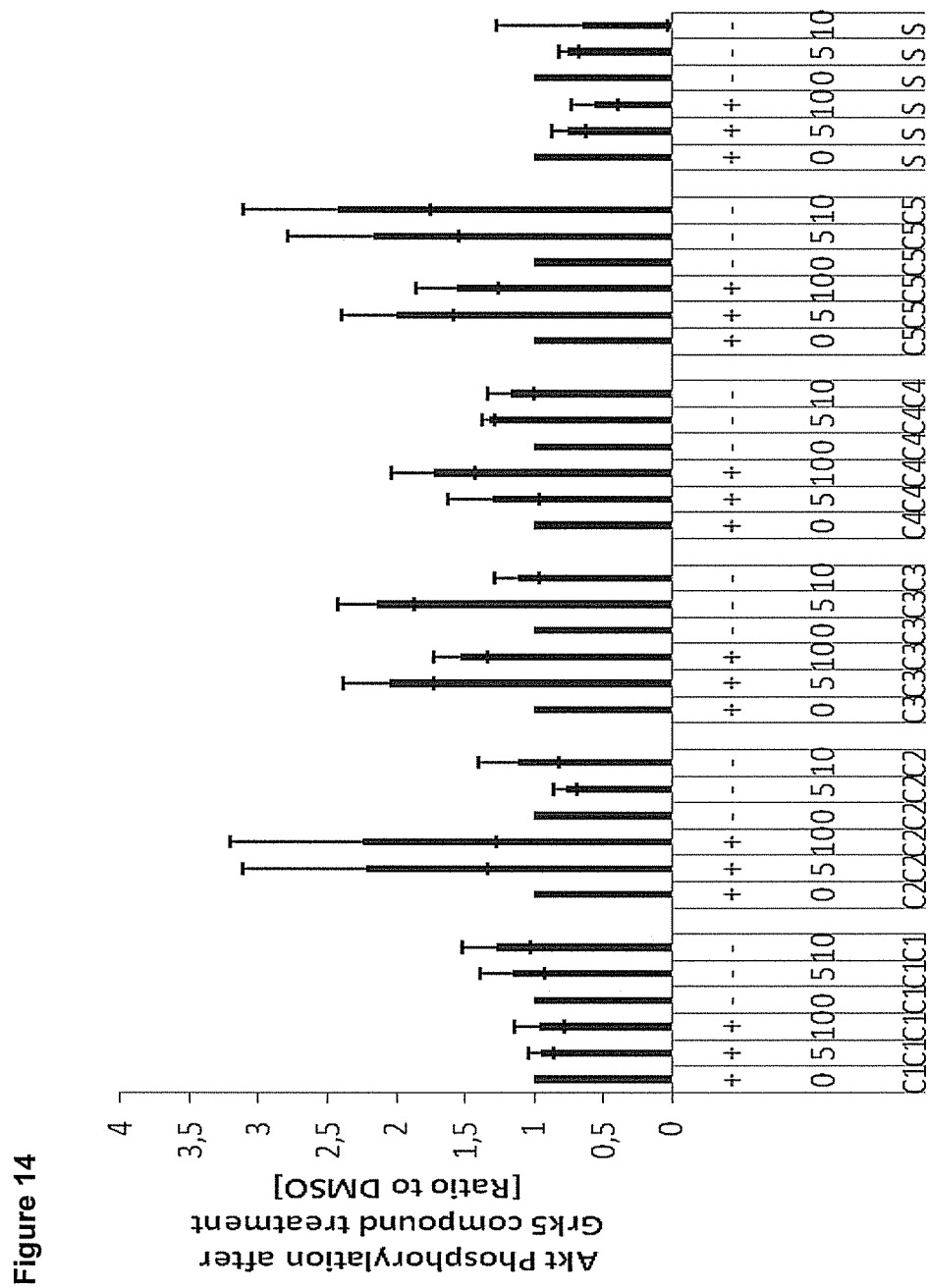
FIG. 14: Phosphorylation of AKT in beta-TC6 cells by GRK5 Inhibitor.

The phosphorylation of AKT1 was measured upon GRK5 inhibitor treatment. The beta-TC6 cells were treated by 5 µM respectively 10 µM of appropriate compound and compared to a DMSO control as well as to AKT protein levels. It can be concluded that AKT1 is phosphorylated by a 1 µg/mL insulin treatment and on that the phosphorylation of Akt1 is elevated by treatment with GRK5 inhibitor (FIG. 14). In contrast to this, Sunitinib—as a control—decrease the insulin mediated increase in AKT1 phosphorylation. Together with previously described knock down studies for AKT phosphorylation and 2-NBDG uptake we suggest, that GRK5 plays a role in glucose uptake and thus leads to increased insulin release.

Example 31

Insulin Released by Beta TC6 Cells after Inhibition of GRK5 in Low Glucose Environment (1.25 mM)

Figure 15:
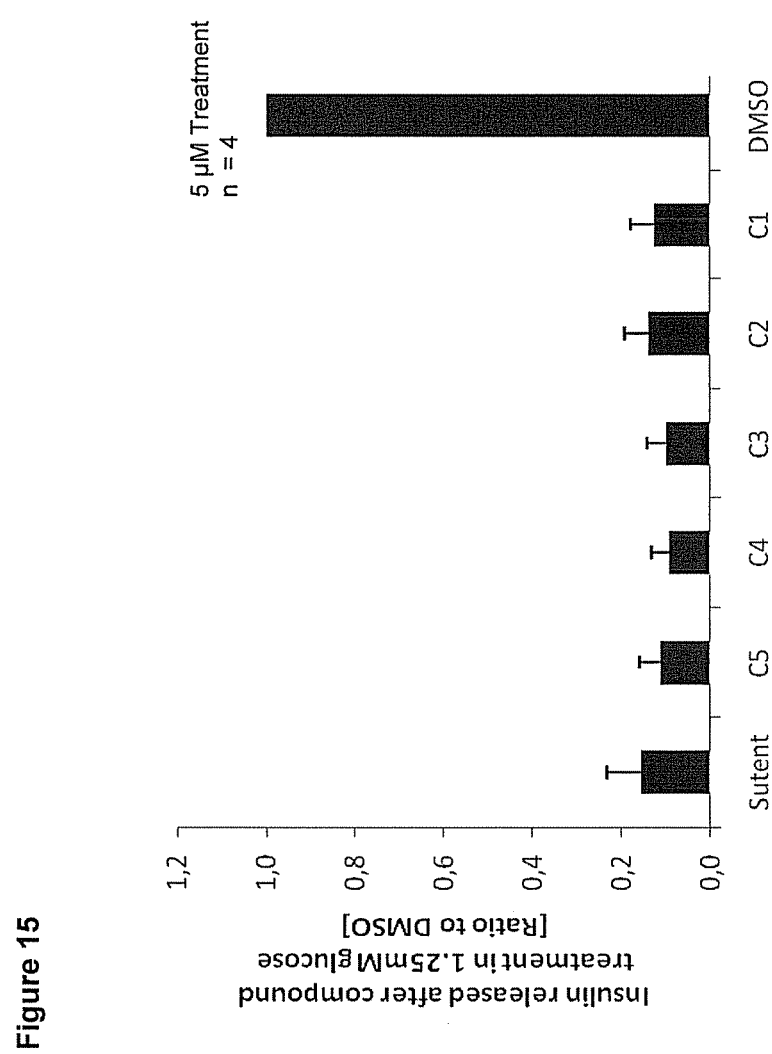
FIG. 15: Insulin released by beta TC6 cells after inhibition of GRK5 in low glucose environment (1.25 mM) with 5 µM compound.
Figure 16:
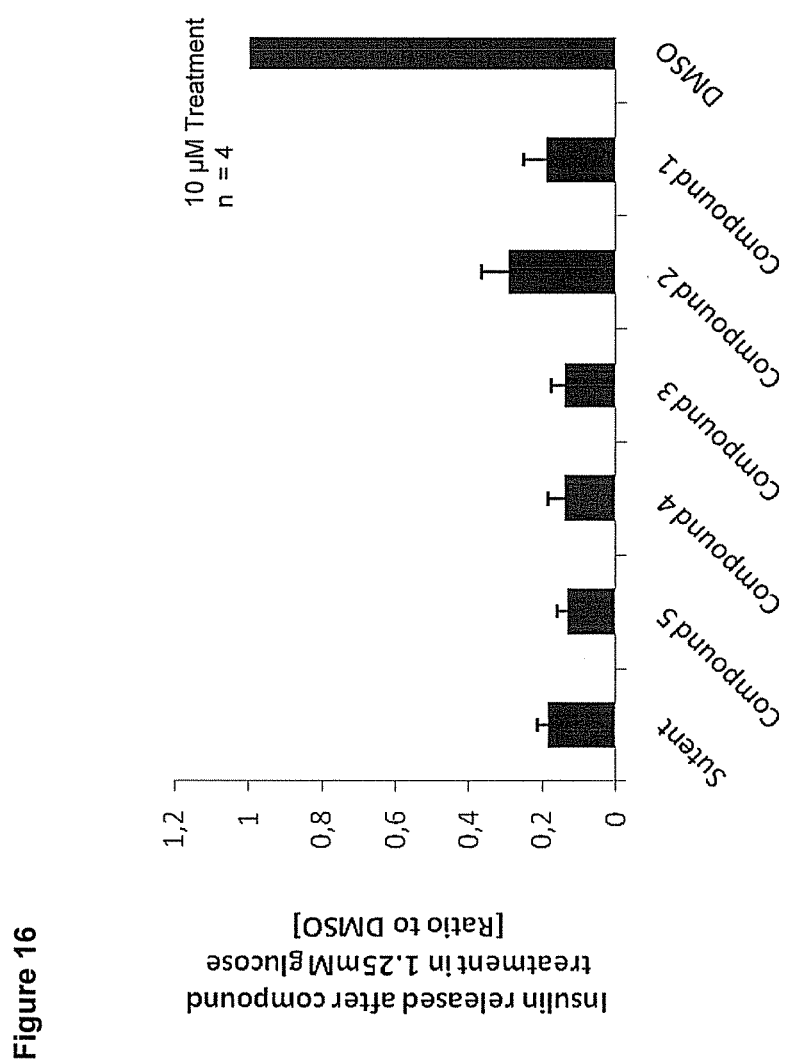
FIG. 16 Insulin released by beta TC6 cells after inhibition of GRK5 in low glucose environment (1.25 mM) with 10 µM compound.

The inhibition of GRK5 in a low glucose environment led to a decreased insulin secretion after a 5 µM treatment (FIG. 15) and 10 µM treatment (FIG. 16). It can be concluded that the inhibition of GRK5 by 5 µM respectively 10 µM of the revealed compounds led to a decrease of insulin release in a low glucose media (1.125 mM). A performed MTT-assay displayed no impaired cell viability.

Example 32

Glucose Uptake Via 2-NBDG after GRK5 Compound Treatment in C2C12, TC6, 3T3-L1 and Cells Inhibition of GRK5 led to an increased uptake of the fluorescent glucose analogue 2-NBDG in C2C12 (FIG. 17) and TC6 (FIG. 18) cells for all five compounds. We suggest that inhibition of GRK5 leads to increased glucose sensitivity without need of insulin. Thus blocking of GRK5 phosphorylation could substitute for insulin.

The increase of glucose uptake in beta TC6 cells incline with previously observed AKT phosphorylation and insulin release. Somehow, the glucose uptake in 3T3-L1 pre-adipocytes (FIG. 18) could only be stimulated by compound 2, suggesting that the cell model is probably not adequate or should be differentiated.

The data are summarized in Table 18:

TABLE 18

Figure 17:
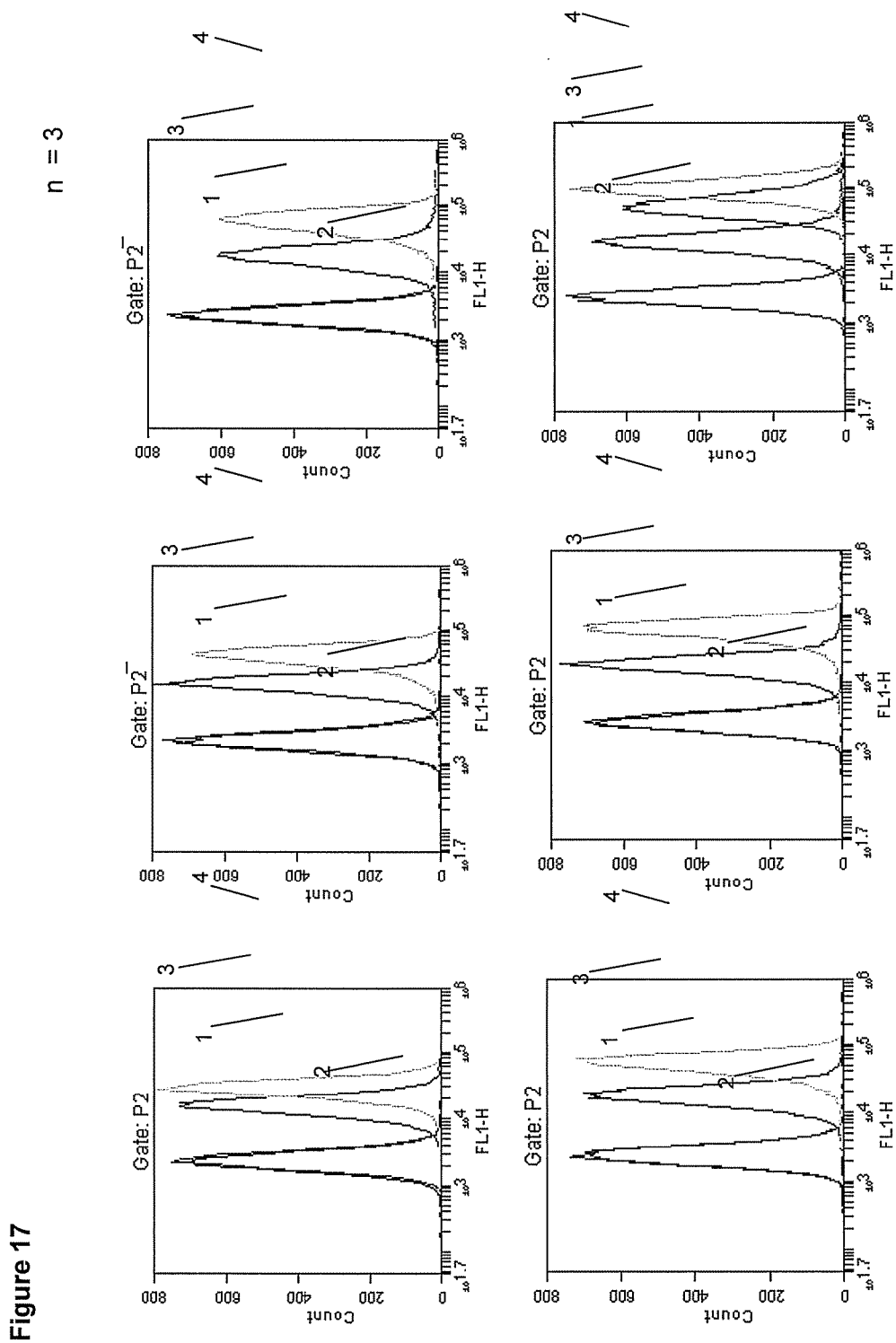
FIG. 17-21:
1=wo 2-NBDG+compound (glucose free medium+compound);
2=wo 2-NBDG (glucose free medium); 3=100 µM 2-NBDG
4=100 µM 2-NBDG+compound
Upper panel left to right shows always compounds 1-3, lower panel left to right compounds 4-5 and Sunitinib.
Figure 18:
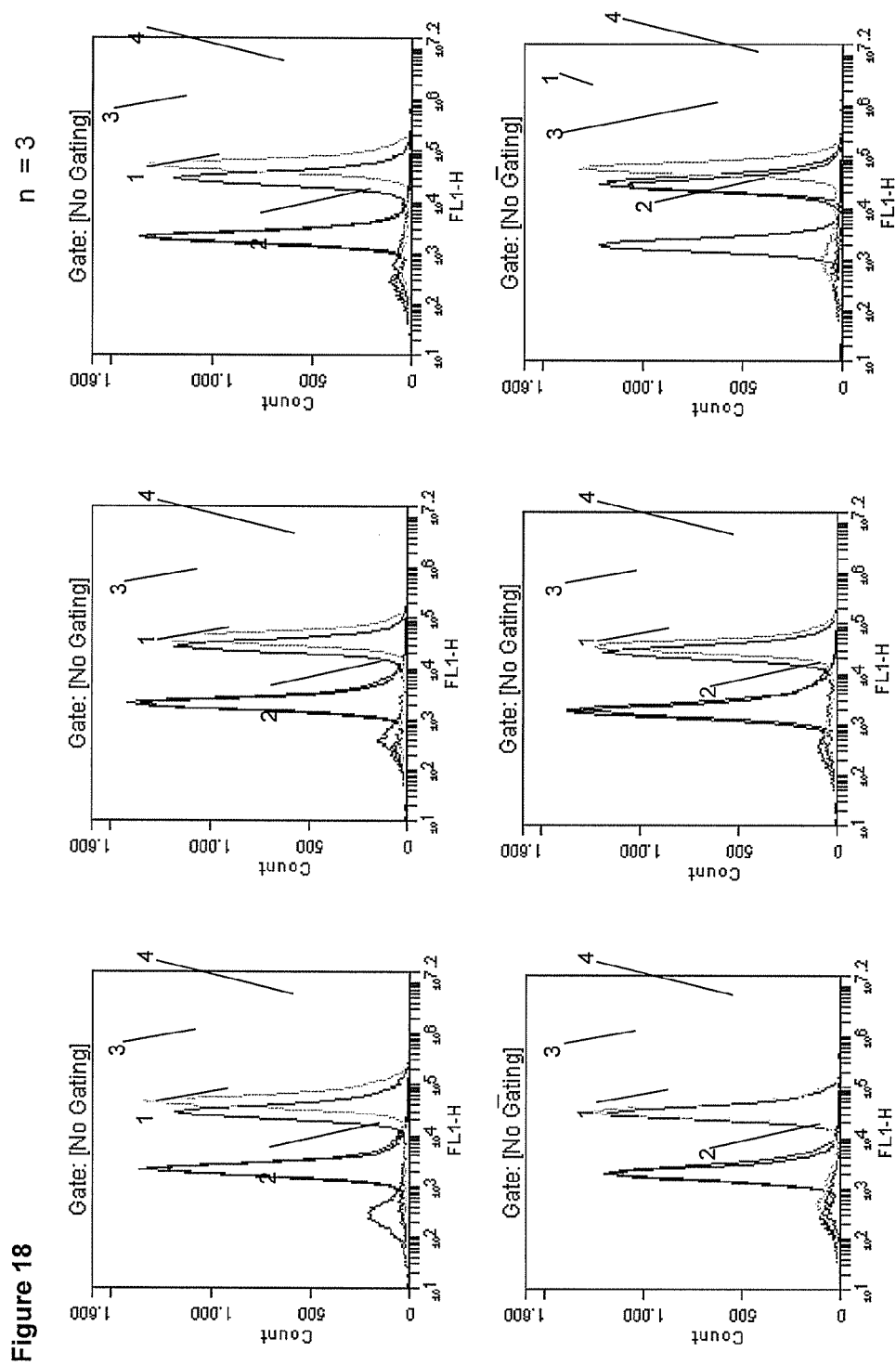
Figure 19:
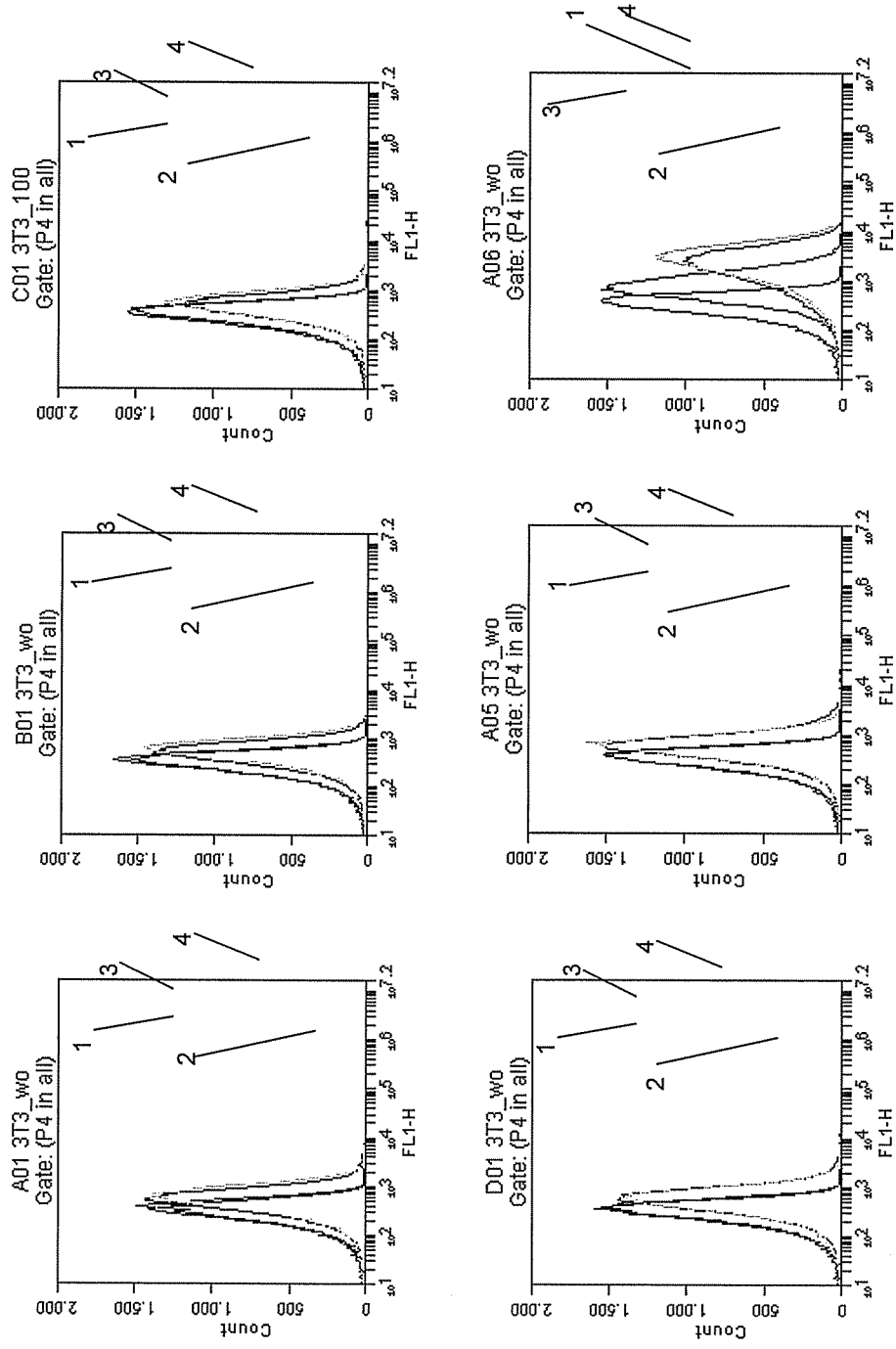

Averages and SEM of FIG. 17-19

|  | C2C12 Ratio | SE | beta TC6 Ratio | SE | 3T3-L1 Ratio | SE |
|---|---|---|---|---|---|---|
| DMSO | 1 | 0 | 1 | 0 | 1 | 0 |
| C1 | 2.346 | 0.53 | 1.567 | 0.12 | 0.989 | 0.07 |
| C2 | 2.127 | 0.44 | 1.529 | 0.07 | 1.111 | 0.03 |
| C3 | 2.325 | 0.46 | 1.683 | 0.21 | 1.022 | 0.03 |
| C4 | 1.774 | 0.43 | 1.284 | 0.09 | 0.930 | 0.07 |
| C5 | 1.47 | 0.17 | 1.259 | 0.02 | 0.926 | 0.04 |
| Sut | 1.511 | 0.4 | 1.084 | 0.19 | 0.533 | 0.10 | n = 3

Example 33

Glucose Uptake Via 2-NBDG after GRK5 Compound Treatment in Matured C2C12 Myotubes and 3T3-L1

Inhibition of GRK5 led to an increased uptake of the fluorescent glucose analogue 2-NBDG in matured C2C12 myotubes (FIG. 20) and 3T3-L1 adipocytes (FIG. 21) for all five compounds (summarized in table 7). In line with C2C12 cells, the matured myotubes display an increase 2-NBDG uptake after inhibition of GRK5 by compounds 1-5. Moreover, also matured adipocytes respond to all five compounds suggesting that glucose metabolism for adipocytes is basically higher and thus could be detected easily.

TABLE 19

Figure 20:
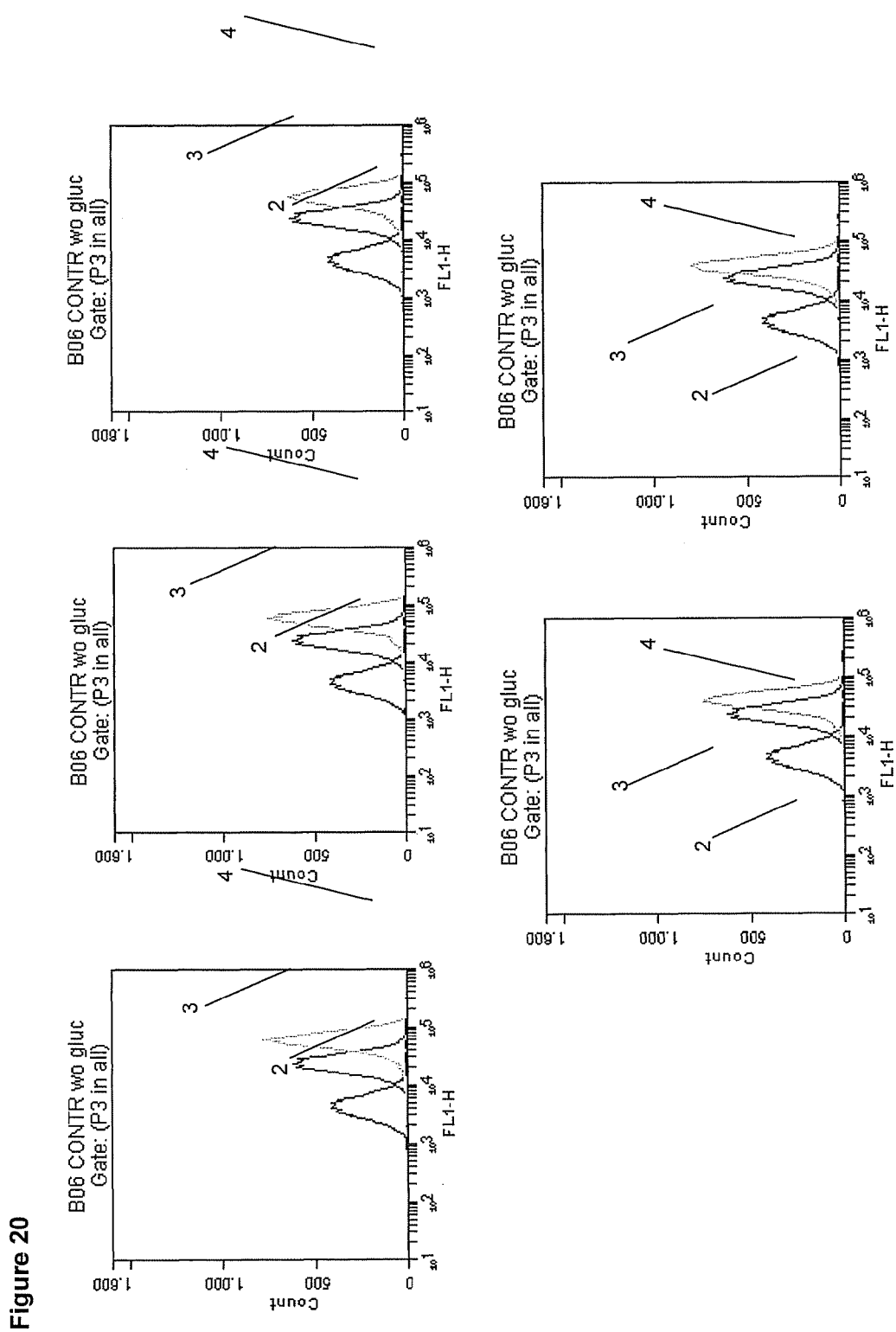
Figure 21:
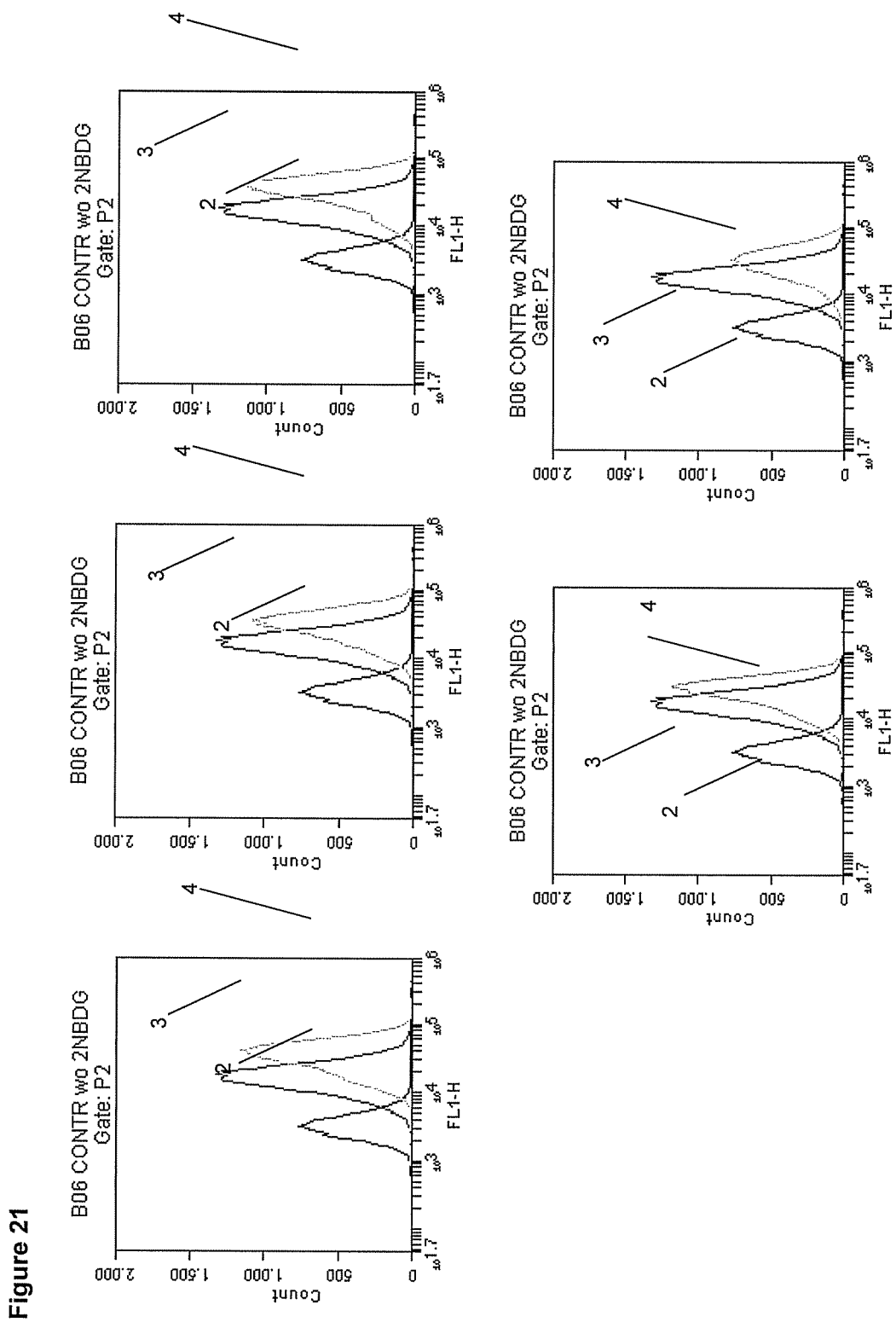

Averages and SEM of FIG. 20 and 21

|  | C2C12 myotubes Ratio | matured SE | 3T3-L1 adipocytes Ratio | matured SE |
|---|---|---|---|---|
| DMSO | 1 | 0 | 1 | 0 |
| C1 | 1.976 | 0.101 | 2.520 | 0.071 |
| C2 | 2.383 | 0.637 | 2.234 | 0.085 |
| C3 | 2.457 | 0.567 | 2.141 | 0.031 |
| C4 | 1.829 | 0.396 | 1.583 | 0.043 |
| C5 | 2.033 | 0.210 | 1.491 | 0.043 | n = 2

The invention claimed is:
1. A method for treatment of diabetes comprising: administering to a subject in need thereof a therapeutically effective amount of at least one inhibitor for: inhibition of G protein-coupled receptor kinase 5, wherein the at least one inhibitor is a small molecule.
2. The method according to claim 1, wherein the diabetes is diabetes mellitus type 2.
3. The method according to claim 1, wherein insulin production and/or release of insulin is up-regulated.
4. The method according to claim 1, wherein the at least one inhibitor is a compound of general formula (I):

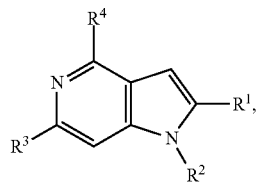

(I)

wherein
$R^1$ represents —$(CH_2)_n$—$R^5$ or —NH—$(CH_2)_n$—$R^5$; and $R^1$ is not —H;
$R^2$ represents —H, —$CH_3$, —$(CH_2)_k$—O—$CH_3$, —$(CH_2)_k$—NHCOCH$_3$, —$(CH_2)_k$-cyclo-$C_3H_5$, —$(CH_2)_k$-Ph, or —$(CH_2)_k$—R*;
R* represents

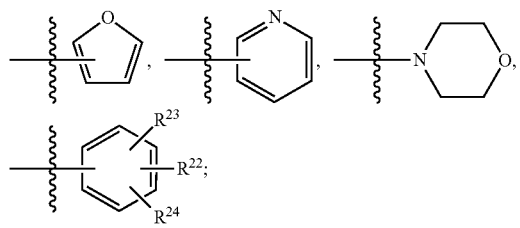

$R^3$ represents —H, —$(CH_2)_m$—$R^6$, or —$NR^7((CH_2)_m$—$R^6)$;
$R^4$ represents —H, —$(CH_2)_p$—$R^8$, or —$NR^9((CH_2)_p$—$R^8)$, wherein $R^3$ or $R^4$ represents —H;
$R^5$ represents —H, —F, —Cl, —Br, —I, —CN, —NO$_2$, —NHCH$_3$, —N(CH$_3$)$_2$, —CH=CH—C$_4$H$_9$, —CH=CH—C$_5$H$_{11}$, —CH=CH-Ph, —CH=CH—C$_6$H$_{13}$, —CH$_2$—OH, —C$_2$H$_4$—OH, —C$_3$H$_6$—OH, —C$_4$H$_9$—OH, —C$_5$H$_{10}$—OH, —C$_6$H$_{12}$—OH, —C$_7$H$_{14}$—OH, —C$_5$H$_{16}$—OH, —CH=CH—C$_3$H$_6$—OH, —CH=CH—C$_4$H$_8$—OH, —CH(CH$_2$OH)$_2$, —CH(C$_2$H$_5$)—CH$_2$—OH, —CH(CH$_3$)—C$_2$H$_4$—OH, —C(CH$_3$)$_2$—OH, —C(CH$_3$)$_2$—CH$_2$—OH, —CH(CH$_3$)OH, —CH$_2$—CH(CH$_3$)OH, —C(OH)(CH$_3$)—C$_2$H$_5$, —C(OH)(CH$_3$)—C$_3$H$_7$, —CH$_2$—C(OH)(CH$_3$)—C$_2$H$_5$, —CH(CH$_3$)—CH(CH$_3$)OH, —C(CH$_3$)$_2$—C$_2$H$_4$OH, —CH$_2$—C(CH$_3$)$_2$OH, —C(OH)(C$_2$H$_5$)$_2$, —C$_2$H$_4$—C(OH)(CH$_3$)$_2$, —C(CH(CH$_3$)$_2$)CH$_2$OH, —C$_3$H$_6$—C(OH)(CH$_3$)$_2$, —CH(CH(CH$_3$)$_2$)CH$_2$—OH, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SO$_3$H, —OCF$_3$, —CH$_2$—OCF$_3$, —C$_2$H$_4$—OCF$_3$, —C$_3$H$_6$—OCF$_3$, —OC$_2$F$_5$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —R$^{10}$, —R$^{11}$,

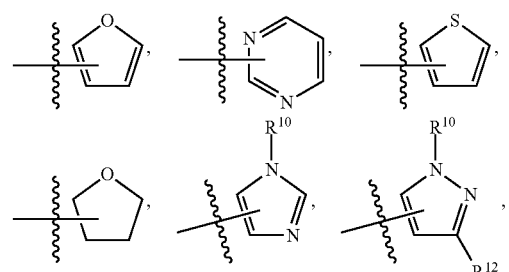

-continued

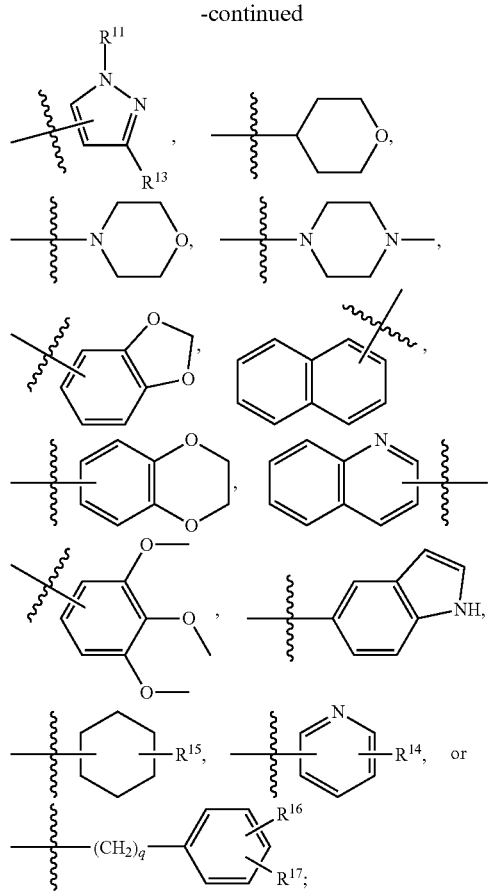

R⁶ represents —H, —F, —CN, —NO₂, —NHCH₃, —N(CH₃)₂, —CH=CH—C₄H₉, —CH=CH—C₅H₁₁, —CH=CH-Ph, —CH=CH—C₆H₁₃, —CH₂—OH, —C₂H₄—OH, —C₃H₆—OH, —C₄H₉—OH, —C₅H₁₀—OH, —C₆H₁₂—OH, —C₇H₁₄—OH, —C₈H₁₆—OH, —CH=CH—C₃H₆—OH, —CH=CH—C₄H₈—OH, —CH(CH₂OH)₂, —CH(C₂H₅)—CH₂—OH, —CH(CH₃)—C₂H₄—OH, —C(CH₃)₂—OH, —C(CH₃)₂—CH₂—OH, —CH(CH₃)OH, —CH₂—CH(CH₃)OH, —C(OH)(CH₃)—C₂H₅, —C(OH)(CH₃)—C₃H₇, —CH₂—C(OH)(CH₃)—C₂H₅, —CH(CH₃)—CH(CH₃)OH, —C(CH₃)₂—C₂H₄OH, —CH₂—C(CH₃)₂OH, —C(OH)(C₂H₅)₂, —C₂H₄—C(OH)(CH₃)₂, —C(CH(CH₃)₂)CH₂OH, —C₃H₆—C(OH)(CH₃)₂, —CH(CH(CH₃)₂)CH₂—OH, —OH, —OCH₃, —OC₂H₅, —OC₃H₇, —O-cyclo-C₃H₅, —OCH(CH₃)₂, —OC(CH₃)₃, —OC₄H₉, —OPh, —OCH₂-Ph, —OCPh₃, —SH, —SCH₃, —SC₂H₅, —SO₃H, —OCF₃, —CH₂—OCF₃, —C₂H₄—OCF₃, —C₃H₆—OCF₃, —OC₂F₅, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —R¹⁰, —R¹¹,

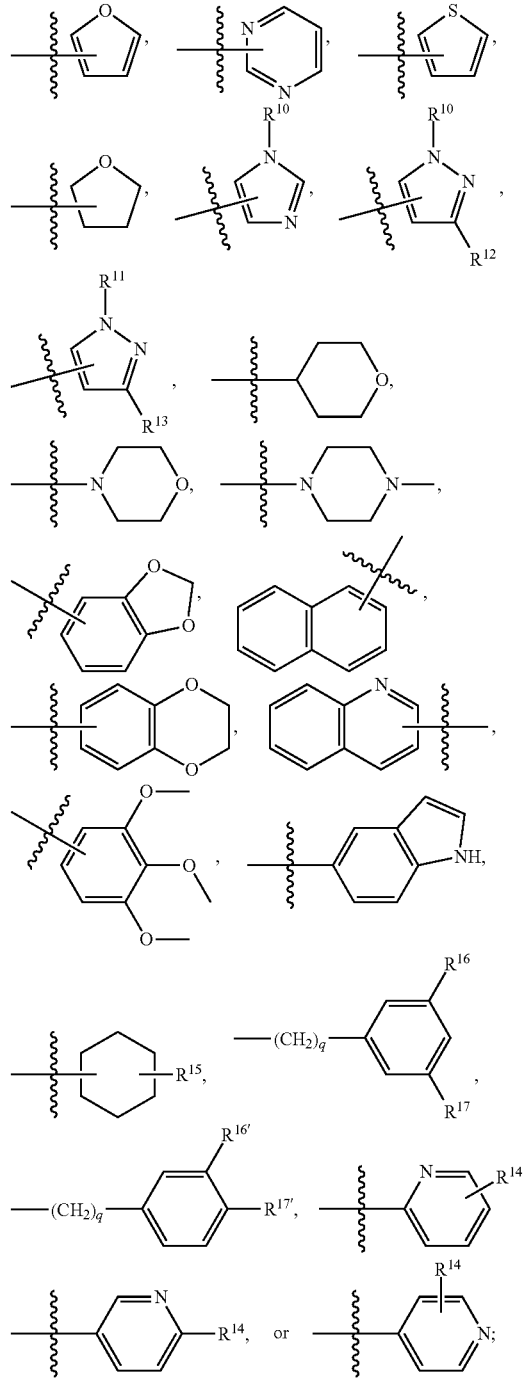

R⁸ represents —H, —F, —CN, —NO₂, —NHCH₃, —N(CH₃)₂, —CH=CH—C₄H₉, —CH=CH—C₅H₁₁, —CH=CH-Ph, —CH=CH—C₆H₁₃, —CH₂—OH, —C₂H₄—OH, —C₃H₆—OH, —C₄H₉—OH, —C₅H₁₀—OH, —C₆H₁₂—OH, —C₇H₁₄—OH, —C₆H₁₆—OH, —CH=CH—C₃H₆—OH, —CH=CH—C₄H₈—OH, —CH(CH₂OH)₂, —CH(C₂H₅)—CH₂—OH, —CH(CH₃)—C₂H₄—OH, —C(CH₃)₂—OH, —C(CH₃)₂—CH₂—OH, —CH(CH₃)OH, —CH₂—CH(CH₃)OH, —C(OH)(CH₃)—

C$_2$H$_5$, —C(OH)(CH$_3$)—C$_3$H$_7$, —CH$_2$—C(OH)(CH$_3$)—C$_2$H$_5$, —CH(CH$_3$)—CH(CH$_3$)OH, —C(CH$_3$)$_2$—C$_2$H$_4$OH, —CH$_2$—C(CH$_3$)$_2$OH, —C(OH)(C$_2$H$_5$)$_2$, —C$_2$H$_4$—C(OH)(CH$_3$)$_2$, —C(CH(CH$_3$)$_2$)CH$_2$OH, —C$_3$H$_6$—C(OH)(CH$_3$)$_2$, —CH(CH(CH$_3$)$_2$)CH$_2$—OH, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OPh, —OCH$_2$-Ph, —OCPh$_3$, —SH, —SCH$_3$, —SC$_2$H$_5$, —SO$_3$H, —OCF$_3$, —CH$_2$—OCF$_3$, —C$_2$H$_4$—OCF$_3$, —C$_3$H$_6$—OCF$_3$, —OC$_2$F$_5$, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —R$^{10}$, —R$^{11}$,

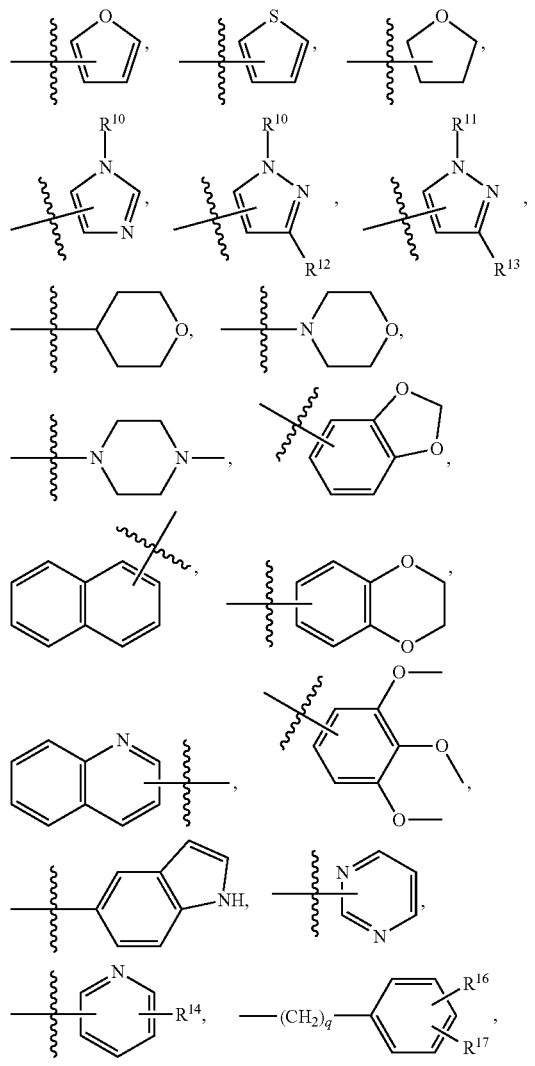

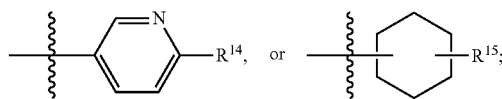

R$^7$ and R$^9$ are independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, or —C(CH$_3$)$_3$;

R$^{14}$ and R$^{15}$ are independently of each other —H, —NH$_2$, —OH, or —OMe;

R$^{16}$ and R$^{16'}$ are independently of each other —H, —F, —Br, —Cl, —OH, —CN, —R$^{18}$, —R$^{19}$, —OR$^{18}$, —OR$^{19}$, —CH$_2$OH, —CH$_2$NH$_2$, —CH$_2$CN; —CH$_2$N(R$^{18}$)$_2$, —CH$_2$N(R$^{19}$)$_2$, —CH$_2$NH(R$^{18}$), —CH$_2$NH(R$^{19}$), —O(CH$_2$)$_3$N(CH$_3$)$_2$, —SCH$_3$, —NH$_2$, —NH(R$^{18}$), —NH(R$^{19}$), —NR$^{18}$COR$^{19}$, —NHSO$_2$CH$_3$, —N(R$^{18}$)$_2$, —N(R$^{19}$)$_2$, —SO$_2$CH$_3$, —SO$_2$NH$_2$, —CH$_2$CO$_2$H, —C$_2$H$_4$CO$_2$H, —CH=CH—CO$_2$H, —COR$^{20}$,

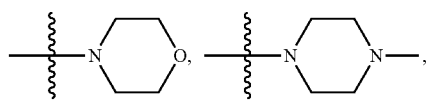

R$^{17}$ and R$^{17'}$ are independently of each other —H, —F, —Br, —Cl, —OH, —CN, —R$^{18}$, —R$^{19}$, —OR$^{18}$, —OR$^{19}$, —CH$_2$OH, —CH$_2$NH$_2$, —CH$_2$CN; —CH$_2$N(R$^{18}$)$_2$, —CH$_2$N(R$^{19}$)$_2$, —CH$_2$NH(R$^{18}$), —CH$_2$NH(R$^{19}$), —O(CH$_2$)$_3$N(CH$_3$)$_2$, —SCH$_3$, —NH$_2$, —NH(R$^{18}$), —NH(R$^{19}$), —NR$^{18}$COR$^{19}$, —NHSO$_2$CH$_3$, —N(R$^{18}$)$_2$, —N(R$^{19}$)$_2$, —SO$_2$CH$_3$, —SO$_2$NH$_2$, —CH$_2$CO$_2$H, —C$_2$H$_4$CO$_2$H, —CH=CH—CO$_2$H, —COR$^{20}$,

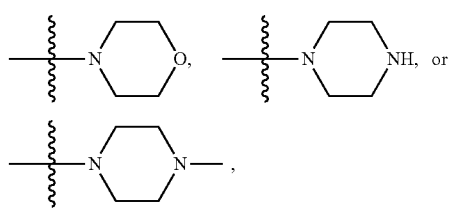

wherein R$^{17'}$ is not —F, —CN, —OCH$_3$, —OC$_2$H$_4$OCH$_3$, —CON(CH$_3$)$_2$ or —CF$_3$, when R$^5$ is 1H-pyrazol-4-yl or 1-methyl-1H-pyrazol-4-yl;

R$^{20}$ is —OH, —R$^{21}$, —OR$^{21}$, —NH$_2$, —NHR$^{21}$, —N(R$^{21}$)$_2$, —NHC$_2$H$_4$OH,

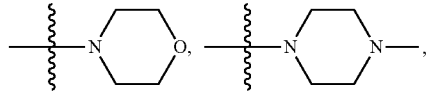

—NHC$_2$H$_4$OCH$_3$, or —NH(CH$_2$)$_r$N(R$^{21}$)$_2$;

R$^{10}$, R$^{11}$, R$^{12}$, R$^{13}$, R$^{18}$, R$^{19}$, and R$^{21}$ are independently of each other

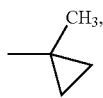

cyclo-C$_3$H$_5$, cyclo-C$_4$H$_7$, cyclo-C$_5$H$_9$, cyclo-C$_6$H$_{11}$, cyclo-C$_7$H$_{13}$, —H, —CH$_2$—OCH$_3$, —C$_2$H$_4$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —CH$_2$—OC$_4$H$_9$, —C$_2$H$_4$—OC$_4$H$_9$, —C$_3$H$_6$—OC$_4$H$_9$, —CH$_2$—OPh, —C$_2$H$_4$—OPh, —C$_3$H$_6$—OPh, —CH$_2$—OCH$_2$-Ph, —C$_2$H$_4$—OCH$_2$-Ph, —C$_3$H$_6$—OCH$_2$-Ph, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, cyclo-C$_8$H$_{15}$, -Ph, —CH$_2$-Ph, —CH═CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH(CH$_3$))—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH═CH$_2$, —CH$_2$—CH═CH$_2$, —C(CH$_3$)═CH$_2$, —CH═CH—CH$_3$, —C$_2$H$_4$—CH═CH$_2$, —CH$_2$—CH═CH—CH$_3$, —CH═CH—C$_2$H$_5$, —CH$_2$—C(CH$_3$)═CH$_2$, —CH(CH$_3$)—CH═CH, —CH═C(CH$_3$)$_2$, —C(CH$_3$)═CH—CH$_3$, —CH═CH—CH═CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —CH(CH$_3$)Ph, or —C(CH$_3$)$_2$Ph;

R$^{22}$, R$^{23}$ and R$^{24}$ represent independently of each other —H, —F, —Cl, —Br, —OCH$_3$, or —CF$_3$;

k is the integer 0, 1 or 2;

m, n, p, q and r are independently of each other integer selected from 0, 1, 2, or 3; and enantiomers, stereoisomeric forms, mixtures of enantiomers, anomers, diastereomers, mixtures of diastereomers, tautomers, hydrates, solvates and racemates of the above mentioned compounds and pharmaceutically acceptable salts thereof.

5. The method according to claim 4, wherein the at least one inhibitor is selected from the group consisting of: 2-(3-aminophenyl)-N-(6-methoxy-3-pyridyl)-1H-pyrrolo[3,2-c]pyridin-6-amine, 2-(3-aminophenyl)-N-(3-pyridyl)-1H-pyrrolo[3,2-c]pyridin-6-amine, 2-(3-aminophenyl)-N-[4-(4-methylpiperazin-1-yl)phenyl]-1H-pyrrolo[3,2-c]pyridin-6-amine, 6-(4-methylpiperazin-1-yl)-2-[3-(trifluoromethyl)phenyl]-1H-pyrrolo[3,2-c]pyridine, N-[3-[[2-[3-(trifluoromethyl)phenyl]-1H-pyrrolo[3,2-c]pyridin-6-yl]amino]phenyl]methanesulfonamide, 4-[[2-(3-fluorophenyl)-1H-pyrrolo[3,2-c]pyridin-6-yl]amino]benzamide, N-(3,4-dimethoxyphenyl)-2-(3-fluorophenyl)-1H-pyrrolo[3,2-c]pyridin-6-amine, 2-(3-fluorophenyl)-N-(6-methoxy-3-pyridyl)-1H-pyrrolo[3,2-c]pyridin-6-amine, N-(3-chloro-4-fluoro-phenyl)-2-(3-fluorophenyl)-1H-pyrrolo[3,2-c]pyridin-6-amine, 3-[[2-(3-fluorophenyl)-1H-pyrrolo[3,2-c]pyridin-6-yl]amino]phenol, 5-[[2-(3-fluorophenyl)-1H-pyrrolo[3,2-c]pyridin-6-yl]amino]-2-methoxy-phenol, 4-[2-(3-fluorophenyl)-1H-pyrrolo[3,2-c]pyridin-6-yl]morpholine, N-[3-[[2-(3-fluorophenyl)-1H-pyrrolo[3,2-c]pyridin-6-yl]amino]phenyl]methanesulfonamide, 4-[[2-(3-fluorophenyl)-1H-pyrrolo[3,2-c]pyridin-6-yl]amino]-N,N-dimethyl-benzamide, N-[3-[[2-(3-fluorophenyl)-1H-pyrrolo[3,2-c]pyridin-6-yl]amino]phenyl]acetamide, 2-(3-fluorophenyl)-N-(4-methylsulfonylphenyl)-1H-pyrrolo[3,2-c]pyridin-6-amine, 4-[[2-(3-fluorophenyl)-1-methyl-pyrrolo[3,2-c]pyridin-6-yl]amino]phenol, N,N-dimethyl-4-[6-(3,4,5-trimethoxyanilino)-1H-pyrrolo[3,2-c]pyridin-2-yl]benzamide, 4-[6-(3-methoxyanilino)-1H-pyrrolo[3,2-c]pyridin-2-yl]-N,N-dimethyl-benzamide, 4-[6-(3,4-dimethoxyanilino)-1H-pyrrolo[3,2-c]pyridin-2-yl]-N,N-dimethyl-benzamide, N,N-dimethyl-4-[6-(3-pyridylamino)-1H-pyrrolo[3,2-c]pyridin-2-yl]benzamide, 4-[6-(3-chloroanilino)-1H-pyrrolo[3,2-c]pyridin-2-yl]-N,N-dimethyl-benzamide, 4-(6-anilino-1H-pyrrolo[3,2-c]pyridin-2-yl)-N,N-dimethyl-benzamide, N,N-dimethyl-4-[6-(4-phenoxyanilino)-1H-pyrrolo[3,2-c]pyridin-2-yl]benzamide, N,N-dimethyl-4-[6-[4-(4-methylpiperazin-1-yl)anilino]-1H-pyrrolo[3,2-c]pyridin-2-yl]benzamide, 4-[6-[3-(dimethylamino)anilino]-1H-pyrrolo[3,2-c]pyridin-2-yl]-N,N-dimethyl-benzamide, N,N-dimethyl-4-[6-(3-methylanilino)-11H-pyrrolo[3,2-c]pyridin-2-yl]benzamide, methyl 4-[[2-[4-(dimethylcarbamoyl)phenyl]-1H-pyrrolo[3,2-c]pyridin-6-yl]amino]benzoate, N,N-dimethyl-4-[6-(3-methylsulfonylanilino)-1H-pyrrolo[3,2-c]pyridin-2-yl]benzamide, 4-[6-(3-hydroxyanilino)-1H-pyrrolo[3,2-c]pyridin-2-yl]-N,N-dimethyl-benzamide, N,N-dimethyl-4-[6-[4-(trifluoromethyl)anilino]-1H-pyrrolo[3,2-c]pyridin-2-yl]benzamide, N,N-dimethyl-4-[6-[3-(trifluoromethoxy)anilino]-1H-pyrrolo[3,2-c]pyridin-2-yl]benzamide, N,N-dimethyl-4-[6-[4-(trifluoromethoxy)anilino]-1H-pyrrolo[3,2-c]pyridin-2-yl]benzamide, N,N-dimethyl-4-[6-(3-phenoxyanilino)-1H-pyrrolo[3,2-c]pyridin-2-yl]benzamide, 4-[6-(3-isopropylanilino)-1H-pyrrolo[3,2-c]pyridin-2-yl]-N,N-dimethyl-benzamide, 4-[6-(4-isopropylanilino)-1H-pyrrolo[3,2-c]pyridin-2-yl]-N,N-dimethyl-benzamide, 4-[6-[3-(methanesulfonamido)anilino]-1H-pyrrolo[3,2-c]pyridin-2-yl]-N,N-dimethyl-benzamide, 4-[6-[4-(dimethylcarbamoyl)anilino]-1H-pyrrolo[3,2-c]pyridin-2-yl]-N,N-dimethyl-benzamide, 4-[6-(3-acetamidoanilino)-1H-pyrrolo[3,2-c]pyridin-2-yl]-N,N-dimethyl-benzamide, 4-[6-(3-acetylanilino)-1H-pyrrolo[3,2-c]pyridin-2-yl]-N,N-dimethyl-benzamide, N,N-dimethyl-4-[6-(4-methylsulfonylanilino)-1H-pyrrolo[3,2-c]pyridin-2-yl]benzamide, 4-[6-(3-isopropoxyanilino)-1H-pyrrolo[3,2-c]pyridin-2-yl]-N,N-dimethyl-benzamide, 4-[6-(3-methoxyanilino)-1-methyl-pyrrolo[3,2-c]pyridin-2-yl]-N,N-dimethyl-benzamide, 4-[6-(3,4-dimethoxyanilino)-1-methyl-pyrrolo[3,2-c]pyridin-2-yl]-N,N-dimethyl-benzamide, N,N-dimethyl-4-[1-methyl-6-(3-pyridylamino)pyrrolo[3,2-c]pyridin-2-yl]benzamide, 4-(6-anilino-1-methyl-pyrrolo[3,2-c]pyridin-2-yl)-N,N-dimethyl-benzamide, N,N-dimethyl-4-[1-methyl-6-[4-(4-methylpiperazin-1-yl)anilino]pyrrolo[3,2-c]pyridin-2-yl]benzamide, 4-[6-[3-(dimethylamino)anilino]-1-methyl-pyrrolo[3,2-c]pyridin-2-yl]-N,N-dimethyl-benzamide, N,N-dimethyl-4-[1-methyl-6-(2-pyridylamino)pyrrolo[3,2-c]pyridin-2-yl]benzamide, N,N-dimethyl-4-[1-methyl-6-(N-methylanilino)pyrrolo[3,2-c]pyridin-2-yl]benzamide, 4-[6-(3-hydroxyanilino)-1-methyl-pyrrolo[3,2-c]pyridin-2-yl]-N,N-dimethyl-benzamide, 4-[6-(3-hydroxy-4-methoxyanilino)-1-methyl-pyrrolo[3,2-c]pyridin-2-yl]-N,N-dimethyl-benzamide, 4-[6-[3-(methanesulfonamido)anilino]-1-methyl-pyrrolo[3,2-c]pyridin-2-yl]-N,N- dimethyl-benzamide, 4-[6-(3-acetamidoanilino)-1-methyl-pyrrolo[3,2-c]pyridin-2-yl]-N,N-dimethyl-benzamide, 4-[6-(4-acetamidoanilino)-1-benzyl-pyrrolo[3,2-c]pyridin-2-yl]-N,N-dimethyl-benzamide, 4-[1-benzyl-6-(pyrimidin-4-ylamino)pyrrolo[3,2-c]pyridin-2-yl]-N,N-dimethyl-benzamide, 2-(4-dimethylaminophenyl)-1-methyl-N-(2-pyridyl)pyrrolo[3,2-c]pyridin-6-amine, 3-[[1-benzyl-2-(4-dimethylaminophenyl)pyrrolo[3,2-c]pyridin-6-yl]amino]phenol, 1-benzyl-2-(4-dimethylaminophenyl)-N-pyrimidin-4-yl-pyrrolo[3,2-c]pyridin-6-amine, 2-(2-pyridyl)-N-(3,4,5-trimethoxyphenyl)-1H-pyrrolo[3,2-c]pyridin-6-amine, N-(m-tolyl)-2-(2-pyridyl)-1H-pyrrolo[3,2-c]pyridin-6-amine, N-(4-methoxyphenyl)-2-(2-pyridyl)-1H-pyrrolo[3,2-c]pyridin-6-amine, 2-(2-pyridyl)-N-[3-(trifluoromethyl)phenyl]-1H-pyrrolo[3,2-c]pyridin-6-amine, methyl 4-[[2-(2-pyridyl)-1H-pyrrolo[3,2-c]pyridin-6-yl]amino]benzoate, 4-[[2-(2-pyridyl)-1H-pyrrolo[3,2-c]pyridin-6-yl]amino]benzonitrile, 2-(2-pyridyl)-N-[3-(trifluoromethoxy)phenyl]-11H-pyrrolo[3,2-c]pyridin-6-amine, N,N-dimethyl-4-[[2-(2-pyridyl)-1H-pyrrolo[3,2-c]pyridin-6-yl]amino]benzamide, N-(3-fluorophenyl)-2-(2-pyridyl)-1H-pyrrolo[3,2-c]pyridin-6-amine, N-(4-methylsulfonylphenyl)-2-(2-pyridyl)-1H-pyrrolo[3,2-c]pyridin-6-amine, N-(3-isopropoxyphenyl)-2-(2-pyridyl)-1H-pyrrolo[3,2-c]pyridin-6-amine, N-[4-[[2-(3-pyridyl)-1H-pyrrolo[3,2-c]pyridin-6-yl]amino]phenyl]acetamide, N-(6-methoxy-3-pyridyl)-2-(3-pyridyl)-1H-pyrrolo[3,2-c]pyridin-6-amine, 2-(3-pyridyl)-N-(4-pyridyl)-1H-pyrrolo[3,2-c]pyridin-6-amine, 4-[2-(3-pyridyl)-1H-pyrrolo[3,2-c]pyridin-6-yl]morpholine, N-[3-[[2-(3-pyridyl)-1H-pyrrolo[3,2-c]pyridin-6-yl]amino]phenyl]acetamide, N-(4-isopropoxyphenyl)-2-(3-pyridyl)-1H-pyrrolo[3,2-c]pyridin-6-amine, 1-methyl-2-(3-pyridyl)-N-(3,4,5-trimethoxyphenyl)pyrrolo[3,2-c]pyridin-6-amine, N-(2,3-dihydro-1,4-benzodioxin-6-yl)-1-methyl-2-(3-pyridyl)pyrrolo[3,2-c]pyridin-6-amine, N-(3,4-dimethoxyphenyl)-1-methyl-2-(3-pyridyl)pyrrolo[3,2-c]pyridin-6-amine, N-(6-methoxy-3-pyridyl)-1-methyl-2-(3-pyridyl)pyrrolo[3,2-c]pyridin-6-amine, 1-methyl-N,2-bis(3-pyridyl)pyrrolo[3,2-c]pyridin-6-amine, 1-methyl-N-phenyl-2-(3-pyridyl)pyrrolo[3,2-c]pyridin-6-amine, N1,N1-dimethyl-N3-[1-methyl-2-(3-pyridyl)pyrrolo[3,2-c]pyridin-6-yl]benzene-1,3-diamine, 1-methyl-N-(m-tolyl)-2-(3-pyridyl)pyrrolo[3,2-c]pyridin-6-amine, N-(4-methoxyphenyl)-1-methyl-2-(3-pyridyl)pyrrolo[3,2-c]pyridin-6-amine, N-(4-fluorophenyl)-1-methyl-2-(3-pyridyl)pyrrolo[3,2-c]pyridin-6-amine, N-(1,3-benzodioxol-5-yl)-1-methyl-2-(3-pyridyl)pyrrolo[3,2-c]pyridin-6-amine, 4-[1-methyl-2-(3-pyridyl)pyrrolo[3,2-c]pyridin-6-yl]morpholine, N,N-dimethyl-4-[[1-methyl-2-(3-pyridyl)pyrrolo[3,2-c]pyridin-6-yl]amino]benzamide, N-[3-[[1-methyl-2-(3-pyridyl)pyrrolo[3,2-c]pyridin-6-yl]amino]phenyl]acetamide, 1-[3-[[1-methyl-2-(3-pyridyl)pyrrolo[3,2-c]pyridin-6-yl]amino]phenyl]ethanone, 1-benzyl-N-(2-pyridyl)-2-(3-pyridyl)pyrrolo[3,2-c]pyridin-6-amine, 1-benzyl-2-(3-pyridyl)-N-pyrimidin-4-yl-pyrrolo[3,2-c]pyridin-6-amine, 2-(3-methylimidazol-4-yl)-N-(3,4,5-trimethoxyphenyl)-1H-pyrrolo[3,2-c]pyridin-6-amine, N-(3-methoxyphenyl)-2-(3-methylimidazol-4-yl)-1H-pyrrolo[3,2-c]pyridin-6-amine, N-(3-chlorophenyl)-2-(3-methylimidazol-4-yl)-1H-pyrrolo[3,2-c]pyridin-6-amine, N1,N1-dimethyl-N3-[2-(3-methylimidazol-4-yl)-1H-pyrrolo[3,2-c]pyridin-6-yl]benzene-1,3-diamine, 2-(3-methyl-imidazol-4-yl)-N-(m-tolyl)-1H-pyrrolo[3,2-c]pyridin-6-amine, 1-[3-[[2-(3-methylimidazol-4-yl)-1H-pyrrolo[3,2-c]pyridin-6-yl]amino]phenyl]ethanone, N-(3-fluorophenyl)-2-(3-methylimidazol-4-yl)-1H-pyrrolo[3,2-c]pyridin-6-amine, N-(4-isopropoxyphenyl)-2-(3-methylimidazol-4-yl)-1H-pyrrolo[3,2-c]pyridin-6-amine, N-(3-methoxyphenyl)-2-(1H-pyrazol-4-yl)-1H-pyrrolo[3,2-c]pyridin-6-amine, N1,N1-dimethyl-N3-[2-(1H-pyrazol-4-yl)-1H-pyrrolo[3,2-c]pyridin-6-yl]benzene-1,3-diamine, N-(m-tolyl)-2-(1H-pyrazol-4-yl)-1H-pyrrolo[3,2-c]pyridin-6-amine, 2-(1H-pyrazol-4-yl)-N-(2-pyridyl)-1H-pyrrolo[3,2-c]pyridin-6-amine, N-[3-methoxy-5-(trifluoromethyl)phenyl]-2-(1H-pyrazol-4-yl)-1H-pyrrolo[3,2-c]pyridin-6-amine, N-[3-[[2-(1H-pyrazol-4-yl)-1H-pyrrolo[3,2-c]pyridin-6-yl]amino]phenyl]acetamide, 1-[3-[[2-(1H-pyrazol-4-yl)-1H-pyrrolo[3,2-c]pyridin-6-yl]amino]phenyl]ethanone, N-(3-fluorophenyl)-2-(1H-pyrazol-4-yl)-1H-pyrrolo[3,2-c]pyridin-6-amine, N-(4-methylsulfonylphenyl)-2-(1H-pyrazol-4-yl)-1H-pyrrolo[3,2-c]pyridin-6-amine, N-[4-[[2-(1-methylpyrazol-4-yl)-1H-pyrrolo[3,2-c]pyridin-6-yl]amino]phenyl]acetamide, N-(2,3-dihydro-1,4-benzodioxin-6-yl)-2-(1-methylpyrazol-4-yl)-1H-pyrrolo[3,2-c]pyridin-6-amine, 1-[3-[[2-(1-methylpyrazol-4-yl)-1H-pyrrolo[3,2-c]pyridin-6-yl]amino]phenyl]ethanone, 1-methyl-2-(1-methylpyrazol-4-yl)-N-(3,4,5-trimethoxyphenyl)pyrrolo[3,2-c]pyridin-6-amine, N-[4-[[1-methyl-2-(1-methylpyrazol-4-yl)pyrrolo[3,2-c]pyridin-6-yl]amino]phenyl]acetamide, N-(3-methoxyphenyl)-1-methyl-2-(1-methylpyrazol-4-yl)pyrrolo[3,2-c]pyridin-6-amine, N-(2,3-dihydro-1,4-benzodioxin-6-yl)-1-methyl-2-(1-methylpyrazol-4-yl)pyrrolo[3,2-c]pyridin-6-amine, N-(6-methoxy-3-pyridyl)-1-methyl-2-(1-methylpyrazol-4-yl)pyrrolo[3,2-c]pyridin-6-amine, 1-methyl-2-(1-methylpyrazol-4-yl)-N-(3-pyridyl)pyrrolo[3,2-c]pyridin-6-amine, 1-methyl-2-(1-methylpyrazol-4-yl)-N-phenyl-pyrrolo[3,2-c]pyridin-6-amine, 1-methyl-N-[4-(4-methylpiperazin-1-yl)phenyl]-2-(1-methylpyrazol-4-yl)pyrrolo[3,2-c]pyridin-6-amine, N1,N1-dimethyl-N3-[1-methyl-2-(1-methylpyrazol-4-yl)pyrrolo[3,2-c]pyridin-6-yl]benzene-1,3-diamine, 1-methyl-2-(1-methylpyrazol-4-yl)-N-(4-pyridyl)pyrrolo[3,2-c]pyridin-6-amine, 1-methyl-2-(1-methylpyrazol-4-yl)-N-(m-tolyl)pyrrolo[3,2-c]pyridin-6-amine, 1-methyl-2-(1-methylpyrazol-4-yl)-N-(2-pyridyl)pyrrolo[3,2-c]pyridin-6-amine, N,1-dimethyl-2-(1-methylpyrazol-4-yl)-N-phenyl-pyrrolo[3,2-c]pyridin-6-amine, methyl 4-[[1-methyl-2-(1-methylpyrazol-4-yl)pyrrolo[3,2-c]pyridin-6-yl]amino]benzoate, N-(1,3-benzodioxol-5-yl)-1-methyl-2-(1-methylpyrazol-4-yl)pyrrolo[3,2-c]pyridin-6-amine, 3-[[1-methyl-2-(1-methylpyrazol-4-yl)pyrrolo[3,2-c]pyridin-6-yl]amino]phenol, 4-[1-methyl-2-(1-methylpyrazol-4-yl)pyrrolo[3,2-c]pyridin-6-yl]morpholine, 1-methyl-2-(1-methylpyrazol-4-yl)-N-[3-(trifluoromethoxy)phenyl]pyrrolo[3,2-c]pyridin-6-amine, 1-methyl-2-(1-methylpyrazol-4-yl)-N-pyrimidin-4-yl-pyrrolo[3,2-c]pyridin-6-amine, N-[3-[[1-methyl-2-(1-methylpyrazol-4-yl)pyrrolo[3,2-c]pyridin-6-yl]amino]phenyl]acetamide, 1-[3-[[1-methyl-2-(1-methylpyrazol-4-yl)pyrrolo[3,2-c]pyridin-6-yl]amino]phenyl]ethanone, N-(3-fluorophenyl)-1-methyl-2-(1-methylpyrazol-4-yl)pyrrolo[3,2-c]pyridin-6-amine, 1-methyl-2-(1-methylpyrazol-4-yl)-N-(4-methylsulfonylphenyl)pyrrolo[3,2-c]pyridin-6-amine, 1-methyl-2-(1-methylpyrazol-4-yl)-N-(4-methylsulfanylphenyl)pyrrolo[3,2-c]pyridin-6-amine, 1-benzyl-6-(4-methylpiperazin-1-yl)-2-(1-methylpyrazol-4-yl)pyrrolo[3,2-c]pyridine, 4-[1-benzyl-2-(1-methylpyrazol-4-yl)pyrrolo[3,2-c]pyridin-6-yl]morpholine, N-[3-[[1-benzyl-2-(1-methylpyrazol-4-yl)pyrrolo[3,2-c]pyridin-6-yl]amino]phenyl]methanesulfonamide, N-[3-[[1-benzyl-2-(1-methylpyrazol-4-yl)pyrrolo[3,2-c]pyridin-6-yl]amino]phenyl]acetamide, N-methyl-N-[3-[1-methyl-6-(3,4,5-trimethoxyanilino)pyrrolo[3,2-c]pyridin-2-yl]phenyl]acetamide, 4-[[2-[3-[acetyl(methyl)amino]phenyl]-1-methyl-pyrrolo[3,2-c]pyridin-6-yl]amino]benzamide, N-[3-

[6-(3,4-dimethoxyanilino)-1-methyl-pyrrolo[3,2-c]pyridin-2-yl]phenyl]-N-methyl-acetamide, N-[3-[6-[(6-methoxy-3-pyridyl)amino]-1-methyl-pyrrolo[3,2-c]pyridin-2-yl]phenyl]-N-methyl-acetamide, N-methyl-N-[3-[1-methyl-6-(3-pyridylamino)pyrrolo[3,2-c]pyridin-2-yl]phenyl]acetamide, N-methyl-N-[3-[1-methyl-6-(4-morpholinoanilino)pyrrolo[3,2-c]pyridin-2-yl]phenyl]acetamide, N-methyl-N-[3-[1-methyl-6-[4-(4-methylpiperazin-1-yl)anilino]pyrrolo[3,2-c]pyridin-2-yl]phenyl]acetamide, N-[3-[6-[3-(dimethylamino)anilino]-1-methyl-pyrrolo[3,2-c]pyridin-2-yl]phenyl]-N-methyl-acetamide, N-[3-[6-(4-methoxyanilino)-1-methyl-pyrrolo[3,2-c]pyridin-2-yl]phenyl]-N-methyl-acetamide, N-methyl-N-[3-[1-methyl-6-(2-pyridylamino)pyrrolo[3,2-c]pyridin-2-yl]phenyl]acetamide, N-[3-[6-(4-cyanoanilino)-1-methyl-pyrrolo[3,2-c]pyridin-2-yl]phenyl]-N-methyl-acetamide, N-[3-[6-(1,3-benzodioxol-5-ylamino)-1-methyl-pyrrolo[3,2-c]pyridin-2-yl]phenyl]-N-methyl-acetamide, N-[3-[6-(3-hydroxyanilino)-1-methyl-pyrrolo[3,2-c]pyridin-2-yl]phenyl]-N-methyl-acetamide, N-methyl-N-[3-(1-methyl-6-morpholino-pyrrolo[3,2-c]pyridin-2-yl)phenyl]acetamide, 4-[[2-[3-[acetyl(methyl)amino]phenyl]-1-methyl-pyrrolo[3,2-c]pyridin-6-yl]amino]-N,N-dimethyl-benzamide, N-methyl-N-[3-[1-methyl-6-(4-methylsulfonylanilino)pyrrolo[3,2-c]pyridin-2-yl]phenyl]acetamide, 2-phenyl-N-(3,4,5-trimethoxyphenyl)-1H-pyrrolo[3,2-c]pyridin-6-amine, N-(3,4-dimethoxyphenyl)-2-phenyl-1H-pyrrolo[3,2-c]pyridin-6-amine, N-(4-morpholinophenyl)-2-phenyl-1H-pyrrolo[3,2-c]pyridin-6-amine, N-[4-(4-methylpiperazin-1-yl)phenyl]-2-phenyl-1H-pyrrolo[3,2-c]pyridin-6-amine, 2-phenyl-N-(4-pyridyl)-1H-pyrrolo[3,2-c]pyridin-6-amine, N-(4-fluorophenyl)-2-phenyl-1H-pyrrolo[3,2-c]pyridin-6-amine, 3-[(2-phenyl-1H-pyrrolo[3,2-c]pyridin-6-yl)amino]phenol, 4-(2-phenyl-1H-pyrrolo[3,2-c]pyridin-6-yl)morpholine, N,N-dimethyl-4-[(2-phenyl-1H-pyrrolo[3,2-c]pyridin-6-yl)amino]benzamide, N-[3-[(2-phenyl-1H-pyrrolo[3,2-c]pyridin-6-yl)amino]phenyl]acetamide, 1-benzyl-2-phenyl-N-pyrimidin-4-yl-pyrrolo[3,2-c]pyridin-6-amine, 1-methyl-4-(4-methylpiperazin-1-yl)-2-[3-(trifluoromethyl)phenyl]pyrrolo[3,2-c]pyridine, 2-(3-fluorophenyl)-4-(4-methylpiperazin-1-yl)-1H-pyrrolo[3,2-c]pyridine, 4-[2-(3-fluorophenyl)-1H-pyrrolo[3,2-c]pyridin-4-yl]morpholine, N,N-dimethyl-4-(1-methyl-4-morpholino-pyrrolo[3,2-c]pyridin-2-yl)benzamide, N,N-dimethyl-4-(4-morpholino-1H-pyrrolo[3,2-c]pyridin-2-yl)aniline, 4-(4-methylpiperazin-1-yl)-2-(3-thienyl)-1H-pyrrolo[3,2-c]pyridine, 4-[2-(3-thienyl)-1H-pyrrolo[3,2-c]pyridin-4-yl]morpholine, 4-[2-(3,5-dimethoxyphenyl)-1-methyl-pyrrolo[3,2-c]pyridin-4-yl]morpholine, 4-[2-(2-methoxyphenyl)-1H-pyrrolo[3,2-c]pyridin-4-yl]morpholine, 2-(3-methoxyphenyl)-1-methyl-4-(4-methylpiperazin-1-yl)pyrrolo[3,2-c]pyridine, 4-[2-(3-chlorophenyl)-1-methyl-pyrrolo[3,2-c]pyridin-4-yl]morpholine, N-(3-pyridyl)-2-[3-(trifluoromethyl)phenyl]-1H-pyrrolo[3,2-c]pyridin-4-amine, N-(4-methylsulfonylphenyl)-2-[3-(trifluoromethyl)phenyl]-1H-pyrrolo[3,2-c]pyridin-4-amine, N-[4-[[2-(3-fluorophenyl)-1H-pyrrolo[3,2-c]pyridin-4-yl]amino]phenyl]acetamide, 4-[[2-(3-fluorophenyl)-1H-pyrrolo[3,2-c]pyridin-4-yl]amino]phenol, 2-(3-fluorophenyl)-N-(3-pyridyl)-1H-pyrrolo[3,2-c]pyridin-4-amine, 2-(3-fluorophenyl)-N-[4-(4-methylpiperazin-1-yl)phenyl]-1H-pyrrolo[3,2-c]pyridin-4-amine, 2-(3-fluorophenyl)-N-(3-methylsulfonylphenyl)-1H-pyrrolo[3,2-c]pyridin-4-amine, N-(1,3-benzodioxol-5-yl)-2-(3-fluorophenyl)-1H-pyrrolo[3,2-c]pyridin-4-amine, 5-[[2-(3-fluorophenyl)-1H-pyrrolo[3,2-c]pyridin-4-yl]amino]-2-methoxy-phenol, N-[3-[[2-(3-fluorophenyl)-1H-pyrrolo[3,2-c]pyridin-4-yl]amino]phenyl]methanesulfonamide, N-[3-[[2-(3-fluorophenyl)-1H-pyrrolo[3,2-c]pyridin-4-yl]amino]phenyl]acetamide, 2-(3-fluorophenyl)-N-(4-methylsulfonylphenyl)-1H-pyrrolo[3,2-c]pyridin-4-amine, N-(3,4-dimethoxyphenyl)-2-(3-fluorophenyl)-1-methyl-pyrrolo[3,2-c]pyridin-4-amine, 2-(3-fluorophenyl)-1-methyl-N-[4-(4-methylpiperazin-1-yl)phenyl]pyrrolo[3,2-c]pyridin-4-amine, N-[3-[[2-(3-fluorophenyl)-1-methyl-pyrrolo[3,2-c]pyridin-4-yl]amino]phenyl]acetamide, 4-[4-(4-acetamidoanilino)-1-methyl-pyrrolo[3,2-c]pyridin-2-yl]-N,N-dimethyl-benzamide, 4-[4-(3-methoxyanilino)-1-methyl-pyrrolo[3,2-c]pyridin-2-yl]-N,N-dimethyl-benzamide, 4-[4-(4-carbamoylanilino)-1-methyl-pyrrolo[3,2-c]pyridin-2-yl]-N,N-dimethyl-benzamide, 4-[4-(2,3-dihydro-1,4-benzodioxin-6-ylamino)-1-methyl-pyrrolo[3,2-c]pyridin-2-yl]-N,N-dimethyl-benzamide, 4-[4-(3,4-dimethoxyanilino)-1-methyl-pyrrolo[3,2-c]pyridin-2-yl]-N,N-dimethyl-benzamide, 4-[4-[(6-methoxy-3-pyridyl)amino]-1-methyl-pyrrolo[3,2-c]pyridin-2-yl]-N,N-dimethyl-benzamide, N,N-dimethyl-4-[1-methyl-4-(4-phenoxyanilino)pyrrolo[3,2-c]pyridin-2-yl]benzamide, 4-[4-[3-(dimethylamino)anilino]-1-methyl-pyrrolo[3,2-c]pyridin-2-yl]-N,N-dimethyl-benzamide, N,N-dimethyl-4-[1-methyl-4-(2-pyridylamino)pyrrolo[3,2-c]pyridin-2-yl]benzamide, N,N-dimethyl-4-[1-methyl-4-(3-methoxy-5-(trifuloromethyl)phenylamino)pyrrolo[3,2-c]pyridin-2-yl]benzamide, 4-[4-(3-hydroxyanilino)-1-methyl-pyrrolo[3,2-c]pyridin-2-yl]-N,N-dimethyl-benzamide, N,N-dimethyl-4-[1-methyl-4-[3-(trifluoromethoxy)anilino]pyrrolo[3,2-c]pyridin-2-yl]benzamide, N,N-dimethyl-4-[1-methyl-4-(3-phenoxyanilino)pyrrolo[3,2-c]pyridin-2-yl]benzamide, 4-[4-(3-isopropylanilino)-1-methyl-pyrrolo[3,2-c]pyridin-2-yl]-N,N-dimethyl-benzamide, 4-[4-[3-(methanesulfonamido)anilino]-1-methyl-pyrrolo[3,2-c]pyridin-2-yl]-N,N-dimethyl-benzamide, 4-[[2-(4-dimethylaminophenyl)-1-methyl-pyrrolo[3,2-c]pyridin-4-yl]amino]phenol, 4-[[2-(4-dimethylaminophenyl)-1-methyl-pyrrolo[3,2-c]pyridin-4-yl]amino]benzamide, 5-[[2-(4-dimethylaminophenyl)-1-methyl-pyrrolo[3,2-c]pyridin-4-yl]amino]-2-methoxy-phenol, 2-(4-dimethylaminophenyl)-1-methyl-N-pyrimidin-4-yl-pyrrolo[3,2-c]pyridin-4-amine, 2-(4-dimethylaminophenyl)-1-methyl-N-(4-methylsulfonylphenyl)pyrrolo[3,2-c]pyridin-4-amine, N-[4-[[2-(3-pyridyl)-1H-pyrrolo[3,2-c]pyridin-4-yl]amino]phenyl]acetamide, N-(2,3-dihydro-1,4-benzodioxin-6-yl)-2-(3-pyridyl)-1H-pyrrolo[3,2-c]pyridin-4-amine, N-(6-methoxy-3-pyridyl)-2-(3-pyridyl)-1H-pyrrolo[3,2-c]pyridin-4-amine, N,2-bis(3-pyridyl)-1H-pyrrolo[3,2-c]pyridin-4-amine, N-[4-(4-methylpiperazin-1-yl)phenyl]-2-(3-pyridyl)-1H-pyrrolo[3,2-c]pyridin-4-amine, 2-methoxy-5-[[2-(3-pyridyl)-1H-pyrrolo[3,2-c]pyridin-4-yl]amino]phenol, 1-methyl-2-(3-pyridyl)-N-(3,4,5-trimethoxyphenyl)pyrrolo[3,2-c]pyridin-4-amine, N-(3,4-dimethoxyphenyl)-1-methyl-2-(3-pyridyl)pyrrolo[3,2-c]pyridin-4-amine, N1,N1-dimethyl-N3-[1-methyl-2-(3-pyridyl)pyrrolo[3,2-c]pyridin-4-yl]benzene-1,3-diamine, N-(4-methoxy-2-methylphenyl)-1-methyl-2-(3-pyridyl)pyrrolo[3,2-c]pyridin-4-amine, 1-methyl-N-(m-tolyl)-2-(3-pyridyl)pyrrolo[3,2-c]pyridin-4-amine, N-(4-fluorophenyl)-1-methyl-2-(3-pyridyl)pyrrolo[3,2-c]pyridin-4-amine, 1-methyl-2-(3-pyridyl)-N-[3-(trifluoromethyl)phenyl]pyrrolo[3,2-c]pyridin-4-amine, N-[3-[[1-methyl-2-(3-pyridyl)pyrrolo[3,2-c]pyridin-4-yl]amino]phenyl]methanesulfonamide, N-[3-[[1-methyl-2-(3-pyridyl)pyrrolo[3,2-c]pyridin-4-yl]amino]phenyl]acetamide, 2-(1-methylpyrazol-4-yl)-N-(4-methylsulfonylphenyl)-1H-pyrrolo[3,2-c]pyridin-4-amine, 1-methyl-2-(1-methylpyrazol-4-yl)-N-(3-pyridyl)pyrrolo[3,2-c]pyridin-4-amine, N-methyl-N-[3-[1-methyl-4-[4-(trifluoromethoxy)anilino]pyrrolo[3,2-c]pyridin-2-yl]phenyl]

acetamide, N-[4-[[2-(3-thienyl)-1H-pyrrolo[3,2-c]pyridin-4-yl]amino]phenyl]acetamide, 4-[[12-(3-thienyl)-1H-pyrrolo[3,2-c]pyridin-4-yl]amino]benzamide, N-(2,4-dimethoxyphenyl)-2-(3-thienyl)-1H-pyrrolo[3,2-c]pyridin-4-amine, N-(2,3-dihydro-1,4-benzodioxin-6-yl)-2-(3-thienyl)-1H-pyrrolo[3,2-c]pyridin-4-amine, N-(3,4-dimethoxyphenyl)-2-(3-thienyl)-1H-pyrrolo[3,2-c]pyridin-4-amine, N-(6-methoxy-3-pyridyl)-2-(3-thienyl)-1H-pyrrolo[3,2-c]pyridin-4-amine, N-(3-pyridyl)-2-(3-thienyl)-1H-pyrrolo[3,2-c]pyridin-4-amine, N-(4-morpholinophenyl)-2-(3-thienyl)-1H-pyrrolo[3,2-c]pyridin-4-amine, N-[4-(4-methylpiperazin-1-yl)phenyl]-2-(3-thienyl)-1H-pyrrolo[3,2-c]pyridin-4-amine, N-(4-pyridyl)-2-(3-thienyl)-1H-pyrrolo[3,2-c]pyridin-4-amine, N-(4-methoxyphenyl)-2-(3-thienyl)-1H-pyrrolo[3,2-c]pyridin-4-amine, N-(2-pyridyl)-2-(3-thienyl)-1H-pyrrolo[3,2-c]pyridin-4-amine, methyl 4-[[2-(3-thienyl)-1H-pyrrolo[3,2-c]pyridin-4-yl]amino]benzoate, N-(3-methylsulfonylphenyl)-2-(3-thienyl)-1H-pyrrolo[3,2-c]pyridin-4-amine, N-(1,3-benzodioxol-5-yl)-2-(3-thienyl)-1H-pyrrolo[3,2-c]pyridin-4-amine, 3-[[2-(3-thienyl)-11H-pyrrolo[3,2-c]pyridin-4-yl]amino]phenol, N-[3-[[2-(3-thienyl)-1H-pyrrolo[3,2-c]pyridin-4-yl]amino]phenyl]methanesulfonamide, N-[3-[[2-(3-thienyl)-1H-pyrrolo[3,2-c]pyridin-4-yl]amino]phenyl]acetamide, 1-[3-[[2-(3-thienyl)-1H-pyrrolo[3,2-c]pyridin-4-yl]amino]phenyl]ethanone, N-(4-methylsulfonylphenyl)-2-(3-thienyl)-1H-pyrrolo[3,2-c]pyridin-4-amine, N-(4-isopropoxyphenyl)-2-(3-thienyl)-1H-pyrrolo[3,2-c]pyridin-4-amine, N-[4-[[1-methyl-2-(3-thienyl)pyrrolo[3,2-c]pyridin-4-yl]amino]phenyl]acetamide, 4-[[1-methyl-2-(3-thienyl)pyrrolo[3,2-c]pyridin-4-yl]amino]phenol, N-(2,4-dimethoxyphenyl)-1-methyl-2-(3-thienyl)pyrrolo[3,2-c]pyridin-4-amine, N-(2,3-dihydro-1,4-benzodioxin-6-yl)-1-methyl-2-(3-thienyl)pyrrolo[3,2-c]pyridin-4-amine, N-(3,4-dimethoxyphenyl)-1-methyl-2-(3-thienyl)pyrrolo[3,2-c]pyridin-4-amine, N-(6-methoxy-3-pyridyl)-1-methyl-2-(3-thienyl)pyrrolo[3,2-c]pyridin-4-amine, 1-methyl-N-(3-pyridyl)-2-(3-thienyl)pyrrolo[3,2-c]pyridin-4-amine, N1,N1-dimethyl-N3-[1-methyl-2-(3-thienyl)pyrrolo[3,2-c]pyridin-4-yl]benzene-1,3-diamine, 1-methyl-N-(4-pyridyl)-2-(3-thienyl)pyrrolo[3,2-c]pyridin-4-amine, N-(4-methoxyphenyl)-1-methyl-2-(3-thienyl)pyrrolo[3,2-c]pyridin-4-amine, 1-methyl-N-(2-pyridyl)-2-(3-thienyl)pyrrolo[3,2-c]pyridin-4-amine, 4-[[1-methyl-2-(3-thienyl)pyrrolo[3,2-c]pyridin-4-yl]amino]benzonitrile, 1-methyl-N-(3-methylsulfonylphenyl)-2-(3-thienyl)pyrrolo[3,2-c]pyridin-4-amine, N-(1,3-benzodioxol-5-yl)-1-methyl-2-(3-thienyl)pyrrolo[3,2-c]pyridin-4-amine, 2-methoxy-5-[[I-methyl-2-(3-thienyl)pyrrolo[3,2-c]pyridin-4-yl]amino]phenol, 1-methyl-N-pyrimidin-4-yl-2-(3-thienyl)pyrrolo[3,2-c]pyridin-4-amine, N-[3-[[1-methyl-2-(3-thienyl)pyrrolo[3,2-c]pyridin-4-yl]amino]phenyl]methanesulfonamide, N-[3-[[1-methyl-2-(3-thienyl)pyrrolo[3,2-c]pyridin-4-yl]amino]phenyl]acetamide, 1-[3-[[1-methyl-2-(3-thienyl)pyrrolo[3,2-c]pyridin-4-yl]amino]phenyl]ethanone, 1-methyl-N-(4-methylsulfonylphenyl)-2-(3-thienyl)pyrrolo[3,2-c]pyridin-4-amine, 4-[[2-(3,5-dimethoxyphenyl)-1H-pyrrolo[3,2-c]pyridin-4-yl]amino]benzamide, 2-(3,5-dimethoxyphenyl)-N-(4-pyridyl)-1H-pyrrolo[3,2-c]pyridin-4-amine, N-[3-[[2-(3,5-dimethoxyphenyl)-1H-pyrrolo[3,2-c]pyridin-4-yl]amino]phenyl]methanesulfonamide, 2-(3,5-dimethoxyphenyl)-N-(4-methylsulfonylphenyl)-1H-pyrrolo[3,2-c]pyridin-4-amine, 4-[[2-(2-methoxyphenyl)-1H-pyrrolo[3,2-c]pyridin-4-yl]amino]benzamide, 2-(2-methoxyphenyl)-N-(4-pyridyl)-1H-pyrrolo[3,2-c]pyridin-4-amine, N-(1,3-benzodioxol-5-yl)-2-(2-methoxyphenyl)-1H-pyrrolo[3,2-c]pyridin-4-amine, 3-[[2-(2-methoxyphenyl)-1H-pyrrolo[3,2-c]pyridin-4-yl]amino]phenol, N-[3-[[2-(2-methoxyphenyl)-1H-pyrrolo[3,2-c]pyridin-4-yl]amino]phenyl]methanesulfonamide, N-[3-[[2-(2-methoxyphenyl)-1H-pyrrolo[3,2-c]pyridin-4-yl]amino]phenyl]acetamide, 2-(2-methoxyphenyl)-N-(4-methylsulfonylphenyl)-1H-pyrrolo[3,2-c]pyridin-4-amine, N-[4-[[2-(2-methoxyphenyl)-1-methyl-pyrrolo[3,2-c]pyridin-4-yl]amino]phenyl]acetamide, N-(2,4-dimethoxyphenyl)-2-(2-methoxyphenyl)-1-methyl-pyrrolo[3,2-c]pyridin-4-amine, 2-(2-methoxyphenyl)-1-methyl-N-(3-pyridyl)pyrrolo[3,2-c]pyridin-4-amine, 2-(2-methoxyphenyl)-1-methyl-N-(2-pyridyl)pyrrolo[3,2-c]pyridin-4-amine, 2-(2-methoxyphenyl)-1-methyl-N-(4-methylsulfanylphenyl)pyrrolo[3,2-c]pyridin-4-amine, N-[4-[[2-(3-methoxyphenyl)-1H-pyrrolo[3,2-c]pyridin-4-yl]amino]phenyl]acetamide, 2-(3-methoxyphenyl)-N-(6-methoxy-3-pyridyl)-11H-pyrrolo[3,2-c]pyridin-4-amine, 2-(3-methoxyphenyl)-N-(3-pyridyl)-1H-pyrrolo[3,2-c]pyridin-4-amine, 2-(3-methoxyphenyl)-N-phenyl-1H-pyrrolo[3,2-c]pyridin-4-amine, 2-(3-methoxyphenyl)-N-[4-(4-methylpiperazin-1-yl)phenyl]-1H-pyrrolo[3,2-c]pyridin-4-amine, 2-(3-methoxyphenyl)-N-(3-methylsulfonylphenyl)-1H-pyrrolo[3,2-c]pyridin-4-amine, 2-methoxy-5-[[2-(3-methoxyphenyl)-1H-pyrrolo[3,2-c]pyridin-4-yl]amino]phenol, 4-[[2-(3-methoxyphenyl)-1H-pyrrolo[3,2-c]pyridin-4-yl]amino]-N,N-dimethyl-benzamide, N-(3-isopropoxyphenyl)-2-(3-methoxyphenyl)-1-methyl-pyrrolo[3,2-c]pyridin-4-amine, 2-(3-chlorophenyl)-N-(3-pyridyl)-1H-pyrrolo[3,2-c]pyridin-4-amine, 2-(3-chlorophenyl)-1-methyl-N-pyrimidin-4-yl-pyrrolo[3,2-c]pyridin-4-amine, 4-[(2-phenyl-1H-pyrrolo[3,2-c]pyridin-4-yl)amino]phenol, 4-[(2-phenyl-1H-pyrrolo[3,2-c]pyridin-4-yl)amino]benzamide, 2-phenyl-N-(3-pyridyl)-1H-pyrrolo[3,2-c]pyridin-4-amine, N-[4-(4-methylpiperazin-1-yl)phenyl]-2-phenyl-1H-pyrrolo[3,2-c]pyridin-4-amine, 2-phenyl-N-(2-pyridyl)-1H-pyrrolo[3,2-c]pyridin-4-amine, N,N-dimethyl-4-[(2-phenyl-1H-pyrrolo[3,2-c]pyridin-4-yl)amino]benzamide, N-[3-[(2-phenyl-1H-pyrrolo[3,2-c]pyridin-4-yl)amino]phenyl]acetamide, N-(4-methylsulfonylphenyl)-2-phenyl-1H-pyrrolo[3,2-c]pyridin-4-amine, 4-[(1-methyl-2-phenyl-pyrrolo[3,2-c]pyridin-4-yl)amino]benzamide, N-(3,4-dimethoxyphenyl)-1-methyl-2-phenyl-pyrrolo[3,2-c]pyridin-4-amine, 1-methyl-2-phenyl-N-(2-pyridyl)pyrrolo[3,2-c]pyridin-4-amine, and 3-[(1-methyl-2-phenyl-pyrrolo[3,2-c]pyridin-4-yl)amino]phenol.

6. The method according to claim 1, wherein the at least one inhibitor is a compound of general formula (IV):

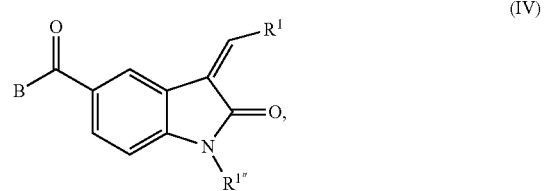

wherein,

B represents

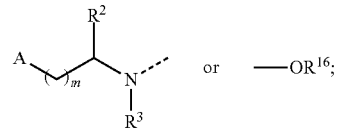

$R^1$ represents

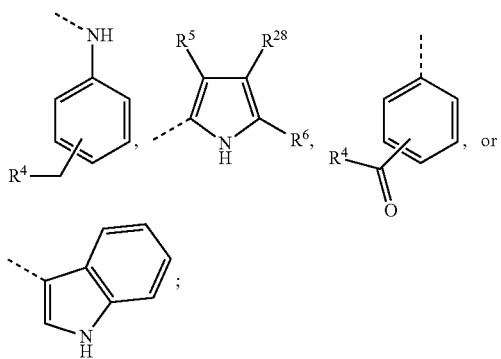

$R^{1''}$ represents —H or —C(O)$R^{18}$;
$R^2$ represents —$R^{19}$, —C(O)NH$_2$, or —CO$_2R^{20}$;
$R^{19}$ and $R^{20}$ are independently of each other selected from —H, —CH$_3$, —C$_2$H$_5$, —C$_3$H$_7$, —C$_4$H$_9$, —C$_5$H$_{11}$, -Ph, and —CH$_2$Ph;
$R^3$, $R^5$ and $R^6$ are independently of each other selected from —H, —CH$_3$, —C$_2$H$_5$, and —C$_3$H$_7$;
$R^{28}$ represents —H or —(CH$_2$)$_q$—C(O)$R^4$;
$R^4$ represents —O$R^{29}$, —$R^7$, —NH—(CH$_2$)$_p$—$R^{17}$, —NH—(CH$_2$)$_n$—$R^7$,

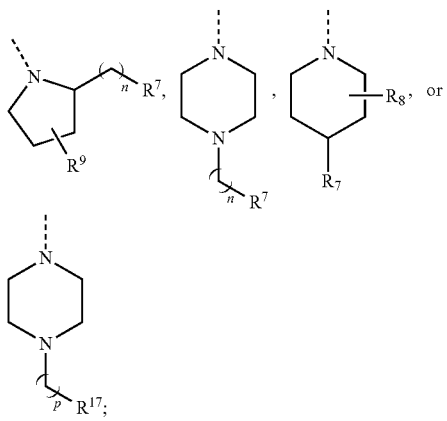

$R^7$ represents —NH—CH($R^{30}$)—CO$_2R^{31}$, —N$R^{10}R^{11}$, —NH—CH($R^{30}$)Ph,

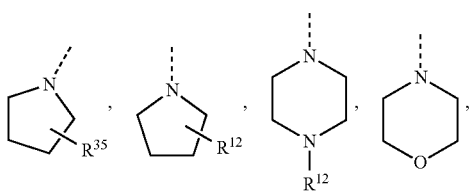

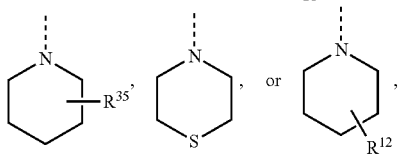

wherein at least one of the residues $R^{10}$ and $R^{11}$ is different of —H;

$R^{30}$ represents —H, —CH$_2R^{32}$, or —CH$_2$O$R^{33}$;
$R^{32}$ represents —H, —CH$_3$, —C$_2$H$_5$, —C$_3$H$_7$, —CH(CH$_3$)$_2$, —C$_4$H$_9$, —CH(CH$_3$)—C$_2$H$_5$, —CH$_2$—CH(CH$_3$)$_2$, —C(CH$_3$)$_3$, -Ph, —CH$_2$—CO$R^{34}$, —C$_2$H$_4$—CO$R^{34}$, or —C$_3$H$_6$—CO$R^{34}$;
$R^{33}$ represents —H, —CH$_3$, —C$_2$H$_5$, —C$_3$H$_7$, —CH(CH$_3$)$_2$, —C$_4$H$_9$, —CH(CH$_3$)—C$_2$H$_5$, —CH$_2$—CH(CH$_3$)$_2$, —C(CH$_3$)$_3$, -Ph, or —CH$_2$-Ph;
$R^{34}$ represents —N$R^{10}R^{11}$, —OH, —OCH$_3$, —OC$_2$H$_5$, —OC$_3$H$_7$, —OCH(CH$_3$)$_2$, or —OCH$_2$Ph;
$R^{35}$ represents —OH, —OCH$_3$, —OC$_2$H$_5$, —NH$_2$, —N(CH$_3$)$_2$, or —N(CH$_3$)(C$_2$H$_5$);
$R^{17}$ represents:

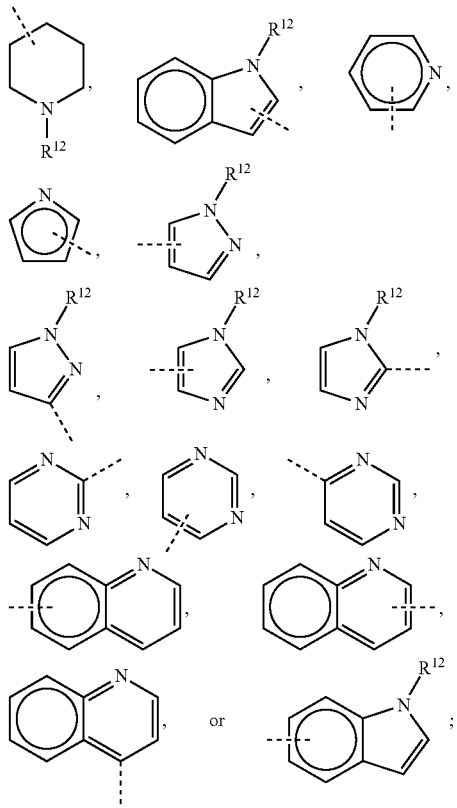

$R^{29}$ and $R^{31}$ are independently of each other selected from —H, —CH$_3$, —C$_2$H$_5$, —C$_3$H$_7$, and —CH$_2$Ph;
A represents or

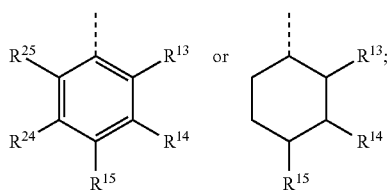

$R^{13}$, $R^{14}$, $R^{15}$, $R^{24}$ and $R^{25}$ are independently of each other selected from the group consisting of: —$R^{21}$, —$R^{22}$, —$R^{23}$, —$R^{26}$, —$R^{27}$, —O$R^{21}$, —O$R^{22}$, —O$R^{23}$, —O$R^{26}$, —O$R^{27}$, —F, —Cl, —Br and —I;
$R^{14}$ together with $R^{15}$ may form with the two carbon of the benzene or cyclohexane they are attached to a carbocyclic 4-, 5- or 6-membered ring and that 4-, 5- or 6-membered ring can be saturated or unsaturated, or a heterocyclic 5- or 6-membered ring and that 5- or 6-membered ring can be saturated or unsaturated;

$R^{13}$ together with $R^2$ may form a carbocyclic 4-, 5- or 6-membered ring and that 4-, 5- or 6-membered ring can be saturated or unsaturated, or a heterocyclic 5- or 6-membered ring and that 5- or 6-membered ring can be saturated or unsaturated;

$R^8$, $R^9$, $R^{10}$, $R^{11}$, $R^{12}$, $R^{16}$, $R^{18}$, $R^{21}$, $R^{22}$, $R^{23}$, $R^{26}$ and $R^{27}$ are independently of each other selected from: —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)— C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH (CH$_3$)$_2$, -Ph, —CH═CH$_2$, —CH$_2$—CH═CH$_2$, —C(CH$_3$)═CH$_2$, —CH═CH—CH$_3$, —C$_2$H$_4$— CH═CH$_2$, —CH$_2$—CH═CH—CH$_3$, —CH═CH— C$_2$H$_5$, —CH$_2$—C(CH$_3$)═CH$_2$, —CH(CH$_3$)— CH═CH, —CH═C(CH$_3$)$_2$, —C(CH$_3$)═CH—CH$_3$, —CH═CH—CH═CH$_2$, —C≡CH, —C≡C—CH$_3$, —CH$_2$—C≡CH, —C$_2$H$_4$—C≡CH, —CH$_2$— C≡C—CH$_3$, —C≡C—C$_2$H$_5$, and —CH$_2$Ph;

m is an integer number selected from 0 and 1;

n is an integer number selected from 1, 2, 3, 4, 5 and 6;

p is an integer number selected from 0, 1, 2, 3 and 4;

q is an integer number selected from 0, 1, 2, 3 and 4; and enantiomers, mixtures of enantiomers, diastereomers, mixtures of diastereomers, tautomers, hydrates, solvates and racemates of the above mentioned compounds and pharmaceutically acceptable salts thereof.

7. The method according to claim 6, wherein the at least one inhibitor is selected from the group consisting of: (3Z)-3-{[3,5-dimethyl-4-(piperidin-1-ylcarbonyl)-1H-pyrrol-2-yl]methylene}-2-oxoindoline-5-carboxylic acid, ((3Z)-3-({3,5-dimethyl-4-[(2-pyrrolidin-1-ylethyl)carbamoyl]-1H-pyrrol-2-yl}methylene)-2-oxoindoline-5-carboxylic acid, (3Z)-3-[(4-{[2-(diethylamino)ethyl]carbamoyl}-3,5-dimethyl-1H-pyrrol-2-yl)methylene]-2-oxoindoline-5-carboxylic acid, (3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxoindoline-5-carboxylic acid, (3Z)-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxylic acid, (3Z)-3-({3,5-dimethyl-4-[(2-pyrrolidin-1-ylethyl)carbamoyl]-1H-pyrrol-2-yl}methylene)-2-oxo-N-[(1R)-1-phenylpropyl]indoline-5-carboxamide, (3Z)-3-({3,5-dimethyl-4-[(4-methylpiperazin-1-yl)carbonyl]-1H-pyrrol-2-yl}methylene)-2-oxo-N-[(1R)-1-phenylpropyl]indoline-5-carboxamide, (3Z)—N-[1-(3-chlorophenyl)propyl]-3-({3,5-dimethyl-4-[(4-methylpiperazin-1-yl)carbonyl]-1H-pyrrol-2-yl}methylene)-2-oxoindoline-5-carboxamide, (3Z)—N-[1-(3,4-difluorophenyl)propyl]-3-({3,5-dimethyl-4-[(4-methylpiperazin-1-yl)carbonyl]-1H-pyrrol-2-yl}methylene)-2-oxoindoline-5-carboxamide, (3Z)—N-[1-(3,4-difluorophenyl)propyl]-3-({3,5-dimethyl-4-[(2-pyrrolidin-1-ylethyl)carbamoyl]-1H-pyrrol-2-yl}methylene)-2-oxoindoline-5-carboxamide, (3Z)—N-[1-(3-chlorophenyl)propyl]-3-({3,5-dimethyl-4-[(2-pyrrolidin-1-ylethyl)carbamoyl]-1H-pyrrol-2-yl}methylene)-2-oxoindoline-5-carboxamide, (3Z)—N-[1-(4-chlorophenyl)propyl]-3-({3,5-dimethyl-4-[(4-methylpiperazin-1-yl)carbonyl]-1H-pyrrol-2-yl}methylene)-2-oxoindoline-5-carboxamide, (3Z)—N-[1-(4-chlorophenyl)propyl]-3-({3,5-dimethyl-4-[(2-pyrrolidin-1-ylethyl)carbamoyl]-1H-pyrrol-2-yl}methylene)-2-oxoindoline-5-carboxamide, (3Z)-3-{[3,5-dimethyl-4-(piperidin-1-ylcarbonyl)-1H-pyrrol-2-yl]methylene}-2-oxo-N-[(1R)-1-phenylethyl]indoline-5-carboxamide, (3Z)-3-({3,5-dimethyl-4-[(4-methylpiperazin-1-yl)carbonyl]-1H-pyrrol-2-yl}methylene)-2-oxo-N-[(1R)-1-phenylethyl]indoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1R)-1-phenylethyl]indoline-5-carboxamide, (3Z)-3-[(3,5-dimethyl-4-{[(2R)-2-(pyrrolidin-1-ylmethyl)pyrrolidin-1-yl]carbonyl}-1H-pyrrol-2-yl)methylene]-2-oxo-N-[(1R)-1-phenylethyl]indoline-5-carboxamide, (3Z)-3-[(3,5-dimethyl-4-{[(2R)-2-(pyrrolidin-1-ylmethyl)pyrrolidin-1-yl]carbonyl}-1H-pyrrol-2-yl)methylene]-2-oxo-N-[(1S)-1-phenylethyl]indoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1S)-1-phenylethyl]indoline-5-carboxamide, (3Z)-3-({3,5-dimethyl-4-[(4-methylpiperazin-1-yl)carbonyl]-1H-pyrrol-2-yl}methylene)-N-[(1S)-1-(4-methoxyphenyl)ethyl]-2-oxoindoline-5-carboxamide, (3Z)-3-({3,5-dimethyl-4-[(4-methylpiperazin-1-yl)carbonyl]-1H-pyrrol-2-yl}methylene)-N-[(1R)-1-(4-methoxyphenyl)ethyl]-2-oxoindoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1R)-1-(4-methoxyphenyl)ethyl]-2-oxoindoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1R)-1-(3-methoxyphenyl)ethyl]-2-oxoindoline-5-carboxamide, (3Z)—N-[(1R)-1-cyclohexylethyl]-3-({3,5-dimethyl-4-[(4-methylpiperazin-1-yl)carbonyl]-1H-pyrrol-2-yl}methylene)-2-oxoindoline-5-carboxamide, (3Z)—N-[(1R)-1-(3-chlorophenyl)ethyl]-3-({3,5-dimethyl-4-[(4-methylpiperazin-1-yl)carbonyl]-1H-pyrrol-2-yl}methylene)-2-oxoindoline-5-carboxamide, (3Z)—N-[(1R)-1-(3-chlorophenyl)ethyl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide, (3Z)-3-({3,5-dimethyl-4-[(4-methylpiperazin-1-yl)carbonyl]-1H-pyrrol-2-yl}methylene)-N-[(1R)-1-(2-naphthyl)ethyl]-2-oxoindoline-5-carboxamide, (3Z)-3-[(3,5-dimethyl-4-{[(2R)-2-(pyrrolidin-1-ylmethyl)pyrrolidin-1-yl]carbonyl}-1H-pyrrol-2-yl)methylene]-N-[(1R)-1-(2-naphthyl)ethyl]-2-oxoindoline-5-carboxamide, (3Z)—N-[(1S)-2,3-dihydro-1H-inden-1-yl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide, (3Z)—N-[(1R)-2,3-dihydro-1H-inden-1-yl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide, (3Z)-3-({3,5-dimethyl-4-[(4-methylpiperazin-1-yl)carbonyl]-1H-pyrrol-2-yl}methylene)-N-methyl-2-oxo-N-[(1R)-1-phenylethyl]indoline-5-carboxamide, (3Z)-3-({3,5-dimethyl-4-[(4-methylpiperazin-1-yl)carbonyl]-1H-pyrrol-2-yl}methylene)-N-[(1R)-1-(4-methylphenyl)ethyl]-2-oxoindoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1R)-1-(4-methylphenyl)ethyl]-2-oxoindoline-5-carboxamide, (3Z)-3-({3,5-dimethyl-4-[(4-methylpiperazin-1-yl)carbonyl]-1H-pyrrol-2-yl}methylene)-N-[(1R)-1-(4-methylphenyl)ethyl]-2-oxoindoline-5-carboxamide, (3Z)—N-[(1R)-1-(4-chlorophenyl)ethyl]-3-({3,5-dimethyl-4-[(4-methylpiperazin-1-yl)carbonyl]-1H-pyrrol-2-yl}methylene)-2-oxoindoline-5-carboxamide, (3Z)—N-[(1S)-1-(4-chlorophenyl)ethyl]-3-[(3,5-dimethyl-4-{[(2S)-2-(pyrrolidin-1-ylmethyl)pyrrolidin-1-yl]carbonyl}-1H- pyrrol-2-yl)methylene]-2-oxoindoline-5-carboxamide, (3Z)—N-[(1R)-1-(4-chlorophenyl)ethyl]-3-[(3,5-dimethyl-4-{[(2R)-2-(pyrrolidin-1-ylmethyl)pyrrolidin-1-yl]carbonyl}-1H-pyrrol-2-yl)methylene]-2-oxoindoline-5-carboxamide, (3Z)—N-[(1R)-1-(3-chlorophenyl)ethyl]-3-[(3,5-dimethyl-4-{[(2S)-2-(pyrrolidin-1-ylmethyl)pyrrolidin-1-yl]carbonyl}-1H-pyrrol-2-yl)methylene]-2-oxoindoline-5-carboxamide, (3Z)—N-[(1R)-1-(3-bromophenyl)ethyl]-3-({3,5-dimethyl-4-[(4-methylpiperazin-1-yl)carbonyl]-1H-pyrrol-2-yl}methylene)-2-oxoindoline-5-carboxamide, (3Z)—N-[(1S)-1-(3-chlorophenyl)ethyl]-3-({3,5-dimethyl-4-[(4-methylpiperazin-1-yl)carbonyl]-1H-pyrrol-2-yl}methylene)-2-oxoindoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-N-[(1S)-1-(4-fluorophenyl)ethyl]-2-oxoindoline-5-carboxamide, (3Z)-3-[(3,5-dimethyl-4-{[(2R)-2-(pyrrolidin-1-ylmethyl)pyrrolidin-1-yl]carbonyl}-1H-pyrrol-2-yl)methylene]-N-[(1S)-1-(4-fluorophenyl)ethyl]-2-oxoindoline-5-carboxamide,)-3-[(3,5-dimethyl-4-{[(2R)-2-(pyrrolidin-1-ylmethyl)pyrrolidin-1-yl]carbonyl}-1H-pyrrol-2-yl)methylene]-N-[(1R)-1-(4-fluorophenyl)ethyl]-2-oxoindoline-5-carboxamide, (3Z)-3-[(3,5-dimethyl-4-{[4-(4-methylpiperazin-1-yl)piperidin-1-yl]carbonyl}-1H-pyrrol-2-yl)methylene]-2-oxo-N-[(1R)-1-phenylethyl]indoline-5-carboxamide, (3Z)-3-({3,5-dimethyl-4-[(4-methylpiperazin-1-yl)carbonyl]-1H-pyrrol-2-yl}methylene)-2-oxo-N-[(1S)-1-phenylpropyl]indoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1R)-1-phenylpropyl]indoline-5-carboxamide, (3Z)-3-[(3,5-dimethyl-4-{[(2S)-2-(pyrrolidin-1-ylmethyl)pyrrolidin-1-yl]carbonyl}-1H-pyrrol-2-yl)methylene]-2-oxo-N-[(1S)-1-phenylpropyl]indoline-5-carboxamide, (3Z)-3-[(3,5-dimethyl-4-{[(2R)-2-(pyrrolidin-1-yl methyl)pyrrolidin-1-yl]carbonyl}-1H-pyrrol-2-yl)methylene]-2-oxo-N-[(1R)-1-phenylpropyl]indoline-5-carboxamide, (3Z)—N-[(1S)-1-(3-bromophenyl)ethyl]-3-({3,5-dimethyl-4-[(4-methylpiperazin-1-yl)carbonyl]-1H-pyrrol-2-yl}methylene)-2-oxoindoline-5-carboxamide, (3Z)-3-{[3,5-dimethyl-4-(pyrrolidin-1-ylcarbonyl)-1H-pyrrol-2-yl]methylene}-N-[(1S)-1-(4-methoxyphenyl)ethyl]-2-oxoindoline-5-carboxamide, (3Z)-3-({3,5-dimethyl-4-[(4-methylpiperazin-1-yl)carbonyl]-1H-pyrrol-2-yl}methylene)-N-[1-(3-methylphenyl)ethyl]-2-oxoindoline-5-carboxamide, (3Z)-3-[(3,5-dimethyl-4-{[4-(4-methylpiperazin-1-yl)piperidin-1-yl]carbonyl}-1H-pyrrol-2-yl)methylene]-2-oxo-N-[(1S)-1-phenylpropyl]indoline-5-carboxamide, (3Z)-3-[(3,5-dimethyl-4-{[4-(4-methylpiperazin-1I-yl)piperidin-1-yl]carbonyl}-1H-pyrrol-2-yl)methylene]-2-oxo-N-[(1R)-1-phenylpropyl]indoline-5-carboxamide, (3Z)-3-{[3,5-dimethyl-4-(piperidin-1-ylcarbonyl)-1H-pyrrol-2-yl]methylene}-2-oxo-N-[(1S)-1-phenylethyl]indoline-5-carboxamide, (3Z)—N-[(1R)-1-(3-chlorophenyl)ethyl]-3-{[3,5-dimethyl-4-(piperidin-1-ylcarbonyl)-1H-pyrrol-2-yl]methylene}-2-oxoindoline-5-carboxamide, (3Z)—N-[(1S)-1-(3-chlorophenyl)ethyl]-3-{[3,5-dimethyl-4-(piperidin-1-ylcarbonyl)-1H-pyrrol-2-yl]methylene}-2-oxoindoline-5-carboxamide, (3Z)-3-{[3,5-dimethyl-4-(piperidin-1-ylcarbonyl)-1H-pyrrol-2-yl]methylene}-2-oxo-N-[(1S)-1-phenylpropyl]indoline-5-carboxamide, (3Z)-3-{4-[(4-methylpiperazin-1-yl)carbonyl]benzylidene}-2-oxo-N-[(1S)-1-phenylpropyl]indoline-5-carboxamide (3Z)-3-({4-{[2-(diethylamino)ethyl]carbamoyl}-3,5-dimethyl-1H-pyrrol-2-yl)methylene]-2-oxo-N-[(1R)-1-phenylethyl]indoline-5-carboxamide, (3Z)-3-[(4-{[2-(diethylamino)ethyl]carbamoyl}-3,5-dimethyl-1H-pyrrol-2-yl)methylene]-2-oxo-N-[(1S)-1-phenylethyl]indoline-5-carboxamide, (3Z)-3-[(4-{[2-(diethylamino)ethyl]carbamoyl}-3,5-dimethyl-1H-pyrrol-2-yl)methylene]-2-oxo-N-[(1R)-1-phenylpropyl]indoline-5-carboxamide, (3Z)-3-[(4-{[12-(diethylamino)ethyl]carbamoyl}-3,5-dimethyl-1H-pyrrol-2-yl)methylene]-2-oxo-N-[(1S)-1-phenylpropyl]indoline-5-carboxamide, (3Z)-3-{[3,5-dimethyl-4-(piperidin-1-ylcarbonyl)-1H-pyrrol-2-yl]methylene}-2-oxo-N-[(1R)-1-phenylpropyl]indoline-5-carboxamide, (3Z)-3-{[3,5-dimethyl-4-(piperidin-1-ylcarbonyl)-1H-pyrrol-2-yl]methylene}-N-[(1S)-1-(4-fluorophenyl)ethyl]-2-oxoindoline-5-carboxamide, (3Z)-3-{[3,5-dimethyl-4-(piperidin-1-ylcarbonyl)-1H-pyrrol-2-yl]methylene}-N-[(1S)-1-(4-methoxyphenyl)ethyl]-2-oxoindoline-5-carboxamide, (3Z)—N-[(1R)-1-(4-chlorophenyl)ethyl]-3-{[3,5-dimethyl-4-(piperidin-1-ylcarbonyl)-1H-pyrrol-2-yl]methylene}-2-oxoindoline-5-carboxamide, (3Z)—N-[(1R)-1-(4-chlorophenyl)ethyl]-3-{[3,5-dimethyl-4-(pyrrolidin-1-ylcarbonyl)-1H-pyrrol-2-yl]methylene}-2-oxoindoline-5-carboxamide, (3Z)-2-oxo-3-({[4-(piperidin-1-ylmethyl)phenyl]amino}methylene)indoline-5-carboxylic acid, (3Z)-2-oxo-N-[(1R)-1-phenylpropyl]-3-({[4-(piperidin-1-ylmethyl)phenyl]amino}methylene)-indoline-5-carboxamide, (3Z)—N-[(1R)-1-(4-methoxyphenyl)ethyl]-2-oxo-3-({[4-(piperidin-1-ylmethyl)phenyl]amino}methylene)indoline-5-carboxamide, (3Z)—N-methyl-2-oxo-N-[(1S)-1-phenylethyl]-3-({[4-(piperidin-1-ylmethyl)phenyl]amino}methylene)indoline-5-carboxamide, (3Z)—N-[(1R)-1-(4-methylphenyl)ethyl]-2-oxo-3-({[4-(piperidin-1-ylmethyl)phenyl]amino}methylene)indoline-5-carboxamide, (3Z)—N-[(1R)-1-(4-chlorophenyl)ethyl]-2-oxo-3-({[4-(piperidin-1-ylmethyl)phenyl]amino}methylene)indoline-5-carboxamide, (3Z)-2-oxo-N-[(1S)-1-phenylpropyl]-3-({[4-(piperidin-1-ylmethyl)phenyl]amino}methylene)indoline-5-carboxamide, (3Z)-2-oxo-N-[(1S)-1-phenylethyl]-3-({[4-(piperidin-1-ylmethyl)phenyl]amino}methylene)indoline-5-carboxamide, (3Z)-2-oxo-3-({[4-(piperidin-1-ylmethyl)phenyl]amino}methylene)-N-[(1S)-1,2,3,4-tetrahydronaphthalen-1-yl]indoline-5-carboxamide, (3Z)—N-[(1R)-1-cyclohexylethyl]-2-oxo-3-({[4-(piperidin-1-ylmethyl)phenyl]amino}methylene)indoline-5-carboxamide, (3Z)-2-oxo-N-[(1R)-1-phenylethyl]-3-({[4-(piperidin-1-ylmethyl)phenyl]amino}methylene)indoline-5-carboxamide, (3Z)—N-[(1R)-1-(3-methoxyphenyl)ethyl]-2-oxo-3-({[4-(piperidin-1-ylmethyl)phenyl]amino}methylene)indoline-5-carboxamide, (3Z)—N-[(1R)-1-(3-chlorophenyl)ethyl]-2-oxo-3-({[4-(piperidin-1-ylmethyl)phenyl]amino}methylene)indoline-5-carboxamide, (3Z)—N-[(1R)-1-(4-methoxyphenyl)ethyl]-2-oxo-3-({[4-(piperidin-1-ylmethyl)phenyl]amino}methylene)indoline-5-carboxamide, (3Z)—N-[(1S)-1-(4-fluorophenyl)ethyl]-2-oxo-3-({[4-(piperidin-1-ylmethyl)phenyl]amino}methylene)indoline-5-carboxamide, (3Z)—N-[(1R)-1-(3-methoxyphenyl)ethyl]-2-oxo-3-({[4-(piperidin-1-ylmethyl)phenyl]amino}methylene)indoline-5-carboxamide, (3Z)—N-[(1R)-1-(4-fluorophenyl)ethyl]-2-oxo-3-({[4-(piperidin-1-ylmethyl)phenyl]amino}methylene)indoline-5-carboxamide, (3Z)—N-[(1R)-1-(3-chlorophenyl)ethyl]-2-oxo-3-({[4-(piperidin-1-ylmethyl)phenyl]amino}methylene)indoline-5-carboxamide, (3Z)-3-({[3-(morpholin-4-ylmethyl)phenyl]amino}methylene)-2-oxoindoline-5-carboxylic acid, (3Z)-3-({[3-(morpholin-4-ylmethyl)phenyl]amino}methylene)-2-oxo-N-[(1R)-1-phenylpropyl]indoline-5-carboxamide, (3Z)-3-({[3-(morpholin-4-ylmethyl)phenyl]amino}methylene)-2-oxo- N-[(1S)-1-phenylpropyl]indoline-5-carboxamide, (3Z)-3-({[3-(morpholin-4-ylmethyl)phenyl]amino}methylene)-2-oxo-N-[(1S)-1-phenylethyl]indoline-5-carboxamide, (3Z)-3-({[3-(morpholin-4-ylmethyl)phenyl]amino}methylene)-2-oxo-N-[(1R)-1-phenylethyl]indoline-5-carboxamide, (3Z)—N-[(1R)-1-(4-fluorophenyl)ethyl]-3-({[3-(morpholin-4-ylmethyl)phenyl]amino}methylene)-2-oxoindoline-5-carboxamide, (3Z)—N-[(1S)-1-(4-fluorophenyl)ethyl]-3-({[3-(morpholin-4-ylmethyl)phenyl]amino}methylene)-2-oxoindoline-5-carboxamide, (3Z)—N-[(1S)-1-(4-methoxyphenyl)ethyl]-3-({[3-(morpholin-4-ylmethyl)phenyl]amino}methylene)-2-oxoindoline-5-carboxamide 3Z)—N-[(1R)-1-(4-methoxyphenyl)ethyl]-3-({[3-(morpholin-4-ylmethyl)phenyl]amino}methylene)-2-oxoindoline-5-carboxamide, (3Z)-2-oxo-3-({[4-(piperidin-1-ylmethyl)phenyl]amino}methylene)indoline-6-carboxylic acid, (3Z)-2-oxo-N-[(1R)-1-phenylethyl]-3-({[4-(piperidin-1-ylmethyl)phenyl]amino}methylene)indoline-6-carboxamide, (3Z)-2-oxo-N-[(1S)-1-phenylethyl]-3-({[4-(piperidin-1-ylmethyl)phenyl]amino}methylene)indoline-6-carboxamide, (3Z)-2-oxo-N-[(1S)-1-phenylpropyl]-3-({[4-(piperidin-1-ylmethyl)phenyl]amino}methylene)indoline-6-carboxamide, (3Z)-2-oxo-N-[(1R)-1-phenylpropyl]-3-({[4-(piperidin-1-ylmethyl)phenyl]amino}methylene)indoline-6-carboxamide, (3Z)—N-[(1R)-1-(4-fluorophenyl)ethyl]-2-oxo-3-({[4-(piperidin-1-ylmethyl)phenyl]amino}methylene)indoline-6-carboxamide, (3Z)—N-[(1S)-1-(4-fluorophenyl)ethyl]-2-oxo-3-({[4-(piperidin-1-ylmethyl)phenyl]amino}methylene)indoline-6-carboxamide, (3Z)—N-[(1S)-1-(3-methoxyphenyl)ethyl]-2-oxo-3-({[4-(piperidin-1-ylmethyl)phenyl]amino}methylene)indoline-6-carboxamide, (3Z)—N-[(1R)-1-(3-methoxyphenyl)ethyl]-2-oxo-3-({[4-(piperidin-1-ylmethyl)phenyl]amino}methylene)indoline-6-carboxamide, (3Z)-3-({3,5-dimethyl-4-[(2-pyrrolidin-1-ylethyl)carbamoyl]-1H-pyrrol-2-yl}methylene)-2-oxo-N-[(1R)-1-phenylethyl]indoline-5-carboxamide, (3Z)-3-({3,5-dimethyl-4-[(2-pyrrolidin-1-ylethyl)carbamoyl]-1H-pyrrol-2-yl}methylene)-2-oxo-N-[(1S)-1-phenylethyl]indoline-5-carboxamide, (3Z)-3-({3,5-dimethyl-4-[(2-pyrrolidin-1-ylethyl)carbamoyl]-1H-pyrrol-2-yl}methylene)-N-[(1S)-1-(4-fluorophenyl)ethyl]-2-oxoindoline-5-carboxamide, (3Z)-3-({3,5-dimethyl-4-[(2-pyrrolidin-1-ylethyl)carbamoyl]-1H-pyrrol-2-yl}methylene)-N-[(1R)-1-(4-fluorophenyl)ethyl]-2-oxoindoline-5-carboxamide, (3Z)-3-({3,5-dimethyl-4-[(2-pyrrolidin-1-ylethyl)carbamoyl]-1H-pyrrol-2-yl}methylene)-N-[(1S)-1-(4-methoxyphenyl)ethyl]-2-oxoindoline-5-carboxamide, (3Z)-3-({3,5-dimethyl-4-[(2-pyrrolidin-1-ylethyl)carbamoyl]-1H-pyrrol-2-yl}methylene)-N-[(1S)-1-(4-methoxyphenyl)ethyl]-2-oxoindoline-5-carboxamid, (3Z)-3-({3,5-dimethyl-4-[(2-pyrrolidin-1-ylethyl)carbamoyl]-1H-pyrrol-2-yl}methylene)-N-[(1S)-1-(3-methoxyphenyl)ethyl]-2-oxoindoline-5-carboxamide, (3Z)-3-({3,5-dimethyl-4-[(2-pyrrolidin-1-ylethyl)carbamoyl]-1H-pyrrol-2-yl}methylene)-N-[(1R)-1-(3-methoxyphenyl)ethyl]-2-oxoindoline-5-carboxamide, (3Z)-3-({3,5-dimethyl-4-[(2-pyrrolidin-1-ylethyl)carbamoyl]-1H-pyrrol-2-yl}methylene)-2-oxo-N-[(1R)-1-phenylethyl]indoline-6-carboxamide, (3Z)-3-({3,5-dimethyl-4-[(2-pyrrolidin-1-ylethyl)carbamoyl]-1H-pyrrol-2-yl}methylene)-2-oxo-N-[(1S)-1-phenylethyl]indoline-6-carboxamide, (3Z)-3-({3,5-dimethyl-4-[(2-pyrrolidin-1-ylethyl)carbamoyl]-1H-pyrrol-2-yl}methylene)-2-oxo-N-[(1S)-1-phenylpropyl]indoline-6-carboxamide, (3Z)-3-({3,5-dimethyl-4-[(2-pyrrolidin-1-ylethyl)carbamoyl]-1H-pyrrol-2-yl}methylene)-2-oxo-N-[(1R)-1-phenylpropyl]indoline-6-carboxamide, (3Z)-3-({3,5-dimethyl-4-[(2-pyrrolidin-1-ylethyl)carbamoyl]-1H-pyrrol-2-yl}methylene)-N-[(1R)-1-(4-fluorophenyl)ethyl]-2-oxoindoline-6-carboxamide, (3Z)-3-({3,5-dimethyl-4-[(2-pyrrolidin-1-ylethyl)carbamoyl]-1H-pyrrol-2-yl}methylene)-N-[(1S)-1-(4-fluorophenyl)ethyl]-2-oxoindoline-6-carboxamide, (3Z)-3-({3,5-dimethyl-4-[(2-pyrrolidin-1-ylethyl)carbamoyl]-1H-pyrrol-2-yl}methylene)-N-[(1S)-1-(4-methoxyphenyl)ethyl]-2-oxoindoline-6-carboxamide, (3Z)-3-({3,5-dimethyl-4-[(2-pyrrolidin-1-ylethyl)carbamoyl]-1H-pyrrol-2-yl}methylene)-N-[(1R)-1-(4-methoxyphenyl)ethyl]-2-oxoindoline-6-carboxamide, (3Z)-3-({3,5-dimethyl-4-[(1-methylpiperidin-4-yl)carbamoyl]-1H-pyrrol-2-yl}methylene)-2-oxo-N-[(1R)-1-phenylpropyl]indoline-5-carboxamide, (3Z)-3-{[3,5-dimethyl-4-(piperidin-4-ylcarbamoyl)-1H-pyrrol-2-yl]methylene}-2-oxo-N-[(1R)-1-phenylpropyl]indoline-5-carboxamide, (3Z)-3-[(3,5-dimethyl-4-{[(3S)-1-methylpiperidin-3-yl]carbamoyl}-1H-pyrrol-2-yl)methylene]-2-oxo-N-[(1R)-1-phenylpropyl]indoline-5-carboxamide, (3Z)-3-{[4-({(2S)-2-[(diethylamino)methyl]pyrrolidin-1-yl}carbonyl)-3,5-dimethyl-1H-pyrrol-2-yl]methylene}-2-oxo-N-[(1R)-1-phenylpropyl]indoline-5-carboxamide, (3Z)-3-{[4-({(2S)-2-[(dimethylamino)methyl]pyrrolidin-1-yl}carbonyl)-3,5-dimethyl-1H-pyrrol-2-yl]methylene}-2-oxo-N-[(1R)-1-phenylpropyl]indoline-5-carboxamide, (3Z)-3-({3,5-dimethyl-4-[(3S)-piperidin-3-ylcarbamoyl]-1H-pyrrol-2-yl}methylene)-2-oxo-N-[(1R)-1-phenylpropyl]indoline-5-carboxamide, (3Z)-3-{[4-({(2R)-2-[(diethylamino)methyl]pyrrolidin-1-yl}carbonyl)-3,5-dimethyl-1H-pyrrol-2-yl]methylene}-2-oxo-N-[(1R)-1-phenylpropyl]indoline-5-carboxamide, (3Z)-3-({3,5-dimethyl-4-[(2-piperidin-1-ylethyl)carbamoyl]-1H-pyrrol-2-yl}methylene)-2-oxo-N-[(1R)-1-phenylpropyl]indoline-5-carboxamide, (3Z)-3-[(3,5-dimethyl-4-{[2-(4-methylpiperazin-1-yl)ethyl]carbamoyl}-1H-pyrrol-2-yl)methylene]-2-oxo-N-[(1R)-1-phenylpropyl]indoline-5-carboxamide, (3Z)-3-({3,5-dimethyl-4-[(2-morpholin-4-ylethyl)carbamoyl]-1H-pyrrol-2-yl}methylene)-2-oxo-N-[(1R)-1-phenylpropyl]indoline-5-carboxamide, (3Z)-3-{2,4-dimethyl-5-[2-oxo-5-(1R)-(1-phenyl-propylcarbamoyl)-1,2-dihydro-indol-3-ylidenemethyl]-1H-pyrrol-3-yl}-propionic acid, (3Z)-3-{4-[2-(2-diethylamino-ethylcarbamoyl)-ethyl]-3,5-dimethyl-1H-pyrrol-2-ylmethylene}-2-oxo-2,3-dihydro-1H-indole-5-carboxylic acid (1-phenyl-propyl)-amide, (3Z)-3-(5-{5-[1-(4-chloro-phenyl)-propylcarbamoyl]-2-oxo-1,2-dihydro-indol-3-ylidenemethyl}-2,4-dimethyl-1H-pyrrol-3-yl)-propionic acid, (3Z)-3-(5-{5-[1-(3,4-difluoro-phenyl)-propylcarbamoyl]-2-oxo-1,2-dihydro-indol-3-ylidenemethyl}-2,4-dimethyl-1H-pyrrol-3-yl)-propionic acid, (3Z)-3-(5-{5-[1-(3-chloro-phenyl)-propylcarbamoyl]-2-oxo-1,2-dihydro-indol-3-ylidenemethyl}-2,4-dimethyl-1H-pyrrol-3-yl)-propionic acid, (3Z)-3-{4-[2-(2-diethyl-amino-ethylcarbamoyl)-ethyl]-3,5-dimethyl-1H-pyrrol-2-ylmethylene}-2-oxo-2,3-dihydro-1H-indole-5-carboxylic acid [1-(3-chloro-phenyl)-propyl]-amide, (3Z)-3-[4-(1S)-1-ethoxycarbonyl-ethylcarbamoyl)-3,5-dimethyl-1H-pyrrol-2-ylmethylene]-2-oxo-2,3-dihydro-1H-indole-5-carboxylic acid, (3Z)-3-[3,5-dimethyl-4-((1R)-1-phenyl-ethylcarbamoyl)-1H-pyrrol-2-ylmethylene]-2-oxo-2,3-dihydro-1H-indole-5-carboxylic acid, (3Z)-3-[3,5-dimethyl-4-((1R)-1-phenyl-ethylcarbamoyl)-1H-pyrrol-2-ylmethylene]-2-oxo-2,3-dihydro-1H-indole-5-carboxylic acid, (3Z)-3-(4-carboxy-3,5-dimethyl-1H-pyrrol-2-ylmethylene)-2-oxo-2,3-dihydro-1H-indole-5-carboxylic acid, (3Z)-3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5- carboxylic acid, (3Z)-3-[4-(2-tert-butoxy-(1S)-1-methoxy-carbonyl-ethylcarbamoyl)-3,5-dimethyl-1H-pyrrol-2-ylmethylene]-2-oxo-2,3-dihydro-1H-indole-5-carboxylic acid, (3Z)-3-[4-(4-methyl-piperazine-1-carbonyl)-benzylidene]-2-oxo-2,3-dihydro-1H-indole-5-carboxylic acid, (3Z)-3-[4-(4-methyl-piperazine-1-carbonyl)-benzylidene]-2-oxo-2,3-dihydro-1H-indole-5-carboxylic acid (1R)-(1-phenyl-ethyl)-amide, (3Z)-3-[4-(4-methyl-piperazine-1-carbonyl)-benzylidene]-2-oxo-2,3-dihydro-1H-indole-5-carboxylic acid (1S)-(1-phenyl-ethyl)-amide, (3Z)-5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carboxylic acid, (3Z)-2-({3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2R)-3-phenyl-propionic acid methyl ester, (3Z)-2-({3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2R)-3-phenyl-propionic acid methyl ester, (3Z)-3-[4-(1-carboxy-(1R)-ethylcarbamoyl)-3,5-dimethyl-1H-pyrrol-2-ylmethylene]-2-oxo-2,3-dihydro-1H-indole-5-carboxylic acid, (3Z)-5-[5-((1S)-1-carboxy-2-phenyl-ethylcarbamoyl)-2-oxo-1,2-dihydro-indol-3-ylidenemethyl]-2,4-dimethyl-1H-pyrrole-3-carboxylic acid ethyl ester, (3Z)-3-[4-(4-methyl-piperazine-1-carbonyl)-benzylidene]-2-oxo-2,3-dihydro-1H-indole-5-carboxylic acid ((1S)-1-phenyl-propyl)-amide, (3Z)-3-[4-((3S)-3-hydroxy-pyrrolidine-1-carbonyl)-benzylidene]-2-oxo-2,3-dihydro-1H-indole-5-carboxylic acid ((1S)-1-phenyl-propyl)-amide, (3Z)-2-oxo-3-[(4-piperidin-1-ylmethyl-phenylamino)-methylene]-2,3-dihydro-1H-indole-5-carboxylic acid ((1R)-1-cyclohexyl-ethyl)-amide, (3Z)-3-[4-((1R)-1-carboxy-2-phenyl-ethylcarbamoyl)-3,5-dimethyl-1H-pyrrol-2-ylmethylene]-2-oxo-2,3-dihydro-1H-indole-5-carboxylic acid, (3Z)-3-[4-((1S)-1-carboxy-2-phenyl-ethylcarbamoyl)-3,5-dimethyl-1H-pyrrol-2-ylmethylene]-2-oxo-2,3-dihydro-1H-indole-5-carboxylic acid, (3Z)-({3-[3,5-dimethyl-4-(piperidine-1-carbonyl)-1H-pyrrol-2-ylmethylene]-2-oxo-2,3-dihydro-1H-indole-5-carbonyl}-amino)-(S)-phenyl-acetic acid methyl ester, (3Z)-3-[4-((3S)-3-dimethylamino-pyrrolidine-1-carbonyl)-3,5-dimethyl-1H-pyrrol-2-ylmethylene]-2-oxo-2,3-dihydro-1H-indole-5-carboxylic acid ((S)-1-phenyl-propyl)-amide, (3Z)-5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carboxylic II.acid ethyl ester, (3Z)-5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carboxylic acid, (3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-3-phenyl-(2S)-propionic acid, (3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-3-phenyl-(2R)-propionic acid, (3Z)-5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carboxylic acid ethyl ester, (3Z)-2-({5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-(2S)-3-phenyl-propionic acid, (3Z)-2-({5-[5-((1R)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-(2R)-3-phenyl-propionic acid, (3Z)-2-({3-[4-((1S)-2-tert-butoxy-1-methoxycarbonyl-ethylcarbamoyl)-3,5-dimethyl-1H-pyrrol-2-ylmethylene]-2-oxo-2,3-dihydro-1H-indole-5-carbonyl}-amino)-(2S)-3-phenyl-propionic acid methyl ester, II., (3Z)-2-({3-[4-((1S)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2S)-3-phenyl-propionic acid methyl ester, (3Z)-2-({3-[4-((1R)-1-methoxycarbonyl-2-phenyl-ethylcarbamoyl)-3,5-dimethyl-1H-pyrrol-2-ylmethylene]-2-oxo-2,3-dihydro-1H-indole-5-carbonyl}-amino)-(2S)-3-phenyl-propionic acid methyl ester, (3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-(S)-pentanedioic acid dimethyl ester, (3Z)-2-({5-[5-((1S)-1-methoxycarbonyl-2-phenyl-ethylcarbamoyl)-2-oxo-1,2-dihydro-indol-3-ylidenemethyl]-2,4-dimethyl-1H-pyrrole-3-carbonyl}-amino)-(R)-pentanedioic acid dimethyl ester, (3Z)-3-[3,5-dimethyl-4-((3R)-piperidin-3-ylcarbamoyl)-1H-pyrrol-2-ylmethylene]-2-oxo-2,3-dihydro-1H-indole-5-carboxylic acid ((1R)-1-phenyl-propyl)-amide, (3Z)-3-(3,5-dimethyl-1H-pyrrol-2-ylmethylene)-2-oxo-2,3-dihydro-1H-indole-5-carboxylic acid [(1R)-1-(4-methoxy-phenyl)-ethyl]-amide, (3Z)-3-[3,5-dimethyl-4-(2-pyrrolidin-1-yl-ethylcarbamoyl)-1H-pyrrol-2-ylmethylene]-2-oxo-2,3-dihydro-1H-indole-5-carboxylic acid [(1S)-1-(3-chloro-phenyl)-ethyl]-amide, (3Z)-3-{3,5-dimethyl-4-[4-(2-piperidin-1-yl-ethyl)-piperazine-1-carbonyl]-1H-pyrrol-2-ylmethylene}-2-oxo-2,3-dihydro-1H-indole-5-carboxylic acid ((1R)-1-phenyl-propyl)-amide, (3Z)-3-[3,5-dimethyl-4-(2-piperidin-1-yl-ethylcarbamoyl)-1H-pyrrol-2-ylmethylene]-2-oxo-2,3-dihydro-1H-indole-5-carboxylic acid ((1R)-1-phenyl-propyl)-amide, 5-{5-[(R)-(carbamoyl-phenyl-methyl)-carbamoyl]-2-oxo-1,2-dihydro-indol-3-ylidenemethyl}-2,4-dimethyl-1H-pyrrole-3-carboxylic acid, (3Z)-2,4-dimethyl-5-[2-oxo-5-((1R)-1-phenyl-ethylcarbamoyl)-1,2-dihydro-indol-3-ylidenemethyl]-1H-pyrrole-3-carboxylic acid, (3Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid (R)-(carbamoyl-phenyl-methyl)-amide, (3Z)-2,4-dimethyl-5-[2-oxo-5-((1S)-1-phenyl-ethylcarbamoyl)-1,2-dihydro-indol-3-ylidenemethyl]-1H-pyrrole-3-carboxylic acid, (3Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid ((1S)-1-phenyl-ethyl)-amide, (3Z)-3-{3,5-dimethyl-4-[4-(1-methyl-piperidin-4-yl)-pip)-piperazine-1-carbonyl]-1H-pyrrol-2-ylmethylene}-2-oxo-2,3-dihydro-1H-indole-5-carboxylic acid methyl-((1R)-1-phenyl-ethyl)-amide, (3Z)-3-[4-((3R)-3-hydroxy-pyrrolidine-1-carbonyl)-3,5-dimethyl-1H-pyrrol-2-ylmethylene]-2-oxo-2,3-dihydro-1H-indole-5-carboxylic acid ((1R)-1-p-tolyl-ethyl)-amide, (3Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid ((1R)-1-phenyl-propyl)-amide, (Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid ((1R)-1-p-tolyl-ethyl)-amide, (3Z)-3-[3,5-dimethyl-4-((2R)-2-pyrrolidin-1-ylmethyl-pyrrolidine-1-carbonyl)-1H-pyrrol-2-ylmethylene]-2-oxo-2,3-dihydro-1H-indole-5-carboxylic acid 3-chloro-2,6-difluoro-benzylamide, (3Z)-5-[5-(3-chloro-2,6-difluoro-benzylcarbamoyl)-2-oxo-1,2-dihydro-indol-3-ylidenemethyl]-2,4-dimethyl-1H-pyrrole-3-carboxylic acid, (3Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid 3-chloro-2,6-difluoro-benzylamide, (3Z)-3-[3,5-dimethyl-4-(1'-methyl-

[4,4']bipiperidinyl-1-carbonyl)-1H-pyrrol-2-ylmethylene]-2-oxo-2,3-dihydro-1H-indole-5-carboxylic acid 3-chloro-2,6-difluoro-benzylamide, (3Z)-3-[3,5-dimethyl-4-((2S)-2-pyrrolidin-1-ylmethyl-pyrrolidine-1-carbonyl)-1H-pyrrol-2-ylmethylene]-2-oxo-2,3-dihydro-1H-indole-5-carboxylic acid 3-chloro-2,6-difluoro-benzylamide, (3Z)-3-{3,5-dimethyl-4-[4-(1-methyl-piperidin-4-yl)-piperazine-1-carbonyl]-1H-pyrrol-2-ylmethylene}-2-oxo-2,3-dihydro-1H-indole-5-carboxylic acid ((1S)-1-phenyl-propyl)-amide, (3Z)-3-[3,5-dimethyl-4-((2S)-2-pyrrolidin-1-ylmethyl-pyrrolidine-1-carbonyl)-1H-pyrrol-2-ylmethylene]-2-oxo-2,3-dihydro-1H-indole-5-carboxylic acid 2,6-difluoro-benzylamide, (3Z)-3-[4-((3S)-3-dimethylamino-pyrrolidine-1-carbonyl)-3,5-dimethyl-1H-pyrrol-2-ylmethylene]-2-oxo-2,3-dihydro-1H-indole-5-carboxylic acid 2,6-difluoro-benzylamide, (3Z)-3-[3,5-dimethyl-4-((2R)-2-pyrrolidin-1-ylmethyl-pyrrolidine-1-carbonyl)-1H-pyrrol-2-ylmethylene]-2-oxo-2,3-dihydro-1H-indole-5-carboxylic acid 2,6-difluoro-benzylamide, (3Z)-3-[3,5-dimethyl-4-(2-piperidin-1-yl-ethylcarbamoyl)-1H-pyrrol-2-ylmethylene]-2-oxo-2,3-dihydro-1H-indole-5-carboxylic acid 2,6-difluoro-benzylamide, and (3Z)-3-(1H-indol-3-yl-methylene)-2-oxo-2,3-dihydro-1H-indole-5-carboxylic acid [(1R)-1-(4-methoxy-phenyl)-ethyl]-amide.

8. The method according to claim 1, wherein the at least one inhibitor is a compound of general formula(X):

(X)

wherein
$A^1$, $A^2$ and $A^3$ represent independently of each other C—H or N, wherein one of $A^1$, $A^2$ and $A^3$ represents N;
$R^1$ represents —$(CH_2)_n$—$R^3$ or —NH—$(CH_2)_n$—$R^3$;
$R^2$ represents —$(CH_2)_m$—$R^4$ or —NHCO—$(CH_2)_m$—$R^4$;
$R^3$ and $R^4$ are independently of each other
—H, —F, —Cl, —Br, —I, —CN, —$NO_2$, —$NHCH_3$, —$N(CH_3)_2$, —CH=CH—$C_4H_9$, —CH=CH—$C_5H_{11}$, —CH=CH-Ph, —CH=CH—$C_6H_{13}$, —$CH_2$—OH, —$C_2H_4$—OH, —$C_3H_6$—OH, —$C_4H_9$—OH, —$C_5H_{10}$—OH, —$C_6H_{12}$—OH, —$C_7H_{14}$—OH, —$C_8H_{16}$—OH, —CH=CH—$C_3H_6$—OH, —CH=CH—$C_4H_8$—OH, —$CH(CH_2OH)_2$, —CH($C_2H_5$)—$CH_2$—OH, —$CH(CH_3)$—$C_2H_4$—OH, —$C(CH_3)_2$—OH, —$C(CH_3)_2$—$CH_2$—OH, —CH($CH_3$)OH, —$CH_2$—$CH(CH_3)$OH, —C(OH)($CH_3$)—$C_2H_5$, —C(OH)($CH_3$)—$C_3H_7$, —$CH_2$—C(OH)($CH_3$)—$C_2H_5$, —$CH(CH_3)$—$CH(CH_3)$OH, —C($CH_3$)$_2$—$C_2H_4$OH, —$CH_2$—C($CH_3$)$_2$OH, —C(OH)($C_2H_5$)$_2$, —$C_2H_4$—C(OH)($CH_3$)$_2$, —C(CH($CH_3$)$_2$)$CH_2$OH, —$C_3H_6$—C(OH)($CH_3$)$_2$, —CH(CH($CH_3$)$_2$)$CH_2$—OH, —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —OPh, —$OCH_2$-Ph, —$OCPh_3$, —SH, —$SCH_3$, —$SC_2H_5$, —$COCH_3$, —$COC_2H_5$, —$COC_3H_7$, —CO-cyclo-$C_3H_5$, —$COCH(CH_3)_2$, —$COC(CH_3)_3$, —COOH, —$OCF_3$, —$CH_2$—$OCF_3$, —$C_2H_4$—$OCF_3$, —$C_3H_6$—$OCF_3$, —$OC_2F_5$, —$COOCH_3$, —$COOC_2H_5$, —$COOC_3H_7$, —COO-cyclo-$C_3H_5$, —$COOCH(CH_3)_2$, —$COOC(CH_3)_3$, —OOC—$CH_3$, —OOC—$C_2H_5$, —OOC—$C_3H_7$, —OOC-cyclo-$C_3H_5$, —OOC—$CH(CH_3)_2$, —OOC—$C(CH_3)_3$, —$CONH_2$, —$CONHCH_3$, —$CONHC_2H_5$, —$CONHC_3H_7$, —CONH-cyclo-$C_3H_5$, —$CONH[CH(CH_3)_2]$, —$CONH[C(CH_3)_3]$, —$CON(CH_3)_2$, —$CON(C_2H_5)_2$, —$CON(C_3H_7)_2$, —CON(cyclo-$C_3H_5$)$_2$, —$CON[CH(CH_3)_2]_2$, —$CON[C(CH_3)_3]_2$, —$NHCOCH_3$, —$NHCOC_2H_5$, —$NHCOC_3H_7$, —NHCO-cyclo-$C_3H_5$, —NHCO—$CH(CH_3)_2$, —NHCO—$C(CH_3)_3$, —NHCO—$OCH_3$, —NHCO—$OC_2H_5$, —NHCO—$OC_3H_7$, —NHCO—O-cyclo-$C_3H_5$, —NHCO—$OCH(CH_3)_2$, —NHCO—$O(CH_3)_3$, —$NH_2$, —$NHCH_3$, —$NHC_2H_5$, —$NHC_3H_7$, —NH-cyclo-$C_3H_5$, —$NHCH(CH_3)_2$, —$NHC(CH_3)_3$, —$N(CH_3)_2$, —$N(C_2H_5)_2$, —$N(C_3H_7)_2$, —N(cyclo-$C_3H_5$)$_2$, —$N[CH(CH_3)_2]_2$, —$N[C(CH_3)_3]_2$, —C≡C—$R^5$, —$R^{11}$, —$R^{12}$;

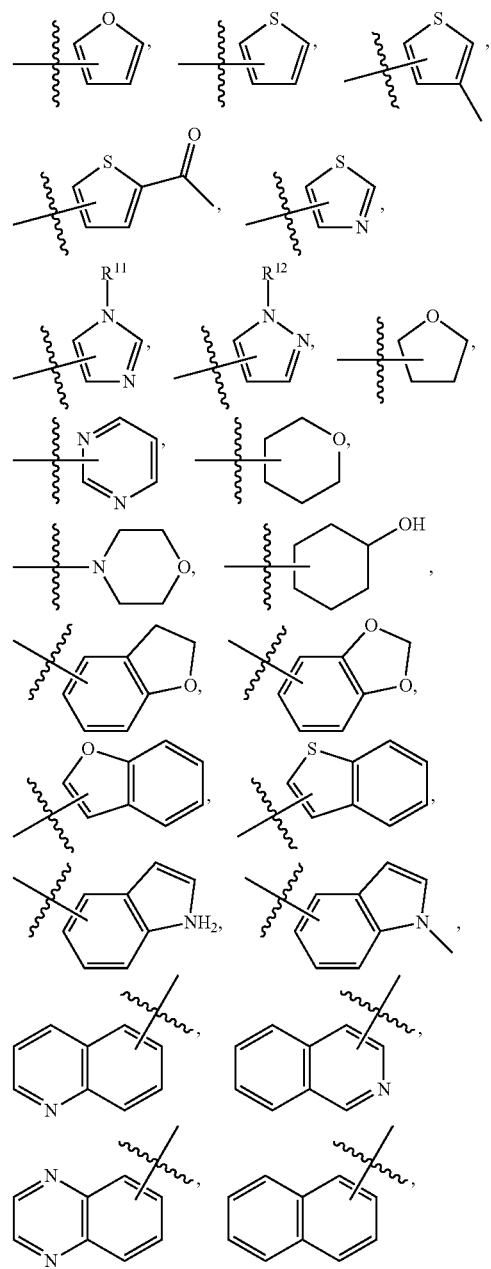

-continued

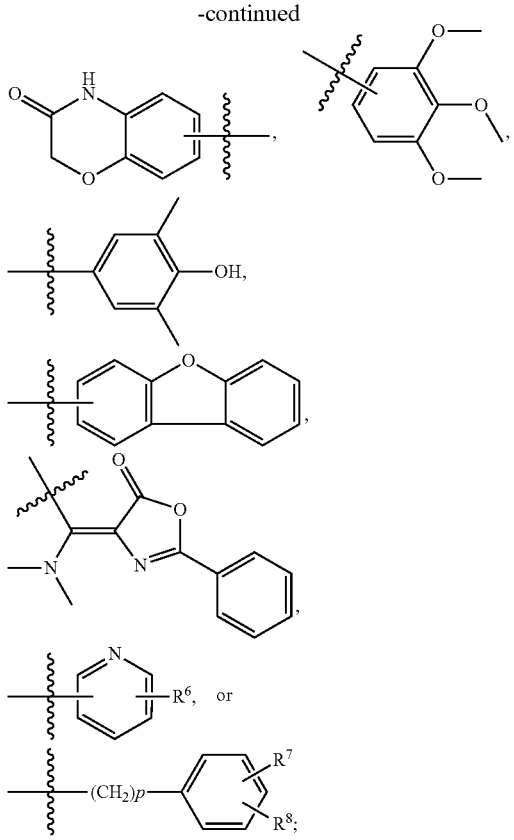

R⁶ is —H, —CH₂OH, —CH₂N(R¹³)₂, —R¹³,

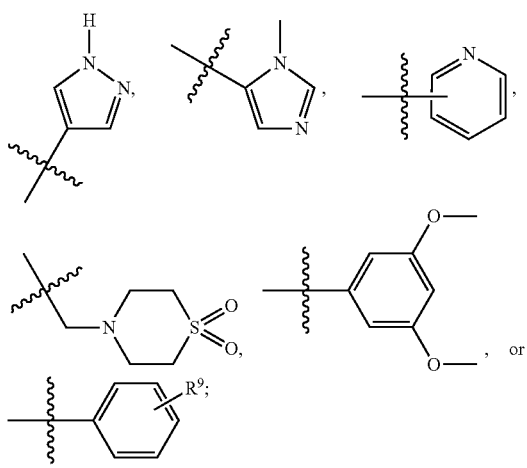

R⁶ is —H, —NH₂, —OMe, —O—(CH₂)₃N(CH₃)₂,

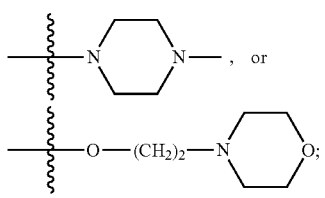

R⁷ and R⁸ are independently of each other
—H, —F, —Br, —Cl, —OH, —CN, —NO₂, —R¹⁴, —R¹⁵, —OR¹⁴, —OR¹⁵, —CH₂OH, —CH₂NH₂, —CH₂CN, —CH₂N(R¹⁴)₂, —CH₂N(R¹⁵)₂, —CH₂NH(R¹⁴), —CH₂NH(R¹⁵), —O(CH₂)₃N(CH₃)₂, —SCH₃, —NH₂, —NH(R¹⁴), —NH(R¹⁵), —NHOCH₃, —NHSO₂CH₃, —N(R¹⁴)₂, —N(R¹⁵)₂, —SO₂CH₃, —SO₂NH₂, —CH₂CO₂H, —C₂H₄CO₂H, —CH=CH—CO₂H, —COR¹⁰,

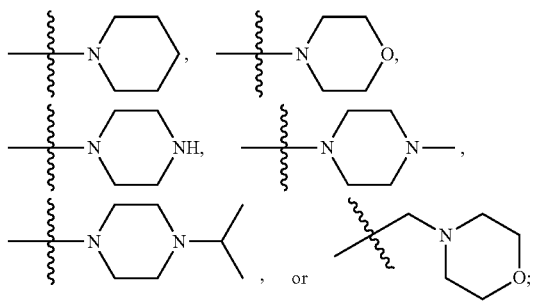

R⁹ is —H, —F, —Br, —Cl, —OH, —ON, —R¹⁶, —OR¹⁶, —NHCOCH₃, or —CON(CH₃)₂;
R¹⁰ is —OH, —R¹⁷, —OR¹⁷, —NH₂, —NHR¹⁷, —N(R¹⁷)₂, —NHC₂H₄OH, —NH(CH₂)$_q$N(R¹⁷)₂,

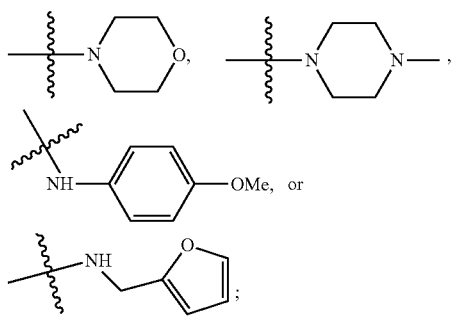

R¹¹, R¹², R¹³, R¹⁴, R¹⁵, R¹⁶ and R¹⁷ are independently of each other

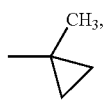

cyclo-C₃H₅, cyclo-C₄H₇, cyclo-C₅H₉, cyclo-C₆H₁₁, cyclo-C₇H₁₃, —H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cycl-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, cyclo-C₈H₁₅, -Ph, —CH₂-Ph, —CH₂—CH₂-Ph, —CH=CH-Ph, —CPh₃, —CH₃, —C$_2$H$_5$, —C$_3$H$_7$, —CH(CH$_3$)$_2$, —C$_4$H$_9$, —CH$_2$—CH (CH$_3$)$_2$, —CH(CH$_3$)—C$_2$H$_5$, —C(CH$_3$)$_3$, —C$_5$H$_{11}$, —CH (CH$_3$)—C$_3$H$_7$, —CH(CH$_3$)—C$_2$H$_5$, —CH$_2$—CH(CH$_3$)—CH(CH$_3$)$_2$, —C(CH$_3$)$_2$—C$_2$H$_5$, —CH$_2$—C(CH$_3$)$_3$, —CH (C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH (CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —CH(CH$_3$)Ph, or —C(CH$_3$)$_2$Ph;

m, n, p and q are independently of each other an integer from 0 to 3; and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof.

9. The method according to claim A, wherein the at least one inhibitor is selected from the group consisting of: 4-(6-benzylimidazo[1,2-b]pyridazin-3-yl)benzamide, 6-(1-methylpyrazol-4-yl)-3-(2-thienyl)imidazo[1,2-b]pyridazine, N-(2-dimethylaminoethyl)-3-[6-(4-hydroxy-3-methoxyphenyl)imidazo[1,2-b]pyridazin-3-yl]benzamide, (2S)-2-[[3-(4-aminophenyl)imidazo[1,2-b]pyridazin-6-yl]amino]-3-methyl-butan-1-ol, 3-(2,4-dimethoxyphenyl)-N-(2-thienylmethyl)imidazo[1,2-b]pyridazin-6-amine, 4-[6-(2-methoxyethylamino)imidazo[1,2-b]pyridazin-3-yl]-N-(4-methoxyphenyl)benzamide, 2-[[3-[(E)-hex-1-enyl]imidazo[1,2-b]pyridazin-6-yl]amino]butan-1-ol, 2-[[3-(2-chlorophenyl)imidazo[1,2-b]pyridazin-6-yl]amino]butan-1-ol, 3-(3-pyridyl)-6-(3,4,5-trimethoxyphenyl)imidazo[1,2-b]pyridazine, 6-(3,4-dimethoxyphenyl)-3-(4-pyridyl)imidazo[1,2-b]pyridazine, N-[3-[3-(3-acetamidophenyl)imidazo[1,2-b]pyridazin-6-yl]phenyl]acetamide, 2-methoxy-4-[6-(3,4,5-trimethoxyphenyl)imidazo[1,2-b]pyridazin-3-yl]phenol, N-(2-dimethylaminoethyl)-3-[6-[3-(methanesulfonamido) phenyl]imidazo[1,2-b]pyridazin-3-yl]benzamide, N-[(3-chlorophenyl)methyl]-3-[4-(trifluoromethoxy)phenyl]imidazo[1,2-b]pyridazin-6-amine, 4-[6-[(3-chlorophenyl) methylamino]imidazo[1,2-b]pyridazin-3-yl]-2-methoxy-phenol, methyl 4-[6-[(3-chlorophenyl)methylamino] imidazo[1,2-b]pyridazin-3-yl]benzoate, N-[(4-fluorophenyl)methyl]-3-(3-thienyl)imidazo[1,2-b] pyridazin-6-amine, N-[3-[6-[(4-fluorophenyl)methylamino] imidazo[1,2-b]pyridazin-3-yl]phenyl]acetamide, 4-[6-(propylamino)imidazo[1,2-b]pyridazin-3-yl]benzoic acid, (E)-3-[3-[6-(propylamino)imidazo[1,2-b]pyridazin-3-yl] phenyl]prop-2-enoic acid, 3-(3-aminophenyl)-N-[(3,4-dichlorophenyl)methyl]imidazo[1,2-b]pyridazin-6-amine, 3-(4-fluorophenyl)-N-(2-methoxyethyl)imidazo[1,2-b] pyridazin-6-amine, 3-(4-morpholinophenyl)-N-[2-(3-pyridyl)ethyl]imidazo[1,2-b]pyridazin-6-amine, 3-(2-naphthyl)-N-[2-(3-pyridyl)ethyl]imidazo[1,2-b]pyridazin-6-amine, N-(1,3-benzodioxol-5-ylmethyl)-3-(4-morpholinophenyl)imidazo[1,2-b]pyridazin-6-amine, N-(1,3-benzodioxol-5-ylmethyl)-3-(8-quinolyl)imidazo[1,2-b] pyridazin-6-amine, N-(1,3-benzodioxol-5-ylmethyl)-3-(4-chlorophenyl)imidazo[1,2-b]pyridazin-6-amine, 3-(2-fluorophenyl)-N-(2-methoxyethyl)imidazo[1,2-b]pyridazin-6-amine, (E)-3-[3-[6-(1,3-benzodioxol-5-ylmethylamino) imidazo[1,2-b]pyridazin-3-yl]phenyl]prop-2-enoic acid, 3-(2-phenoxyphenyl)-N-(4-pyridylmethyl) imidazo[1,2-b] pyridazin-6-amine, 4-[(3-bromoimidazo[1,2-b]pyridazin-6-yl)amino]cyclohexanol, 3-(3-aminophenyl)-N-tetrahydropyran-4-yl-imidazo[1,2-b]pyridazin-6-amine, 3-(4-phenoxyphenyl)-N-tetrahydropyran-4-yl-imidazo[1,2-b] pyridazin-6-amine, 3-(benzofuran-2-yl)-N-[(4-methoxyphenyl)methyl]imidazo[1,2-b]pyridazin-6-amine, 4-[6-[(4-methoxyphenyl)methylamino]imidazo[1,2-b] pyridazin-3-yl]phenol, 3-(1H-indol-5-yl)-N-[(4-methoxyphenyl)methyl]imidazo[1,2-b]pyridazin-6-amine, 3-(1-naphthyl)-N-[2-(2-pyridyl)ethyl]imidazo[1,2-b]pyridazin-6-amine, 3-(2,4-dimethoxyphenyl)-N-[(4-methoxyphenyl) methyl]imidazo[1,2-b]pyridazin-6-amine, 3-[[3-(2-furyl) imidazo[1,2-b]pyridazin-6-yl]amino]propan-1-ol, 3-[[3-(4-methoxyphenyl)imidazo[1,2-b]pyridazin-6-yl]amino] propan-1-ol, 3-[[3-(2,4-dimethoxyphenyl)imidazo[1,2-b] pyridazin-6-yl]amino]propan-1-ol, N-(3-morpholinopropyl)-3-(3,4,5-trimethoxyphenyl)imidazo[1,2-b]pyridazin-6-amine, 3-bromo-N-(3-morpholinopropyl) imidazo[1,2-b]pyridazin-6-amine (2S)-3-methyl-2-[[3-(2-naphthyl)imidazo[1,2-b]pyridazin-6-yl]amino]butan-1-ol, (2S)-2-[[3-(2,4-dimethoxyphenyl)imidazo[1,2-b]pyridazin-6-yl]amino]-3-methyl-butan-1-ol, 3-(3,4-dimethoxyphenyl)-N-(2-pyridylmethyl)imidazo[1,2-b]pyridazin-6-amine, 3-(5-isopropyl-2-methoxy-phenyl)-N-(2-pyridylmethyl) imidazo[1,2-b]pyridazin-6-amine, 3-(4-dimethylaminophenyl)-N-[(3,4,5-trimethoxyphenyl)methyl]imidazo[1,2-b] pyridazin-6-amine, N',N'-dimethyl-N-[3-(p-tolyl)imidazo[1,2-b]pyridazin-6-yl]ethane-1,2-diamine, N-(cyclopropylmethyl)-3-(6-methoxy-3-pyridyl)imidazo[1,2-b]pyridazin-6-amine, 4-[6-[(2,4-dimethylphenyl)methylamino]imidazo[1,2-b]pyridazin-3-yl]phenol, 3-[4-[6-[(2,4-dimethylphenyl)methylamino]imidazo[1,2-b]pyridazin-3-yl]phenyl]propanoic acid, N-(2-dimethylaminoethyl)-4-[6-[(2,4-dimethylphenyl)methylamino]imidazo[1,2-b] pyridazin-3-yl]benzamide, N-[(2,4-dimethylphenyl) methyl]-3-(3-methoxyphenyl)imidazo[1,2-b]pyridazin-6-amine, 4-[[[3-(1,3-benzodioxol-5-yl)imidazo[1,2-b] pyridazin-6-yl]amino]methyl]benzenesulfonamide, 4-[[[3-(1-benzylpyrazol-4-yl)imidazo[1,2-b]pyridazin-6-yl]amino] methyl]benzenesulfonamide, 4-[6-[[4-(4-methylpiperazin-1-yl)phenyl]methylamino]imidazo[1,2-b]pyridazin-3-yl] benzonitrile, (Z)-5-[6-(methylamino)imidazo[1,2-b] pyridazin-3-yl]pent-4-en-1-ol, 2-[6-(methylamino)imidazo [1,2-b]pyridazin-3-yl]phenol, N,N-dimethyl-3-[6-(methylamino)imidazo[1,2-b]pyridazin-3-yl]benzamide, 1-[2-[6-(methylamino)imidazo[1,2-b]pyridazin-3-yl]phenyl]ethanone, 3-[4-(dimethylaminomethyl)phenyl]-N-methyl-imidazo[1,2-b]pyridazin-6-amine, 3-(3,3-dimethylbut-1-ynyl)-N-methyl-imidazo[1,2-b]pyridazin-6-amine, N-[2-[6-(methylamino)imidazo[1,2-b]pyridazin-3-yl]phenyl]acetamide, 3-methyl-4-[6-(methylamino)imidazo[1,2-b] pyridazin-3-yl]phenol, 3-[(5-imidazo[1,2-b]pyridazin-3-yl-2-pyridyl)oxy]-N,N-dimethyl-propan-1-amine, 1-(2-imidazo[1,2-b]pyridazin-3-ylphenyl)-N,N-dimethyl-methanamine, 3-[6-(4-methylpiperazin-1-yl)-3-pyridyl] imidazo[1,2-b]pyridazine, 3-(benzothiophen-2-yl)-N-[(3,4,5-trimethoxyphenyl)methyl]imidazo[1,2-b]pyridazin-6-amine, 3-dibenzofuran-4-ylimidazo[1,2-b]pyridazine, 3-(4-methylsulfanylphenyl)imidazo[1,2-b]pyridazine, 3-(4-chlorophenyl)imidazo[1,2-b]pyridazine, 3-[(E)-styryl] imidazo[1,2-b]pyridazine, 2-imidazo[1,2-b]pyridazin-3-ylbenzoic acid, 3-(3-ethoxyphenyl)imidazo[1,2-b] pyridazine, 4-imidazo[1,2-b]pyridazin-3-yl-2,6-dimethyl-phenol, N-(2-hydroxyethyl)-4-imidazo[1,2-b]pyridazin-3- yl-benzamide, (4-imidazo[1,2-b]pyridazin-3-ylphenyl)-(4-methylpiperazin-1-yl)methanone, 3-(2,3-dihydrobenzofuran-5-yl)imidazo[1,2-b]pyridazine, 3-(3-fluoro-4-methyl-phenyl)imidazo[1,2-b]pyridazine, 3-imidazo[1,2-b]pyridazin-3-ylbenzonitrile, 3-(3,4-difluorophenyl)imidazo[1,2-b]pyridazine, 3-(m-tolyl)imidazo[1,2-b]pyridazine, 3-(4-ethoxyphenyl)imidazo[1,2-b]pyridazine, 3-(2-methylsulfanylphenyl)imidazo[1,2-b]pyridazine, 1-(4-imidazo[1,2-b]pyridazin-3-ylphenyl)ethanone, 5-imidazo[1,2-b]pyridazin-3-ylquinoline, N-cyclopropyl-4-imidazo[1,2-b]pyridazin-3-yl-benzamide, 4-imidazo[1,2-b]pyridazin-3-ylisoquinoline, (2-imidazo[1,2-b]pyridazin-3-ylphenyl)methanol, 3-(2-fluoro-3-methoxy-phenyl)imidazo[1,2-b]pyridazine, (3-imidazo[1,2-b]pyridazin-3-ylphenyl)-morpholino-methanone, 2-(4-imidazo[1,2-b]pyridazin-3-ylphenyl)acetonitrile, N-(2-furylmethyl)-3-imidazo[1,2-b]pyridazin-3-yl-benzamide, N-(4-imidazo[1,2-b]pyridazin-3-ylphenyl)methanesulfonamide, 4-[(4-imidazo[1,2-b]pyridazin-3-ylphenyl)methyl]morpholine, 3-(1-isobutylpyrazol-4-yl)imidazo[1,2-b]pyridazine, N-cyclopropyl-3-imidazo[1,2-b]pyridazin-3-yl-benzamide, 4-(3-phenylimidazo[1,2-b]pyridazin-6-yl)benzamide, 3-(1,3-benzodioxol-5-yl)-6-phenyl-imidazo[1,2-b]pyridazine, 3-(1,3-benzodioxol-5-yl)-6-[3-(trifluoromethyl)phenyl]imidazo[1,2-b]pyridazine, 3-(3,4-dimethylphenyl)-N-[(3,4,5-trimethoxyphenyl)methyl]imidazo[1,2-b]pyridazin-6-amine, 3-(1,3-benzodioxol-5-yl)-6-(3-fluorophenyl)imidazo[1,2-b]pyridazine, N-[3-[3-(4-pyridyl)imidazo[1,2-b]pyridazin-6-yl]phenyl]methanesulfonamide, [4-[3-(3-pyridyl)imidazo[1,2-b]pyridazin-6-yl]phenyl]methanol, 6-(3-furyl)-3-(3-pyridyl)imidazo[1,2-b]pyridazine, 3-(3-pyridyl)-6-(2-thienyl)imidazo[1,2-b]pyridazine, N-[3-[6-(3-pyridyl)imidazo[1,2-b]pyridazin-3-yl]phenyl]acetamide, N-[3-[6-(3-acetylphenyl)imidazo[1,2-b]pyridazin-3-yl]phenyl]acetamide, N-[3-[6-[(3,4-difluorophenyl)methyl]imidazo[1,2-b]pyridazin-3-yl]phenyl]acetamide, 3-[3-(3-acetamidophenyl)imidazo[1,2-b]pyridazin-6-yl]-N-methyl-benzamide, 3-(3-chloro-4-fluoro-phenyl)-6-(2-methoxyphenyl)imidazo[1,2-b]pyridazine, 3-(3-chloro-4-fluoro-phenyl)-6-(3,4,5-trimethoxyphenyl)imidazo[1,2-b]pyridazine, 6-(2-methoxyphenyl)-3-[3-(trifluoromethoxy)phenyl]imidazo[1,2-b]pyridazine, N-(2-dimethylaminoethyl)-3-[3-[3-(trifluoromethoxy)phenyl]imidazo[1,2-b]pyridazin-6-yl]benzamide, 4-[3-[3-(trifluoromethoxy)phenyl]imidazo[1,2-b]pyridazin-6-yl]benzamide, 3-(4-methyl-2-thienyl)-N-[(3,4,5-trimethoxyphenyl)methyl]imidazo[1,2-b]pyridazin-6-amine, 6-benzyl-3-(4-methylsulfonylphenyl)imidazo[1,2-b]pyridazine, 3-[6-(3-chlorophenyl)imidazo[1,2-b]pyridazin-3-yl]-N-(2-dimethylaminoethyl)benzamide, N-(2-dimethylaminoethyl)-3-[6-[3-(hydroxymethyl)phenyl]imidazo[1,2-b]pyridazin-3-yl]benzamide, 6-[(4-fluorophenyl)methyl]-3-(5-methoxy-3-pyridyl)imidazo[1,2-b]pyridazine, 3-[3-(3-chlorophenyl)imidazo[1,2-b]pyridazin-6-yl]aniline, 3-(3-chlorophenyl)-6-(3,4-dimethoxyphenyl)imidazo[1,2-b]pyridazine, 3-(3-chlorophenyl)-6-(4-methoxy-2-methyl-phenyl)imidazo[1,2-b]pyridazine, 3-(3-chlorophenyl)-6-(3-methoxyphenyl)imidazo[1,2-b]pyridazine, 3-[6-(4-fluorophenyl)imidazo[1,2-b]pyridazin-3-yl]phenol, 3-[6-(5-quinolyl)imidazo[1,2-b]pyridazin-3-yl]phenol, [4-[6-(4-dimethylaminophenyl)imidazo[1,2-b]pyridazin-3-yl]phenyl]methanol, [4-(6-pyrimidin-5-ylimidazo[1,2-b]pyridazin-3-yl)phenyl]methanol, [4-[6-(1-methylpyrazol-4-yl)imidazo[1,2-b]pyridazin-3-yl]phenyl]methanol, N-(2-hydroxyethyl)-3-[3-[3-(hydroxymethyl)phenyl]imidazo[1,2-b]pyridazin-6-yl]benzamide, [3-[6-(3-phenoxyphenyl)imidazo[1,2-b]pyridazin-3-yl]phenyl]methanol, 6-(4-pyridyl)-3-[3-(trifluoromethyl)phenyl]imidazo[1,2-b]pyridazine, 3-[3-[3-(trifluoromethyl)phenyl]imidazo[1,2-b]pyridazin-6-yl]phenol, 6-cyclopropyl-3-[3-(trifluoromethyl)phenyl]imidazo[1,2-b]pyridazine, 3-(3-fluorophenyl)-6-[(4-fluorophenyl)methyl]imidazo[1,2-b]pyridazine, 2-methoxy-4-[6-[3-(trifluoromethoxy)phenyl]imidazo[1,2-b]pyridazin-3-yl]phenol, 3-[3-(dimethylamino)phenyl]-N-(2-furylmethyl)imidazo[1,2-b]pyridazin-6-amine, 4-[6-(2-furylmethylamino)imidazo[1,2-b]pyridazin-3-yl]benzoic acid, N-[3-[3-(3-furyl)imidazo[1,2-b]pyridazin-6-yl]phenyl]acetamide, 3-[3-(3-furyl)imidazo[1,2-b]pyridazin-6-yl]benzoic acid, 3-(3-furyl)-6-(5-methoxy-3-pyridyl)imidazo[1,2-b]pyridazine, N-[4-[(3-furyl)imidazo[1,2-b]pyridazin-6-yl]phenyl]acetamide, 4-[6-[(3,4-difluorophenyl)methyl]imidazo[1,2-b]pyridazin-3-yl]benzamide, 4-[6-(m-tolylmethyl)imidazo[1,2-b]pyridazin-3-yl]benzamide, N-[4-[6-(4-morpholinophenyl)imidazo[1,2-b]pyridazin-3-yl]phenyl]acetamide, N-[4-[6-(1,3-benzodioxol-5-yl)imidazo[1,2-b]pyridazin-3-yl]phenyl]acetamide, N-[4-[6-(4-methylsulfonylphenyl)imidazo[1,2-b]pyridazin-3-yl]phenyl]acetamide, 6-benzyl-3-pyrimidin-5-yl-imidazo[1,2-b]pyridazine, 6-[(4-fluorophenyl)methyl]-3-(4-methoxy-2-methyl-phenyl)imidazo[1,2-b]pyridazine, 6-[(4-fluorophenyl)methyl]-3-(3-phenoxyphenyl)imidazo[1,2-b]pyridazine, 1-[3-[6-(6-amino-3-pyridyl)imidazo[1,2-b]pyridazin-3-yl]phenyl]ethanone, 3-[3,5-bis(trifluoromethyl)phenyl]-N-(2-thienylmethyl)imidazo[1,2-b]pyridazin-6-amine, N,N-dimethyl-3-[3-(2-thienyl)imidazo[1,2-b]pyridazin-6-yl]aniline, 6-(3-chloro-4-fluoro-phenyl)-3-(2-thienyl)imidazo[1,2-b]pyridazine, 2-methoxy-4-[3-(2-thienyl)imidazo[1,2-b]pyridazin-6-yl]phenol, 6-(2-chlorophenyl)-3-(2-thienyl)imidazo[1,2-b]pyridazine, N-[3-[6-[(4-fluorophenyl)methyl]imidazo[1,2-b]pyridazin-3-yl]phenyl]methanesulfonamide, 3-(1-methylpyrazol-4-yl)-6-(m-tolylmethyl)imidazo[1,2-b]pyridazine, 5-(6-benzylimidazo[1,2-b]pyridazin-3-yl)pyridin-2-amine, (4Z)-4-[dimethylamino(imidazo[1,2-b]pyridazin-3-yl)methylene]-2-phenyl-oxazol-5-one, 3-(3-bromophenyl)-N-(2-thienylmethyl)imidazo[1,2-b]pyridazin-6-amine, 6-(1,3-benzodioxol-5-yl)-3-phenyl-[1,2,4]triazolo[4,3-a]pyridine, N-[3-(3-phenyl-[1,2,4]triazolo[4,3-a]pyridin-6-yl)phenyl]acetamide, 6-(4-methoxy-2-methyl-phenyl)-3-phenyl-[1,2,4]triazolo[4,3-a]pyridine, 3-phenyl-6-[2-(2-pyridyl)ethynyl]-[1,2,4]triazolo[4,3-a]pyridine, N,N-dimethyl-3-(3-phenyl-[1,2,4]triazolo[4,3-a]pyridin-6-yl)prop-2-yn-1-amine, N-[3-(3-phenyl-[1,2,4]triazolo[4,3-a]pyridin-6-yl)phenyl]methanesulfonamide, 3-(1,3-benzodioxol-5-yl)-6-(3-chlorophenyl)-[1,2,4]triazolo[4,3-a]pyridine, 3-(1,3-benzodioxol-5-yl)-6-(3-furyl)-[1,2,4]triazolo[4,3-a]pyridin, 3-(1,3-benzodioxol-5-yl)-6-[2-(3-methylimidazol-4-yl)ethynyl]-[1,2,4]triazolo[4,3-a]pyridine, 3-[3-(1,3-benzodioxol-5-yl)-[1,2,4]triazolo[4,3-a]pyridin-6-yl]prop-2-yn-1-ol, 3-(1,3-benzodioxol-5-yl)-6-(1-methylpyrazol-4-yl)-[1,2,4]triazolo[4,3-a]pyridine, 3-[3-(1,3-benzodioxol-5-yl)-[1,2,4]triazolo[4,3-a]pyridin-6-yl]-N-methyl-benzamide, 4-[4-[3-(4-pyridyl)-[1,2,4]triazolo[4,3-a]pyridin-6-yl]phenyl]morpholine, 6-(3,4-dimethoxyphenyl)-3-(4-pyridyl)-[1,2,4]triazolo[4,3-a]pyridine, 3-(4-pyridyl)-6-[3-(trifluoromethoxy)phenyl]-[1,2,4]triazolo[4,3-a]pyridine, [4-[3-(4-pyridyl)-[1,2,4]triazolo[4,3-a]pyridin-6-yl]phenyl]methanol, 3-(4-pyridyl)-6-[2-[3-(trifluoromethyl)phenyl]ethynyl]-[1,2,4]triazolo[4,3-a]pyridine, 6-(3-phenoxyphenyl)-3-(4-pyridyl)-[1,2,4]triazolo[4,3-a]pyridine, N,N-dimethyl-4-[3-(3-pyridyl)-[1,2,4]triazolo[4,3-a]pyridin-6-yl]aniline, 6-(3-isopropylphenyl)-3-(3-pyridyl)-[1,2,4]triazolo[4,3-a]pyridine, 6-(2-chlorophenyl)-3-(3-pyridyl)-

[1,2,4]triazolo[4,3-a]pyridine, 3-[3-(3,4-dimethoxyphenyl)-[1,2,4]triazolo[4,3-a]pyridin-6-yl]-N,N-dimethyl-aniline, 3-(3,4-dimethoxyphenyl)-6-(4-methylsulfonylphenyl)-[1,2,4]triazolo[4,3-a]pyridine, 3-(3,4-dimethoxyphenyl)-6-(3-fluorophenyl)-[1,2,4]triazolo[4,3-a]pyridine, 3-[3-(3,4-dimethoxyphenyl)-[1,2,4]triazolo[4,3-a]pyridin-6-yl]-N,N-dimethyl-benzamide, 3-(3,4-dimethoxyphenyl)-6-[2-(3-pyridyl)ethynyl]-[1,2,4]triazolo[4,3-a]pyridine, 3-(3,4-dimethoxyphenyl)-6-[2-(4-pyridyl)ethynyl]-[1,2,4]triazolo[4,3-a]pyridine, 3-(3,4-dimethoxyphenyl)-6-(2-thienyl)-[1,2,4]triazolo[4,3-a]pyridine, 6-(5-methoxy-3-pyridyl)-3-[3-(trifluoromethoxy)phenyl]-[1,2,4]triazolo[4,3-a]pyridine, 6-(3-methylsulfonylphenyl)-3-[3-(trifluoromethoxy)phenyl]-[1,2,4]triazolo[4,3-a]pyridine, 6-[2-(3-methoxyphenyl)ethynyl]-3-[3-(trifluoromethoxy)phenyl]-[1,2,4]triazolo[4,3-a]pyridine, 6-(2-thienyl)-3-[3-(trifluoromethoxy)phenyl]-[1,2,4]triazolo[4,3-a]pyridine, 6-(2-phenylethynyl)-3-[3-(trifluoromethoxy)phenyl]-[1,2,4]triazolo[4,3-a]pyridine, 3-[3-(3-chlorophenyl)-[1,2,4]triazolo[4,3-a]pyridin-6-yl]aniline, 6-(1,3-benzodioxol-5-yl)-3-(3-chlorophenyl)-[1,2,4]triazolo[4,3-a]pyridine, 3-(3-chlorophenyl)-6-(4-pyridyl)-[1,2,4]triazolo[4,3-a]pyridine, 3-(3-chlorophenyl)-6-(3-pyridyl)-[1,2,4]triazolo[4,3-a]pyridine, 3-(3-chlorophenyl)-6-(3-furyl)-[1,2,4]triazolo[4,3-a]pyridine, N-[4-[3-(3-chlorophenyl)-[1,2,4]triazolo[4,3-a]pyridin-6-yl]phenyl]acetamide, 3-(3-chlorophenyl)-6-pyrimidin-5-yl-[1,2,4]triazolo[4,3-a]pyridin, 3-(3-chlorophenyl)-6-pyrimidin-2-yl-[1,2,4]triazolo[4,3-a]pyridine, 4-[3-(3-chlorophenyl)-[1,2,4]triazolo[4,3-a]pyridin-6-yl]isoquinoline, 4-[3-(3-hydroxyphenyl)-[1,2,4]triazolo[4,3-a]pyridin-6-yl]benzonitrile, 3-[6-(4-isopropylphenyl)-[1,2,4]triazolo[4,3-a]pyridin-3-yl]phenol, 3-[6-(4-fluorophenyl)-[1,2,4]triazolo[4,3-a]pyridin-3-yl]phenol, 3-[6-(5-quinolyl)-[1,2,4]triazolo[4,3-a]pyridin-3-yl]phenol, 3-[3-(trifluoromethyl)phenyl]-6-(3,4,5-trimethoxyphenyl)-[1,2,4]triazolo[4,3-a]pyridine, N-[3-(dimethylamino)propyl]-4-[3-[3-(trifluoromethyl)phenyl]-[1,2,4]triazolo[4,3-a]pyridin-6-yl]benzamide, morpholino-[4-[3-[3-(trifluoromethyl)phenyl]-[1,2,4]triazolo[4,3-a]pyridin-6-yl]phenyl]methanone, N,N-dimethyl-4-[3-[3-(trifluoromethyl)phenyl]-[1,2,4]triazolo[4,3-a]pyridin-6-yl]benzamide, 5-[3-[3-(trifluoromethyl)phenyl]-[1,2,4]triazolo[4,3-a]pyridin-6-yl]pyridin-2-amine, 2-methoxy-4-[6-[4-(4-methylpiperazin-1-yl)phenyl]-[1,2,4]triazolo[4,3-a]pyridin-3-yl]phenol, 2-methoxy-4-[6-(6-methoxy-3-pyridyl)-[1,2,4]triazolo[4,3-a]pyridin-3-yl]phenol, 4-[6-(3-fluorophenyl)-[1,2,4]triazolo[4,3-a]pyridin-3-yl]-2-methoxy-phenol, 2-methoxy-4-[6-(o-tolyl)-[1,2,4]triazolo[4,3-a]pyridin-3-yl]phenol, 3-(3-furyl)-6-(3,4,5-trimethoxyphenyl)-[1,2,4]triazolo[4,3-a]pyridine, 3-(3-furyl)-6-(4-methoxyphenyl)-[1,2,4]triazolo[4,3-a]pyridine, 3-(3-furyl)-6-(2-thienyl)-[1,2,4]triazolo[4,3-a]pyridine, 3-[6-(2-pyridyl)-[1,2,4]triazolo[4,3-a]pyridin-3-yl]benzonitrile, 6-(3,4-dimethoxyphenyl)-3-(o-tolyl)-[1,2,4]triazolo[4,3-a]pyridine, N-(2-hydroxyethyl)-3-[3-(o-tolyl)-[1,2,4]triazolo[4,3-a]pyridin-6-yl]benzamide, 4-[3-(o-tolyl)-[1,2,4]triazolo[4,3-a]pyridin-6-yl]benzamide, 4-[4-(3-thiazol-4-yl-[1,2,4]triazolo[4,3-a]pyridin-6-yl)phenyl]morpholine, N,N-dimethyl-3-(3-thiazol-4-yl-[1,2,4]triazolo[4,3-a]pyridin-6-yl)aniline, 4-[6-(3-chloro-4-fluorophenyl)-[1,2,4]triazolo[4,3-a]pyridin-3-yl]thiazole, 4-[6-(1H-indol-5-yl)-[1,2,4]triazolo[4,3-a]pyridin-3-yl]thiazole, 3-(3-thiazol-4-yl-[1,2,4]triazolo[4,3-a]pyridin-6-yl)benzamide, 4-[6-(4-methoxy-2-methyl-phenyl)-[1,2,4]triazolo[4,3-a]pyridin-3-yl]thiazole, 4-[3-(3-thiazol-4-yl-[1,2,4]triazolo[4,3-a]pyridin-6-yl)prop-2-ynyl]-1,4-thiazinane 1,1-dioxide, 4-[6-(2-chlorophenyl)-[1,2,4]triazolo[4,3-a]pyridin-3-yl]thiazole, 4-[6-(3-methoxyphenyl)-[1,2,4]triazolo[4,3-a]pyridin-3-yl]thiazole, 4-[6-(6-quinolyl)-[1,2,4]triazolo[4,3-a]pyridin-3-yl]thiazole, 3-[4-[6-(3,4-dimethoxyphenyl)-[1,2,4]triazolo[4,3-a]pyridin-3-yl]phenoxy]-N,N-dimethyl-propan-1-amine, 3-[4-[6-(4-chlorophenyl)-[1,2,4]triazolo[4,3-a]pyridin-3-yl]phenoxy]-N,N-dimethyl-propan-1-amine, 4-[2-[3-[4-[3-(dimethylamino)propoxy]phenyl]-[1,2,4]triazolo[4,3-a]pyridin-6-yl]ethynyl]-N,N-dimethyl-benzamide, 3-[4-[6-[2-(3,5-dimethoxyphenyl)ethynyl]-[1,2,4]triazolo[4,3-a]pyridin-3-yl]phenoxy]-N,N-dimethyl-propan-1-amine, 4-[3-[4-[3-(dimethylamino)propoxy]phenyl]-[1,2,4]triazolo[4,3-a]pyridin-6-yl]-N-methyl-benzamide, N-[3-(3-quinoxalin-6-yl-[1,2,4]triazolo[4,3-a]pyridin-6-yl)phenyl]acetamide, N-(2-dimethylaminoethyl)-3-(3-quinoxalin-6-yl-[1,2,4]triazolo[4,3-a]pyridin-6-yl)benzamide, (4-methylpiperazin-1-yl)-[3-(3-quinoxalin-6-yl-[1,2,4]triazolo[4,3-a]pyridin-6-yl)phenyl]methanone, 2-methoxy-4-(3-quinoxalin-6-yl-[1,2,4]triazolo[4,3-a]pyridin-6-yl)phenol, 6-[6-(3-furyl)-[1,2,4]triazolo[4,3-a]pyridin-3-yl]quinoxaline, N,N-dimethyl-3-(3-quinoxalin-6-yl-[1,2,4]triazolo[4,3-a]pyridin-6-yl)benzamide, 3-[3-(2-pyridyl)-[1,2,4]triazolo[4,3-a]pyridin-6-yl]phenol, [3-[3-(2-pyridyl)-[1,2,4]triazolo[4,3-a]pyridin-6-yl]phenyl]methanol, 6-(3-methylsulfonylphenyl)-3-(2-pyridyl)-[1,2,4]triazolo[4,3-a]pyridine, N-[6-(2,3-dichlorophenyl)imidazo[1,2-a]pyrazin-3-yl]-2-(2-methoxyphenyl)acetamide, N-[6-(4-isopropylphenyl)imidazo[1,2-a]pyrazin-3-yl]-2-(2-methoxyphenyl)acetamide, N-[6-[2-(dimethylaminomethyl)phenyl]imidazo[1,2-a]pyrazin-3-yl]-2-(3-methoxyphenyl)acetamide, N-[6-[(E)-hex-1-enyl]imidazo[1,2-a]pyrazin-3-yl]-2-(3-methoxyphenyl)acetamide, N-[6-(1H-indol-5-yl)imidazo[1,2-a]pyrazin-3-yl]-2-(3-methoxyphenyl)acetamide, N-[6-[3-(hydroxymethyl)phenyl]imidazo[1,2-a]pyrazin-3-yl]-2-(3-methoxyphenyl)acetamide, 2-(3-methoxyphenyl)-N-[6-[3-(trifluoromethyl)phenyl]imidazo[1,2-a]pyrazin-3-yl]acetamide, N-[6-(4-fluorophenyl)imidazo[1,2-a]pyrazin-3-yl]-2-(3-methoxyphenyl)acetamide, N-[6-(3-furyl)imidazo[1,2-a]pyrazin-3-yl]-2-(3-methoxyphenyl)acetamide, 2-(3-methoxyphenyl)-N-[6-(4-phenoxyphenyl)imidazo[1,2-a]pyrazin-3-yl]acetamide, 2-(3-methoxyphenyl)-N-[6-(2-thienyl)imidazo[1,2-a]pyrazin-3-yl]acetamide, 2-(3-methoxyphenyl)-N-[6-(1-methylpyrazol-4-yl)imidazo[1,2-a]pyrazin-3-yl]acetamide, N-[6-[(E)-hex-1-enyl]imidazo[1,2-a]pyrazin-3-yl]pyridine-4-carboxamide, N-[6-(3-thienyl)imidazo[1,2-a]pyrazin-3-yl]thiophene-2-carboxamide, N-[6-(4-isopropylphenyl)imidazo[1,2-a]pyrazin-3-yl]acetamide, N-[6-[3-(2-dimethylaminoethylcarbamoyl)phenyl]imidazo[1,2-a]pyrazin-3-yl]furan-2-carboxamide, N-[6-(1-benzylpyrazol-4-yl)imidazo[1,2-a]pyrazin-3-yl]-2-methyl-propanamide, N-[6-(2-methoxyphenyl)imidazo[1,2-a]pyrazin-3-yl]benzamide, N-[6-[3-(dimethylamino)phenyl]imidazo[1,2-a]pyrazin-3-yl]benzamide, N-[6-(4-aminophenyl)imidazo[1,2-a]pyrazin-3-yl]benzamide, N-[6-(1,3-benzodioxol-5-yl)imidazo[1,2-a]pyrazin-3-yl]-2-phenyl-propanamide, N-[6-(3-nitrophenyl)imidazo[1,2-a]pyrazin-3-yl]-2-phenyl-propanamide, 2-(o-tolyl)-N-[6-(1H-pyrazol-4-yl)imidazo[1,2-a]pyrazin-3-yl]acetamide, N-[6-(1-benzylpyrazol-4-yl)imidazol[1,2-a]pyrazin-3-yl]cyclobutanecarboxamide, N-[6-(3-acetylphenyl)imidazo[1,2-a]pyrazin-3-yl]-2-cyclopropyl-acetamide, N-[6-(2-naphthyl)imidazo[1,2-a]pyrazin-3-yl]tetrahydrofuran-3-carboxamide, N-[6-(4-methoxyphenyl)imidazo[1,2-a]pyrazin-3-yl]tetrahydrofuran-3-carboxamide, N-[6-(3-aminophenyl)imidazo[1,2-a]pyrazin-3-yl]-2-(3,4-difluorophenyl)acetamide, N-[6-(2-fluorophenyl)imidazo[1,2-a]pyrazin-3-yl]-2-(3-thienyl)acetamide, N-[6-(3-methoxyphenyl)imidazo[1,2-a]pyrazin-3-yl]-2-(3-thienyl)acetamide, N-[6-(2,4-dimethoxyphenyl)

imidazo[1,2-a]pyrazin-3-yl]-2-(3-thienyl)acetamide, 4-[6-[6-[3-(dimethylamino)propoxy]-3-pyridyl]imidazo[1,2-a]pyrazin-3-yl]-N,N-dimethyl-aniline, 5-[3-(4-dimethylaminophenyl)imidazo[1,2-a]pyrazin-6-yl]-N-(2-morpholinoethyl)pyridin-2-amine, 2-[3-(4-dimethylaminophenyl)imidazo[1,2-a]pyrazin-6-yl]-N,N-dimethyl-aniline, 4-[3-(4-dimethylaminophenyl)imidazo[1,2-a]pyrazin-6-yl]phenol, 4-[3-(4-dimethylaminophenyl)imidazo[1,2-a]pyrazin-6-yl]-N-[3-(dimethylamino)propyl]benzamide, 3-[3-(4-dimethylaminophenyl)imidazo[1,2-a]pyrazin-6-yl]-N-(2-hydroxyethyl)benzamide, [4-[3-(4-dimethylaminophenyl)imidazo[1,2-a]pyrazin-6-yl]phenyl]methanol, 4-[6-(6-methoxy-3-pyridyl)imidazo[1,2-a]pyrazin-3-yl]-N,N-dimethyl-aniline, N-(2-dimethylaminoethyl)-4-[3-(4-dimethylaminophenyl)imidazo[1,2-a]pyrazin-6-yl]benzamide, 4-[3-(4-dimethylaminophenyl)imidazo[1,2-a]pyrazin-6-yl]-N-(2-hydroxyethyl)benzamide, [4-[3-(4-dimethylaminophenyl)imidazo[1,2-a]pyrazin-6-yl]phenyl]-morpholino-methanone, 3-[3-(4-dimethyl aminophenyl)imidazo[1,2-a]pyrazin-6-yl]benzamide, 3-[3-(4-dimethylaminophenyl)imidazo[1,2-a]pyrazin-6-yl]-N,N-dimethyl-benzamide, 4-[6-(2-chlorophenyl)imidazo[1,2-a]pyrazin-3-yl]-N,N-dimethyl-aniline, N-[3-[3-(4-dimethylaminophenyl)imidazo[1,2-a]pyrazin-6-yl]phenyl]methanesulfonamide, 3-phenyl-6-(3-thienyl)imidazo[1,2-a]pyrazine, 6-(3-fluorophenyl)-3-phenyl-imidazo[1,2-a]pyrazine, 3-phenyl-6-(2-thienyl)imidazo[1,2-a]pyrazine, N-cyclopropyl-4-(3-phenylimidazo[1,2-a]pyrazin-6-yl)benzamide, 3-(1,3-benzodioxol-5-yl)-6-phenyl-imidazo[1,2-a]pyrazine, 3-(1,3-benzodioxol-5-yl)-6-(3-thienyl)imidazo[1,2-a]pyrazine, 3-(1,3-benzodioxol-5-yl)-6-(3-ethoxyphenyl)imidazo[1,2-a]pyrazine, 3-(1,3-benzodioxol-5-yl)-6-(3-chlorophenyl)imidazo[1,2-a]pyrazine, 3-(1,3-benzodioxol-5-yl)-6-(3-fluorophenyl)imidazo[1,2-a]pyrazine, 3-(1,3-benzodioxol-5-yl)-6-(o-tolyl)imidazo[1,2-a]pyrazine, 3-(1,3-benzodioxol-5-yl)-6-(2-thienyl)imidazo[1,2-a]pyrazine, 3-(1,3-benzodioxol-5-yl)-6-(1-benzylpyrazol-4-yl)imidazo[1,2-a]pyrazine, 3-(1,3-benzodioxol-5-yl)-6-(3,5-dimethoxyphenyl)imidazo[1,2-a]pyrazine, 5-[3-(1,3-benzodioxol-5-yl)imidazo[1,2-a]pyrazin-6-yl]pyridin-2-amine, 3-(1,3-benzodioxol-5-yl)-6-(3-isopropoxyphenyl)imidazo[1,2-a]pyrazine, 6-(2-phenoxyphenyl)-3-(4-pyridyl)imidazo[1,2-a]pyrazine, 2,6-dimethyl-4-[3-(4-pyridyl)imidazo[1,2-a]pyrazin-6-yl]phenol, morpholino-[4-[3-(4-pyridyl)imidazo[1,2-a]pyrazin-6-yl]phenyl]methanone, 3-(4-pyridyl)-6-(2-thienyl)imidazo[1,2-a]pyrazine, 4-[4-[3-(3-pyridyl)imidazo[1,2-a]pyrazin-6-yl]phenyl]morpholine, 6-(benzothiophen-2-yl)-3-(3-pyridyl)imidazo[1,2-a]pyrazine, 6-(4-methylsulfanylphenyl)-3-(3-pyridyl)imidazo[1,2-a]pyrazine, N-[3-[3-(3-pyridyl)imidazo[1,2-a]pyrazin-6-yl]phenyl]methanesulfonamide, 6-(2-furyl)-3-(3-thienyl)imidazo[1,2-a]pyrazine, 6-(3-chloro-4-fluoro-phenyl)-3-(3-thienyl)imidazo[1,2-a]pyrazine, N-(2-hydroxyethyl)-4-[3-(3-thienyl)imidazo[1,2-a]pyrazin-6-yl]benzamide, 6-(2-thienyl)-3-(3-thienyl)imidazo[1,2-a]pyrazine, 6-(3,5-dimethoxyphenyl)-3-(3-thienyl)imidazo[1,2-a]pyrazine, 4-[6-(4-chlorophenyl)imidazo[1,2-a]pyrazin-3-yl]phenol, 4-[6-[4-(4-isopropylpiperazin-1-yl)phenyl]imidazo[1,2-a]pyrazin-3-yl]phenol, N-cyclopropyl-4-[3-(4-hydroxyphenyl)imidazo[1,2-a]pyrazin-6-yl]benzamide, 4-[6-(1-methyl-pyrazol-4-yl)imidazo[1,2-a]pyrazin-3-yl]phenol, 3-[4-[6-(3-ethoxyphenyl)imidazo[1,2-a]pyrazin-3-yl]phenyl]propanoic acid, 3-[4-[6-(3-chlorophenyl)imidazo[1,2-a]pyrazin-3-yl]phenyl]propanoic acid, 3-[4-[6-(o-tolyl)imidazo[1,2-a]pyrazin-3-yl]phenyl]propanoic acid, 3-[4-[6-(2-chlorophenyl)imidazo[1,2-a]pyrazin-3-yl]phenyl]propanoic acid, 3-[4-[6-(2-thienyl)imidazo[1,2-a]pyrazin-3-yl]phenyl]propanoic acid, 3-[4-[6-[2-(hydroxymethyl)phenyl]imidazo[1,2-a]pyrazin-3-yl]phenyl]propanoic acid, 3-[4-[6-(2,3-dimethylphenyl)imidazo[1,2-a]pyrazin-3-yl]phenyl]propanoic acid, 4-(6-phenylimidazo[1,2-a]pyrazin-3-yl)benzonitrile, 4-[6-(3-thienyl)imidazo[1,2-a]pyrazin-3-yl]benzonitrile, 4-[6-(4-chlorophenyl)imidazo[1,2-a]pyrazin-3-yl]benzonitrile, 4-[6-[4-(hydroxymethyl)phenyl]imidazo[1,2-a]pyrazin-3-yl]benzonitrile, 4-[6-(2-thienyl)imidazo[1,2-a]pyrazin-3-yl]benzonitrile, 6-[6-(4-methylpiperazin-1-yl)-3-pyridyl]-3-(3,4,5-trimethoxyphenyl)imidazo[1,2-a]pyrazine, 3-[6-[6-[3-(dimethylamino)propoxy]-3-pyridyl]imidazo[1,2-a]pyrazin-3-yl]-N,N-dimethyl-aniline, N,N-dimethyl-3-[6-(4-pyridyl)imidazo[1,2-a]pyrazin-3-yl]aniline, N,N-dimethyl-3-[6-(3-thienyl)imidazo[1,2-a]pyrazin-3-yl]aniline, [4-[3-[3-(dimethylamino)phenyl]imidazo[1,2-a]pyrazin-6-yl]phenyl]methanol, N,N-dimethyl-3-[6-(2-thienyl)imidazo[1,2-a]pyrazin-3-yl]aniline, 3-[6-(3,5-dimethoxyphenyl)imidazo[1,2-a]pyrazin-3-yl]-N,N-dimethyl-aniline, 3-(4-chlorophenyl)-6-(4-pyridyl)imidazo[1,2-a]pyrazine, 3-(4-chlorophenyl)-6-(3-thienyl)imidazo[1,2-a]pyrazine, 3-(4-chlorophenyl)-6-(2-thienyl)imidazo[1,2-a]pyrazine, N-[3-[3-(3-chloro-4-fluoro-phenyl)imidazo[1,2-a]pyrazin-6-yl]phenyl]acetamide, 3-(3-chloro-4-fluoro-phenyl)-6-(2-furyl)imidazo[1,2-a]pyrazine, 6-(3-pyridyl)-3-[3-(trifluoromethoxy)phenyl]imidazo[1,2-a]pyrazine, N-(2-hydroxyethyl)-3-[3-[3-(trifluoromethoxy)phenyl]imidazo[1,2-a]pyrazin-6-yl]benzamide, (4-methylpiperazin-1-yl)-[3-[6-(2-phenoxyphenyl)imidazo[1,2-a]pyrazin-3-yl]phenyl]methanone, [3-[6-(1,3-benzodioxol-5-yl)imidazo[1,2-a]pyrazin-3-yl]phenyl]-(4-methylpiperazin-1-yl)methanone, (4-methylpiperazin-1-yl)-[3-[6-[4-(trifluoromethoxy)phenyl]imidazo[1,2-a]pyrazin-3-yl]phenyl]methanone, [3-[6-(3-chlorophenyl)imidazo[1,2-a]pyrazin-3-yl]phenyl]-(4-methylpiperazin-1-yl)methanone, [3-[6-(1-methylindol-5-yl)imidazo[1,2-a]pyrazin-3-yl]phenyl]-(4-methylpiperazin-1-yl)methanone, [3-[6-[4-(anilinomethyl)phenyl]imidazo[1,2-a]pyrazin-3-yl]phenyl]-(4-methylpiperazin-1-yl)methanone, [4-[3-(3-chlorophenyl)imidazo[1,2-a]pyrazin-6-yl]phenyl]methanol, [4-[3-(4-methoxyphenyl)imidazo[1,2-a]pyrazin-6-yl]phenyl]methanol, 3-(4-methoxyphenyl)-6-(2-thienyl)imidazo[1,2-a]pyrazine, 5-[3-(4-methoxyphenyl)imidazo[1,2-a]pyrazin-6-yl]pyridin-2-amine, 3-[6-(benzothiophen-2-yl)imidazo[1,2-a]pyrazin-3-yl]phenol, 3-[6-(4-chlorophenyl)imidazo[1,2-a]pyrazin-3-yl]phenol, 3-[6-[(E)-styryl]imidazo[1,2-a]pyrazin-3-yl]phenol, 3-[6-[4-(4-methylpiperazin-1-yl)phenyl]imidazo[1,2-a]pyrazin-3-yl]phenol, 3-[6-(3-chlorophenyl)imidazo[1,2-a]pyrazin-3-yl]phenol, 3-[6-(6-methoxy-3-pyridyl)imidazo[1,2-a]pyrazin-3-yl]phenol, 3-[6-(2-thienyl)imidazo[1,2-a]pyrazin-3-yl]phenol, 3-[6-(3,5-dimethoxyphenyl)imidazo[1,2-a]pyrazin-3-yl]phenol, 3-[6-(2-fluoro-3-methoxy-phenyl)imidazo[1,2-a]pyrazin-3-yl]phenol, [4-[6-(2-furyl)imidazo[1,2-a]pyrazin-3-yl]phenyl]methanol, [4-[6-(2,4-dichlorophenyl)imidazo[1,2-a]pyrazin-3-yl]phenyl]methanol, N-cyclopentyl-4-[3-[4-(hydroxymethyl)phenyl]imidazo[1,2-a]pyrazin-6-yl]benzamide, [3-(6-phenylimidazo[1,2-a]pyrazin-3-yl)phenyl]methanol, [3-[6-(4-methylsulfanylphenyl)imidazo[1,2-a]pyrazin-3-yl]phenyl]methanol, [3-[6-(3-ethoxyphenyl)imidazo[1,2-a]pyrazin-3-yl]phenyl]methanol, [3-[6-(2-thienyl)imidazo[1,2-a]pyrazin-3-yl]phenyl]methanol, [3-[6-(3-isopropoxyphenyl)imidazo[1,2-a]pyrazin-3-yl]phenyl]methanol, 3-(6-methoxy-3-pyridyl)-6-[4-(4-methylpiperazin-1-yl)phenyl]imidazo[1,2-a]pyrazine, 3,6-bis(6-methoxy-3-pyridyl)imidazo[1,2-a]pyrazine, 3-[3-(6- methoxy-3-pyridyl)imidazo[1,2-a]pyrazin-6-yl]benzamide, 3-[3-(3-fluorophenyl)imidazo[1,2-a]pyrazin-6-yl]aniline, 3-(3-fluorophenyl)-6-phenyl-imidazo[1,2-a]pyrazine, 6-(1,3-benzodioxol-5-yl)-3-(3-fluorophenyl)imidazo[1,2-a]pyrazine, 3-(3-fluorophenyl)-6-(4-piperazin-1-ylphenyl)imidazo[1,2-a]pyrazine, 6-(4-chlorophenyl)-3-(3-fluorophenyl)imidazo[1,2-a]pyrazine, [4-[3-(3-fluorophenyl)imidazo[1,2-a]pyrazin-6-yl]phenyl]methanol, 3-(3-fluorophenyl)-6-(2-thienyl)imidazo[1,2-a]pyrazine, 4-[6-[6-[3-(dimethylamino)propoxy]-3-pyridyl]imidazo[1,2-a]pyrazin-3-yl]-2-methoxy-phenol, 2-methoxy-4-[6-[6-(2-morpholinoethylamino)-3-pyridyl]imidazo[1,2-a]pyrazin-3-yl]phenol, 2-methoxy-4-[6-[6-(4-methylpiperazin-1-yl)-3-pyridyl]imidazo[1,2-a]pyrazin-3-yl]phenol, 4-[6-(1,3-benzodioxol-5-yl)imidazo[1,2-a]pyrazin-3-yl]-2-methoxy-phenol, 4-[6-(3-ethoxyphenyl)imidazo[1,2-a]pyrazin-3-yl]-2-methoxy-phenol, 4-[6-(6-amino-3-pyridyl) imidazo[1,2-a]pyrazin-3-yl]-2-methoxy-phenol, 2-methoxy-4-[6-(1-methylpyrazol-4-yl)imidazo[1,2-a]pyrazin-3-yl]phenol, N-[3-(dimethylamino)propyl]-4-[3-(1-methylindol-5-yl)imidazo[1,2-a]pyrazin-6-yl]benzamide, N-(2-hydroxyethyl)-3-[3-(1-methylindol-5-yl)imidazo[1,2-a]pyrazin-6-yl]benzamide, 2-methoxy-4-[3-(1-methylindol-5-yl)imidazo[1,2-a]pyrazin-6-yl]phenol, 3-[3-(1-methylindol-5-yl)imidazo[1,2-a]pyrazin-6-yl]benzamide, (4-methylpiperazin-1-yl)-[4-[6-[(E)-styryl]imidazo[1,2-a]pyrazin-3-yl]phenyl]methanone, N-[3-[3-(4-phenoxyphenyl)imidazo[1,2-a]pyrazin-6-yl]phenyl]methanesulfonamide, 6-(3-fluorophenyl)-3-(o-tolyl)imidazo[1,2-a]pyrazine, 3-(o-tolyl)-6-(2-thienyl)imidazo[1,2-a]pyrazine, 4-[3-(2-chlorophenyl)imidazo[1,2-a]pyrazin-6-yl]-2-methoxy-phenol, 3-[3-(4-tert-butylphenyl)imidazo[1,2-a]pyrazin-6-yl]-N,N-dimethyl-benzamide, 5-[3-(4-tert-butylphenyl)imidazo[1,2-a]pyrazin-6-yl]pyridin-2-amine, 1-[3-[6-(3-pyridyl)imidazo[1,2-a]pyrazin-3-yl]phenyl]ethanone, 1-[3-[6-(3-fluorophenyl)imidazo[1,2-a]pyrazin-3-yl]phenyl]ethanone, 4-[3-(3-acetylphenyl)imidazo[1,2-a]pyrazin-6-yl]-N-(2-dimethylaminoethyl)benzamide, 1-[3-[6-(2-thienyl)imidazo[1,2-a]pyrazin-3-yl]phenyl]ethanone, N,N-dimethyl-2-[3-(2-thienyl)imidazo[1,2-a]pyrazin-6-yl]aniline, 6-(4-pyridyl)-3-(2-thienyl)imidazo[1,2-a]pyrazine, 3-(2-thienyl)-6-(3-thienyl)imidazo[1,2-a]pyrazine, 6-(benzothiophen-2-yl)-3-(2-thienyl)imidazo[1,2-a]pyrazine, 4-[3-(2-thienyl)imidazo[1,2-a]pyrazin-6-yl]phenol, 3-(2-thienyl)-6-[4-(trifluoromethoxy)phenyl]imidazo[1,2-a]pyrazine, 6-[(E)-styryl]-3-(2-thienyl)imidazo[1,2-a]pyrazine, N-(2-hydroxyethyl)-3-[3-(2-thienyl)imidazo[1,2-a]pyrazin-6-yl]benzamide, 6-(3-chlorophenyl)-3-(2-thienyl)imidazo[1,2-a]pyrazine, [4-[3-(2-thienyl)imidazo[1,2-a]pyrazin-6-yl]phenyl]methanol, N-(2-hydroxyethyl)-4-[3-(2-thienyl)imidazo[1,2-a]pyrazin-6-yl]benzamide, 3,6-bis(2-thienyl)imidazo[1,2-a]pyrazine, N-[3-[3-(2-thienyl)imidazo[1,2-a]pyrazin-6-yl]phenyl]methanesulfonamide, 6-(3,5-dimethoxyphenyl)-3-(2-thienyl)imidazo[1,2-a]pyrazine, 5-[3-(2-thienyl)imidazo[1,2-a]pyrazin-6-yl]pyridin-2-amine, 6-(3-isopropoxyphenyl)-3-(2-thienyl)imidazo[1,2-a]pyrazine, N,N-dimethyl-4-[6-[6-(4-methylpiperazin-1-yl)-3-pyridyl]imidazo[1,2-a]pyrazin-3-yl]benzamide, N,N-dimethyl-4-[6-(2-phenoxyphenyl)imidazo[1,2-a]pyrazin-3-yl]benzamide, N,N-dimethyl-4-[6-(3-thienyl)imidazo[1,2-a]pyrazin-3-yl]benzamide, 4-[6-(3-acetamidophenyl)imidazo[1,2-a]pyrazin-3-yl]-N,N-dimethyl-benzamide, N,N-dimethyl-4-[6-(1-methylindol-5-yl)imidazo[1,2-a]pyrazin-3-yl]benzamide, 4-[6-(5-acetyl-2-thienyl) imidazo[1,2-a]pyrazin-3-yl]-N-cyclopropyl-benzamide, N-cyclopropyl-4-[6-[4-(4-isopropylpiperazin-1-yl)phenyl]imidazo[1,2-a]pyrazin-3-yl]benzamide, 2-[3-(3,5-dimethoxyphenyl)imidazo[1,2-a]pyrazin-6-yl]-N,N-dimethyl-aniline, 3-(3,5-dimethoxyphenyl)-6-(3-isopropoxyphenyl)imidazo[1,2-a]pyrazine, 3-(1-methylpyrazol-4-yl)-6-(4-pyridyl)imidazo[1,2-a]pyrazine, 6-(benzothiophen-2-yl)-3-(1-methylpyrazol-4-yl)imidazo[1,2-a]pyrazine, 6-[6-(3,4,5-trimethoxyphenyl)imidazo[1,2-a]pyrazin-3-yl]quinoline, 2-methoxy-4-[3-(6-quinolyl)imidazo[1,2-a]pyrazin-6-yl]phenol, 2,6-dimethyl-4-[3-(6-quinolyl) imidazo[1,2-a]pyrazin-6-yl]phenol, 6-[6-(1-methylindol-5-yl)imidazo[1,2-a]pyrazin-3-yl]quinoline, and N-[3-[3-(6-quinolyl)imidazo[1,2-a]pyrazin-6-yl]phenyl]methanesulfonamide, 4-[3-[6-(2-thienyl)imidazo[1,2-a]pyrazin-3-yl]phenyl]morpholine, N-[3-[6-(2-thienyl)imidazo[1,2-a]pyrazin-3-yl]phenyl]methanesulfonamide, 3-(benzothiophen-2-yl)-6-(2-thienyl)imidazo[1,2-a]pyrazine, 3-[6-(2-thienyl)imidazo[1,2-a]pyrazin-3-yl]aniline, 5-[6-(2-thienyl)imidazo[1,2-a]pyrazin-3-yl]pyridin-2-amine, 3-(3-isopropoxyphenyl)-6-(2-thienyl)imidazo[1,2-a]pyrazine, 3-[4-(1-piperidyl)phenyl]-6-(2-thienyl)imidazo[1,2-a]pyrazine, (2S)-3-methyl-2-[[3-[4-(1-piperidyl)phenyl]imidazo[1,2-b]pyridazin-6-yl]amino]butan-1-ol, (2S)-2-[[3-[3-(dimethylamino)phenyl]imidazo[1,2-b]pyridazin-6-yl]amino]-3-methyl-butan-1-ol, (2S)-3-methyl-2-[[3-(3-morpholinophenyl)imidazo[1,2-b]pyridazin-6-yl]amino]butan-1-ol, (2S)-2-[[3-(6-amino-3-pyridyl)imidazo[1,2-b]pyridazin-6-yl]amino]-3-methyl-butan-1-ol, (2S)-2-[[3-(3-isopropoxyphenyl)imidazo[1,2-b]pyridazin-6-yl]amino]-3-methyl-butan-1-ol, N,N-dimethyl-3-(3-thiazol-4-ylimidazo[1,2-a]pyrazin-6-yl)aniline, 4-[3-(3-thiazol-4-ylimidazo[1,2-a]pyrazin-6-yl)phenyl]morpholine, 5-(3-thiazol-4-ylimidazo[1,2-a]pyrazin-6-yl)pyridin-2-amine, 4-[6-(3-isopropoxyphenyl)imidazo[1,2-a]pyrazin-3-yl]thiazole, N-[3-(3-thiazol-4-ylimidazo[1,2-a]pyrazin-6-yl)phenyl]methanesulfonamide, and 3-(3-thiazol-4-ylimidazo[1,2-a]pyrazin-6-yl)aniline.

* * * * *

SEQUENCE LISTING

<160> NUMBER OF SEQ ID NOS: 12

<210> SEQ ID NO 1
<211> LENGTH: 23
<212> TYPE: DNA
<213> ORGANISM: Mus musculus

<400> SEQUENCE: 1
cggcggcgac gatgtggttc ttt                                             23

<210> SEQ ID NO 2
<211> LENGTH: 22
<212> TYPE: DNA
<213> ORGANISM: Mus musculus

<400> SEQUENCE: 2
cggcgttgcc ctgtgccgag ta                                              22

<210> SEQ ID NO 3
<211> LENGTH: 23
<212> TYPE: DNA
<213> ORGANISM: Mus musculus

<400> SEQUENCE: 3
ctgacacggg caaggctgag att                                    23

<210> SEQ ID NO 4
<211> LENGTH: 23
<212> TYPE: DNA
<213> ORGANISM: Mus musculus

<400> SEQUENCE: 4
gcgccctgat acaacaccga gac                                    23

<210> SEQ ID NO 5
<211> LENGTH: 22
<212> TYPE: DNA
<213> ORGANISM: Mus musculus

<400> SEQUENCE: 5
gccgggtgct ggagactgag ga                                     22

<210> SEQ ID NO 6
<211> LENGTH: 24
<212> TYPE: DNA
<213> ORGANISM: Mus musculus

<400> SEQUENCE: 6
tggcggttct ggaggctgac ttct                                   24

<210> SEQ ID NO 7
<211> LENGTH: 2637
<212> TYPE: DNA
<213> ORGANISM: Mus musculus

<400> SEQUENCE: 7
cccgccccgc ccggctcgg gcggccggag acccggagt ggaggctccc gagcccgtgg      60
cggcggcgac gatgtggttc tttgcccggg acccggtccg ggacttcccg ttcgagctga   120
gccctgagcc ccccgaaggc gggccgcccg ggccctggat cctgcaccga ggccgcaaaa   180
aggccacagg cagcgcagtg tccatcttcg tgtatgatgt gaaaccggga gctgaagagc   240
agacccaggt ggccaaagct gccttcaaac gcctcaaaac tctccgacac cccaacatcc   300
tggcctatat cgatgggttg gagacagaaa agtgcctcca catcgtgaca gaggctgtga   360 ccccctggg aacatacctc aaggcacgag cagaagcagg tggcctgaag gagcaggagc   420
tgtcatgggg gttacaccag atcgtgaaag ccctcagctt cctggtcaac gactgcaacc   480
tcatccacaa taatgtctgc atggccgctg tgtttgtgga cagggctggc gagtggaaac   540
ttgggggtct ggactacatg tactcggcac agggcaacgg cggggaccca cccagcaagg   600
ggatcccgga gctcgagcag tatgatcccc cggagctggc tgacagcagt agcagagcag   660
tcagagagaa gtggtcagca gacatgtggc gcttgggctg cctcatctgg gaagttttca   720
atgggtctct acctcgggca gctgccctgc gcaaccctgg aagatccccc aaatccctgg   780
tgacccatta ctgtgaactg gtgggagcta acccaaaagt acgtcccaac ccggcccgct   840
tcctgcagaa ctgccgggca cccggtggct tcatgagcaa ccgctttgtt gagaccaacc   900

| | |
|---|---|
| tcttcctgga ggagattcag atcaaagagc cagctgagaa gcagaagttc ttccaagagc | 960 |
| tgagcaagag tctagactca tttcccgaag atttctgtcg acacaaggtg ctgccccagc | 1020 |
| tactgactgc ctttgagttt ggcaatgctg gggccgtggt cctcacacct ctcttcaagg | 1080 |
| tgggaaaatc cctccgtgct gaagagtacc aggagaagat catccccgtg gtagttaaga | 1140 |
| tgttctcatc caccgaccgg gccatgcgca tccgcctcct ccagcagatg gagcagttca | 1200 |
| tccaataccT tgatgagcca acagtcaaca cgcagatttt cccccacgtc acacatggct | 1260 |
| tcctggacac caaccccgcc atccgcgagc agacggtcaa gtccatgctg ctcttggccc | 1320 |
| caaagctgaa tgaggccaat ctcaatgtgg aactgatgaa gcactttgca aggctacaag | 1380 |
| ccaaggacga ccagggtcct atccgctgca acaccacggt ctgcttgggc aaaatcggct | 1440 |
| cctatctcag tgctagtact agacacaggg tcctcacctc cgccttcagc agagccacta | 1500 |
| aggacccatt tgcaccatcc cgggttgcgg gtgtcctggg ctttgctgcc acacacaatc | 1560 |
| tctattcgat ggacgactgt gcccataaga tcctgcctgt gctctgtggc cttactgtgg | 1620 |
| accctgagaa atctgtgcgg gaccaggcct ttaagaccat tcgaagcttc ctgtccaaat | 1680 |
| tagagtctgt gtcagaggat cccacccagc tggcagaagt agagaaggat gtccatgcag | 1740 |
| cgtccagtcc tggaacagga ggagctgcag ccagctgggc aggctgggct gtgactgggg | 1800 |
| tatcctctct cacctccaag ctgatccgag cacaccccac gcctgtgccg tctgatacca | 1860 |
| ctgtgcccca gagaccagtg ccagagggaa atcctgctcc agccctgcc cttgcccaag | 1920 |
| ctatccctgc aacctcaggg cactgggaga cacaggaaga caaggacact gcagaagaca | 1980 |
| gcgccactgc tgacagatgg gacgatgagg actgggcag cttggagcag gaagctgaat | 2040 |
| ccgtgttggc acagcaggat gactggagtg ccaagggcca aggaagccga gctggacaga | 2100 |
| tcaaccaccc agaccacaaa tctctggaat cacattggag cagctgggaa gttgagggct | 2160 |
| cctgggacca gggctggcag gaacccagct ctgtggagcc acctccagaa ggcactcggc | 2220 |
| tagctagcga atataactgg ggtggtgcag agcccagtga caagggcgac cccttttgctg | 2280 |
| ccctgtctgt tcgtcccagc gctcagccca ggccagaccc agactcctgg ggtgaagaca | 2340 |
| actgggaagg cttggaggct gagagcagac aggtaaaggc agagctggcc cggaaaaagc | 2400 |
| gagaggaaag gagaagagaa atggaagcca acgggcaga gaaaaagacc accaagggc | 2460 |
| ccatgaagct gggagcccgg aagctggact gacaacccca cccccaagcc actgggcttc | 2520 |
| caaccactgg agagcaggcc cggcggatgt atttattgta caaaccatgt gagcctggtc | 2580 |
| agcaggtcag gcacatctag tgtacataat cagagccaca ataaattcta tttcaca | 2637 |

<210> SEQ ID NO 8
<211> LENGTH: 3182
<212> TYPE: DNA
<213> ORGANISM: Mus musculus

<400> SEQUENCE: 8

| | |
|---|---|
| gcggccgcca ggtcgccccg ggctggccga acccccttgct gccccggaaac aaagtgcacc | 60 |
| tttgtcagag acctggcgcg tgtgagcggc agacggcggg ccgcgcggaa ccccaggagc | 120 |
| gcgccttcgc tcgggtctca gctcactcct gggcctccca cagcagcgtt ctgccgcctt | 180 |
| ggcttgtgct ttccgctttc tcggatcttg gcgggacagg aaagggactc tgcgctccag | 240 |
| gagtgggggt ttcgttttgg ctgagtcgtt tttgactcct gccggcgagg ctgggccgcc | 300 |
| tgggctcagc gccataccgg cagcagtcct gctccacagt cccggtgcaa tagagccctc | 360 |
| gccccgtcag acgcgggact acaattccca gcactcctcg cgttcagagc gcgcggtggg | 420 |

| | |
|---|---:|
| agttgcctcc gggcagacgc ctgcgcgctg cagcggctcg agcctggagt accacacccc | 480 |
| cgggagggga acgaggggag gctgaagcat ccgaagcatt aaagcatccg agggagccgg | 540 |
| aggggaggag aatggagtga cagagacgcg cggagggtgg ggggtggggg ggaaagtgtt | 600 |
| gagggagggg ggagggggga cacagaggga ggaagaagcg gcggcggcgt ctcttcggtg | 660 |
| cagagggga aactccgcgg gctccgagaa agaataatgc ggtagcaggc aggctgcttg | 720 |
| ctctggggtt tggcagcagc ggcggcagct cgagcagtgg cagcggcagc ggcatcaccc | 780 |
| cagacgctga cagcacagcc ggccggctcc ctcgctgact gccgactgtc aatggagctg | 840 |
| gaaaacatcg tggccaacac ggtcttgctg aaagcccggg aaggggtgg aggaaagcgc | 900 |
| aaagggaaaa gcaagaagtg gaaggaaatc ctgaagtttc ctcacatcag ccagtgtgaa | 960 |
| gacctccgaa ggaccataga cagagattac tacagtctat gtgacaagca accaattggg | 1020 |
| agactgcttt ttcgacagtt ctgtgaaacc aggcctgggc tggagtgcta cattcagttc | 1080 |
| ctggacttag tggcagaata tgaaattact ccagatgaaa accttggggc gaaggggaag | 1140 |
| gaaataatga ccaagtacct cactccaaag tccccagtct tcattgccca agttggacag | 1200 |
| gacctggtct cccagacaga gaagaagctc ctgcagagcc cctgcaaaga actcttctct | 1260 |
| gcttgtgctc agtctgtcca tgactacttg aagggagacc ccttccacga gtacctggat | 1320 |
| agcatgtatt ttgaccgttt tctgcagtgg aaatggttag aaagacaacc agtgaccaaa | 1380 |
| aacactttcc ggcagtaccg agtgctgggc aaaggggct ttggagaggt ctgtgcctgc | 1440 |
| caggttcggg ccactggtaa aatgtatgct tgtaaacgct tagagaagaa gaggatcaaa | 1500 |
| aagaggaaag gcgaatccat ggcactcaac gaaaagcaga ttcttgagaa ggtcaacagc | 1560 |
| cagtttgtgg tcaacctggc ctatgcctat gaaaccaaag atgcactatg cctggttctg | 1620 |
| accattatga atggtggtga cctgaagttt cacatctaca atatggggaa tcctggcttt | 1680 |
| gaggaagagc gagccttatt ttatgcagct gagatcctct gtggcctaga agacttacac | 1740 |
| cgtgagaaca ctgtctatag agatctaaaa cccgaaaaca tcttgctgga tgattatggc | 1800 |
| cacataagga tctcagacct cggactggcc gtgaagatcc ccgagggaga ccttatccgt | 1860 |
| ggccgggtag gcactgttgg ctacatggcc ccagaagttc tgaacaacca gcgatatgga | 1920 |
| ctgagccctg actactgggg cctgggctgc ctcatctatg agatgattga aggccagtca | 1980 |
| ccatttcgag gtcgcaagga gaaggttaag cgggaagagg tggatcgccg ggtgctggag | 2040 |
| actgaggaag tgtattcctc caagttctct gaagaggcca agtccatctg caacatgctg | 2100 |
| ctcaccaaag actcgaagca gaggctgggc tgccaggagg aggggccgc cgaggtcaag | 2160 |
| aggcacccct tcttcaggaa catgaacttt aagcgcctgg aggctgggat gttggaccct | 2220 |
| ccccttcgttc cagatccccg ggctgtatac tgcaaggatg tgctggacat tgagcagttc | 2280 |
| tccactgtga aggtgtcaa cctggaccat acggacgatg attttactc aaagttctct | 2340 |
| acaggctctg tgccaattcc atggcaaaat gagatgatag aaacagaatg tttcaaggag | 2400 |
| ctgaatgtgt tcggacctaa cggtaccctc tcaccagacc tgaacagaag tcagcctcca | 2460 |
| gaaccgccaa agaaagggct gttccacaga ctcttcaggc gtcagcatca aagcaattcc | 2520 |
| aagagttcac ctactcctaa gaccagttgt aaccaccgaa taaattcaaa ccacatcaat | 2580 |
| tcaaactcca ctggaagcag ctagtttcgg ctctggcctt gaagtcaaaa gtggaaccag | 2640 |
| ctcagagcct tctacttgga agcagaactt gtagccaggg gagcttccac tgtggctcag | 2700 |
| tggccagcaa agctccagtg ggaactaaga taggagaccg ttcccccaat aacaaacctc | 2760 |

| | |
|---|---|
| caagtttctc aaagaaattt ccactcaggt ctgttttcca aggtggcccc aagctggggt | 2820 |
| ggactagaat tttccttgtt gaacattgca atagaaaccc aatgggatat gacagcttgc | 2880 |
| acggatttta atagcatcct aactagaact gaattttgtc tttattattt ttaaaggaaa | 2940 |
| gttttgtaaa tttctctatt gtctctgttt acattttgta tatttgtatt taagtgaaag | 3000 |
| tcagactttg agggtgtata ttttctgtgc agccactgtt aagccatgtg ttttaagaca | 3060 |
| ttttagattg gaggggggt tacaaaaatg tgactctaga cttccagagc ctcaaaagag | 3120 |
| ataatgtttt tattaaatat agaaaatatc tcactttta cctttaaaaa aaaaaaaaa | 3180 |
| aa | 3182 |

<210> SEQ ID NO 9
<211> LENGTH: 2287
<212> TYPE: DNA
<213> ORGANISM: Mus musculus

<400> SEQUENCE: 9

| | |
|---|---|
| gcccccttgg ctgtgactct ctcgctcggt gtcctagagg tccttagtgt ggactggcca | 60 |
| cttgggtggc ccaaccttgc gtgccctgga gtaggcagag gtgaagaggg gctacgagtg | 120 |
| gctccgccgg cagccttcag acatcggtga ccttgtgggc tcccacgcag agggtctgga | 180 |
| gacatggcca gaaaggctct caagcttgct tcatggacca gcgtggctct tgctgcctcc | 240 |
| ggtgtctacc tctacagtaa caactacttg gaccctaatg actttggcgc tgtcagggtg | 300 |
| ggcagagctg ttgctacgac agctgtcatc agctatgact acctcacctc cctgaggagt | 360 |
| gtcccatatg gctctgagga gtatttgcag cgtcgatccc aggtgcacct ccgctctgcc | 420 |
| aggcgtctct ttgagctctg ctgtgccaac cggggcactt tcatcaaggt gggccagcac | 480 |
| ctgggggcgc tggactacct gctgccagaa gagtacacca gcacactgaa ggtgttgcac | 540 |
| agtcaagccc cacagagcag catgcaagag gtccggcagg tcatccgaga agacctgggc | 600 |
| aaggagatcc acgatttgtt cctgagcttc gatgacaccc ctcttggggc agcctccctg | 660 |
| gcccaggtcc acaaggcggt gttgcatgat ggtcggacag tggcagttaa ggtccagcac | 720 |
| ccgaaggttc aggctcaaag ctctaaggac attctcctga tggaggtgct tgtcctggcc | 780 |
| gtgaagcaac ttttcccaga ttttgaattc atgtggctgg tggatgaagc gaagaagaac | 840 |
| ctgcctctcg agttggactt cctgaatgaa gggaggaacg ctgagaaagt ggcccacatg | 900 |
| ctcaggcact ttgacttcct aaaggttccc cagatccact gggagctgtc taccaagagg | 960 |
| gtgctcctga tggaatttgt agagggaggt caagtcaacg acagggccta catggagaag | 1020 |
| aaccagatcg atgtgaatga gatctcctgc cacctgggca gatgtacag tgagatgatc | 1080 |
| tttgtcaatg gcttcgtgca ctgtgacccc cacccaggca acgtactggt acggaagcgt | 1140 |
| cctgacacgg gcaaggctga gattgtcctc ttagaccatg gctttacca ggtgctcacg | 1200 |
| gaggagttcc gcctggacta ctgccatctg tggcagtctc tgatctggac tgacatggac | 1260 |
| gggctgaaac agtacagcca gcgcctggga gctgcagacc tctacccact gtttgcctgt | 1320 |
| atgctgacag cccggtcctg ggactcagtc aaacagggca ttgggcaagc tccagtctct | 1380 |
| gctactgagg actcagagat tcgcaataat gcagcctgct acctgcctga gatcagccag | 1440 |
| ctccttaacc atgtgcctcg ccagatgctg ctcatcctga agactaatga tctactccgt | 1500 |
| agcattgaga ccaccctggg cacgcgctcc agtgccagtt ccttcctcaa catgtctcgg | 1560 |
| tgttgtatca gggcgctggc tgaacacaag aagagggat ccggctcttt cttcagaagg | 1620 |
| actcagatat cttcagtga ggcctttagc ctgtggcaga tcaaccttca tgaacttctg | 1680 |

-continued

```
cttcgagtga gggccttgag gctagcttgc tgggtctcag ctctcctggg ctggctgact    1740
cgggctccac acagaatgtg atggtctttc cctgcccctt cgtagtgtct ttccacacct    1800
cattccttcc ttcacgctgg gacgacccac tgacccatgg ctgcctaggg ttggctgtgg    1860
tcccagagtg gtcatccatg gcaccctcat gctctgccat ggagcccct gccttggggt     1920 ggccttgtct tgaggtcctg gaatgtcctg gagagtgaga tgggataaag caacctctct    1980
cccatctcct gtgtgtgcca ttgacttggt catccctact tttatgagga ctgtgagaat    2040
ggaccaacca cctgtgtcac aggggcgtgt ttaacttgta gggaataagt agaaactcag    2100
aacctgcaga gaacagactt tatattttg ctgtatcact cccaaagttg tctcgcctca     2160
gtgaggaaga ctgcatctga gagggaacga tgcaactgtg ggctcatgct gtcatggtga    2220
caccttcagt gttatatgta ttgtatatat tgtttattgt aataaaccaa taaacagttt    2280
caaggtt                                                              2287
```

<210> SEQ ID NO 10
<211> LENGTH: 806
<212> TYPE: PRT
<213> ORGANISM: Mus musculus

<400> SEQUENCE: 10

```
Met Trp Phe Phe Ala Arg Asp Pro Val Arg Asp Phe Pro Phe Glu Leu
1               5                   10                  15

Ser Pro Glu Pro Pro Glu Gly Gly Pro Pro Gly Pro Trp Ile Leu His
            20                  25                  30

Arg Gly Arg Lys Lys Ala Thr Gly Ser Ala Val Ser Ile Phe Val Tyr
        35                  40                  45

Asp Val Lys Pro Gly Ala Glu Glu Gln Thr Gln Val Ala Lys Ala Ala
    50                  55                  60

Phe Lys Arg Leu Lys Thr Leu Arg His Pro Asn Ile Leu Ala Tyr Ile
65                  70                  75                  80

Asp Gly Leu Glu Thr Glu Lys Cys Leu His Ile Val Thr Glu Ala Val
                85                  90                  95

Thr Pro Leu Gly Thr Tyr Leu Lys Ala Arg Ala Glu Ala Gly Gly Leu
            100                 105                 110

Lys Glu Gln Glu Leu Ser Trp Gly Leu His Gln Ile Val Lys Ala Leu
        115                 120                 125

Ser Phe Leu Val Asn Asp Cys Asn Leu Ile His Asn Asn Val Cys Met
    130                 135                 140

Ala Ala Val Phe Val Asp Arg Ala Gly Glu Trp Lys Leu Gly Gly Leu
145                 150                 155                 160

Asp Tyr Met Tyr Ser Ala Gln Gly Asn Gly Gly Pro Pro Ser Lys
                165                 170                 175

Gly Ile Pro Glu Leu Glu Gln Tyr Asp Pro Pro Glu Leu Ala Asp Ser
            180                 185                 190

Ser Ser Arg Ala Val Arg Glu Lys Trp Ser Ala Asp Met Trp Arg Leu
        195                 200                 205

Gly Cys Leu Ile Trp Glu Val Phe Asn Gly Ser Leu Pro Arg Ala Ala
    210                 215                 220

Ala Leu Arg Asn Pro Gly Lys Ile Pro Lys Ser Leu Val Thr His Tyr
225                 230                 235                 240

Cys Glu Leu Val Gly Ala Asn Pro Lys Val Arg Pro Asn Pro Ala Arg
                245                 250                 255
```

```
Phe Leu Gln Asn Cys Arg Ala Pro Gly Phe Met Ser Asn Arg Phe
            260                 265                 270

Val Glu Thr Asn Leu Phe Leu Glu Glu Ile Gln Ile Lys Glu Pro Ala
        275                 280                 285

Glu Lys Gln Lys Phe Phe Gln Glu Leu Ser Lys Ser Leu Asp Ser Phe
    290                 295                 300

Pro Glu Asp Phe Cys Arg His Lys Val Leu Pro Gln Leu Leu Thr Ala
305                 310                 315                 320

Phe Glu Phe Gly Asn Ala Gly Ala Val Val Leu Thr Pro Leu Phe Lys
                325                 330                 335

Val Gly Lys Ser Leu Arg Ala Glu Glu Tyr Gln Glu Lys Ile Ile Pro
            340                 345                 350

Val Val Val Lys Met Phe Ser Ser Thr Asp Arg Ala Met Arg Ile Arg
        355                 360                 365

Leu Leu Gln Gln Met Glu Gln Phe Ile Gln Tyr Leu Asp Glu Pro Thr
    370                 375                 380

Val Asn Thr Gln Ile Phe Pro His Val Thr His Gly Phe Leu Asp Thr
385                 390                 395                 400

Asn Pro Ala Ile Arg Glu Gln Thr Val Lys Ser Met Leu Leu Leu Ala
                405                 410                 415

Pro Lys Leu Asn Glu Ala Asn Leu Asn Val Glu Leu Met Lys His Phe
            420                 425                 430

Ala Arg Leu Gln Ala Lys Asp Asp Gln Gly Pro Ile Arg Cys Asn Thr
        435                 440                 445

Thr Val Cys Leu Gly Lys Ile Gly Ser Tyr Leu Ser Ala Ser Thr Arg
    450                 455                 460

His Arg Val Leu Thr Ser Ala Phe Ser Arg Ala Thr Lys Asp Pro Phe
465                 470                 475                 480

Ala Pro Ser Arg Val Ala Gly Val Leu Gly Phe Ala Ala Thr His Asn
                485                 490                 495

Leu Tyr Ser Met Asp Asp Cys Ala His Lys Ile Leu Pro Val Leu Cys
            500                 505                 510

Gly Leu Thr Val Asp Pro Glu Lys Ser Val Arg Asp Gln Ala Phe Lys
        515                 520                 525

Thr Ile Arg Ser Phe Leu Ser Lys Leu Glu Ser Val Ser Glu Asp Pro
    530                 535                 540

Thr Gln Leu Ala Glu Val Glu Lys Asp Val His Ala Ala Ser Ser Pro
545                 550                 555                 560

Gly Thr Gly Gly Ala Ala Ser Trp Ala Gly Trp Ala Val Thr Gly
                565                 570                 575

Val Ser Ser Leu Thr Ser Lys Leu Ile Arg Ala His Pro Thr Pro Val
            580                 585                 590

Pro Ser Asp Thr Thr Val Pro Gln Arg Pro Val Pro Glu Gly Asn Pro
        595                 600                 605

Ala Pro Ala Pro Ala Leu Ala Gln Ala Ile Pro Ala Thr Ser Gly His
    610                 615                 620

Trp Glu Thr Gln Glu Asp Lys Asp Thr Ala Glu Asp Ser Ala Thr Ala
625                 630                 635                 640

Asp Arg Trp Asp Asp Glu Asp Trp Gly Ser Leu Glu Gln Glu Ala Glu
                645                 650                 655

Ser Val Leu Ala Gln Gln Asp Asp Trp Ser Ala Lys Gly Gln Gly Ser
            660                 665                 670

Arg Ala Gly Gln Ile Asn His Pro Asp His Lys Ser Leu Glu Ser His
```

```
                    675                 680                 685
Trp Ser Ser Trp Glu Val Glu Gly Ser Trp Asp Gln Gly Trp Gln Glu
        690                 695                 700

Pro Ser Ser Val Glu Pro Pro Glu Gly Thr Arg Leu Ala Ser Glu
705                 710                 715                 720

Tyr Asn Trp Gly Gly Ala Glu Pro Ser Asp Lys Gly Asp Pro Phe Ala
                725                 730                 735

Ala Leu Ser Val Arg Pro Ser Ala Gln Pro Arg Pro Asp Pro Asp Ser
                740                 745                 750

Trp Gly Glu Asp Asn Trp Glu Gly Leu Glu Ala Glu Ser Arg Gln Val
                755                 760                 765

Lys Ala Glu Leu Ala Arg Lys Lys Arg Glu Glu Arg Arg Glu Met
770                 775                 780

Glu Ala Lys Arg Ala Glu Lys Lys Thr Thr Lys Gly Pro Met Lys Leu
785                 790                 795                 800

Gly Ala Arg Lys Leu Asp
                805

<210> SEQ ID NO 11
<211> LENGTH: 590
<212> TYPE: PRT
<213> ORGANISM: Mus musculus

<400> SEQUENCE: 11

Met Glu Leu Glu Asn Ile Val Ala Asn Thr Val Leu Leu Lys Ala Arg
1               5                   10                  15

Glu Gly Gly Gly Gly Lys Arg Lys Gly Lys Ser Lys Lys Trp Lys Glu
                20                  25                  30

Ile Leu Lys Phe Pro His Ile Ser Gln Cys Glu Asp Leu Arg Arg Thr
            35                  40                  45

Ile Asp Arg Asp Tyr Tyr Ser Leu Cys Asp Lys Gln Pro Ile Gly Arg
        50                  55                  60

Leu Leu Phe Arg Gln Phe Cys Glu Thr Arg Pro Gly Leu Glu Cys Tyr
65                  70                  75                  80

Ile Gln Phe Leu Asp Leu Val Ala Glu Tyr Glu Ile Thr Pro Asp Glu
                85                  90                  95

Asn Leu Gly Ala Lys Gly Lys Glu Ile Met Thr Lys Tyr Leu Thr Pro
            100                 105                 110

Lys Ser Pro Val Phe Ile Ala Gln Val Gly Gln Asp Leu Val Ser Gln
        115                 120                 125

Thr Glu Lys Lys Leu Leu Gln Ser Pro Cys Lys Glu Leu Phe Ser Ala
130                 135                 140

Cys Ala Gln Ser Val His Asp Tyr Leu Lys Gly Asp Pro Phe His Glu
145                 150                 155                 160

Tyr Leu Asp Ser Met Tyr Phe Asp Arg Phe Leu Gln Trp Lys Trp Leu
                165                 170                 175

Glu Arg Gln Pro Val Thr Lys Asn Thr Phe Arg Gln Tyr Arg Val Leu
            180                 185                 190

Gly Lys Gly Gly Phe Gly Glu Val Cys Ala Cys Gln Val Arg Ala Thr
        195                 200                 205

Gly Lys Met Tyr Ala Cys Lys Arg Leu Glu Lys Lys Arg Ile Lys Lys
210                 215                 220

Arg Lys Gly Glu Ser Met Ala Leu Asn Glu Lys Gln Ile Leu Glu Lys
225                 230                 235                 240
```

```
Val Asn Ser Gln Phe Val Asn Leu Ala Tyr Ala Tyr Glu Thr Lys
                245                 250                 255

Asp Ala Leu Cys Leu Val Leu Thr Ile Met Asn Gly Gly Asp Leu Lys
            260                 265                 270

Phe His Ile Tyr Asn Met Gly Asn Pro Gly Phe Glu Glu Glu Arg Ala
        275                 280                 285

Leu Phe Tyr Ala Ala Glu Ile Leu Cys Gly Leu Glu Asp Leu His Arg
    290                 295                 300

Glu Asn Thr Val Tyr Arg Asp Leu Lys Pro Glu Asn Ile Leu Leu Asp
305                 310                 315                 320

Asp Tyr Gly His Ile Arg Ile Ser Asp Leu Gly Leu Ala Val Lys Ile
                325                 330                 335

Pro Glu Gly Asp Leu Ile Arg Gly Arg Val Gly Thr Val Gly Tyr Met
            340                 345                 350

Ala Pro Glu Val Leu Asn Asn Gln Arg Tyr Gly Leu Ser Pro Asp Tyr
        355                 360                 365

Trp Gly Leu Gly Cys Leu Ile Tyr Glu Met Ile Glu Gly Gln Ser Pro
    370                 375                 380

Phe Arg Gly Arg Lys Glu Lys Val Lys Arg Glu Glu Val Asp Arg Arg
385                 390                 395                 400

Val Leu Glu Thr Glu Glu Val Tyr Ser Ser Lys Phe Ser Glu Glu Ala
                405                 410                 415

Lys Ser Ile Cys Asn Met Leu Leu Thr Lys Asp Ser Lys Gln Arg Leu
            420                 425                 430

Gly Cys Gln Glu Glu Gly Ala Ala Glu Val Lys Arg His Pro Phe Phe
        435                 440                 445

Arg Asn Met Asn Phe Lys Arg Leu Glu Ala Gly Met Leu Asp Pro Pro
    450                 455                 460

Phe Val Pro Asp Pro Arg Ala Val Tyr Cys Lys Asp Val Leu Asp Ile
465                 470                 475                 480

Glu Gln Phe Ser Thr Val Lys Gly Val Asn Leu Asp His Thr Asp Asp
                485                 490                 495

Asp Phe Tyr Ser Lys Phe Ser Thr Gly Ser Val Pro Ile Pro Trp Gln
            500                 505                 510

Asn Glu Met Ile Glu Thr Glu Cys Phe Lys Glu Leu Asn Val Phe Gly
        515                 520                 525

Pro Asn Gly Thr Leu Ser Pro Asp Leu Asn Arg Ser Gln Pro Pro Glu
    530                 535                 540

Pro Pro Lys Lys Gly Leu Phe His Arg Leu Phe Arg Arg Gln His Gln
545                 550                 555                 560

Ser Asn Ser Lys Ser Ser Pro Thr Pro Lys Thr Ser Cys Asn His Arg
                565                 570                 575

Ile Asn Ser Asn His Ile Asn Ser Asn Ser Thr Gly Ser Ser
            580                 585                 590

<210> SEQ ID NO 12
<211> LENGTH: 551
<212> TYPE: PRT
<213> ORGANISM: Mus musculus

<400> SEQUENCE: 12

Met Ala Arg Lys Ala Leu Lys Leu Ala Ser Trp Thr Ser Val Ala Leu
1               5                   10                  15

Ala Ala Ser Gly Val Tyr Leu Tyr Ser Asn Asn Tyr Leu Asp Pro Asn
            20                  25                  30
```

```
Asp Phe Gly Ala Val Arg Val Gly Arg Ala Val Ala Thr Thr Ala Val
        35                  40                  45

Ile Ser Tyr Asp Tyr Leu Thr Ser Leu Arg Ser Val Pro Tyr Gly Ser
 50                  55                  60

Glu Glu Tyr Leu Gln Arg Arg Ser Gln Val His Leu Arg Ser Ala Arg
 65                  70                  75                  80

Arg Leu Phe Glu Leu Cys Cys Ala Asn Arg Gly Thr Phe Ile Lys Val
                 85                  90                  95

Gly Gln His Leu Gly Ala Leu Asp Tyr Leu Leu Pro Glu Glu Tyr Thr
                100                 105                 110

Ser Thr Leu Lys Val Leu His Ser Gln Ala Pro Gln Ser Ser Met Gln
                115                 120                 125

Glu Val Arg Gln Val Ile Arg Glu Asp Leu Gly Lys Glu Ile His Asp
                130                 135                 140

Leu Phe Leu Ser Phe Asp Asp Thr Pro Leu Gly Ala Ala Ser Leu Ala
145                 150                 155                 160

Gln Val His Lys Ala Val Leu His Asp Gly Arg Thr Val Ala Val Lys
                165                 170                 175

Val Gln His Pro Lys Val Gln Ala Gln Ser Ser Lys Asp Ile Leu Leu
                180                 185                 190

Met Glu Val Leu Val Leu Ala Val Lys Gln Leu Phe Pro Asp Phe Glu
                195                 200                 205

Phe Met Trp Leu Val Asp Glu Ala Lys Lys Asn Leu Pro Leu Glu Leu
        210                 215                 220

Asp Phe Leu Asn Glu Gly Arg Asn Ala Glu Lys Val Ala His Met Leu
225                 230                 235                 240

Arg His Phe Asp Phe Leu Lys Val Pro Gln Ile His Trp Glu Leu Ser
                245                 250                 255

Thr Lys Arg Val Leu Leu Met Glu Phe Val Glu Gly Gly Gln Val Asn
                260                 265                 270

Asp Arg Ala Tyr Met Glu Lys Asn Gln Ile Asp Val Asn Glu Ile Ser
                275                 280                 285

Cys His Leu Gly Lys Met Tyr Ser Glu Met Ile Phe Val Asn Gly Phe
        290                 295                 300

Val His Cys Asp Pro His Pro Gly Asn Val Leu Val Arg Lys Arg Pro
305                 310                 315                 320

Asp Thr Gly Lys Ala Glu Ile Val Leu Leu Asp His Gly Leu Tyr Gln
                325                 330                 335

Val Leu Thr Glu Glu Phe Arg Leu Asp Tyr Cys His Leu Trp Gln Ser
                340                 345                 350

Leu Ile Trp Thr Asp Met Asp Gly Leu Lys Gln Tyr Ser Gln Arg Leu
        355                 360                 365

Gly Ala Ala Asp Leu Tyr Pro Leu Phe Ala Cys Met Leu Thr Ala Arg
        370                 375                 380

Ser Trp Asp Ser Val Lys Gln Gly Ile Gly Gln Ala Pro Val Ser Ala
385                 390                 395                 400

Thr Glu Asp Ser Glu Ile Arg Asn Asn Ala Ala Cys Tyr Leu Pro Glu
                405                 410                 415

Ile Ser Gln Leu Leu Asn His Val Pro Arg Gln Met Leu Leu Ile Leu
                420                 425                 430

Lys Thr Asn Asp Leu Leu Arg Ser Ile Glu Thr Thr Leu Gly Thr Arg
                435                 440                 445
```

```
Ser Ser Ala Ser Ser Phe Leu Asn Met Ser Arg Cys Cys Ile Arg Ala
        450             455             460

Leu Ala Glu His Lys Lys Arg Asp Ala Gly Ser Phe Phe Arg Arg Thr
465             470             475                     480

Gln Ile Ser Phe Ser Glu Ala Phe Ser Leu Trp Gln Ile Asn Leu His
            485             490                     495

Glu Leu Leu Leu Arg Val Arg Ala Leu Arg Leu Ala Cys Trp Val Ser
            500             505             510

Ala Leu Leu Gly Trp Leu Thr Arg Ala Pro His Arg Met Arg Arg Glu
        515             520             525

Met Glu Ala Lys Arg Ala Glu Lys Lys Thr Thr Lys Gly Pro Met Lys
530             535             540

Leu Gly Ala Arg Lys Leu Asp
545             550
```